US012637493B2

(12) United States Patent
Ngo et al.

(10) Patent No.: US 12,637,493 B2
(45) Date of Patent: May 26, 2026

(54) ENGINEERED MCP AND PCP PROTEINS AND SYSTEMS AND METHODS THEREOF

(71) Applicant: TRUSTEES OF BOSTON UNIVERSITY, Boston, MA (US)

(72) Inventors: John T. Ngo, Boston, MA (US); Christopher Joseph Kuffner, Boston, MA (US); Alex Marzilli, Boston, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 18/813,643

(22) Filed: Aug. 23, 2024

(65) Prior Publication Data

US 2025/0084130 A1 Mar. 13, 2025

Related U.S. Application Data

(60) Provisional application No. 63/578,836, filed on Aug. 25, 2023.

(51) Int. Cl.
*C07K 14/005* (2006.01)
*C12N 15/11* (2006.01)

(52) U.S. Cl.
CPC ............ C07K 14/005 (2013.01); C12N 15/11 (2013.01); *C07K 2319/00* (2013.01); *C07K 2319/03* (2013.01); *C07K 2319/735* (2013.01); *C07K 2319/85* (2013.01); *C07K 2319/95* (2013.01); *C12N 2310/3513* (2013.01); *C12N 2310/531* (2013.01); *C12N 2795/00022* (2013.01)

(58) Field of Classification Search
CPC .............. C07K 14/005; C07K 2319/00; C07K 2319/03; C07K 2319/735; C07K 2319/85; C07K 2319/95; C12N 15/11; C12N 2310/3513; C12N 2310/531; C12N 2795/00022
See application file for complete search history.

(56) References Cited

U.S. PATENT DOCUMENTS

| | | | | |
|---|---|---|---|---|
| 2020/0390700 | A1* | 12/2020 | Leonard | C12N 15/88 |
| 2021/0080472 | A1* | 3/2021 | Linghu | G01N 33/6872 |
| 2021/0139964 | A1* | 5/2021 | Singer | C12Q 1/6841 |
| 2021/0206880 | A1* | 7/2021 | Steyaert | G01N 33/6845 |
| 2022/0204975 | A1* | 6/2022 | Liu | C12N 15/907 |
| 2022/0290161 | A1* | 9/2022 | Jaffrey | C12Q 1/6816 |
| 2023/0076395 | A1 | 3/2023 | Horns et al. | |
| 2023/0183678 | A1 | 6/2023 | Ramos et al. | |
| 2023/0226213 | A1* | 7/2023 | Cameron | C12N 5/0006 |
| | | | | 424/93.21 |

FOREIGN PATENT DOCUMENTS

| | | | | |
|---|---|---|---|---|
| WO | 2016054106 | A1 | 4/2016 | |
| WO | 2018195254 | A1 | 10/2018 | |
| WO | 2019217943 | A1 | 11/2019 | |
| WO | 2020191248 | A1 | 9/2020 | |
| WO | 2021072328 | A1 | 4/2021 | |
| WO | WO-2022197621 | A1 * | 9/2022 | ......... A61K 39/4611 |
| WO | 2024137990 | A2 | 6/2024 | |

OTHER PUBLICATIONS

"Polyubiquitin-B precursor [*Homo sapiens*]"; NCBI Reference Sequence: NP_001268645.1; accessed on Mar. 11, 2025. Assembly date of Sep. 21, 2024. 3 pages total. (Year: 2024).*
Wu et al. "Live imaging of mRNA using RNA-stabilized fluorogenic proteins." Nat. Methods 16: 862-865 (2019).
Xia et al. "Single-molecule live-cell RNA imaging with CRISPR-Csm", BioRxiv Preprint available on the world wide web at https://doi.org/10.1101/2024.07.14.603457 (2024).
Zhang et al. "Fluorogenic CRISPR for genomic DNA imaging." Nat. Commun. 15: 934 (2024).
Zhang et al. "Optogenetic control with a photocleavable protein, PhoCl." Nat Methods 14: 391-394 (2017).
Zielke et al. "FUCCI sensors: powerful new tools for analysis of cell proliferation." Wiley Interdiscip Rev Dev Biol. 4(5): 469-487 (2015).
Akiyama et al. "Structured RNAs that evade or confound exonucleases: function follows form." Curr Opin Struct Biol. 36: 40-47 (2016).
Bachmair et al. "In vivo half-life of a protein is a function of its amino-terminal residue." Science 234(4773): 179-186 (1986).
Bertrand et al. "Localization of ASH1 mRNA particles in living yeast." Mol. Cell 2: 437-445 (1998).
Bery et al. "A potent KRAS macromolecule degrader specifically targeting tumours with mutant KRAS." Nat. Commun. 11: 3233 (2020).
Bonger et al. "General Method for Regulating Protein Stability with Light." ACS Chem. Biol. 9: 111-115 (2014).
Bonger et al. "Small-molecule displacement of a cryptic degron causes conditional protein degradation." Nat. Chem. Biol. 7: 531-537 (2011).
Borbolis et al. "Biological implications of decapping: beyond bulk mRNA decay." FEBS J. 289(6): 1457-1475 (2022).

(Continued)

*Primary Examiner* — Anand U Desai
*Assistant Examiner* — Andrew T Moehlman
(74) *Attorney, Agent, or Firm* — Nixon Peabody LLP; Ronald I. Eisenstein; Alissa R. Young

(57) ABSTRACT

The technology described herein is directed to engineered MCP proteins and engineered PCP proteins, which are degraded when the proteins are not bound to an MS2 or PP7 RNA hairpin loop, respectively. Also described herein are fusion proteins comprising such engineered MCP proteins and engineered PCP proteins linked to various effector proteins. The linkage to the effector proteins can be modulated through of specialized linker domains. In addition, described herein are complexes and systems comprising the fusion proteins in combination with synthetic RNA molecules, in order to modulate the structure and/or function the synthetic RNA molecules.

27 Claims, 69 Drawing Sheets

Specification includes a Sequence Listing.

(56) References Cited

OTHER PUBLICATIONS

Borchardt et al. "Controlling mRNA stability and translation with the CRISPR endoribonuclease Csy4." RNA 21 (11): 1921-1930 (2015).

Brouns et al. "Small CRISPR RNAs guide antiviral defense in prokaryotes." Science 321(5891): 960-964 (2008).

Carte et al. "Cas6 is an endoribonuclease that generates guide RNAs for invader defense in prokaryotes." Genes Dev. 22(24): 3489-3496 (2008).

Cawte et al. "Live cell imaging of single RNA molecules with fluorogenic Mango II arrays." Nat. Commun. 11: 1283 (2020).

Chen et al. "CRISPR/Pepper-tDeg: A Live Imaging System Enables Non-Repetitive Genomic Locus Analysis with One Single-Guide RNA." Adv. Sci. 11: e2402534 (2024).

Chen et al. "Symbolic recording of signalling and cis-regulatory element activity to DNA." Nature 632: 1073-1081 (2024).

Choi et al. "Third-generation in situ hybridization chain reaction: multiplexed, quantitative, sensitive, versatile, robust." Dev. Camb. Engl. 145: dev165753 (2018).

Chubb et al. "Transcriptional Pulsing of a Developmental Gene." Curr. Biol. 16: 1018-1025 (2006).

Deng et al. "Tunable light and drug induced depletion of target proteins." Nat. Commun. 11: 304 (2020).

Dohmen et al. "Heat-inducible degron: a method for constructing temperature-sensitive mutants." Science 263: 1273-1276 (1994).

Foight et al. "Multi-input chemical control of protein dimerization for programming graded cellular responses." Nat Biotechnol. 37(10): 1209-1216 (2019).

Gayet et al. "Autocatalytic base editing for RNA-responsive translational control." Nat. Commun. 14: 1339 (2023).

Grant et al. "Accurate delineation of cell cycle phase transitions in living cells with PIP-FUCCI." Cell Cycle 17(21-22): 2496-2516 (2018).

Halstead et al. "An RNA biosensor for imaging the first round of translation from single cells to living animals." Science 347: 1367-1671 (2015).

Han et al. "Engineered exosomes with a photoinducible protein delivery system enable CRISPR-Cas-based epigenome editing in Alzheimer's disease." Sci Transl Med. 6(759): eadi4830 (2024).

Helgstrand et al. "Investigating the structural basis of purine specificity in the structures of MS2 coat protein RNA translational operator hairpins." Nucleic Acids Res. 30: 2678-2685 (2002).

Hill et al. "Human antibody-based chemically induced dimerizers for cell therapeutic applications." Nat Chem Biol 14: 112-117 (2018).

Hu et al. "Enhanced Single RNA Imaging Reveals Dynamic Gene Expression in Live Animals." BioRxiv Preprint available on the world wide web at https://doi.org/10.1101/2022.07.26.501631 (2022).

Kaseniit et al. "Modular and programmable RNA sensing using ADAR editing in living cells." BioRxiv Preprint available on the world wide web at https://doi.org/10.1101/2022.01.28.478207 (2022).

Katrekar et al. "In vivo RNA editing of point mutations via RNA-guided adenosine deaminases." Nat. Methods 16, 239-242 (2019).

Kim et al. "Luciferase-LOV BRET enables versatile and specific transcriptional readout of cellular protein-protein interactions." eLife 8: e43826 (2019).

Koren et al. "The Eukaryotic Proteome is Shaped by E3 Ubiquitin Ligases Targeting C-Terminal Degrons." Cell 173: 1622-1635.e14 (2018).

Li et al. "An improved MS2-MCP imaging system with minimal perturbation of mRNA stability." BioRxiv Preprint available on the world wide web at https://www.biorxiv.org/content/10.1101/2022.02.05.479257v1 (2022).

Lim et al. "Exquisitely Specific anti-KRAS Biodegraders Inform on the Cellular Prevalence of Nucleotide-Loaded States." ACS Cent. Sci. 7: 274-291 (2021).

Long et al. "Interaction of human immunodeficiency virus type 1 Tat-derived peptides with TAR RNA." Biochemistry 34: 8885-8895 (1995).

Lowary et al. "An RNA mutation that increases the affinity of an RNA-protein interaction." Nucleic Acids Res. 15: 10483-10493 (1987).

Lyons et al. "Morphogenesis in sea urchin embryos: linking cellular events to gene regulatory network states." Wiley Interdiscip Rev Dev Biol. 1(2): 231-252 (2012).

Mcshane et al. "Kinetic Analysis of Protein Stability Reveals Age-Dependent Degradation." Cell 167: 803-815.e21 (2016).

Nakanishi et al. "Caliciviral protein-based artificial translational activator for mammalian gene circuits with RNA-only delivery." Nat Commun. 11(1): 1297 (2020).

Nam et al. "Cas5d protein processes pre-crRNA and assembles into a cascade-like interference complex in subtype I-C/Dvulg CRISPR-Cas system." Structure 20(9): 1574-1584 (2012).

Negi et al. "An engineered cell line with a hRpn1-attached handle to isolate proteasomes." J Biol Chem. 299(8): 104948 (2023).

Peabody et al. "Complementation of RNA binding site mutations in MS2 coat protein heterodimers." Nucleic Acids Res. 24: 2352-2359 (1996).

Reynaud et al. "Surveying the global landscape of post-transcriptional regulators." Nat Struct Mol Biol 30: 740-752 (2023).

Shao et al. "Engineered poly(A)-surrogates for translational regulation and therapeutic biocomputation in mammalian cells." Cell Res. 34(1): 31-46 (2024).

Skeparnias et al. "Expanding the repertoire of deadenylases." RNA Biol. 14(10): 1320-1325 (2017).

Stephens et al. "Engineering single pan-specific ubiquibodies for targeted degradation of all forms of endogenous ERK protein kinase." BioRxiv Preprint available on the world wide web at https://www.biorxiv.org/content/10.1101/2021.04.16.440242v1 (2021).

Sternberg et al. "Mechanism of substrate selection by a highly specific CRISPR endoribonuclease." RNA 18(4): 661-672 (2012).

Tague et al. "Chemogenetic control of gene expression and cell signaling with antiviral drugs." Nat Methods. 15(7): 519-522 (2018).

Tang et al. "Detection and manipulation of live antigen-expressing cells using conditionally stable nanobodies." eLife 5: e15312 (2016).

Thurm et al. "High-throughput discovery of regulatory effector domains in human RNA-binding proteins." BioRxiv Preprint available on the world wide web at https://www.biorxiv.org/content/10.1101/2024.07.19.604317v1 (2024).

Vallecillo-Viejo et al. "Abundant off-target edits from site-directed RNA editing can be reduced by nuclear localization of the editing enzyme." RNA Biol. 15: 104-114 (2018).

Waymack et al. "Shadow enhancers can suppress input transcription factor noise through distinct regulatory logic." eLife 9: e59351 (2020).

Wu et al. "Fluorescence Fluctuation Spectroscopy Enables Quantitative Imaging of Single mRNAs in Living Cells." Biophys. J. 102: 2936-2944 (2012).

* cited by examiner 3.2: TetR-LID Negative Feedback For Reduced Variability in MCPQ Expression 3.1: MCPQ Transcript Autoinhibition For
Reduced Variability in MCPQ Expression 5' MS2 FP-MCPQ mRNA

FP-MCPQ

RRRG

MS2 transcript

E3 Ligase

After 2h in CHX d-td-MCP

*unbound protein copies are degraded*

MS2 hairpin

*Selective preservation of MS2-bound copies via degron masking*

MS2 Bound, Degron Masked

Stop Codons: 0
MS2 Loop: None

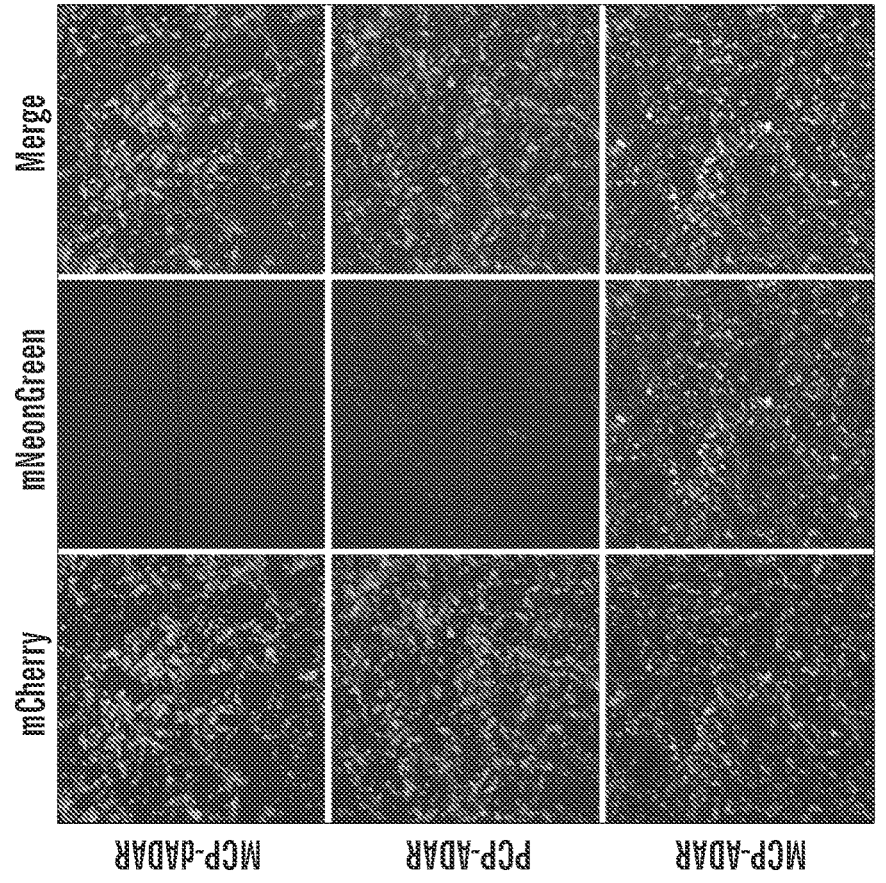
*FIG. 40*
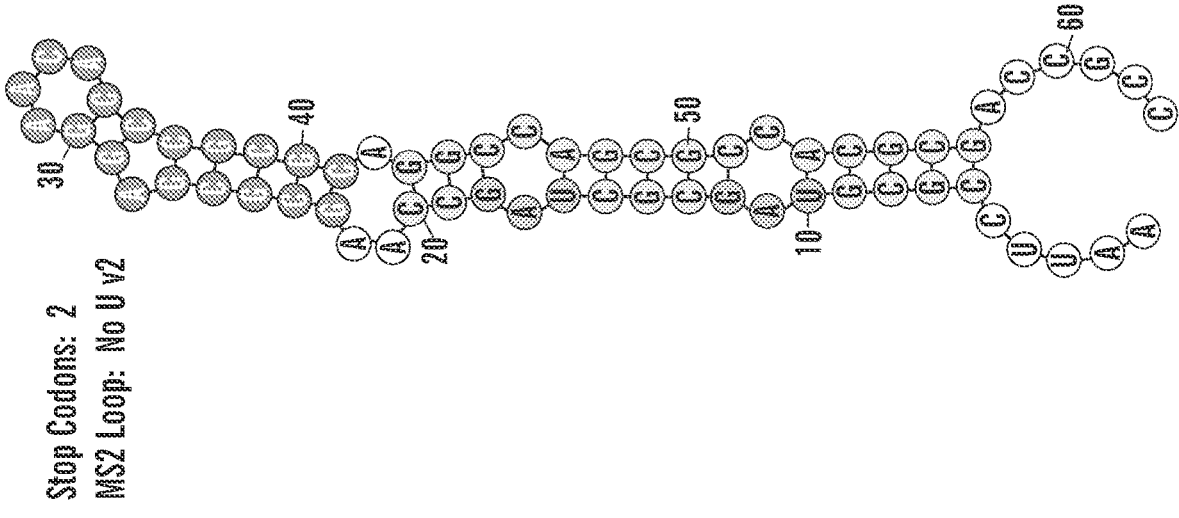
Stop Codons: 2
MS2 Loop: No U V2

SEQUENCE LISTING

Sequence total quantity: 56
SEQ ID NO: 1             moltype = DNA   length = 765
FEATURE                  Location/Qualifiers
source                   1..765
                         mol_type = other DNA
                         organism = synthetic construct
SEQUENCE: 1
tccaagactg cgtatagagt aaacctgaaa ctggatcaag ccgatgtcgt agatagtggg  60
gctcctaaag tgaggtatac tcaagtctgg tcacatgacg taacgatagt cgctaactct  120
acggaagcga gccgaaaaag cctctacgat ctcacgaagt ccctcgtggc tacttctcaa  180
gtcgaggatc tcgtagtcaa tcttgtcccg cttgggcgcg cggatccgct agcctcaaag  240
acaatagtgt tgagtgtggg ggaagctacg cggaccttga ctgaaataca acgcaccgca  300
gatcggcaga ttttcgagga gaaggtgggg cctgctgtcg gccgcttgag gcttaccgct  360
tcactgcgac agaacggagc taaaaccgcc tataggtca acttgaaatt ggatcaggca  420
gacgtcgttg attctcgggc gccaaaggta aggtataccc aagtatggtc ccacgacgtt  480
acgattgtag ccaattctac tgaggcttca cgaaagtcac tctacgactt gaccaaatct  540
cttgttgcaa catcacaggt ggaggacctt gtcgtcaatt tggtgccact cgggcgagcg  600
ggcgccctag ccagtaagac cattgtgctt agcgtagggg aagccacacg gacgcttacc  660
gaaatacaga gaacggccga ccggcagatt tttgaagaaa aagtaggccc cgcagttgga  720
cgcctgaggc ttacggcttc ccttcgacag aggcgtcgag gataa                 765

SEQ ID NO: 2             moltype = AA   length = 254
FEATURE                  Location/Qualifiers
source                   1..254
                         mol_type = protein
                         organism = synthetic construct
SEQUENCE: 2
SKTAYRVNLK LDQADVVDSG APKVRYTQVW SHDVTIVANS TEASRKSLYD LTKSLVATSQ  60
VEDLVVNLVP LGRADPLASK TIVLSVGEAT RTLTEIQRTA DRQIFEEKVG PAVGRLRLTA  120
SLRQNGAKTA YRVNLKLDQA DVVDSGAPKV RYTQVWSHDV TIVANSTEAS RKSLYDLTKS  180
LVATSQVEDL VVNLVPLGRA GALASKTIVL SVGEATRTLT EIQRTADRQI FEEKVGPAVG  240
RLRLTASLRQ RRRG                                                    254

SEQ ID NO: 3             moltype = DNA   length = 696
FEATURE                  Location/Qualifiers
source                   1..696
                         mol_type = other DNA
                         organism = synthetic construct
SEQUENCE: 3
gcccaaaaca ggaaatacac catcaaagtg gaggtgccaa agggtgcctg gcggagctac  60
ctgaacatgg agctgactat tccaatcttc gctactaatt ccgattgcga actgatagta  120
aaagcgatgc aaggtttgct gaaagacggc aacccaattc ccagcgcaat cgccgccaat  180
agcggcatct acgctaattt cacacagttc gtgctggtcg acaacggcgg caccggcgac  240
gttacggtgg ccccctcaaa ctttgccaac gggattgccg agtggataag cagcaatagc  300
aggtcccagg cctacaaggt tacctgtagc gtaaggcaga gcagcgccca gaaccgaaag  360
tacacgatta aggtggaagt ccccaaaggc gcatggagga gctatcttaa tatggaactg  420
accatcccca tattcgcgac aaacagcgac tgtgagctga tcgtgaaggc tatgcagggc  480
ctcctcaagg atgggaaccc gatccgtctc gccatcgcca ctaactccgg catttatgca  540
aacttcactc aatttgttct ggtggacaat ggtgggaccg gggatgttac cgtggctccc  600
agcaattttg ctaacggtat cgcagaatgg atcagtagta acagcaggag ccaagcctat  660
aaagtgacgt gcagcgtacg gcagaggaga agaggc                           696

```
SEQ ID NO: 4              moltype = AA   length = 232
FEATURE                   Location/Qualifiers
source                    1..232
                          mol_type = protein
                          organism = synthetic construct
SEQUENCE: 4
AQNRKYTIKV EVPKGAWRSY LNMELTIPIF ATNSDCELIV KAMQGLLKDG NPIPSAIAAN   60
SGIYANFTQF VLVDNGGTGD VTVAPSNFAN GIAEWISSNS RSQAYKVTCS VRQSSAQNRK   120
YTIKVEVPKG AWRSYLNMEL TIPIFATNSD CELIVKAMQG LLKDGNPIPS AIAANSGIYA   180
NFTQFVLVDN GGTGDVTVAP SNFANGIAEW ISSNSRSQAY KVTCSVRQRR RG           232

SEQ ID NO: 5              moltype = AA   length = 235
FEATURE                   Location/Qualifiers
source                    1..235
                          mol_type = protein
                          organism = synthetic construct
SEQUENCE: 5
ASNFTQFVLV DNGGTGDVTV APSNFANGIA EWISSNSRSQ AYKVTCSVRQ SSAQNRKYTI   60
KVEVPKGAWR SYLNMELTIP IFATNSDCEL IVKAMQGLLK DGNPIPSAIA ANSGIYAMAS   120
NFTQFVLVDN GGTGDVTVAP SNFANGIAEW ISSNSRSQAY KVTCSVRQSS AQNRKYTIKV   180
EVPKGAWRSY LNMELTIPIF ATNSDCELIV KAMQGLLKDG NPIPSAIAAN SGIYA        235

SEQ ID NO: 6              moltype = AA   length = 249
FEATURE                   Location/Qualifiers
source                    1..249
                          mol_type = protein
                          organism = synthetic construct
SEQUENCE: 6
LASKTIVLSV GEATRTLTEI QSTADRQIFE EKVGPLVGRL RLTASLRQNG AKTAYRVNLK   60
LDQADVVDSG LPKVRYTQVW SHDVTIVANS TEASRKSLYD LTKSLVATSQ VEDLVVNLVP   120
LGRADPLASK TIVLSVGEAT RTLTEIQSTA DRQIFEEKVG PLVGRLRLTA SLRQNGAKTA   180
YRVNLKLDQA DVVDSGLPKV RYTQVWSHDV TIVANSTEAS RKSLYDLTKS LVATSQVEDL   240
VVNLVPLGR                                                          249

SEQ ID NO: 7              moltype = DNA   length = 263
FEATURE                   Location/Qualifiers
source                    1..263
                          mol_type = other DNA
                          organism = synthetic construct
SEQUENCE: 7
cggtcccaag cccggataaa atgggagggg gcgggaaacc gcctaaccat gccgagtgcg   60
gccgcttgcc atgtgtatgt gggacgcgtt gccacgtttc ccacatactc tgatgatccg   120
ctagcaaagg ctcgtctgag ctcattagct ccgagcccga ggtaccggat cattcatggc   180
aagcggccgc ggtcggcgtg gactgtagaa cactgccaat gccggtccca agcccggata   240
aaagtggagg gtacagtcca cgc                                          263

SEQ ID NO: 8              moltype = DNA   length = 253
FEATURE                   Location/Qualifiers
source                    1..253
                          mol_type = other DNA
                          organism = synthetic construct
SEQUENCE: 8
cggtcccaag cccggataaa atgggagggg gcgggaaacc gcctaaccat gccgagtgcg   60
gccgcttgcc atgtgtatgt gggacgcgtt gccacgtttc ccacatactc tgatgatccg   120
ctagcaaagc acgagcatca gccgtgccga ggtaccggat cattcatggc aagcggccgc   180
ggtcggcgtg gactgtagaa cactgccaat gccggtccca agcccggata aaagtggagg   240
gtacagtcca cgc                                                     253

SEQ ID NO: 9              moltype = DNA   length = 259
FEATURE                   Location/Qualifiers
source                    1..259
                          mol_type = other DNA
                          organism = synthetic construct
SEQUENCE: 9
cggtcccaag cccggataaa atgggagggg gcgggaaacc gcctaaccat gccgagtgcg   60
gccgcttgcc atgtgtatgt gggacgcgtt gccacgtttc ccacatactc tgatgatccg   120
ctagcaaagg agcagacgat atggcgtcgc tcccgaggta ccggatcatt catgcaagc    180
ggccgcggtc ggcgtggact gtagaacact gccaatgccg gtcccaagcc cggataaaag   240
tggagggtac agtccacgc                                               259

SEQ ID NO: 10             moltype = AA   length = 4
FEATURE                   Location/Qualifiers
source                    1..4
                          mol_type = protein
                          organism = synthetic construct
SEQUENCE: 10
RRRG                                                               4

SEQ ID NO: 11             moltype = AA   length = 73
```

```
FEATURE                  Location/Qualifiers
source                   1..73
                         mol_type = protein
                         organism = synthetic construct
SEQUENCE: 11
SKTAYRVNLK LDQADVVDSG APKVRYTQVW SHDVTIVANS TEASRKSLYD LTKSLVATSQ  60
VEDLVVNLVP LGR                                                      73

SEQ ID NO: 12            moltype = AA  length = 120
FEATURE                  Location/Qualifiers
source                   1..120
                         mol_type = protein
                         organism = synthetic construct
SEQUENCE: 12
SKTIVLSVGE ATRTLTEIQR TADRQIFEEK VGPAVGRLRL TASLRQNGAK TAYRVNLKLD  60
QADVVDSGAP KVRYTQVWSH DVTIVANSTE ASRKSLYDLT KSLVATSQVE DLVVNLVPLG  120

SEQ ID NO: 13            moltype = AA  length = 46
FEATURE                  Location/Qualifiers
source                   1..46
                         mol_type = protein
                         organism = synthetic construct
SEQUENCE: 13
SKTIVLSVGE ATRTLTEIQR TADRQIFEEK VGPAVGRLRL TASLRQ                 46

SEQ ID NO: 14            moltype = DNA  length = 765
FEATURE                  Location/Qualifiers
source                   1..765
                         mol_type = other DNA
                         organism = synthetic construct
SEQUENCE: 14
tccaagactg cgtatagagt aaacctgaaa ctggatcaag ccgatgtcgt agatagtggg  60
cttcctaaag tgaggtatac tcaagtctgg tcacatgacg taacgatagt cgctaactct  120
acggaagcga gccgaaaaag cctctacgat ctcacgacgt ccctcgtggc tacttctcaa  180
gtcgaggatc tcgtagtcaa tcttgtcccg cttgggcgcg cggatccgct agcctcaaag  240
acaatagtgt tgagtgtggg ggaagctacg cggaccttga ctgaaataca aagcaccgca  300
gatcggcaga ttttcgagga gaaggtgggg cctcttgtcg gccgcttgag gcttaccgct  360
tcactgcgac agaacggagc taaaaccgcc tatagggtca acttgaaatt ggatcaggca  420
gacgtcgttg attctgggct gccaaaggta aggtataccc aagtatggtc ccacgacgtt  480
acgattgtag ccaattctac tgaggcttca cgaaagtcac tctacgactt gaccaaatct  540
cttgttgcaa catcacaggt ggaggacctt gtcgtcaatt tggtgccact cgggcgagcg  600
ggcgccctag ccagtaagac cattgtgctt agcgtagggg aagccacacg gacgcttacc  660
gaaatacaga gtacggccga ccggcagatt tttgaagaaa aagtaggccc cctagttgga  720
cgcctgaggc ttacggcttc ccttcgacag aggcgtcgag gataa                 765

SEQ ID NO: 15            moltype = AA  length = 254
FEATURE                  Location/Qualifiers
source                   1..254
                         mol_type = protein
                         organism = synthetic construct
SEQUENCE: 15
SKTAYRVNLK LDQADVVDSG LPKVRYTQVW SHDVTIVANS TEASRKSLYD LTKSLVATSQ  60
VEDLVVNLVP LGRADPLASK TIVLSVGEAT RTLTEIQSTA DRQIFEEKVG PLVGRLRLTA  120
SLRQNGAKTA YRVNLKLDQA DVVDSGLPKV RYTQVWSHDV TIVANSTEAS RKSLYDLTKS  180
LVATSQVEDL VVNLVPLGRA GALASKTIVL SVGEATRTLT EIQSTADRQI FEEKVGPLVG  240
RLRLTASLRQ RRRG                                                    254

SEQ ID NO: 16            moltype = AA  length = 73
FEATURE                  Location/Qualifiers
source                   1..73
                         mol_type = protein
                         organism = synthetic construct
SEQUENCE: 16
SKTAYRVNLK LDQADVVDSG LPKVRYTQVW SHDVTIVANS TEASRKSLYD LTKSLVATSQ  60
VEDLVVNLVP LGR                                                      73

SEQ ID NO: 17            moltype = AA  length = 121
FEATURE                  Location/Qualifiers
source                   1..121
                         mol_type = protein
                         organism = synthetic construct
SEQUENCE: 17
SKTIVLSVGE ATRTLTEIQS TADRQIFEEK VGPLVGRLRL TASLRQNGAK TAYRVNLKLD  60
QADVVDSGLP KVRYTQVWSH DVTIVANSTE ASRKSLYDLT KSLVATSQVE DLVVNLVPLG  120
R                                                                   121

SEQ ID NO: 18            moltype = AA  length = 46
FEATURE                  Location/Qualifiers
source                   1..46
```

-continued

```
                          mol_type = protein
                          organism = synthetic construct
SEQUENCE: 18
SKTIVLSVGE ATRTLTEIQS TADRQIFEEK VGPLVGRLRL TASLRQ                      46

SEQ ID NO: 19            moltype = AA   length = 64
FEATURE                  Location/Qualifiers
source                   1..64
                         mol_type = protein
                         organism = synthetic construct
SEQUENCE: 19
AQNRKYTIKV EVPKGAWRSY LNMELTIPIF ATNSDCELIV KAMQGLLKDG NPIPSAIAAN       60
SGIY                                                                    64

SEQ ID NO: 20            moltype = AA   length = 114
FEATURE                  Location/Qualifiers
source                   1..114
                         mol_type = protein
                         organism = synthetic construct
SEQUENCE: 20
NFTQFVLVDN GGTGDVTVAP SNFANGIAEW ISSNSRSQAY KVTCSVRQSS AQNRKYTIKV       60
EVPKGAWRSY LNMELTIPIF ATNSDCELIV KAMQGLLKDG NPIPSAIAAN SGIY             114

SEQ ID NO: 21            moltype = AA   length = 48
FEATURE                  Location/Qualifiers
source                   1..48
                         mol_type = protein
                         organism = synthetic construct
SEQUENCE: 21
NFTQFVLVDN GGTGDVTVAP SNFANGIAEW ISSNSRSQAY KVTCSVRQ                    48

SEQ ID NO: 22            moltype = AA   length = 117
FEATURE                  Location/Qualifiers
source                   1..117
                         mol_type = protein
                         organism = synthetic construct
SEQUENCE: 22
ASNFTQFVLV DNGGTGDVTV APSNFANGIA EWISSNSRSQ AYKVTCSVRQ SSAQNRKYTI       60
KVEVPKGAWR SYLNMELTIP IFATNSDCEL IVKAMQGLLK DGNPIPSAIA ANSGIYA          117

SEQ ID NO: 23            moltype = AA   length = 118
FEATURE                  Location/Qualifiers
source                   1..118
                         mol_type = protein
                         organism = synthetic construct
SEQUENCE: 23
MASNFTQFVL VDNGGTGDVT VAPSNFANGI AEWISSNSRS QAYKVTCSVR QSSAQNRKYT       60
IKVEVPKGAW RSYLNMELTI PIFATNSDCE LIVKAMQGLL KDGNPIPSAI AANSGIYA         118

SEQ ID NO: 24            moltype = AA   length = 123
FEATURE                  Location/Qualifiers
source                   1..123
                         mol_type = protein
                         organism = synthetic construct
SEQUENCE: 24
LASKTIVLSV GEATRTLTEI QSTADRQIFE EKVGPLVGRL RLTASLRQNG AKTAYRVNLK       60
LDQADVVDSG LPKVRYTQVW SHDVTIVANS TEASRKSLYD LTKSLVATSQ VEDLVVNLVP       120
LGR                                                                     123

SEQ ID NO: 25            moltype = AA   length = 8
FEATURE                  Location/Qualifiers
source                   1..8
                         mol_type = protein
                         organism = synthetic construct
SEQUENCE: 25
VRQSSAQN                                                                8

SEQ ID NO: 26            moltype = AA   length = 5
FEATURE                  Location/Qualifiers
source                   1..5
                         mol_type = protein
                         organism = synthetic construct
SEQUENCE: 26
VRQSS                                                                   5

SEQ ID NO: 27            moltype = DNA   length = 21
FEATURE                  Location/Qualifiers
source                   1..21
                         mol_type = other DNA
```

```
                        organism = synthetic construct
SEQUENCE: 27
aaacatgagg attacccatg t                                              21

SEQ ID NO: 28          moltype =    length =
SEQUENCE: 28
000

SEQ ID NO: 29          moltype = DNA   length = 19
FEATURE                Location/Qualifiers
source                 1..19
                       mol_type = other DNA
                       organism = synthetic construct
SEQUENCE: 29
gcgcgaggaa cacccgcgc                                                 19

SEQ ID NO: 30          moltype = DNA   length = 4887
FEATURE                Location/Qualifiers
source                 1..4887
                       mol_type = other DNA
                       organism = synthetic construct
SEQUENCE: 30
ggagacccaa gctggctaga ggatcgaacc cttaaggcca ccatggcgtc caatttcact   60
cagtttgtgc tggttgacaa cggcgggacc ggggacgtta cggtagcccc ctcaaacttt   120
gccaacggta tagcggagtg gataagcagc aattctagga gtcaagcata caaagttaca   180
tgcagcgtgc gccaatctag cgctcagaat cgcaagtaca ccattaaagt agaggtcccc   240
aagggagcct ggagaagcta tcttaacatg gagttgacca taccaatctt cgctaccaac   300
tctgactgtg aactcattgt gaaagccatg caaggtctgc tcaaggatgg taacccaatt   360
ccgtccgcta tcgctgccaa ctctgggatt tacgggggca gtgggagcgg tgcaggatct   420
ggtagtccag ctgggggagg agcaccgggt agcggtgggt ggtctcagct gcacctgccc   480
caggttctcg cagacgccgt atcccgcctt gtactgggca agtttggtga tcttactgac   540
aattttttcat ctcctcatgc gaggcggaaa gtactcgcag gcgtcgtcat gacgaccgga   600
actgacgtga aagacgccaa agtcatctct gtctccacgg gcacaaagtg cataaacggg   660
gagtacatga gcgaccgggg gctggcactg aatgattgtc acgctgaaat aatatctagg   720
cgatctctgc ttagatttct ctacactcaa ctcgaattgt accttaacaa caaagatgac   780
cagaaacgca gtatatttca gaaatcagaa cgcggcggat ttcgacttaa ggaaaacgtt   840
cagttccact tgtatatcag cacatccct tgcggtgacg cccgaatctt ttccccgcac   900
gagccgatat tggaggagcc cgcggacaga catcctaata ggaaggctag aggccaactt   960
cggacgaaga ttgaaagtgg ccaggtgact atcccggtgc ggtccaacgc tagtattcaa   1020
acgtgggacg gagtccttca aggtgaacgg ctgttgacaa tgagctgctc agacaaaatc   1080
gcgcgctgga atgtagtggg aatccaaggc agcctcttga gcatattcgt agaacccata   1140
tatttctcat ccattatttt gggctctctg tatcatggtg accatctgtc aagggctatg   1200
taccaacgaa tttctaatat cgaggatctt cctccactct atacactcaa taagcctctc   1260
ttgtccggga tatcaaacgc tgaggcccgc cagccaggga aagctcctaa cttcagtgtt   1320
aactggaccg ttggtgattc tgcgatagag gtcatcaacg ccacgacagg taaggatgag   1380
ctcggtagag cctcacgcct gtgtaaacac gcgttgtatt gtagatggat gagagtacat   1440
gggaaggtcc catctcactt gctccgaagc aagatcacta gcctaatgt gtatcatgag   1500
tcaaaactcg cggctaaaga ataccaggca gccaaagctc gacttttac agctttttatt   1560
aaggcagggc tcgggcatg ggtcgagaag ccgaccgagc aggaccaatt ctctctgacg   1620
gggagcggat ccagcgagct gattaaggag aacatgcaca tgaagcgccc atcggtcgcc   1680
accatggtga gcaagggcga ggaggataac atggccatca tcaaggagtt catgcgcttc   1740
aaggtgcaca tggagggctc cgtgaacggc cacgagttcg agatcgaggg cgagggcgag   1800
ggccgccct acgagggcac ccagaccgcc aagctgaagg tgaccaaggg tggcccctg   1860
ccccttcgcct gggacatcct gtcccctcag ttcatgtacg gctccaaggc ctacgtgaag   1920
caccccgccg acatccccga ctacttgaag ctgtccttcc ccgagggctt caagtgggag   1980
cgcgtgatga acttcgagga cggcggcgtg gtgaccgtga cccaggactc ctccctgcag   2040
gacggcgagt catctacaa ggtgaagctg cgcggcacca acttcccctc cgacggcccc   2100
gtaatgcaga agaagaccat gggctgggag gcctcctccg agcggatgta ccccgaggac   2160
ggcgccctga aggcgagat caagcagagg ctgaagctga aggacggcgg ccactacgac   2220
gctgaggtca agaccaccta caaggccaag aagcccgtgc agctgcccgg cgcctacaac   2280
gtcaacatca gttggacat cacctccac aacgaggact acaccatcgt ggaacagtac   2340
gaacgcgccg agggccgcca ctccaccggc ggcatgacg agctgtacaa ggattacaag   2400
gatgacgatg acaaaggtag cggggcaact aattttagct tactcaaaca ggctggggac   2460
gtcgaggaa atccaggccc tgcatccgct ggctctgaga aggacgagg ctccttgcca   2520
acctgtggag atgtcgaaga aacccaggt cctgcaaccg ggaattccgc gtagcgctag   2580
ctttgccagc gccacgcgaa acatgaggat cacccatgtg ccgctatggc agaaatcggt   2640
actggctttc cattcgaccc ccattatgtg gaagtcctgg gcgagcgcat gcactacgtc   2700
gatgttggtc cgcgcgatgg caccctgtg ctgttcctgc acggtaaccc gacctcctcc   2760
tacgtgtggc gcaacatcat cccgcatgtt gcaccgaccc atcgctgcat tgctccagac   2820
ctgatcggta tgggcaaatc cgacaaacca gacctgggtt atttcttcga cgaccacgtc   2880
cgcttcatgg atgccttcat cgaagccctg ggtctggaag aggtcgtcct ggtcattcac   2940
gactgggggct ccgctctggg tttccactgg gccaagcgca atccagagcg cgtcaaaggt   3000
attgcattta tggagttcat ccgccctatc ccgacctggg acgaatggcc agaatttgcc   3060
cgcgagacct tccaggcctt ccgaccacc gacgtcgggc gcaagctgat catcgatcag   3120
aacgttttta tcgagggtac gctgccgatg ggtgtcgtcc gcccgctgac tgaagtcgag   3180
atggaccatt accgcgagcc gttcctgaat cctgttgacc gcgagccact gtggcgcttc   3240
ccaaacgagc tgccaatcgc cggtgagcca gcgaacatcg tcgcgctggt cgaagaatac   3300
atggactggc tgcaccagtc ccctgtcccg aagctgctgt ctgggggcac cccaggcgtt   3360
ctgatcccac cggccgaagc cgctcgcctg gccaaaagcc tgcctaactg caaggctgtg   3420
```

```
gacatcggcc cgggtctgaa tctgctgcaa gaagacaacc cggacctgat cggcagcgag 3480
atcgcgcgct ggctgtcgac gctcgagatt tctggcaccg gtatggcatc tatgactgga 3540
ggccaacaga tgggtcctgc aaccgggaat tccgcgtagc gctagctttg ccagcgccac 3600
gcgaaacatg aggatcaccc atgtactagt gccacaaact tctctctgct aaagcaagca 3660
ggtgatgttg aagaaaaccc agggcctgga gggtccgagg gcaggggaag tctcctaaca 3720
tgcggggacg tggaggaaaa tcccggccca tccggatatc cctacgatgt gcccgattac 3780
gctgctagct ctagactgga caagagcaaa gtcataaact ctgctctgga attactcaat 3840
gaagtcggta tcgaaggcct gacgacaagg aaactcgctc aaaagctggg agttgagcag 3900
cctaccctgt actggcacgt gaagaacaag cgggccctgc tcgatgccct ggcaatcgag 3960
atgctggaca ggcatcatac ccacttctgc ccctggaag gcgagtcatg gcaagacttt 4020
ctgcggaaca acgccaagtc attccgctgt gctctcctct cacatcgcga cggggctaaa 4080
gtgcatctcg gcacccgccc aacagagaaa cagtacgaaa ccctggaaaa tcagctcgcg 4140
ttcctgtgtc agcaaggctt ctccctggag aacgcactgt acgctctgtc cgccgtgggc 4200
cactttacac tgggctgcgt attggaggat caggagcatc aagtagcaaa agaggaaaga 4260
gagacaccta ccaccgattc tatgcccca cttctgagac aagcaattga gctgttcgac 4320
catcagggag ccgaacctgc cttcctttc ggcctggaac taatcatatg tggcctggag 4380
aaacagctaa agtgcgaaag cggcgggccg gccgacgccc ttgacgattt tgacttagac 4440
atgctcccag ccgatgccct tgacgacttt gaccttgata tgctgcctgc tgacgctctt 4500
gacgattttg accttgacat gctccccggg taatctagag ggcccgcggt tcgaaggtaa 4560
gcctatccct aaccctctcc tcggtctcga ttctacgcgt accggtcatc atcaccatca 4620
ccattgagtt taaacccgct gatcagcctc gactgtgcct tctagttgcc agccatctgt 4680
tgtttgcccc tccccgtgc cttccttgac cctggaaggt gccactccca ctgtcctttc 4740
ctaataaaat gaggaaattg caaaaaaaaa aaaaaaaaa aaaaaaaaa aaaaaaaaa 4800
aaaaaaaaaa aaaaaaaaaa aaaaaaaaaa aaaaaaaaaa aaaaaaaaaa aaaaaaaaaa 4860
aaaaaaaaaa aaaaaaaaaa aaaaaaa                                      4887

SEQ ID NO: 31        moltype = DNA   length = 4887
FEATURE              Location/Qualifiers
source               1..4887
                     mol_type = other DNA
                     organism = synthetic construct
SEQUENCE: 31
ggagacccaa gctggctaga ggatcgaacc cttaaggcca ccatggcgtc caatttcact 60
cagtttgtgc tggttgacaa cggcgggacc ggggacgtta cggtagcccc ctcaaacttt 120
gccaacggta tagcggagtg gataagcagc aattctagga gtcaagcata caaagttaca 180
tgcagcgtgc gccaatctag cgctcagaat cgcaagtaca ccattaaagt agaggtcccc 240
aagggagcct ggagaagcta tcttaacatg gagttgacca taccaatctt cgctaccaac 300
tctgactgtg aactcattgt gaaagccatg caaggtctgc tcaaggatgg taacccaatt 360
ccgtccgcta tcgctgccaa ctctgggatt tacggggcca gtttggagtg tgcaggatct 420
ggtagtccag ctgggggagg agcaccgggt agcggtgggg ggtctcagct gcacctgccc 480
caggttctcg cagacgccgt atcccgcctt gtactgggca agtttggtga tcttactgac 540
aatttttcat ctcctcatgc gaggcggaaa gtactcgcag gcgtcgtcat gacgaccgga 600
actgacgtga aagacgccaa agtcatctct gtctccacgg gcacaaagtg cataaacggg 660
gagtacatga gcgaccgggg gctggcactg aatgattgtc acgctgccat aatatctagg 720
cgatctctgc ttagatttct ctacactcaa ctcgaattgt accttaacaa caaagatgac 780
cagaaacgca gtatatttca gaaatcagaa cgcggcggat ttcgacttaa ggaaaacgtt 840
cagttccact tgtatatcag cacatcccct tgcggtgacg cccgaatctt ttccccgcac 900
gagccgatat tggaggagcc cgcggacaga catcctaata ggaaggctag aggccaactt 960
cggacgaaga ttgaaagtgg ccagggtact atcccggtgc ggtccaacgc tagtattcaa 1020
acgtgggacg gagtccttca aggtgaacgg ctgttgacaa tgagctgctc agacaaaatc 1080
gcgcgctgga atgtagtggg aatccaaggc agcctcttga gcatattcgt agaacccata 1140
tatttctcat ccattatttt gggctctctg tatcatggtg accatctgtc aagggctatg 1200
taccaacgaa tttctaatat cgaggatctt cctccactct atacactcaa taagcctctc 1260
ttgtccggga tatcaaacgc tgaggcccgc cagccaggga aagctcctaa cttcagtgtt 1320
aactggaccg ttggtgattc tgcgatagag gtcatcaacg ccacgacagg taaggatgag 1380
ctcggtagag cctcacgcct gtgtaaacac gcgttgtatt gtagatggat gagagtacat 1440
gggaaggtcc catctcactt gctccgaagc aagatcacta agcctaatgt gtatcatgag 1500
tcaaaactcg cggctaaaga ataccaggca gccaaagctc gacttttac agcttttatt 1560
aaggcagggc tcgggcatg ggtcgagaag ccgaccgagc aggaccaatt ctctctgacg 1620
gggagcggat ccagcgagct gattaaggag aacatgcaca tgaagcgccc atcggtcgcc 1680
accatggtga gcaaagggcga ggaggataac atggccatca tcaaggagtt catgcgcttc 1740
aaggtgcaca tggaggggctc cgtgaacggc cacgagttcg agatcgaggg cgagggcgag 1800
ggccgccct acgagggcac ccagaccgcc aagctgaagg tgaccaaggg tggcccctg 1860
cccttcgcct gggacatcct gtcccctcag ttcatgtacg gctccaagc ctacgtgaag 1920
caccccgccg acatccccga ctacttgaag ctgtccttcc ccgagggctt caagtgggag 1980
cgcgtgatga acttcgagga cggcggcgtg gtgaccgtga cccaggactc ctccctgcag 2040
gacggcgagt tcatctacaa ggtgaagctg cgcggcacca acttcccctc cgacggcccc 2100
gtaatgcaga gaagaccat gggctgggag gcctcctccg agcggatgta ccccgaggac 2160
ggcgccctga agggcgagat caagcagagg ctgaagctga aggacggcgg ccactacgac 2220
gctgaggtca agaccaccta caaggccaag aagcccgtgc agctgccgg cgcctacaac 2280
gtcaacatca agttggacat cacctccac aacgaggact acaccatcgt ggaacagtac 2340
gaacgcgccc agggccgcca ctccaccggc ggcatgacg agctgtacaa ggattacaag 2400
gatgacgatg acaaaggtag cggggcaact aattttagct tactcaaaca ggctgggac 2460
gtcgagggaa atccaggccc tgcatccgct ggctctgga aggacgagg ctccttgctc 2520
acctgtggag atgtcgaaga gaacccaggt cctgcaaccg gaattccgc gtagcgctag 2580
ctttgccagc gccacgcgaa acatgaggat cacccatgtg ccgctatggc agaaatcggt 2640
actggctttc cattcgaccc ccattatgtg gaagtcctgg gcgagcgcat gcactacgtc 2700
gatgttggtc gcgcgatgg cacccctgtg ctgttcctgc acggtaaccc gacctcctcc 2760
tacgtgtggc gcaacatcat cccgcatgtt gcaccgacc atcgctgcat tgctccagac 2820
```

```
ctgatcggta tgggcaaatc cgacaaacca gacctgggtt atttcttcga cgaccacgtc  2880
cgcttcatgg atgccttcat cgaagccctg ggtctggaag aggtcgtcct ggtcattcac  2940
gactggggct ccgctctggg tttccactgg gccaagcgca atccagagcg cgtcaaaggt  3000
attgcattta tggagttcat ccgccctatc ccgacctggg acgaatggcc agaatttgcc  3060
cgcgagacct tccaggcctt ccgcaccacc gacgtcggcc gcaagctgat catcgatcag  3120
aacgttttta tcgagggtac gctgccgatg ggtgtcgtcc gcccgctgac tgaagtcgag  3180
atggaccatt accgcgagcc gttcctgaat cctgttgacc gcgagccact gtggcgcttc  3240
ccaaacgagc tgccaatcgc cggtgagcca gcgaacatcg tcgcgctggt cgaagaatac  3300
atggactggc tgcaccagtc ccctgtcccg aagctgctgt tctggggcac cccaggcgtt  3360
ctgatcccac cggccgaagc cgctcgcctg gccaaaagcc tgcctaactg caaggctgtg  3420
gacatcggcc cgggtctgaa tctgctgcaa gaagacaacc cggacctgat cggcagcgag  3480
atcgcgcgct ggctgtcgac gctcgagatt tctggcaccg gtatggcatc tatgactgga  3540
ggccaacaga tgggtcctgc aaccgggaat tccgcgtagc gctagctttg ccagcgccac  3600
gcgaaacatg aggatcaccc atgtactagt gccacaaact tctctctgct aaagcaagca  3660
ggtgatgttg aagaaaaccc agggcctgga gggtccgagg gcaggggaag tctcctaaca  3720
tgcggggacg tggaggaaaa tcccggccca tccggatatc cctacgatgt gcccgattac  3780
gctgctagct ctagactgga caagagcaaa gtcataaact ctgctctgga attactcaat  3840
gaagtcggta tcgaaggcct gacgacaagg aaactcgctc aaaagctggg agttgagcag  3900
cctaccctgt actggcacgt gaagaacaag cgggccctgc tcgatgccct ggcaatcgag  3960
atgctggaca ggcatcatac ccacttctgc cccctggaag gcgagtcatg gcaagacttt  4020
ctgcggaaca acgccaagtc attccgctgt gctctcctct cacatcgcga cggggctaaa  4080
gtgcatctcg gcacccgccc aacagagaaa cagtacgaaa tcagctcgcg tcagctcgcg  4140
ttcctgtgtc agcaaggctt ctccctggag aacgcactgt acgctctgtc cgccgtgggc  4200
cactttacac tgggctgcgt attggaggat caggagcatc aagtagcaaa agaggaaaga  4260
gagacaccta ccaccgattc tatgccccca cttctgagac aagcaattga gctgttcgac  4320
catcagggag ccgaacctgc cttccttttc ggcctggaac taatcatatg tggcctggag  4380
aaacagctaa agtgcgaaag cggcgggccg gccgacgccc ttgacgattt tgacttagac  4440
atgctcccag ccgatgccct tgacgacttt gaccttgata tgctgcctgc tgacgctctt  4500
gacgattttg accttgacat gctccccggg taatctagag ggcccgcggt tcgaaggtaa  4560
gcctatccct aaccctctcc tcggtctcga ttctacgcgt accggtcatc atcaccatca  4620
ccattgagtt taaacccgct gatcagcctc gactgtgcct tctagttgcc agccatctgt  4680
tgtttgcccc tccccgtgc cttccttgac cctggaaggt gccactccca ctgtcctttc  4740
ctaataaaat gaggaaattg caaaaaaaaa aaaaaaaaaa aaaaaaaaaa aaaaaaaaaa  4800
aaaaaaaaaa aaaaaaaaaa aaaaaaaaaa aaaaaaaaaa aaaaaaaaaa aaaaaaaaaa  4860
aaaaaaaaaa aaaaaaaaaa aaaaaaa                                       4887

SEQ ID NO: 32            moltype = DNA  length = 2017
FEATURE                  Location/Qualifiers
source                   1..2017
                         mol_type = other DNA
                         organism = synthetic construct SEQUENCE: 32
taatacgact cactataggg agacccaagc tggctaggta agcttggtac cgagctcgga  60
tccaccggtc gccaccatgg tgagcaaggg cgaggaggat aacatggcca tcatcaagga  120
gttcatgcgc ttcaaggtgc acatggaggg ctccgtgaac ggccacgagt cgagatcga  180
gggcgagggc gagggccgcc cctacgaggg cacccagacc gccaagctga aggtgaccaa  240
gggtggcccc ctgcccttcg cctgggacat cctgtcccct cagttcatgt acggctccaa  300
ggcctacgtg aagcaccccg ccgacatccc cgactacttg aagctgtcct tccccgaggg  360
cttcaagtgg gagcgcgtga tgaacttcga ggacggcggc gtggtgaccg tgacccagga  420
ctcctccctg caggacggcg agttcatcta caaggtgaag ctgcgcggca ccaacttccc  480
ctccgacggc cccgtaatgc agaagaagac catgggctgg gaggcctcct ccgagcggat  540
gtaccccgag gacggcgccc tgaagggcga gatcaagcag aggctgaagc tgaaggacgg  600
cggccactac gacgctgagg tcaagaccac ctacaaggcc aagaagcccg tgcagctgcc  660
cggcgcctac aacgtcaaca tcaagttgga catcacctcc cacaacgagg actacaccat  720
cgtggaacag tacgaacgcg ccgagggccg ccactccacc ggacgcatgg acgagctgta  780
caaggattac aaggatgacg atgacaaagg tagcgggca actaattta gcttactcaa  840
acaggctggg gacgtcgagg agaatccagg ccctgcatcc gctggctctg agaaggacg  900
aggctccttg ctcacctgtg gagatgtcga agagaaccca ggtcctgcaa ccgggaattc  960
cgcgtggcgc tggcttcctt gccagcgcca cgcgactagt gccacaaact tctctctgct  1020
aaagcaagca ggtgatgttg aagaaaaccc agggcctgga gggtccgagg gcaggggaag  1080
tctcctaaca tgcggggacg tggaggaaaa tcccggccca tccggatatc cctacgatgt  1140
gcccgattac gctcatatgg tgagcaaggg cgaggaggat aacatggcct ctctcccagc  1200
gacacatgag ttacacatct ttggctccat caacggtgtg gactttgaca tggtgggtca  1260
gggcaccgg aatccaaatg atggttatga ggagttaaac ctgaagtcca caaagggtga  1320
cctcagttc tcccccctgg ttctggtccc tcatatcggg tatggcttcc atcagtacct  1380
gcctaccct gacgggatgt cgcctttcca ggccgccatg gtagatggca gcggataccga  1440
agtccatcgc acaatgcagt ttgaagatgg tgcctccctt actgttaact accgctacac  1500
ctacgaggga agccacatca aaggagaggc caggtgaag gggactggtt tccctgctga  1560
cggtcctgtg atgaccaact cgctgaccgc tgcggactta tgcaggtcga agaagactta  1620
ccccaacgac aaaaccatca tcagtaccdtt taagtggagt tacaccactg gaaatggca  1680
gagataccg agcactgcgc ggaccaccta caccttgcc aagccaatgg cggctaacta  1740
tctgaagaac cagccgatgt acgtgttccg taagacggag ctcaagcact ccaagaccga  1800
gctcaacttc aaggagtgc aaaaggcctt taccgatgtg atgggaatgg acgagctgta  1860
taaggctagc taagcggccg ctcgagtcta gagggcccgc ggttcgaagg taagcctatc  1920
cctaacccctc tcctcggtct cgattctacg cgtaccggtc atcatcacca tcaccattga  1980
gtttaaaccc gctgatcagc ctcgactgtg ccttcta                            2017

SEQ ID NO: 33            moltype = DNA  length = 2017
FEATURE                  Location/Qualifiers
```

-continued

```
source                  1..2017
                        mol_type = other DNA
                        organism = synthetic construct
SEQUENCE: 33
taatacgact cactataggg agacccaagc tggctaggta agcttggtac cgagctcgga   60
tccaccggtc gccaccatgg tgagcaaggg cgaggaggat aacatggcca tcatcaagga  120
gttcatgcgc ttcaaggtgc acatggaggg ctccgtgaac ggccacgagt tcgagatcga  180
gggcgagggc gagggccgcc cctacgaggg cacccagacc gccaagctga aggtgaccaa  240
gggtggcccc ctgcccttcg cctgggacat cctgtcccct cagttcatgt acggctccaa  300
ggcctacgtg aagcacccct ccgacatccc cgactacttg aagctgtcct tccccgaggg  360
cttcaagtgg gagcgcgtga tgaacttcga ggacggcggc gtggtgaccg tgacccagga  420
ctcctccctg caggacggcg agttcatcta caaggtgaag ctgcgcggca ccaacttccc  480
ctccgacggc cccgtaatgc agaagaagac catgggctgg gaggcctcct ccgagcggat  540
gtaccccgag gacggcgccc tgaagggcga gatcaagcag aggctgaagc tgaaggacgg  600
cggccactac gacgctgagg tcaagaccac ctacaaggcc aagaagcccg tgcagctgcc  660
cggcgcctac aacgtcaaca tcaagttgga catcacctcc cacaacgagg actacaccat  720
cgtggaacag tacgaacgcg ccgagggccg ccactccacc ggcggcatgg acgagctgta  780
caaggattac aaggatgacg atgacaaagg tagcggggca actaatttta gcttactcaa  840
acaggctggg gacgtcgagg agaatccagg ccctgcatcc gctggctctg gagaaggacg  900
aggctccttg ctcacctgtg gagatgtcga agagaaccca ggtcctgcaa ccgggaattc  960
cgcgtagcgc tagcttcctt gccagcgcca cgcgactagt gccacaaact tctctctgct 1020
aaagcaagca ggtgatgttg aagaaaaccc agggcctgga ggtccgagg gcaggggaag 1080
tctcctaaca tgcggggacg tggaggaaaa tcccggccca tccggatatc cctacgatgt 1140
gcccgattac gctcatatgg tgagcaaggg cgaggaggat aacatggcct ctctcccagc 1200
gacacatgag ttacacatct ttggctccat caacggtgtg gactttgaca tggtgggtca 1260
gggcaccggc aatccaaatg atggttatga ggagttaaac ctgaagtcca ccaagggtga 1320
cctccagttc tccccctgga ttctggtccc tcatatcggg tatggcttcc atcagtacct 1380
gccctaccct gacgggatgt cgcctttcca ggccgccatg gtagatggca gcggatacca 1440
agtccatcgc acaatgcagt ttgaagatgg tgcctccctt actgttaact accgctacac 1500
ctacgaggga agccacatca aaggagaggc ccaggtgaag gggactggtt tccctgctga 1560
cggtcctgtg atgaccaact cgctgaccgc tgcggactgg tgcaggtcga agaagactta 1620
ccccaacgac aaaaccatca tcagtacctt taagtggagt tacaccactg gaaatggcaa 1680
gagataccgc agcactgcgc ggaccaccta cacctttgcc aagccaatgg cggctaacta 1740
tctgaagaac cagccgatgt acgtgttccg taagacggag ctcaagcact ccaagaccga 1800
gctcaacttc aaggagtggc aaaaggcctt taccgatgtg atgggaatgg acgagctgta 1860
taaggctagc taagcggccg ctcgagtcta gagggcccgc ggttcgaagg taagcctatc 1920
cctaaccctc tcctcggtct cgattctacg cgtaccggtc atcatcacca tcaccattga 1980
gtttaaaccc gctgatcagc ctcgactgtg ccttcta                          2017
```

```
SEQ ID NO: 34          moltype = DNA  length = 2035
FEATURE                Location/Qualifiers
source                 1..2035
                       mol_type = other DNA
                       organism = synthetic construct
SEQUENCE: 34
taatacgact cactataggg agacccaagc tggctaggta agcttggtac cgagctcgga   60
tccaccggtc gccaccatgg tgagcaaggg cgaggaggat aacatggcca tcatcaagga  120
gttcatgcgc ttcaaggtgc acatggaggg ctccgtgaac ggccacgagt tcgagatcga  180
gggcgagggc gagggccgcc cctacgaggg cacccagacc gccaagctga aggtgaccaa  240
gggtggcccc ctgcccttcg cctgggacat cctgtcccct cagttcatgt acggctccaa  300
ggcctacgtg aagcacccct ccgacatccc cgactacttg aagctgtcct tccccgaggg  360
cttcaagtgg gagcgcgtga tgaacttcga ggacggcggc gtggtgaccg tgacccagga  420
ctcctccctg caggacggcg agttcatcta caaggtgaag ctgcgcggca ccaacttccc  480
ctccgacggc cccgtaatgc agaagaagac catgggctgg gaggcctcct ccgagcggat  540
gtaccccgag gacggcgccc tgaagggcga gatcaagcag aggctgaagc tgaaggacgg  600
cggccactac gacgctgagg tcaagaccac ctacaaggcc aagaagcccg tgcagctgcc  660
cggcgcctac aacgtcaaca tcaagttgga catcacctcc cacaacgagg actacaccat  720
cgtggaacag tacgaacgcg ccgagggccg ccactccacc ggcggcatgg acgagctgta  780
caaggattac aaggatgacg atgacaaagg tagcggggca actaatttta gcttactcaa  840
acaggctggg gacgtcgagg agaatccagg ccctgcatcc gctggctctg gagaaggacg  900
aggctccttg ctcacctgtg gagatgtcga agagaaccca ggtcctgcaa ccgggaattc  960
cgcgtagcgc tagctttgcc agcgccacgc gaaacatgag gatcacccat gtactagtgc 1020
cacaaacttc tctctgctaa agcaagcagg tgatgttgaa gaaaacccag gcctggagg 1080
gtccgagggc aggggaagtc tcctaacatg cggggaaatc ccgcccatc 1140
cggatatccc tacgatgtgc ccgattacgc tcatatggtg agcaagggcg aggaggataa 1200
catggcctct ctcccagcga cacatgagtt acacatcttt ggctccatca cggtgtgga 1260
ctttgacatg gtgggtcagg gcaccggcaa tccaaatgat ggttatgagg agttaaacct 1320
gaagtccacc aagggtgacc tccagttctc ccctggatt ctggtccctc atatcgggta 1380
tggcttccat cagtacctgc cctaccctga cgggatgtcg cctttccag gccgccatg 1440
agatggcagc ggataccaag tccatcgcac aatgcagttt gaagatggtg cctccttac 1500
tgttaactac cgctacacct acgagggaag ccacatcaaa ggagaggccc aggtgaaggg 1560
gactggtttc cctgctgacg gtcctgtgat gaccaactcg ctgaccgctg cggactggtg 1620
caggtcgaag aagacttacc ccaacgacaa aaccatcatc agtacctta agtggagtta 1680
caccactgga aatggcaaga taccggagc acctgccaa cctttgccaa 1740
gccaatggcg gctaactatc tgaagaacca gccgatgtac gtgttccgta agacggagct 1800
caagcactcc aagaccgagc tcaacttcaa ggagtggcaa aaggccttta ccgatgtgat 1860
gggaatggac gagctgtata aggctagcta agcggccgct cgagtctaga gggcccgcgg 1920
ttcgaaggta agcctatccc taaccctctc tcggtctcg attctacgcg taccggtcat 1980
catcaccatc accattgagt ttaaacccgc tgatcagcct cgactgtgcc ttcta       2035
```

```
SEQ ID NO: 35              moltype = DNA  length = 2035
FEATURE                    Location/Qualifiers
source                     1..2035
                           mol_type = other DNA
                           organism = synthetic construct
SEQUENCE: 35
taatacgact cactataggg agacccaagc tggctaggta agcttggtac cgagctcgga   60
tccaccggtc gccaccatgg tgagcaaggg cgaggaggat aacatggcca tcatcaagga  120
gttcatgcgc ttcaaggtgc acatggaggg ctccgtgaac ggccacgagt tcgagatcga  180
gggcgagggc gagggccgcc cctacgaggg cacccagacc gccaagctga aggtgaccaa  240
gggtggcccc ctgcccttcg cctgggacat cctgtcccct cagttcatgt acggctccaa  300
ggcctacgtg aagcaccccg ccgacatccc cgactacttg aagctgtcct tccccgaggg  360
cttcaagtgg gagcgcgtga tgaacttcga ggacggcggc gtggtgaccg tgacccagga  420
ctcctccctg caggacggcg agttcatcta caaggtgaag ctgcgcggca ccaacttccc  480
ctccgacggc cccgtaatgc agaagaagac catgggctgg gaggcctcct ccgagcggat  540
gtaccccgag gacggcgccc tgaagggcga gatcaagcag aggctgaagc tgaaggacgg  600
cggccactac gacgctgagg tcaagaccac ctacaaggcc aagaagcccg tgcagctgcc  660
cggcgcctac aacgtcaaca tcaagttgga catcacctcc cacaacgagg actacaccat  720
cgtggaacag tacgaacgcg ccgagggccg ccactccacc ggcggcatgg acgagctgta  780
caaggattac aaggatgacg atgacaaagg tagcggggca actaatttta gcttactcaa  840
acaggctggg gacgtcgagg agaatccagg ccctgcatcc gctgggctctg agaaggacg  900
aggctccttg ctcacctgtg gagatgtcga agagaaccca ggtcctgcaa ccgggaattc  960
cgcgtagcgc tagctttgcc agcgccacgc gaagcgcgag gaacaccgcg cactagtgc  1020
cacaaacttc tctctgctaa agcaagcagg tgatgttgaa gaaaacccag ggcctggagg  1080
gtccgagggc aggggaagtc tcctaacatg cggggacgtg gaggaaaatc cggcccatc  1140
cggatatccc tacgatgtgc ccgattacgc tcatatggtg agcaagggcg aggaggataa  1200
catggcctct ctcccagcga cacatgagtt acacatcttt ggctccatca acggtgtgga  1260
ctttgacatg gtgggtcagg gcaccggcaa tccaaatgat ggttatgagg agttaaacct  1320
gaagtccacc aagggtgacc tccagttctc cccctggatt ctggtccctc atatcgggta  1380
tggcttccat cagtacctgc cctaccctga cgggatgtcg cctttccagg ccgccatggt  1440
agatggcagc ggataccaag tccatcgcac aatgcagttt gaagatggtg cctcccttac  1500
tgttaactac cgctacacct acgagggaag ccacatcaaa ggagaggccc aggtgaaggg  1560
gactggtttc cctgctgacg gtcctgtgat gaccaactcg ctgaccgctg cggactggtg  1620
caggtcgaag aagacttacc ccaacgacaa aaccatcatc agtaccttta agtggagtta  1680
caccactgga aatggcaaga gataccggag cactgcgcgg accacctaca cctttgccaa  1740
gccaatggcg gctaactatc tgaagaacca gccgatgtac gtgttccgta agacggagct  1800
caagcactcc aagaccgagc tcaacttcaa ggagtggcaa aaggcctttta ccgatgtgat  1860
gggaatggac gagctgtata aggctagcta agcggccgct cgagtctaga gggcccgcgg  1920
ttcgaaggta agcctatccc taaccctctc ctcggtctcg attctacgcg taccggtcat  1980
catcaccatc accattgagt ttaaacccgc tgatcagcct cgactgtgcc ttcta         2035

SEQ ID NO: 36              moltype = DNA  length = 2035
FEATURE                    Location/Qualifiers
source                     1..2035
                           mol_type = other DNA
                           organism = synthetic construct
SEQUENCE: 36
taatacgact cactataggg agacccaagc tggctaggta agcttggtac cgagctcgga   60
tccaccggtc gccaccatgg tgagcaaggg cgaggaggat aacatggcca tcatcaagga  120
gttcatgcgc ttcaaggtgc acatggaggg ctccgtgaac ggccacgagt tcgagatcga  180
gggcgagggc gagggccgcc cctacgaggg cacccagacc gccaagctga aggtgaccaa  240
gggtggcccc ctgcccttcg cctgggacat cctgtcccct cagttcatgt acggctccaa  300
ggcctacgtg aagcaccccg ccgacatccc cgactacttg aagctgtcct tccccgaggg  360
cttcaagtgg gagcgcgtga tgaacttcga ggacggcggc gtggtgaccg tgacccagga  420
ctcctccctg caggacggcg agttcatcta caaggtgaag ctgcgcggca ccaacttccc  480
ctccgacggc cccgtaatgc agaagaagac catgggctgg gaggcctcct ccgagcggat  540
gtaccccgag gacggcgccc tgaagggcga gatcaagcag aggctgaagc tgaaggacgg  600
cggccactac gacgctgagg tcaagaccac ctacaaggcc aagaagcccg tgcagctgcc  660
cggcgcctac aacgtcaaca tcaagttgga catcacctcc cacaacgagg actacaccat  720
cgtggaacag tacgaacgcg ccgagggccg ccactccacc ggcggcatgg acgagctgta  780
caaggattac aaggatgacg atgacaaagg tagcggggca actaatttta gcttactcaa  840
acaggctggg gacgtcgagg agaatccagg ccctgcatcc gctggctctg agaaggacg   900
aggctccttg ctcacctgtg gagatgtcga agagaaccca ggtcctgcaa ccgggaattc  960
cgcgtagcgc tagccaagcg cgaggaacac ccgcgcaggc cagcgccacg cgactagtgc  1020
cacaaacttc tctctgctaa agcaagcagg tgatgttgaa gaaaacccag ggcctggagg  1080
gtccgagggc aggggaagtc tcctaacatg cggggacgtg gaggaaaatc ccggccatc  1140
cggatatccc tacgatgtgc ccgattacgc tcatatggtg agcaagggcg aggaggataa  1200
catggcctct ctcccagcga cacatgagtt acacatcttt ggctccatca acggtgtgga  1260
ctttgacatg gtgggtcagg gcaccggcaa tccaaatgat ggttatgagg agttaaacct  1320
gaagtccacc aagggtgacc tccagttctc ccctggatt ctggtccctc atatcgggta  1380
tggcttccat cagtacctgc cctaccctga cgggatgtcg cctttccagg ccgccatggt  1440
agatggcagc ggataccaag tccatcgcac aatgcagttt gaagatggtg cctcccttac  1500
tgttaactac cgctacacct acgagggaag ccacatcaaa ggagaggccc aggtgaaggg  1560
gactggtttc cctgctgacg gtcctgtgat gaccaactcg ctgaccgctg cggactggtg  1620
caggtcgaag aagacttacc ccaacgacaa aaccatcatc agtaccttta agtggagtta  1680
caccactgga aatggcaaga gataccggag cactgcgcgg accacctaca cctttgccaa  1740
gccaatggcg gctaactatc tgaagaacca gccgatgtac gtgttccgta agacggagct  1800
caagcactcc aagaccgagc tcaacttcaa ggagtggcaa aaggcctttta ccgatgtgat  1860
```

```
gggaatggac gagctgtata aggctagcta agcggccgct cgagtctaga gggcccgcgg  1920
ttcgaaggta agcctatccc taaccctctc ctcggtctcg attctacgcg taccggtcat  1980
catcaccatc accattgagt ttaaacccgc tgatcagcct cgactgtgcc ttcta        2035
```

```
SEQ ID NO: 37              moltype = AA  length = 762
FEATURE                    Location/Qualifiers
source                     1..762
                           mol_type = protein
                           organism = synthetic construct
SEQUENCE: 37
MASNFTQFVL VDNGGTGDVT VAPSNFANGI AEWISSNSRS QAYKVTCSVR QSSAQNRKYT   60
IKVEVPKGAW RSYLNMELTI PIFATNSDCE LIVKAMQGLL KDGNPIPSAI AANSGIYGGS   120
GSGAGSGSPA GGGAPGSGGG SQLHLPQVLA DAVSRLVLGK FGDLTDNFSS PHARRKVLAG   180
VVMTTGTDVK DAKVISVSTG TKCINGEYMS DRGLALNDCH AEIISRRSLL RFLYTQLELY   240
LNNKDDQKRS IFQKSERGGF RLKENVQFHL YISTSPCGDA RIFSPHEPIL EEPADRHPNR   300
KARGQLRTKI ESGQGTIPVR SNASIQTWDG VLQGERLLTM SCSDKIARWN VVGIQGSLLS   360
IFVEPIYFSS IILGSLYHGD HLSRAMYQRI SNIEDLPPLY TLNKPLLSGI SNAEARQPGK   420
APNFSVNWTV GDSAIEVINA TTGKDELGRA SRLCKHALYC RWMRVHGKVP SHLLRSKITK   480
PNVYHESKLA AKEYQAAKAR LFTAFIKAGL GAWVEKPTEQ DQFSLTGSGS SELIKENMHM   540
KLYMEGTVDN HHFKCTSEGE GKPYEGTQTM RIKVVEGGPL PFAFDILATS FLYGSKTFIN   600
HTQGIPDFFK QSFPEGFTWE RVTTYEDGGV LTATQDTSLQ DGCLIYNVKI RGVNFTSNGP   660
VMQKKTLGWE AFTETLYPAD GGLEGRNDMA LKLVGGSHLI ANIKTTYRSK KPAKNLKMPG   720
VYYVDYRLER IKEANNETYV EQHEVAVARY CDLPSKLGHK LN                      762
```

```
SEQ ID NO: 38              moltype = AA  length = 762
FEATURE                    Location/Qualifiers
source                     1..762
                           mol_type = protein
                           organism = synthetic construct
SEQUENCE: 38
MASNFTQFVL VDNGGTGDVT VAPSNFANGI AEWISSNSRS QAYKVTCSVR QSSAQNRKYT   60
IKVEVPKGAW RSYLNMELTI PIFATNSDCE LIVKAMQGLL KDGNPIPSAI AANSGIYGGS   120
GSGAGSGSPA GGGAPGSGGG SQLHLPQVLA DAVSRLVLGK FGDLTDNFSS PHARRKVLAG   180
VVMTTGTDVK DAKVISVSTG TKCINGEYMS DRGLALNDCH AAIISRRSLL RFLYTQLELY   240
LNNKDDQKRS IFQKSERGGF RLKENVQFHL YISTSPCGDA RIFSPHEPIL EEPADRHPNR   300
KARGQLRTKI ESGQGTIPVR SNASIQTWDG VLQGERLLTM SCSDKIARWN VVGIQGSLLS   360
IFVEPIYFSS IILGSLYHGD HLSRAMYQRI SNIEDLPPLY TLNKPLLSGI SNAEARQPGK   420
APNFSVNWTV GDSAIEVINA TTGKDELGRA SRLCKHALYC RWMRVHGKVP SHLLRSKITK   480
PNVYHESKLA AKEYQAAKAR LFTAFIKAGL GAWVEKPTEQ DQFSLTGSGS SELIKENMHM   540
KLYMEGTVDN HHFKCTSEGE GKPYEGTQTM RIKVVEGGPL PFAFDILATS FLYGSKTFIN   600
HTQGIPDFFK QSFPEGFTWE RVTTYEDGGV LTATQDTSLQ DGCLIYNVKI RGVNFTSNGP   660
VMQKKTLGWE AFTETLYPAD GGLEGRNDMA LKLVGGSHLI ANIKTTYRSK KPAKNLKMPG   720
VYYVDYRLER IKEANNETYV EQHEVAVARY CDLPSKLGHK LN                      762
```

```
SEQ ID NO: 39              moltype = AA  length = 775
FEATURE                    Location/Qualifiers
source                     1..775
                           mol_type = protein
                           organism = synthetic construct
SEQUENCE: 39
MSKTIVLSVG EATRTLTEIQ STADRQIFEE KVGPLVGRLR LTASLRQNGA KTAYRVNLKL   60
DQADVVDSGL PKVRYTQVWS HDVTIVANST EASRKSLYDL TKSLVATSQV EDLVVNLVPL   120
GRASTGSGIY GGSGSGAGSG SPAGGGAPGS GGGSQLHLPQ VLADAVSRLV LGKFGDLTDN   180
FSSPHARRKV LAGVVMTTGT DVKDAKVISV STGTKCINGE YMSDRGLALN DCHAEIISRR   240
SLLRFLYTQL ELYLNNKDDQ KRSIFQKSER GGFRLKENVQ FHLYISTSPC GDARIFSPHE   300
PILEEPADRH PNRKARGQLR TKIESGQGTI PVRSNASIQT WDGVLQGERL LTMSCSDKIA   360
RWNVVGIQGS LLSIFVEPIY FSSIILGSLY HGDHLSRAMY QRISNIEDLP PLYTLNKPLL   420
SGISNAEARQ PGKAPNFSVN WTVGDSAIEV INATTGKDEL GRASRLCKHA LYCRWMRVHG   480
KVPSHLLRSK ITKPNVYHES KLAAKEYQAA KARLFTAFIK AGLGAWVEKP TEQDQFSLTG   540
SGSSELIKEN MHMKLYMEGT VDNHHFKCTS EGEGKPYEGT QTMRIKVVEG GPLPFAFDIL   600
ATSFLYGSKT FINHTQGIPD FFKQSFPEGF TWERVTTYED GGVLTATQDT SLQDGCLIYN   660
VKIRGVNFTS NGPVMQKKTL GWEAFTETLY PADGGLEGRN DMALKLVGGS HLIANIKTTY   720
RSKKPAKNLK MPGVYYVDYR LERIKEANNE TYVEQHEVAV ARYCDLPSKL GHKLN         775
```

```
SEQ ID NO: 40              moltype = DNA  length = 45
FEATURE                    Location/Qualifiers
source                     1..45
                           mol_type = other DNA
                           organism = synthetic construct
SEQUENCE: 40
aattccgcgt ggcgctggct tccttgccag cgccacgcga ctagt                  45
```

```
SEQ ID NO: 41              moltype = DNA  length = 45
FEATURE                    Location/Qualifiers
source                     1..45
                           mol_type = other DNA
                           organism = synthetic construct
SEQUENCE: 41
aattccgcgt agcgctagct tccttgccag cgccacgcga ctagt                  45
```

```
SEQ ID NO: 42              moltype = DNA   length = 63
FEATURE                    Location/Qualifiers
source                     1..63
                           mol_type = other DNA
                           organism = synthetic construct
SEQUENCE: 42
aattccgcgt agcgctagct ttgccagcgc cacgcgaaac atgaggatca cccatgtact   60
agt                                                                 63

SEQ ID NO: 43              moltype = DNA   length = 63
FEATURE                    Location/Qualifiers
source                     1..63
                           mol_type = other DNA
                           organism = synthetic construct
SEQUENCE: 43
aattccgcgt agcgctagct ttgccagcgc cacgcgaagc gcgaggaaca cccgcgcact   60
agt                                                                 63

SEQ ID NO: 44              moltype = DNA   length = 63
FEATURE                    Location/Qualifiers
source                     1..63
                           mol_type = other DNA
                           organism = synthetic construct
SEQUENCE: 44
aattccgcgt agcgctagcc aagcgcgagg aacacccgcg caggccagcg ccacgcgact   60
agt                                                                 63

SEQ ID NO: 45              moltype = AA   length = 552
FEATURE                    Location/Qualifiers
source                     1..552
                           mol_type = protein
                           organism = synthetic construct
SEQUENCE: 45
MQIFVKTLTG KTITLEVEPS DTIENVKAKI QDKEGIPPDQ QRLIFAGKQL EDGRTLSDYN    60
IQKESTLHLV LRLRGGSAQN RKYTIKVEVP KGAWRSYLNM ELTIPIFATN SDCELIVKAM   120
QGLLKDGNPI PSAIAANSGI YANFTQFVLV DNGGTGDVTV APSNFANGIA EWISSNSRSQ   180
AYKVTCSVRQ SSAQNRKYTI KVEVPKGAWR SYLNMELTIP IFATNSDCEL IVKAMQGLLK   240
DGNPIPSAIA ANSGIYGSVQ LADHYQQNTP IGDGPVLLPD NHYLSYQSKL SKDPNEKRDH   300
MVLLEFVTAA GITLGMDELY KGGTGGSMVS KGEELFTGVV PILVELDGDV NGHKFSVSGE   360
GEGDATYGKL TLKLICTTGK LPVPWPTLVT TLGYGLQCFA RYPDHMKQHD FFKSAMPEGY   420
VQERTIFFKD DGNYKTRAEV KFEGDTLVNR IELKGIDFKE DGNILGHKLE YNYNSHNVYI   480
TADKQKNGIK ANFKIRHNTS ANFTQFVLVD NGGTGDVTVA PSNFANGIAE WISSNSRSQA   540
YKVTCSRQRR RG                                                       552

SEQ ID NO: 46              moltype = DNA   length = 2850
FEATURE                    Location/Qualifiers
source                     1..2850
                           mol_type = other DNA
                           organism = synthetic construct
SEQUENCE: 46
atggtgagca agggcgagga ggataacatg gcctctctcc cagcgacaca tgagttacac    60
atctttggct ccatcaacgg tgtggacttt gacatggtgg tcagggcac cggcaatcca   120
aatgatggtt atgaggagtt aaacctgaag tccaccaagg tgacctcca gttctccccc   180
tggattctgg tccctcatat cgggtatggc ttcatccatg acctgcccta ccctgacggg   240
atgtcgcctt tccaggccgc catggtagat ggctccggat accaagtcca tcgcacaatg   300
cagtttgaag atggtgcctc ccttactgtt aactaccgct acacctacga gggaagccac   360
atcaaaggag aggcccaggt gaaggggact ggtttccctg ctgacggtcc tgtgatgacc   420
aactcgctga ccgctgcgga ctggtgcagg tcgaagaaga cttaccccaa cgacaaaacc   480
atcatcagta cctttaagtg gagttacacc actggaaatg gcaagcgcta ccggagcact   540
gcgcggacca cctacacctt tgccaagcca atggcggcta actatctgaa gaaccagccg   600
atgtacgtgt ccgtaagac ggagctcaag cactccaaga ccgagctcaa cttcaaggag   660
tggcaaaagg cctttaccga tgtgatgggc atggacgagc tgtacaagta acggctctag   720
atcgcgaacg cgtgaattcc tcgagggcgg ccgctctaga gtcgacgggc cgcggtaaca   780
attgttaact aacttaagct agcaacggtt tccctctagc gggatcaatt ccgcccccc   840
cccctaacgt tactggccga agcgcttgg aataaggccg gtgtgcgttt gtctatatgt   900
tattttccac catattgccg tcttttggca atgtgagggc ccggaaacct ggccctgtct  960
tcttgacgag cattcctagg ggtctttccc ctctcgccaa aggaatgcaa ggtctgttga  1020
atgtcgtgaa ggaagcagtt cctctggaag cttcttgaag acaaacaacg tctgtagcga  1080
ccctttgcag gcagcggaac cccccacctg cgcgacaggtg cctctgcggc caaaagccac  1140
gtgtataaga tacacctgca aaggcggcac aaccccagtg ccacgttgtg agttggatag  1200
ttgtggaaag agtcaaatgg ctctcctcaa gcgtattcaa caaggggctg aaggatgccc  1260
agaaggtacc ccattgtatg ggatctgatc tggggcctcg gtgcacatgc tttacatgtg  1320
tttagtcgag gttaaaaaaa cgtctaggcc cccgaaccca catggtttcc tttt         1380
gaaaaacacg ataataccat ggtgagcaag ggcgaggcag tgatcaagga gttcatgcgg  1440
ttcaaggtgc acatggaggg ctccatgaac ggccacgagt cgagatcga gggcgaggc    1500
gagggccgcc cctacgaggg cacccagacc gccaagctga aggtgaccaa gggtggcccc  1560
ctgcccttct cctgggacat cctgtccct cagttcatgt acggctccag ggccttcatc  1620
aagcacccg ccgacatccc cgactactat aagcagtcct tccccgaggg cttcaagtgg  1680
```

```
gagcgcgtga tgaacttcga ggacggcggc gccgtgaccg tgacccagga cacctccctg   1740
gaggacggca ccctgatcta caaggtgaag ctccgcggca ccaacttccc tcctgacggc   1800
cccgtaatgc agaagaagac aatgggctgg gaagcgtcca ccgagcggtt gtaccccgag   1860
gacggcgtgc tgaagggcga cattaagatg gccctgcgcc tgaaggacgg cggccgctac   1920
ctggcggact tcaagaccac ctacaaggcc aagaagcccg tgcagatgcc cggcgcctac   1980
aacgtcgacc gcaagttgga catcacctcc cacaacgagg actacaccgt ggtggaacag   2040
tacgaacgct ccgagggccg ccactccacc ggcggcatgg acgagctgta caagggcggg   2100
agttacccct acgacgtgcc cgactacgcc ggtaccggcg ggagtggcgg tagtgcccaa   2160
aacaggaaat acaccatcaa agtggaggtg ccaaagggtg cctggcggag ctacctgaac   2220
atggagctga ctattccaat cttcgctact aattccgatt gcgaactgat agtaaaagca   2280
atgcaaggtt tgctgaaaga cggcaaccca attcccagcg caatcgccgc caatagcggc   2340
atctacgcta atttcacaca gttcgtgctg gtcgacaacg gcggcaccgg cgacgttacg   2400
gtggccccct caaactttgc caacgggatt gccgagtgga taagcagcaa tagcaggtcc   2460
caggcctaca aggttacctg tagcgtaagg cagagcaggc cccagaaccg aaagtacacg   2520
attaaggtgg aagtccccaa aggcgcatgg aggagctatc ttaatatgga actgaccatc   2580
cccatattcg cgacaaacag cgactgtgag ctgatcgtga aggctatgca gggcctcctc   2640
aaggatggga acccgatccc gtctgccatc gctgctaact ccggcattta tgcaaacttc   2700
actcaatttg ttctggtgga caatggtggg accggggatg ttaccgtggc tcccagcaat   2760
tttgctaacg gtatcgcaga atggatcagt agtaacagca ggagccaagc ctataaagtg   2820
acgtgcagcg tacggcagag gagaagaggc                                    2850

SEQ ID NO: 47           moltype = DNA   length = 19
FEATURE                 Location/Qualifiers
source                  1..19
                        mol_type = other DNA
                        organism = synthetic construct
SEQUENCE: 47
gcacgagcat cagccgtgc                                                 19

SEQ ID NO: 48           moltype = AA   length = 315
FEATURE                 Location/Qualifiers
source                  1..315
                        mol_type = protein
                        organism = synthetic construct
SEQUENCE: 48
MVSSGPRPRG TRGKGRRIRR GGGLADAVTA WFPENKQSDV SQIWHAFEHE EHANTFSAFL   60
DRLSDTVSAR NTSGFREQVA AWLEKLSASA ELRQQSFAVA ADATESCEDR VALTWNNLRK   120
TLLVHQASEG LFDNDTGALL SLGREMFRLE ILEDIARDKV RTLHFVDEIE VYLAFQTMLA   180
EKLQLSTAVK EMRFYGVSGV TANDLRTAEA MVRSREENEF TDWFSLWGPW HAVLKRTEAD   240
RWAQAEEQKY EMLENEYPQR VADRLKASGL SGDADAEREA GAQVMRETEQ QIYRQLTDEV   300
LALRLPENGS QLHHS                                                     315

SEQ ID NO: 49           moltype = AA   length = 116
FEATURE                 Location/Qualifiers
source                  1..116
                        mol_type = protein
                        organism = synthetic construct
SEQUENCE: 49
SAQNRKYTIK VEVPKGAWRS YLNMELTIPI FATNSDCELI VKAMQGLLKD GNPIPSAIAA   60
NSGIYANFTQ FVLVDNGGTG DVTVAPSNFA NGIAEWISSN SRSQAYKVTC SVRQSS        116

SEQ ID NO: 50           moltype = AA   length = 118
FEATURE                 Location/Qualifiers
source                  1..118
                        mol_type = protein
                        organism = synthetic construct
SEQUENCE: 50
SAQNRKYTIK VEVPKGAWRS YLNMELTIPI FATNSDCELI VKAMQGLLKD GNPIPSAIAA   60
NSGIYANFTQ FVLVDNGGTG DVTVAPSNFA NGIAEWISSN SRSQAYKVTC SVRQRRRG     118

SEQ ID NO: 51           moltype = AA   length = 552
FEATURE                 Location/Qualifiers
source                  1..552
                        mol_type = protein
                        organism = synthetic construct
SEQUENCE: 51
MQIFVKTLTG KTITLEVEPS DTIENVKAKI QDKEGIPPDQ QRLIFAGKQL EDGRTLSDYN   60
IQKESTLHLV LRLRGGRASA QNRKYTIKVE VPKGAWRSYL NMELTIPIFA TNSDCELIVK   120
AMQGLLKDGN PIPSAIAANS GIYANFTQFV LVDNGGTGDV TVAPSNFANG IAEWISSNSR   180
SQAYKVTCSV RQSSAQNRKY TIKVEVPKGA WRSYLNMELT IPIFATNSDC ELIVKAMQGL   240
LKDGNPIPSA IAANSGIYGS VQLADHYQQN TPIGDGPVLL PDNHYLSYQS KLSKDPNEKR   300
DHMVLLEFVT AAGITLGMDE LYKGGTGGSM VSKGEELFTG VVPILVELDG DVNGHKFSVS   360
GEGEGDATYG KLTLKLICTT GKLPVPWPTL VTTLGYGLQC FARYPDHMKQ HDFFKSAMPE   420
GYVQERTIFF KDDGNYKTRA EVKFEGDTLV NRIELKGIDF KEDGNILGHK LEYNYNSHNV   480
YITADKQKNG IKANFKIRHN TSANFTQFVL VDNGGTGDVT VAPSNFANGI AEWISSNSRS   540
QAYKVTCSRQ SS                                                        552

SEQ ID NO: 52           moltype = AA   length = 15
FEATURE                 Location/Qualifiers
```

-continued

```
source                  1..15
                        mol_type = protein
                        organism = synthetic construct
SEQUENCE: 52
GLNDIFEAQK IEWHE                                               15

SEQ ID NO: 53           moltype = DNA  length = 25
FEATURE                 Location/Qualifiers
source                  1..25
                        mol_type = other DNA
                        organism = synthetic construct
SEQUENCE: 53
ggagcagacg atatggcgtc gctcc                                   25

SEQ ID NO: 54           moltype = DNA  length = 19
FEATURE                 Location/Qualifiers
source                  1..19
                        mol_type = other DNA
                        organism = synthetic construct
SEQUENCE: 54
gcacgagcat cagccgtgc                                          19

SEQ ID NO: 55           moltype = AA  length = 7
FEATURE                 Location/Qualifiers
source                  1..7
                        mol_type = protein
                        organism = synthetic construct
SEQUENCE: 55
VRQRRRG                                                       7

SEQ ID NO: 56           moltype = DNA  length = 29
FEATURE                 Location/Qualifiers
source                  1..29
                        mol_type = other DNA
                        organism = synthetic construct
SEQUENCE: 56
ggctcgtctg agctcattag ctccgagcc                              29
```

ENGINEERED MCP AND PCP PROTEINS AND SYSTEMS AND METHODS THEREOF

CROSS-REFERENCE TO RELATED APPLICATIONS

This application claims benefit under 35 U.S.C. § 119(e) of U.S. Provisional Application No. 63/578,836 filed Aug. 25, 2023, the contents of which are incorporated herein by reference in their entirety.

GOVERNMENT SUPPORT

This invention was made with government support under contract No. R35-GM128859 awarded by the National Institutes of Health. The government has certain rights in the invention.

SEQUENCE LISTING

The instant application contains a Sequence Listing which has been submitted in XML format via Patent Center and is hereby incorporated by reference in its entirety. Said XML copy, created on Jun. 17, 2025, is named 701586-000120USPT_SL.xml and is 80,973 bytes in size.

TECHNICAL FIELD

The technology described herein relates to engineered MCP and PCP proteins, as well as systems and methods thereof.

BACKGROUND

Subcellular localization of mRNA is necessary for many processes in the cell. For example, localization of beta-actin mRNA enables fibroblast movement through concentrated actin translation at a defined end of the cell, and localization of arc mRNA in neurons allows protein translation at specific dendrites, which can play a role in memory storage. Imaging the subcellular distribution of single mRNA molecules is possible for fixed cells with single-molecule fluorescence in-situ hybridization (smFISH). smFISH stains specific RNAs in fixed cells with a concentrated solution of fluorescent oligo probes, and then excess probes are washed away to reveal punctae where multiple probes have tagged a single RNA target. This approach has yielded insights into RNA translation, splicing, transport, and degradation, with some FISH methods capable of imaging thousands of transcripts in parallel. However, it cannot reveal real-time dynamics of mRNA behavior in live cells.

Single-molecule live cell RNA imaging can be achieved with the MS2-MCP system, in which a bacteriophage MS2 coat protein fused to a fluorophore tags its cognate 'MS2' RNA aptamers attached to an RNA of interest. This specific protein-RNA pair has been used for live cell RNA imaging; see e.g., Bertrand et al. Mol Cell. 1998 October; 2(4):437-45. Its temporal precision has produced insights into dynamic phenomena like transcriptional bursting and translation. The key weakness of MS2-MCP is that excess MCP cannot be washed away when all MS2 has been labeled, so it lingers in the cell and produces high background fluorescence that obscures images.

Single-molecule live RNA imaging systems that overcome this weakness include fluorogenic dyes that fluoresce only upon binding specific RNA aptamers, like the mango II system. However, Mango II is limited to one color and requires exogenous dye addition. This system also lacks the flexibility of genetically encoded systems like MS2-MCP, whose functionality can be customized by mutation and fusion of various protein domains. One genetically encoded "fluorogenic" live-cell single-RNA imaging system is tDeg, a peptide that is stable when bound to TAR RNA aptamers, but degraded when not. tDeg is capable of imaging single mRNA transcripts tagged with an array TAR aptamers in live cells. See e.g., Bertrand et al. Mol. Cell 2, 437-445 (1998); Hu et al. "Enhanced Single RNA Imaging Reveals Dynamic Gene Expression in Live Animals". 2022.07.26.501631 Preprint at doi 10.1101/2022.07.26.501631 (2022); Li et al. "An improved MS2-MCP imaging system with minimal perturbation of mRNA stability." 2022.02.05.479257 Preprint at doi 10.1101/2022.02.05.479257 (2022); Chubb et al. Curr. Biol. CB 16, 1018-1025 (2006); Halstead et al. Science 347, 1367-1671 (2015); Cawte et al. Nat. Commun. 11, 1283 (2020); Wu et al. Nat. Methods 16, 862-865 (2019).

There is thus need for MCP variants that do not linger in the cell when not bound to RNA.

SUMMARY

The technology described herein is directed to engineered MCP proteins and engineered PCP proteins, which are degraded when the proteins are not bound to an MS2 or PP7 RNA hairpin loop, respectively. Also described herein are fusion proteins comprising such engineered MCP proteins and engineered PCP proteins linked to various effector proteins. The linkage to the effector proteins can be modulated through of specialized linker domains. In addition, described herein are complexes and systems comprising the fusion proteins in combination with synthetic RNA molecules, in order to modulate the structure and/or function the synthetic RNA molecules.

In one aspect, described herein is an engineered MS2 coat protein (MCP) comprising an engineered RNA-binding domain and a degron; wherein the degron is hidden upon binding of the engineered RNA-binding domain to an MS2 RNA hairpin loop; wherein when the engineered RNA-binding domain is not bound to the MS2 RNA hairpin loop, the degron is exposed and degradation of the engineered MCP protein increases.

In some embodiments of any of the aspects, the degron is C-terminal of the engineered RNA-binding domain.

In some embodiments of any of the aspects, the C-terminal degron comprises RRRG (SEQ ID NO: 10).

In some embodiments of any of the aspects, the degron is N-terminal of the engineered RNA-binding domain.

In some embodiments of any of the aspects, the N-terminal degron comprises RAS.

In some embodiments of any of the aspects, the engineered RNA-binding domain comprises a tandem dimer of MCP monomers.

In some embodiments of any of the aspects, the engineered RNA-binding domain comprises circular permutation of MCP monomers.

In some embodiments of any of the aspects, the engineered RNA-binding domain comprises: (a) a C-terminal portion of a first MCP monomer; (b) a second MCP monomer; and (c) an N-terminal portion of the first MCP monomer.

In some embodiments of any of the aspects, the engineered RNA-binding domain comprises: (a) a C-terminal portion of a first MCP monomer; and (b) an N-terminal portion of the first MCP monomer.

In some embodiments of any of the aspects, the first MCP monomer is split into the N-terminal portion and the C-terminal portion at a binding pocket for the MS2 RNA hairpin loop.

In some embodiments of any of the aspects, the first MCP monomer is split into the N-terminal portion and the C-terminal portion at residue 48, 49, 50, 51, 52, 53, 54, or 55 of an MCP monomer (SEQ ID NO: 22 or SEQ ID NO: 23).

In some embodiments of any of the aspects, (a) the C-terminal portion of the first MCP monomer comprises at least residues 53-116 of an MCP monomer (SEQ ID NO: 22 or SEQ ID NO: 23); and/or (b) the N-terminal portion of the first MCP monomer comprises at least residues 3-50 of an MCP monomer (SEQ ID NO: 22 or SEQ ID NO: 23).

In some embodiments of any of the aspects, (a) the C-terminal portion of the first MCP monomer comprises SEQ ID NO: 19 or an amino acid sequence that is at least 80% identical to SEQ ID NO: 19; (b) the second MCP monomer comprises SEQ ID NO: 20 or an amino acid sequence that is at least 80% identical to SEQ ID NO: 20; and/or (c) the N-terminal portion of the first MCP monomer comprises SEQ ID NO: 21 or an amino acid sequence that is at least 80% identical to SEQ ID NO: 21.

In some embodiments of any of the aspects, the MS2 RNA hairpin loop comprises one of SEQ ID NOs: 27, 29, 42-44, 47, 54 or a nucleic acid sequence that is at least 80% identical to one of SEQ ID NOs: 27, 29, 42-44, 47, 54.

In some embodiments of any of the aspects, the engineered MCP protein comprises SEQ ID NO: 4, SEQ ID NO: 50, or an amino acid sequence that is at least 80% identical to SEQ ID NO: 4 or SEQ ID NO: 50.

In some embodiments of any of the aspects, the engineered MCP protein comprises from N-terminus to C-terminus: (a) the engineered RNA-binding domain comprising from N-terminus to C-terminus: (i) a C-terminal portion of a first MCP monomer; (ii) a second MCP monomer; and (iii) an N-terminal portion of the first MCP monomer; and (b) the degron.

In some embodiments of any of the aspects, the engineered MCP protein comprises from N-terminus to C-terminus: (a) the engineered RNA-binding domain comprising from N-terminus to C-terminus: (i) a C-terminal portion of a first MCP monomer; and (ii) an N-terminal portion of the first MCP monomer; and (b) the degron.

In one aspect, described herein is an engineered MS2 coat protein (MCP; cpmMCP) comprising an engineered RNA-binding domain; wherein the engineered MCP protein is stable when the engineered RNA-binding domain is bound to an MS2 RNA hairpin loop; wherein when the engineered RNA-binding domain is not bound to the MS2 RNA hairpin loop, the engineered MCP protein is unstable and degradation of the engineered MCP protein increases.

In some embodiments of any of the aspects, the engineered RNA-binding domain comprises: (a) a C-terminal portion of a first MCP monomer; and (b) an N-terminal portion of the first MCP monomer.

In some embodiments of any of the aspects, the engineered MCP protein comprises (a) the engineered RNA-binding domain comprising from N-terminus to C-terminus: (i) a C-terminal portion of a first MCP monomer; and (ii) an N-terminal portion of the first MCP monomer.

In some embodiments of any of the aspects, the engineered MCP protein does not comprise a degron.

In some embodiments of any of the aspects, the engineered RNA-binding domain comprises SEQ ID NO: 49, or an amino acid sequence that is at least 80% identical to SEQ ID NO: 49.

In some embodiments of any of the aspects, the engineered RNA-binding domain further comprises a degron.

In one aspect, described herein is an engineered PP7 coat protein (PCP) comprising an engineered RNA-binding domain and a degron; wherein the degron is hidden upon binding of the engineered RNA-binding domain to a PP7 RNA hairpin loop; wherein when the engineered RNA-binding domain is not bound to the PP7 RNA hairpin loop, the degron is exposed and degradation of the engineered PCP protein increases.

In some embodiments of any of the aspects, the degron is C-terminal of the engineered RNA-binding domain.

In some embodiments of any of the aspects, the C-terminal degron comprises RRRG (SEQ ID NO: 10).

In some embodiments of any of the aspects, the degron is N-terminal of the engineered RNA-binding domain.

In some embodiments of any of the aspects, the N-terminal degron comprises RAS.

In some embodiments of any of the aspects, the engineered RNA-binding domain comprises a tandem dimer of PCP monomers.

In some embodiments of any of the aspects, the engineered RNA-binding domain comprises circular permutation of PCP monomers.

In some embodiments of any of the aspects, the engineered RNA-binding domain comprises: (a) a C-terminal portion of a first PCP monomer; (b) a second PCP monomer; and (c) an N-terminal portion of the first PCP monomer.

In some embodiments of any of the aspects, the engineered RNA-binding domain comprises: (a) a C-terminal portion of a first PCP monomer; and (b) an N-terminal portion of the first PCP monomer.

In some embodiments of any of the aspects, the first PCP monomer is split into the N-terminal portion and the C-terminal portion at a binding pocket for the PP7 RNA hairpin loop.

In some embodiments of any of the aspects, the first PCP monomer is split into the N-terminal portion and the C-terminal portion at residue 48, 49, 50, 51, 52, 53, 54, or 55 of a PCP monomer (SEQ ID NO: 24).

In some embodiments of any of the aspects, (a) the C-terminal portion of the first PCP monomer comprises at least residues 52-123 of a PCP monomer (SEQ ID NO: 24); and/or (b) the N-terminal portion of the first PCP monomer comprises at least residues 3-48 of a PCP monomer (SEQ ID NO: 24).

In some embodiments of any of the aspects, (a) the C-terminal portion of the first PCP monomer comprises SEQ ID NO: 11, SEQ ID NO: 16, or an amino acid sequence that is at least 80% identical to SEQ ID NO: 11 or SEQ ID NO: 16; (b) the second PCP monomer comprises SEQ ID NO: 12, SEQ ID NO: 17, or an amino acid sequence that is at least 80% identical to SEQ ID NO: 12 or SEQ ID NO: 17; and/or (c) the N-terminal portion of the first PCP monomer comprises SEQ ID NO: 13, SEQ ID NO: 18, or an amino acid sequence that is at least 80% identical to SEQ ID NO: 13 or SEQ ID NO: 18.

In some embodiments of any of the aspects, the PP7 RNA hairpin loop comprises SEQ ID NO: 53 (ggagcagacga-tatggcgtcgctcc) or a nucleic acid sequence that is at least 80% identical to SEQ ID NO: 53.

In some embodiments of any of the aspects, the engineered PCP protein comprises SEQ ID NO: 2, SEQ ID NO: 15, or an amino acid sequence that is at least 80% identical to SEQ ID NO: 2 or SEQ ID NO: 15.

In some embodiments of any of the aspects, the first or second PCP monomer, or the N-terminal or C-terminal portions thereof, comprises at least one mutation to decrease self-assembly of dimers into higher order aggregates.

In some embodiments of any of the aspects, the at least one mutation corresponds to S22R, L36A, and/or L71A in SEQ ID NO: 24.

In some embodiments of any of the aspects, the engineered PCP protein comprises from N-terminus to C-terminus: (a) the engineered RNA-binding domain comprising from N-terminus to C-terminus: (i) a C-terminal portion of a first PCP monomer; (ii) a second PCP monomer; and (iii) an N-terminal portion of the first PCP monomer; and (b) the degron.

In some embodiments of any of the aspects, the engineered PCP protein comprises from N-terminus to C-terminus: (a) the engineered RNA-binding domain comprising from N-terminus to C-terminus: (i) a C-terminal portion of a first PCP monomer; and (ii) an N-terminal portion of the first PCP monomer; and (b) the degron.

In one aspect, described herein is an engineered PP7 coat protein (PCP) comprising an engineered RNA-binding domain; wherein the engineered PCP protein is stable when the engineered RNA-binding domain is bound to a PP7 RNA hairpin loop; wherein when the engineered RNA-binding domain is not bound to the PP7 RNA hairpin loop, the engineered PCP protein is unstable and degradation of the engineered PCP protein increases.

In some embodiments of any of the aspects, the engineered RNA-binding domain comprises: (a) a C-terminal portion of a first PCP monomer; and (b) an N-terminal portion of the first PCP monomer.

In some embodiments of any of the aspects, the engineered PCP protein comprises (a) the engineered RNA-binding domain comprising from N-terminus to C-terminus: (i) a C-terminal portion of a first PCP monomer; and (ii) an N-terminal portion of the first PCP monomer.

In some embodiments of any of the aspects, the engineered PCP protein does not comprise a degron.

In some embodiments of any of the aspects, the engineered PCP protein further comprises a degron.

In some embodiments of any of the aspects, the first or second PCP monomer, or the N-terminal or C-terminal portions thereof, comprise at least one mutation to decrease self assembly of dimers into higher order aggregates.

In some embodiments of any of the aspects, the at least one mutation corresponds to S22R, L36A, and/or L71A in SEQ ID NO: 24.

In one aspect, described herein is a fusion protein comprising an engineered MCP protein as described herein linked to at least one effector protein.

In one aspect, described herein is a fusion protein comprising an engineered PCP protein as described herein linked to at least one effector protein.

In some embodiments of any of the aspects, the at least one effector protein is selected from the group consisting of: (a) a detectable marker; (b) a trafficking domain and/or targeting sequence; (c) a Cas protein that binds to an RNA guide sequence; (d) an RNA-cleaving and/or RNA-modifying enzyme; (e) a translation-regulating and translation-associated domain; (f) a cell-cycle regulated degron; (g) a proximity-labeling and/or substrate-labeling enzyme; and (h) an antigen-binding domain.

In some embodiments of any of the aspects, the detectable marker is selected from the group consisting of: a luciferase, a fluorescent protein, and an ultrasound-mediated reporter.

In some embodiments of any of the aspects, the luciferase is selected from the group consisting of: NanoLuc®, RLuc, RLuc8, and Super RLuc8.

In some embodiments of any of the aspects, the fluorescent protein is an infrared fluorescent protein (iRFP).

In some embodiments of any of the aspects, the infrared fluorescent protein (iRFP) is selected from the group consisting of: iRFP-670 and miIRFP-670.

In some embodiments of any of the aspects, the fluorescent protein is fluorescent when bound to a substrate.

In some embodiments of any of the aspects, the fluorescent protein is HALOTAG.

In some embodiments of any of the aspects, the ultrasound-mediated reporter comprises a gas vesicle-based reporter protein.

In some embodiments of any of the aspects, the trafficking domain and/or targeting sequence is selected from the group consisting of: (a) a microtubule motor protein (e.g., a kinesin or dynein); (b) a mitochondrial surface targeting sequence; (c) a nuclear localization signal; (d) a nuclear exclusion signal; (e) a transmembrane domain; (f) a signaling receptor; (g) a lipid-modification substrate; (h) a Pleckstrin homology domain; and (i) a split pleckstrin homology domain.

In some embodiments of any of the aspects, the signaling receptor is selected from the group consisting of: (a) a GPCR; (b) a SynNotch; or (c) a CAR.

In some embodiments of any of the aspects, the lipid-modification substrate comprises a substrate for: (i) myristoylation, (ii) palmitoylation, (iii) myristoylation and palmitoylation, or (iv) prenylation.

In some embodiments of any of the aspects, the Cas protein is selected from the group consisting of: (a) an RNA-guided DNA binding Cas protein; and (b) an RNA-guided RNA binding Cas protein.

In some embodiments of any of the aspects, the RNA-guided DNA binding Cas protein comprises Cas9 or Cas12.

In some embodiments of any of the aspects, the RNA-guided RNA binding Cas protein comprises Cas13 or Cas CSM.

In some embodiments of any of the aspects, the Cas protein is catalytically inactive.

In some embodiments of any of the aspects, the RNA-cleaving and/or RNA-modifying enzyme is selected from the group consisting of: (a) an RNA-cleaving nuclease; (b) a de-adenylating enzyme; (c) a de-capping enzyme; (d) a capping enzyme; (e) an RNA base editor; (f) an enzyme that adds covalent attachments to RNA; and (g) an adduct-forming protein.

In some embodiments of any of the aspects, the RNA-cleaving nuclease is selected from the group consisting of: (i) a pre-crRNA-processing enzyme; (ii) an RNase; and (iii) a sequence comprising a SMG6 PIN domain.

In some embodiments of any of the aspects, the pre-crRNA-processing enzyme is selected from the group consisting of: Csy4 (Cas6f), Cas5d, Cas6e, and Cas6.

In some embodiments of any of the aspects, the RNase is selected from the group consisting of: RNase H, RNase III, RNase A, and RNase T1.

In some embodiments of any of the aspects, the de-adenylating enzyme is selected from the group consisting of: (i) CCR4-Not; and (ii) Poly(A)-specific ribonuclease (PARN).

In some embodiments of any of the aspects, the de-capping enzyme comprises Dcp1/Dcp2.

In some embodiments of any of the aspects, the capping enzyme is selected from the group consisting of: (i) a Faustovirus capping enzyme; (ii) a Vaccinia RNA capping enzyme; and (iii) an HIV capping enzyme.

In some embodiments of any of the aspects, the RNA base editor comprises Adenosine Deaminase Acting on RNA (ADAR).

In some embodiments of any of the aspects, the enzyme that adds covalent attachments to RNA is a poly-adenylating enzyme.

In some embodiments of any of the aspects, the poly-adenylating enzyme is selected from the group consisting of: (i) an *E. coli* Poly(A) polymerase; (ii) a yeast poly(A) polymerase; and (iii) a mammalian poly(A) polymerase.

In some embodiments of any of the aspects, the adduct-forming protein is selected from the group consisting of: (i) a tyrosyl-RNA phosphodiester bond-forming domain; and (ii) a VPg viral protein.

In some embodiments of any of the aspects, the translation-regulating and translation-associated domain is selected from the group consisting of: (a) a cap-independent initiation domain; (b) a translational downregulation domain; (c) an amino acyl tRNA synthetase (aaRS); and (d) a peptide-based sequence that facilitates translation modulation or RNA stability changes when recruited to an RNA molecule.

In some embodiments of any of the aspects, the cap-independent initiation domain comprises a caliciviral VPg protein.

In some embodiments of any of the aspects, the translational downregulation domain comprises eif4e-bp1, or the Eif4E binding domain from CUP, THOR, or 4E-T.

In some embodiments of any of the aspects, the translational downregulation domain blocks ribosome translocation.

In some embodiments of any of the aspects, the translational downregulation domain comprises a stable secondary structure that blocks ribosome translocation.

In some embodiments of any of the aspects, the amino acyl tRNA synthetase (aaRS) is selected from the group consisting of: (a) mutant *E. coli* amino aaRS; (b) mutant endogenous aaRS; (c) mutant *Methanocaldococcus jannaschii* aaRS; (d) mutant yeast aaRS; and (e) mutant pyrrolysine aaRS.

In some embodiments of any of the aspects, the cell-cycle regulated degron is selected from the group consisting of: (a) a CdtI degron domain; (b) a Geminin degron domain; and (c) a FUCCI sensor.

In some embodiments of any of the aspects, the proximity-labeling and/or substrate-labeling enzyme is selected from the group consisting of: (a) a biotin ligase in combination with a biotin ligase substrate; (b) a peroxidase-based enzyme; (c) miniSOG; (d) RNA methyltransferase (e.g., METTL16); (e) 'LITtag', an engineered flavin-mononucleotide-binding LOV domain; and (f) an RNA Transglycosylase.

In some embodiments of any of the aspects, the biotin ligase is *E. coli* biotin ligase (BirA).

In some embodiments of any of the aspects, the biotin ligase is derived from BirA and selected from the group consisting of BioID, BioID2, and TurboID.

In some embodiments of any of the aspects, the biotin ligase substrate is an acceptor peptide (AP), a biotinylated sequence from *Propionibacterium shermanii* transcarboxylase, or AviTag.

In some embodiments of any of the aspects, the peroxidase-based enzyme is selected from the group consisting of APEX, APEX2, and HRP.

In some embodiments of any of the aspects, the RNA Transglycosylase is *E. coli* tRNA guanine transglycosylase (TGT).

In some embodiments of any of the aspects, the antigen-binding domain is comprised by an antibody or nanobody.

In some embodiments of any of the aspects, the antigen-binding domain binds to an endogenous protein.

In some embodiments of any of the aspects, the antigen-binding domain binds to an intracellular protein.

In some embodiments of any of the aspects, the nanobody comprises a destabilized nanobody.

In some embodiments of any of the aspects, the at least one effector protein recruits at least one additional effector protein.

In some embodiments of any of the aspects, the fusion protein further comprises a linker between the engineered RNA-binding domain and the at least one effector protein.

In some embodiments of any of the aspects, the linker is selected from the group consisting of: (a) drug-inducible heterodimerization domains; (b) drug-dissociable heterodimerization domains; (c) drug-preservable domains; (d) a gas-vesicle associated domain that is released by ultrasound; (e) light-regulated protein-protein interaction domains; and (f) protein-protein interaction domains dependent on an extracellular or intracellular signal.

In some embodiments of any of the aspects, the drug-inducible heterodimerization domains are selected from the group consisting of: (a) FKBP and FRB; (b) abscisic acid (ABA)-inducible heterodimeric protein binding domains; (c) gibberellin-inducible heterodimeric protein binding domains; (d) a drug-inducible reader domain that specifically binds to an NS3 protease inhibitor-bound NS3 protease; and (e) human antibody-based dimerizers (AbCIDs).

In some embodiments of any of the aspects, the drug-dissociable heterodimerization domains are selected from the group consisting of: (a) Bcl-xL and BH3 proteins, the interaction of which can dissociated by small molecules (e.g., A-1155463); (b) NS3 protease complexed with an inhibitory peptide, the interaction of which can be dissociated using an NS3 protease inhibitor, optionally wherein the NS3 protease is catalytically inactive; and (c) a drug-dissociable reader domain that specifically binds to a first NS3 protease inhibitor-bound NS3 protease, the interaction of which can dissociated by a second NS3 protease inhibitor that binds to NS3 protease.

In some embodiments of any of the aspects, the drug-preservable domains comprise an active NS3 protease and a cognate cleavage site for the active NS3 protease, wherein the linker is preserved in the presence of an NS3 protease inhibitor, and the linkage is severed in the absence of the NS3 protease inhibitor.

In some embodiments of any of the aspects, the light-regulated protein-protein interaction domains are selected from the group consisting of: (a) PhoCl; (b) mMaple3; (c) LOV domains; (d) luciferase-fused LOV domains; and (e) red light-inducible PPI domains (e.g., PhyB/Pif).

In some embodiments of any of the aspects, the protein-protein interaction domains dependent on an extracellular or intracellular signal are selected from the group consisting of: (a) beta-arrestin, which bind to phosphorylated tails of GPCRs; (b) phosphorylated kinase substrates in combination with domains recognizing such phosphorylated sequences; (c) binding proteins that recognize and undergo protein interactions in response to secondary metabolites (e.g., cAMP) or ions (including Ca2+); and (d) a nanobody that binds the intracellular region of an activated GPCR.

In some embodiments of any of the aspects, the fusion protein further comprises a transmembrane domain.

In some embodiments of any of the aspects, the at least one effector protein is N-terminal of the engineered RNA-binding domain.

In some embodiments of any of the aspects, the at least one effector protein is linked to the N-terminus of the engineered RNA-binding domain.

In some embodiments of any of the aspects, the at least one effector protein is located between: (a) the C-terminal portion of the first MCP monomer and the second MCP monomer; (b) the C-terminal portion of the first MCP monomer and the N-terminal portion of the first MCP monomer; (c) the second MCP monomer and the N-terminal portion of the first MCP monomer; and/or (d) the N-terminal portion of the first MCP monomer and the degron.

In some embodiments of any of the aspects, the at least one effector protein is located between: (a) the C-terminal portion of the first PCP monomer and the second PCP monomer; (b) the C-terminal portion of the first PCP monomer and the N-terminal portion of the first PCP monomer; (c) the second PCP monomer and the N-terminal portion of the first PCP monomer; and/or (d) the N-terminal portion of the first PCP monomer and the degron.

In one aspect, described herein is a nucleic acid encoding a fusion protein as described herein.

In one aspect, described herein is a vector comprising a nucleic acid as described herein.

In one aspect, described herein is a complex comprising a fusion protein as described herein bound to an RNA molecule comprising at least one hairpin loop specifically bound by the engineered RNA-binding domain of the fusion protein.

In one aspect, described herein is a complex comprising a fusion protein as described herein bound to an RNA molecule comprising at least one MS2 RNA hairpin loop or at least one PP7 RNA hairpin loop.

In one aspect, described herein is a system comprising a fusion protein as described herein and an RNA molecule comprising at least one hairpin loop specifically bound by the engineered RNA-binding domain of the fusion protein.

In one aspect, described herein is a system comprising a fusion protein as described herein and an RNA molecule comprising at least one MS2 RNA hairpin loop or at least one PP7 RNA hairpin loop.

In one aspect, described herein is a system comprising: (a) a fusion protein comprising an engineered MCP protein as described herein linked to at least one effector protein; and (b) an RNA molecule comprising at least one MS2 RNA hairpin loop.

In one aspect, described herein is a system comprising: (a) a fusion protein comprising an engineered PCP protein as described herein linked to at least one effector protein; and (b) an RNA molecule comprising at least one PP7 RNA hairpin loop.

In some embodiments of any of the aspects, the engineered RNA-binding domain of the fusion protein is capable of binding to the at least one hairpin loop in the RNA molecule, thereby decreasing degradation of the fusion protein.

In some embodiments of any of the aspects, the at least one hairpin loop is located in an untranslated region of the RNA molecule that is 5' or 3' from an encoded gene of interest.

In some embodiments of any of the aspects, the fusion protein binds to the at least one hairpin loop in the RNA molecule and modulates expression of the encoded gene of interest.

In some embodiments of any of the aspects, the gene of interest encodes for the fusion protein.

In some embodiments of any of the aspects, the fusion protein binds to the at least one hairpin loop in the RNA molecule and decreases expression of the encoded fusion protein, thus resulting in auto-inhibition.

In some embodiments of any of the aspects, the RNA molecule comprises a circular RNA.

In some embodiments of any of the aspects, the RNA molecule comprises a capless linear RNA.

In some embodiments of any of the aspects, the RNA molecule comprises an IRES for cap-independent translation of the encoded gene of interest.

In some embodiments of any of the aspects, the RNA molecule comprises substituted synthetic nucleotides.

In some embodiments of any of the aspects, the substituted synthetic nucleotides are pseudouridine ($\Psi$) and/or 5-methylcytosine ($m^5C$).

In some embodiments of any of the aspects, the at least one hairpin loop does not comprise uridine.

In some embodiments of any of the aspects, the at least one hairpin loop does not comprise substituted synthetic nucleotides.

In one aspect, described herein is a system comprising: (a) a first fusion protein comprising an engineered MCP protein as described herein linked to at least one effector protein; (b) a second fusion protein comprising an engineered PCP protein as described herein linked to at least one effector protein; and (c) an RNA molecule comprising at least one MS2 RNA hairpin loop and at least one PP7 RNA hairpin loop.

In one aspect, described herein is a system comprising: (a) a first fusion protein comprising an engineered MCP protein as described herein linked to at least one effector protein; (b) a second fusion protein comprising an engineered PCP protein as described herein linked to at least one effector protein; (c) a first RNA molecule comprising at least one MS2 RNA hairpin loop; and (d) a second RNA molecule comprising at least one PP7 RNA hairpin loop.

In one aspect, described herein is a method of detecting an RNA molecule, the method comprising contacting the RNA molecule with a fusion protein as described herein; wherein the at least one effector protein comprises a detectable marker; wherein the RNA molecule comprises at least one hairpin loop specifically bound by the engineered RNA-binding domain of the fusion protein.

In one aspect, described herein is a method of detecting an RNA molecule in a cell, the method comprising contacting the cell with a fusion protein as described herein; wherein the at least one effector protein comprises a detectable marker; wherein the RNA molecule comprises at least one hairpin loop specifically bound by the engineered RNA-binding domain of the fusion protein.

In one aspect, described herein is a method of trafficking or targeting an RNA molecule to a specific location in a cell, the method comprising contacting the cell with a fusion protein as described herein; wherein the at least one effector protein comprises a trafficking domain and/or targeting sequence; wherein the RNA molecule comprises at least one hairpin loop specifically bound by the engineered RNA-binding domain of the fusion protein.

In one aspect, described herein is a method of editing an RNA molecule, the method comprising contacting the RNA molecule with a fusion protein as described herein; wherein the at least one effector protein comprises a Cas protein that binds to an RNA guide sequence; wherein the RNA molecule comprises at least one hairpin loop specifically bound by the engineered RNA-binding domain of the fusion protein.

In one aspect, described herein is a method of editing an RNA molecule in a cell, the method comprising contacting the cell with a fusion protein as described herein; wherein the at least one effector protein comprises a Cas protein that binds to an RNA guide sequence; wherein the RNA molecule comprises at least one hairpin loop specifically bound by the engineered RNA-binding domain of the fusion protein.

In one aspect, described herein is a method of cleaving an RNA molecule, the method comprising contacting the RNA molecule with a fusion protein as described herein; wherein the at least one effector protein comprises an RNA-cleaving enzyme; wherein the RNA molecule comprises at least one hairpin loop specifically bound by the engineered RNA-binding domain of the fusion protein.

In one aspect, described herein is a method of cleaving an RNA molecule in a cell, the method comprising contacting the cell with a fusion protein as described herein; wherein the at least one effector protein comprises an RNA-cleaving enzyme; wherein the RNA molecule comprises at least one hairpin loop specifically bound by the engineered RNA-binding domain of the fusion protein.

In one aspect, described herein is a method of modifying an RNA molecule, the method comprising contacting the RNA molecule with a fusion protein as described herein; wherein the at least one effector protein comprises an RNA-modifying enzyme; wherein the RNA molecule comprises at least one hairpin loop specifically bound by the engineered RNA-binding domain of the fusion protein.

In one aspect, described herein is a method of modifying an RNA molecule in a cell, the method comprising contacting the cell with a fusion protein as described herein; wherein the at least one effector protein comprises an RNA-modifying enzyme; wherein the RNA molecule comprises at least one hairpin loop specifically bound by the engineered RNA-binding domain of the fusion protein.

In one aspect, described herein is a method of regulating translation of an RNA molecule, the method comprising contacting the RNA molecule with a fusion protein as described herein; wherein the at least one effector protein comprises a translation-regulating and translation-associated domain; wherein the RNA molecule comprises at least one hairpin loop specifically bound by the engineered RNA-binding domain of the fusion protein.

In one aspect, described herein is a method of regulating translation of an RNA molecule in a cell, the method comprising contacting the cell with a fusion protein as described herein; wherein the at least one effector protein comprises a translation-regulating and translation-associated domain; wherein the RNA molecule comprises at least one hairpin loop specifically bound by the engineered RNA-binding domain of the fusion protein.

In one aspect, described herein is a method of regulating an RNA molecule in a cell according to the cell cycle, the method comprising contacting the cell with a fusion protein as described herein; wherein the at least one effector protein comprises a cell-cycle regulated degron; wherein the RNA molecule comprises at least one hairpin loop specifically bound by the engineered RNA-binding domain of the fusion protein.

In one aspect, described herein is a method of detecting the proximity of an RNA molecule to another molecule, the method comprising contacting the RNA molecule with a fusion protein as described herein; wherein the at least one effector protein comprises a proximity-labeling and/or substrate-labeling enzyme; wherein the RNA molecule comprises at least one hairpin loop specifically bound by the engineered RNA-binding domain of the fusion protein.

In one aspect, described herein is a method of detecting the proximity of an RNA molecule to another molecule in a cell, the method comprising contacting the cell with a fusion protein as described herein; wherein the at least one effector protein comprises a proximity-labeling and/or substrate-labeling enzyme; wherein the RNA molecule comprises at least one hairpin loop specifically bound by the engineered RNA-binding domain of the fusion protein.

In one aspect, described herein is a method of targeting an RNA molecule to an antigen, the method comprising contacting the RNA molecule with a fusion protein as described herein; wherein the at least one effector protein comprises an antigen-binding domain; wherein the RNA molecule comprises at least one hairpin loop specifically bound by the engineered RNA-binding domain of the fusion protein.

In one aspect, described herein is a method of targeting an RNA molecule to an antigen in a cell, the method comprising contacting the cell with a fusion protein as described herein; wherein the at least one effector protein comprises an antigen-binding domain; wherein the RNA molecule comprises at least one hairpin loop specifically bound by the engineered RNA-binding domain of the fusion protein.

In one aspect, described herein is a method of modulating the linker in a fusion protein as described herein, the method comprising inducing a signal that modulates the linker.

In some embodiments of any of the aspects, the linker is between the engineered MCP protein and the at least one effector protein.

In some embodiments of any of the aspects, the linker is between the engineered PCP protein and the at least one effector protein.

In some embodiments of any of the aspects, the linker is selected from the group consisting of: (a) drug-inducible heterodimerization domains; (b) drug-dissociable heterodimerization domains; (c) drug-preservable domains; (d) gas-vesicle associated domains that are released by ultrasound; (e) light-regulated protein-protein interaction domains; and (f) protein-protein interaction domains dependent on an extracellular or intracellular signal.

In some embodiments of any of the aspects, the signal is selected from the group consisting of: (a) a drug that induces heterodimerization of drug-inducible heterodimerization domains; (b) a drug that induces dissociation of drug-dissociable heterodimerization domains; (c) a drug that induces preservation of drug-preservable domains; (d) ultrasound that releases gas-vesicle associated domains; (e) light that induces cleavage (e.g., PhoCL, mMaple3), dissociation (e.g., LOV, luciferase-LOV) or dimerization (e.g., PhyB/PIF); and (f) an extracellular or intracellular signal that induces interaction of protein-protein interaction domains.

BRIEF DESCRIPTION OF THE DRAWINGS

(FIG. 2A) Screen of C-terminal circularly permuted MCP variants, transfected with either H2B-mCherry-16×MS2 (+MS2) or H2B-mCherry RNA (Ctrl). cMCP-Q52 contains the same residues as wildtype MCP, with the C-terminus relocated to Q52. The others have an RRRG (SEQ ID NO: 10) degron domain added after the indicated residue. MCPQ refers to the Q50 variant. (FIG. 2B) Cycloheximide (CHX) chase of an MCPQ cell line revealed strong contrast between RNA-stabilized and unstabilized MCPQ, and no significant degradation of stabilized MCPQ after 2 hours. (FIG. 2C) Western blots of CHX chase HA-tagged MCPQ revealed ~15 min half life of unstable MCPQ. Stabilized MCPQ accumulated to equal concentration as naturally stable tdMCP, even after two hours in CHX.

(FIG. 3A) Imaging of transcripts for proteins targeted to various subcellular locations. (FIG. 3B) HCR-FISH demonstrated overlap of MCPQ and FISH single RNA labeling and lowered background from MCPQ in comparison with tdMCP. (FIG. 3C) HALOTAG-MCPO produced single-molecule images with yellow dye (JF503), red dye (JF552), and far red (JFX646) dye. (FIG. 3D) Frames from a video recording of suspected mitochondria-TOM20 RNA association revealed by MCPQ.

(FIG. 4A) A bidirectional promoter can be used for flow-cytometry analysis of signal-to-noise in MCPQ. (FIG. 4B) TetR autoinhibition can be used in combination with LID rapamycin inducible degradation for noise-reducing, degradation sensitive negative feedback. (FIG. 4C) MCP can repress its own transcript through a 5' UTR MS2 loop, which can reduce variability of MCPQ expression.

(FIG. 6A) MCPQ normally degrades rapidly, but its half-life was greatly extended upon interaction with an MS2 RNA loop. Figure made with BIORENDER. (FIG. 6B) Western blot of HA-tagged MCPQ in a HEK293FT line expressing the protein after addition of cycloheximide (CHX) to halt MCPQ translation. In the absence of MS2 RNA, MCPQ has a half-life of roughly 20 minutes. (FIG. 6C) Blot of HEK293FT transfected to express HA-tagged MCP, HA-tagged MCPQ, and MS2 RNA. In the presence of MS2 RNA, MCPQ showed no significant degradation after two hours of CHX treatment, and its stability was comparable to the stability of MCP. MCPQ without MS2 RNA completely degraded in this timespan. (FIG. 6D) Fluorescence microscopy of HEK 293FT cells transduced to express mNeonGreen tagged MCPQ and transfected with or without MS2 containing RNA revealed increased fluorescent MCPQ signal when MS2 RNA is present (FIG. 7A) Fixed U2OS cells were transfected to express H2B-mCherry-16×MS2 and either 4×mNeonGreen-MCPQ or 4×mNeonGreen-MCP. H2B-mCherry-16×MS2 RNA was stained in far red using HCR-FISH. (FIG. 7B) Frames from a recording of H2B-mCherry-16×MS2 movement in a live U2OS cell as tracked using 4×mNeonGreen-MCPQ at 50 ms exposure. Frames on the right include time of capture in seconds. Traces shown for two punctae. (FIG. 7C) Fixed U2OS expressing H2B-mCherry-16×MS2 RNA and 2×HaloTag®-MCPQ stained with red JF585 dye and far-red JFX646 dye.

FIG. 8A is a schematic of the d-td-MCP protein. FIG. 8B is a series of microscopy images showing use of the d-td-MCP protein for fluorescent intracellular labeling. FIG. 8C is a series of microscopy images showing use of the td-MCP protein for fluorescent intracellular labeling.

FIG. 9A: MCP proteins (blue ovals) interact with MS2 hairpin RNAs (green loop) as a heterodimer with accessible/free N- and C-termini. FIG. 9B: a tandem dimer of MCP (tdMCP) was generated, and circular permutation was used to reorient tdMCP's termini. FIG. 9C: a C-degron was then fused to the C-terminus (Xs). This is a new C-terminus that is distinct from the original tdMCP's C-terminus. The protein created after tdMCP's termini were reoriented is called cpMCP, and the C-degron was fused to cpMCP's C-terminus.

FIG. 10A: The Permutation introduced a new C terminus at S52 (N-term at A53); R49 interacts with the sugar phosphate backbone of MS2 stem loop. FIG. 10B: MS2 bound, degron masked. FIG. 10C: Not bound to MS2, degron exposed.

FIG. 17A is a schematic showing an exemplary assay. FIG. 17B is a series of microscopy images showing labeling of old and new mRNA, e.g., using MCPQ linked to different fluorescent markers.

(FIG. 21A) dMCP fused to a variety of protein domains can be stabilized by a circular tomado-MS2 RNA. (FIG. 21B) dMCP can interact with RNAs exhibiting distinct subcellular transport properties (cytosolic and ER-targeted RNAs displayed, dMCP signal in white).

(FIG. 24A) log scale Relative Light Unit (RLU) values for the indicated co-transfected cells. (FIG. 24B) linear scale comparison of the indicated constructs shown in (FIG. 24A).

FIG. 25 includes SEQ ID NO: 25 (VRQSSAQN; exemplary MCP binding pocket for the MS2 RNA hairpin loop, where the MCP monomer can be split into N-terminal and C-terminal portions) and SEQ ID NO: 26 (VRQSS; exemplary C-terminus in an engineered MCP protein, e.g., without a C-terminal degron added). In some embodiments with a C-terminal degron, the C-terminus of the engineered MCP protein comprises VRQRRRG (SEQ ID NO: 55).

FIG. 30 includes SEQ ID NO: 25 (VRQSSAQN) and SEQ ID NO: 26 (VRQSS). In some embodiments with a C-terminal degron, the C-terminus of the engineered MCP protein comprises VRQRRRG (SEQ ID NO: 55).

FIG. 33A-33B: Exemplary systems comprising MCP-iDAR. FIG. 33C: HEK293FT reporter cell line. FIG. 33D: iDAR editing efficiency.

FIG. 34A includes SEQ ID NO: 27 (AAACAUGAGGAUUACCCAUGU) and NNNNNRN-NANYANNNNNNN where "R" indicates a purine (A or G), "Y" indicates a pyrimidine (C or T/U), and the following "N" nucleotide positions are complementary: 1 and 19, 2 and 18, 3 and 17, 4 and 16, 5 and 15, 7 and 14, 8 and 13). FIG. 34B includes SEQ ID NO: 29 (GCGCGAG-GAACACCCGCGC).

FIG. 40: Testing of MCP-ADAR with reporter variant (stop codons: 2; MS2 loop: no Uv2; SEQ ID NO: 44, AATTCCGCGTAGCGCTAGCCaaGCGCGAG-
GAacACCCGCGCaGGCCAGCGCCACGCGACTAGT).

FIG.
41A) Schematic indicating the ubiquitin fusion construct
that generates the N-degron equipped RAS-cpMCP-cpmVenus (see e.g., Table 9, SEQ ID NO: 51). cpmVenus was
inserted into cpMCP at the site between the C-terminal
fragment of MCP and the fully intact MCP as a fluorescent
reporter.
FIG. 41A includes SEQ ID NO: 26 (VRQSS).

FIG. 41B) Microscopy data indicating MS2-dependent upregulation in RAS-cpMCP-cpmVenus expression.

DETAILED DESCRIPTION

Figure 1:
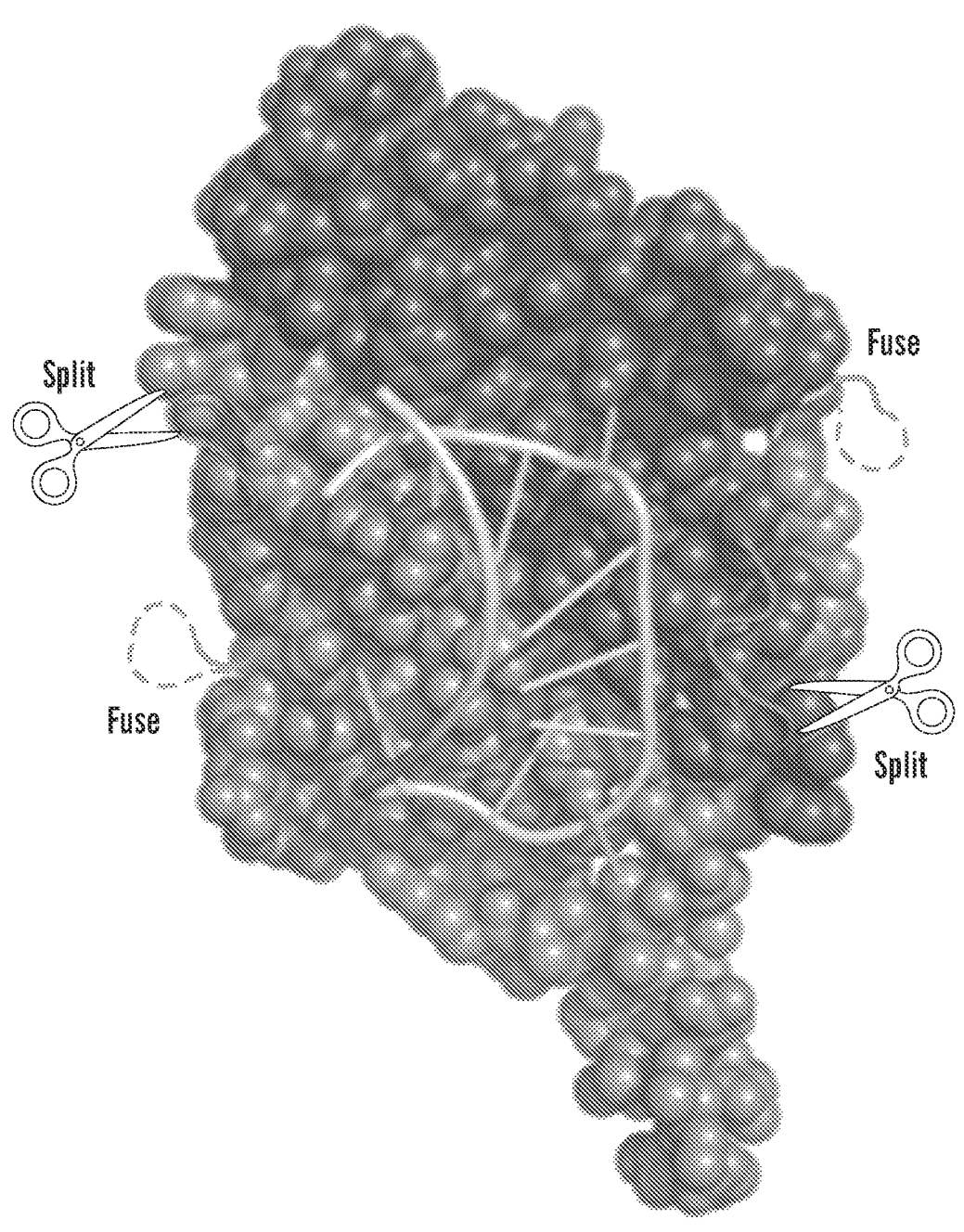
FIG. 1 is a schematic showing sites of fusion and circular permutation for MCP (structure from Helgstrand et al. 2022, Nucleic Acids Res. 30, 2678-2685). Structural depiction of the MCP dimer with cartoons shows where MCP units were fused and how the termini were repositioned.

Embodiments of the technology described herein include
engineered MCP proteins and engineered PCP proteins,
which are degraded when the proteins are not bound to an
MS2 or PP7 RNA hairpin loop, respectively. For example,
the engineered MCP protein can comprise a tandem dimer of
MCP monomers and/or circular permutation of the MCP
monomers, such that an included degron is shielded from
binding to an E3 ligase when the engineered MCP protein is
bound to an MS2 RNA hairpin loop. When the engineered
MCP protein is not bound to the MS2 RNA hairpin loop, the
degron is exposed and degradation of the engineered MCP
protein increases. Also described herein are engineered PCP
proteins and alternative structures of both proteins to allow
for conditional stability.

Also described herein are fusion proteins comprising such
engineered MCP proteins and engineered PCP proteins
linked to various effector proteins, non-limiting examples of
which are provided herein. The linkage to the effector
proteins can be modulated through of specialized linker
domains. In addition, described herein are complexes and systems comprising the fusion proteins in combination with
synthetic RNA molecules, in order to modulate the structure
and/or function the synthetic RNA molecules.

Engineered MCP Proteins

In multiple aspects, described herein are engineered MS2 coat proteins (MCP), including those that are conditionally
stable when bound to a corresponding MS2 hairpin loop.

In one aspect, described herein is an engineered MS2 coat
protein (MCP) comprising an engineered RNA-binding
domain and a degron. In some embodiments, the degron is
hidden upon binding of the engineered RNA-binding
domain to an MS2 RNA hairpin loop. In some embodiments,
when the engineered RNA-binding domain is not bound to
the MS2 RNA hairpin loop, the degron is exposed and
degradation of the engineered MCP protein increases.

Engineered MCP proteins described herein comprise at
least one degron (e.g., 1, 2, 3, 4, 5, or more), which can be
the same or different degrons. As use herein, the term
"degron" refers to a polypeptide sequence or amino acid that
facilitates proteasome-mediated degradation of the linked
polypeptide, including an amino acid or sequence that
facilitates such degradation by serving as a recognition site
for E3 or other ubiquitin ligases. In some embodiments, the
degron is C-terminal of, N-terminal of, or within the engi-
neered RNA-binding domain. In some embodiments, the
engineered MCP protein comprises a C-terminal degron and
an N-terminal degron. In some embodiments, the engineered MCP protein comprises a C-terminal degron, an N-terminal
degron, and an internal degron. In some embodiments, the
engineered MCP protein comprises a C-terminal degron and
an internal degron. In some embodiments, the engineered
MCP protein comprises an N-terminal degron and an inter-
nal degron.

In some embodiments, the degron is C-terminal of the
engineered RNA-binding domain. In some embodiments,
the C-terminal degron comprises RRRG (SEQ ID NO: 10).
In some embodiments, the C-terminal degron follows a
C-end rule. In some embodiments, the C-terminal degron is
known in the art, e.g., selected from Koren et al. Cell 173,
1622-1635.e14 (2018), including but not limited to the
following C-terminal motifs: A, Ax, Vx, EE, Rxx, RxxG,
PG, RG, or GG.

In some embodiments, the degron is N-terminal of the
engineered RNA-binding domain. In some embodiments,
the N-terminal degron comprises RAS. In some embodi-
ments, the N-terminal degron follows an N-end rule, for
example the Cys/Arg N-end rule, the Arg/N-end rule, or the
Pro/N-end rule.

In some embodiments, the engineered RNA-binding
domain comprises a tandem dimer of MCP monomers. In
some embodiments, the engineered RNA-binding domain
comprises circular permutation of MCP monomers. In some
embodiments, the engineered RNA-binding domain com-
prises a tandem dimer and circular permutation of MCP
monomers.

In some embodiments, the engineered RNA-binding
domain comprises: (a) a C-terminal portion of a first MCP
monomer; (b) a second MCP monomer; and (c) an N-ter-
minal portion of the first MCP monomer. In some embodi-
ments, the second MCP monomer described herein com-
prises a full-length, complete or intact MCP monomer. In
some embodiments, the second MCP monomer described
herein comprises a functional portion of a full-length, com-
plete or intact MCP monomer.

In some embodiments, the engineered RNA-binding
domain comprises: (a) a C-terminal portion of a first MCP
monomer; and (b) an N-terminal portion of the first MCP
monomer.

In some embodiments, the first MCP monomer is split
into the N-terminal portion and the C-terminal portion at a
binding pocket for the MS2 RNA hairpin loop. In some
embodiments, the first MCP monomer is split into the
N-terminal portion and the C-terminal portion at residue 48,
49, 50, 51, 52, 53, 54, or 55 of an MCP monomer (SEQ ID
NO: 22 or SEQ ID NO: 23). In some embodiments, the
C-terminal portion of the first MCP monomer comprises at
least residues 48-116, 49-116, 50-116, 51-116, 52-116,
53-116, 54-116, or 55-116 of an MCP monomer (SEQ ID
NO: 22 or SEQ ID NO: 23). In some embodiments, the
N-terminal portion of the first MCP monomer comprises at
least residues 3-48, 3-49, 3-50, 3-51, 3-52, 3-53, 3-54, or
3-55 of an MCP monomer (SEQ ID NO: 22 or SEQ ID NO:
23).

In some embodiments, an MCP monomer comprises SEQ
ID NO: 22, SEQ ID NO: 23, or an amino acid sequence that
is at least 70%, at least 75%, at least 80%, at least 85%, at
least 90%, at least 90%, at least 91%, at least 92%, at least
93%, at least 94%, at least 95%, at least 96%, at least 97%,
at least 98%, or at least 99% identical to SEQ ID NO: 22 or SEQ ID NO: 23, which maintains its function (e.g., RNA-binding).

```
SEQ ID NO: 22, MCP monomer 1, see e.g., SEQ ID[]
NO: 5,
ASNFTQFVLVDNGGTGDVTVAPSNFANGIAEWISSNSRSQAYKVTCSVRQ
SSAQNRKYTIKVEVPKGAWRSYLNMELTIPIFATNSDCELIVKAMQGLLK
DGNPIPSAIAANSGIYA

[SEQ ID NO: 23, MCP monomer 2, see e.g., SEQ ID]
NO: 5,
MASNFTQFVLVDNGGTGDVTVAPSNFANGIAEWISSNSRSQAYKVTCSVR
QSSAQNRKYTIKVEVPKGAWRSYLNMELTIPIFATNSDCELIVKAMQGLL
KDGNPIPSAIAANSGIYA
```

In some embodiments, the C-terminal portion of the first MCP monomer comprises SEQ ID NO: 19 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to SEQ ID NO: 19, which maintains its function (e.g., as part of the engineered RNA-binding domain).

SEQ ID NO: 19, amino acid sequence of C half MCP, see e.g., SEQ ID NO: 4, AQNRKYTIKVEVPKGAWRSYLN-MELTIPIFATNSDCELIVKAMQGLLKDGNPIPSA-IAANSGIY In some embodiments, the second MCP monomer comprises SEQ ID NO: 20 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to SEQ ID NO: 20, which maintains its function (e.g., as part of the engineered RNA-binding domain).

SEQ ID NO: 20, amino acid sequence of MCP monomer, see e.g., SEQ ID NO: 4, NFTQFVLVDNGGTGDVTVAPSNFANGIAEWISSNSR-SQAYKVTCSVRQSSAQNRKYTIKVEVPK GAWR-SYLNMELTIPIFATNSDCELIVKAMQGLLKDGNPIP-SAIAANSGIY In some embodiments, the N-terminal portion of the first MCP monomer comprises SEQ ID NO: 21 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to SEQ ID NO: 21, which maintains its function (e.g., as part of the engineered RNA-binding domain).

SEQ ID NO: 21, amino acid sequence of N half MCP, see e.g., SEQ ID NO: 4, NFTQFVLVDNGGTGDVTVAPSN-FANGIAEWISSNSRSQAYKVTCSVRQ In some embodiments, the MS2 RNA hairpin loop comprises one of SEQ ID NOs: 27, 29, 42-44, 47, 54 or a nucleic acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to one of SEQ ID NOs: 27, 29, 42-44, 47, 54, which maintains its function (e.g., binding to an engineered MCP protein as described herein).

In some embodiments, the engineered MCP protein comprises SEQ ID NO: 4, SEQ ID NO: 50, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to SEQ ID NO: 4 or SEQ ID NO: 50, which maintains its function (e.g., degron shielding when bound to an MS2 hairpin loop).

In some embodiments, the engineered MCP protein comprises from N-terminus to C-terminus: (a) the engineered RNA-binding domain comprising from N-terminus to C-terminus: (i) a C-terminal portion of a first MCP monomer; (ii) a second MCP monomer; and (iii) an N-terminal portion of the first MCP monomer; and (b) the degron.

In some embodiments, the engineered MCP protein comprises from N-terminus to C-terminus: (a) the engineered RNA-binding domain comprising from N-terminus to C-terminus: (i) a C-terminal portion of a first MCP monomer; and (ii) an N-terminal portion of the first MCP monomer; and (b) the degron.

In one aspect, described herein is an engineered MCP protein comprising (e.g., from N-terminus to C-terminus): (a) an engineered RNA-binding domain comprising (e.g., from N-terminus to C-terminus): (i) a C-terminal portion of a first MCP monomer; (ii) a second MCP monomer; and (iii) an N-terminal portion of the first MCP monomer; and (b) a degron. Such an engineered MCP protein can be referred to herein as "destabilized MCP" (also referred herein as d-MCP, dMCP MCP-q, MCPQ, destabilized tdMCP, d-td-MCP).

In one aspect, described herein is an engineered MCP protein comprising (e.g., from N-terminus to C-terminus): (a) an engineered RNA-binding domain comprising (e.g., from N-terminus to C-terminus): (i) a C-terminal portion of a first MCP monomer; and (ii) an N-terminal portion of the first MCP monomer; and (b) a degron. Such an engineered MCP protein can be referred to herein as dmMCP (degron-equipped cpmMCP; cpmMCP-RRRG).

Figure 30:
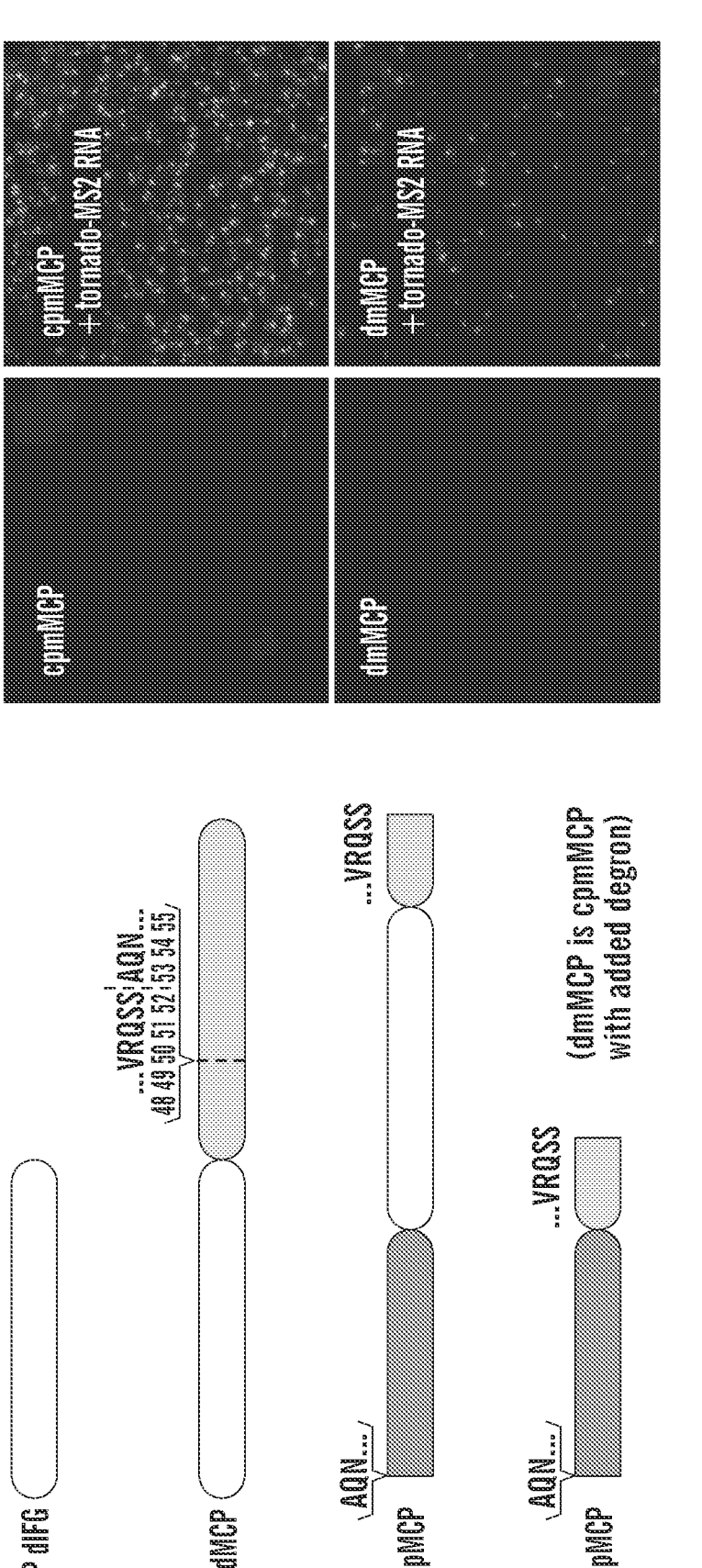
FIG. 30: Design and function of cpmMCP and dmMCP. Left, schematic of how cpmMCP was generated from cpMCP (itself generated from MCP and tdMCP). Right, data indicating that both cpmMCP and dmMCP (degron-equipped cpmMCP) exhibited RNA-dependent stability. In this data, both cpmMCP and dmMCP were fused to mNeon-Green fluorescent protein.

In one aspect, described herein is an engineered MS2 coat protein (MCP) comprising an engineered RNA-binding domain. In some embodiments, wherein the engineered MCP protein is stable when the engineered RNA-binding domain is bound to an MS2 RNA hairpin loop. In some embodiments, when the engineered RNA-binding domain is not bound to the MS2 RNA hairpin loop, the engineered MCP protein is unstable and degradation of the engineered MCP protein increases. Such an engineered MCP protein can be referred to herein as cpmMCP (see e.g., FIG. 30).

In some embodiments, the engineered RNA-binding domain comprises: (a) a C-terminal portion of a first MCP monomer; and (b) an N-terminal portion of the first MCP monomer. In some embodiments, the engineered MCP protein comprises: (a) the engineered RNA-binding domain comprising (e.g., from N-terminus to C-terminus): (i) a C-terminal portion of a first MCP monomer; and (ii) an N-terminal portion of the first MCP monomer. Non-limiting examples of the C-terminal and N-terminal portions of the first MCP monomer are provided herein.

In some embodiments, the engineered MCP protein does not comprise a degron. In some embodiments, the engineered MCP protein comprises SEQ ID NO: 49, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to SEQ ID NO: 49, which maintains its function (e.g., stability when bound to an MS2 hairpin loop). In some embodiments, the engineered MCP protein further comprises a degron, non-limiting examples of which are provided herein.

Engineered PCP Proteins

In multiple aspects, described herein are engineered PP7 coat proteins (PCP), including those that are conditionally stable when bound to a corresponding PP7 hairpin loop.

In one aspect, described herein is an engineered PP7 coat protein (PCP) comprising an engineered RNA-binding domain and a degron. In some embodiments, the degron is hidden upon binding of the engineered RNA-binding domain to a PP7 RNA hairpin loop. In some embodiments, when the engineered RNA-binding domain is not bound to the PP7 RNA hairpin loop, the degron is exposed and degradation of the engineered PCP protein increases.

Engineered PCP proteins described herein comprise at least one degron (e.g., 1, 2, 3, 4, 5, or more), which can be the same or different degrons. As use herein, the term "degron" refers to a polypeptide sequence or amino acid that facilitates proteasome-mediated degradation of the linked polypeptide, including an amino acid or sequence that facilitates such degradation by serving as a recognition site for E3 or other ubiquitin ligases. In some embodiments, the degron is C terminal of, N-terminal of, or within the engineered RNA-binding domain. In some embodiments, the engineered PCP protein comprises a C-terminal degron and an N-terminal degron. In some embodiments, the engineered PCP protein comprises a C-terminal degron, an N-terminal degron, and an internal degron.

In some embodiments, the degron is C-terminal of the engineered RNA-binding domain In some embodiments, the C-terminal degron comprises RRRG (SEQ ID NO: 10). In some embodiments, the C-terminal degron follows a C-end rule. In some embodiments, the C-terminal degron is known in the art, e.g., selected from Koren et al. Cell 173, 1622-1635.e14 (2018), including but not limited to the following C-terminal motifs: A, Ax, Vx, EE, Rxx, RxxG, PG, RG, or GG.

In some embodiments, the degron is N-terminal of the engineered RNA-binding domain. In some embodiments, the N-terminal degron comprises RAS. In some embodiments, the N-terminal degron follows an N-end rule, for example the Cys/Arg N-end rule, the Arg/N-end rule, or the Pro/N-end rule.

In some embodiments, the engineered RNA-binding domain comprises a tandem dimer of PCP monomers. In some embodiments, the engineered RNA-binding domain comprises circular permutation of PCP monomers. In some embodiments, the engineered RNA-binding domain comprises a tandem dimer and circular permutation of PCP monomers.

In some embodiments, the engineered RNA-binding domain comprises: (a) a C-terminal portion of a first PCP monomer; (b) a second PCP monomer; and (c) an N-terminal portion of the first PCP monomer. In some embodiments, the second PCP monomer described herein comprises a full-length, complete or intact PCP monomer. In some embodiments, the second PCP monomer described herein comprises a functional portion of a full-length, complete or intact PCP monomer.

In some embodiments, the engineered RNA-binding domain comprises: (a) a C-terminal portion of a first PCP monomer; and (b) an N-terminal portion of the first PCP monomer.

In some embodiments, the first PCP monomer is split into the N-terminal portion and the C-terminal portion at a binding pocket for the PP7 RNA hairpin loop. In some embodiments, the first PCP monomer is split into the N-terminal portion and the C-terminal portion at residue 48, 49, 50, 51, 52, 53, 54, or 55 of an PCP monomer (SEQ ID NO: 24). In some embodiments, the C-terminal portion of the first PCP monomer comprises at least residues 48-123, 49-123, 50-123, 51-123, 52-123, 53-123, 54-123, or 55-123 of an PCP monomer (SEQ ID NO: 24). In some embodiments, the N-terminal portion of the first PCP monomer comprises at least residues 3-48, 3-49, 3-50, 3-51, 3-52, 3-53, 3-54, or 3-55 of an PCP monomer (SEQ ID NO: 24).

In some embodiments, a PCP monomer comprises SEQ ID NO: 24, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to SEQ ID NO: 24, which maintains its function (e.g., RNA-binding).

```
SEQ ID NO: 24, PCP monomer 1 or PCP monomer 2,
LASKTIVLSVGEATRTLTEIQSTADRQIFEEKVGPLVGRLRLTASLRQNG

AKTAYRVNLKLDQADVVDSGLPKVRYTQVWSHDVTIVANSTEASRKSLYD

LTKSLVATSQVEDLVVNLVPLGR
```

In some embodiments, the C-terminal portion of the first PCP monomer comprises SEQ ID NO: 11, SEQ ID NO: 16, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to SEQ ID NO: 11 or SEQ ID NO: 16, which maintains its function (e.g., as part of the engineered RNA-binding domain).

In some embodiments, the second PCP monomer comprises SEQ ID NO: 12, SEQ ID NO: 17, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to SEQ ID NO: 12 or SEQ ID NO: 17, which maintains its function (e.g., as part of the engineered RNA-binding domain).

In some embodiments, the N-terminal portion of the first PCP monomer comprises SEQ ID NO: 13, SEQ ID NO: 18, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to SEQ ID NO: 13 or SEQ ID NO: 18, which maintains its function (e.g., as part of the engineered RNA-binding domain).

```
SEQ ID NO: 11, amino acid sequence of C half PCP,
see e.g., SEQ ID NO: 2,
SKTAYRVNLKLDQADVVDSGAPKVRYTQVWSHDVTIVANSTEASRKSLY
DLTKSLVATSQVEDLVVNLVPLGR SEQ ID NO: 12, amino acid sequence of PCP monomer,
see e.g., SEQ ID NO: 2,
SKTIVLSVGEATRTLTEIQRTADRQIFEEKVGPAVGRLRLTASLRQNGA
KTAYRVNLKLDQADVVDSGAPKVRYTQVWSHDVTIVANSTEASRKSLYD
LTKSLVATSQVEDLVVNLVPLG SEQ ID NO: 13, amino acid sequence of N half PCP,
see e.g., SEQ ID NO: 2,
SKTIVLSVGEATRTLTEIQRTADRQIFEEKVGPAVGRLRLTASLRQ SEQ ID NO: 16, amino acid sequence of C half PCP,
see e.g., SEQ ID NO: 15,
SKTAYRVNLKLDQADVVDSGLPKVRYTQVWSHDVTIVANSTEASRKSLY
DLTKSLVATSQVEDLVVNLVPLGR SEQ ID NO: 17, amino acid sequence of PCP monomer,
see e.g., SEQ ID NO: 15,
SKTIVLSVGEATRTLTEIQSTADRQIFEEKVGPLVGRLRLTASLRQNGA
KTAYRVNLKLDQADVVDSGLPKVRYTQVWSHDVTIVANSTEASRKSLYD
LTKSLVATSQVEDLVVNLVPLGR
```

-continued

```
SEQ ID NO: 18, amino acid sequence of N half PCP,
see e.g., SEQ ID NO: 15,
SKTIVLSVGEATRTLTEIQSTADRQIFEEKVGPLVGRLRLTASLRQ
```

In some embodiments, the PP7 RNA hairpin loop comprises SEQ ID NO: 53 (ggagcagacgatatggcgtcgctcc) or a nucleic acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to SEQ ID NO: 53, which maintains its function (e.g., binding to an engineered PCP protein as described herein).

In some embodiments, the engineered PCP protein comprises SEQ ID NO: 2, SEQ ID NO: 15, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to SEQ ID NO: 2 or SEQ ID NO: 15, which maintains its function (e.g., degron shielding when bound to a PP7 hairpin loop).

In some embodiments, the first or second PCP monomer, or the N-terminal or C-terminal portions thereof, comprise at least one mutation to decrease self-assembly of dimers into higher order aggregates. In some embodiments, the at least one mutation corresponds to S22R, L36A, and/or L71A in SEQ ID NO: 24. For example, the first or second PCP monomer can comprise: S22R; L36A; L71A; S22R and L36A; S22R and L71A; L36A and L71A; or S22R, L36A, and L71A.

In some embodiments, the engineered PCP protein comprises from N-terminus to C-terminus: (a) the engineered RNA-binding domain comprising from N-terminus to C-terminus: (i) a C-terminal portion of a first PCP monomer; (ii) a second PCP monomer; and (iii) an N-terminal portion of the first PCP monomer; and (b) the degron.

In some embodiments, the engineered PCP protein comprises from N-terminus to C-terminus: (a) the engineered RNA-binding domain comprising from N-terminus to C-terminus: (i) a C-terminal portion of a first PCP monomer; and (ii) an N-terminal portion of the first PCP monomer; and (b) the degron.

In one aspect, described herein is an engineered PCP protein comprising (e.g., from N-terminus to C-terminus): (a) an engineered RNA-binding domain comprising (e.g., from N-terminus to C-terminus): (i) a C-terminal portion of a first PCP monomer; (ii) a second PCP monomer; and (iii) an N-terminal portion of the first PCP monomer; and (b) a degron. Such an engineered PCP protein can be referred to herein as "destabilized PCP" (also referred herein as d-PCP, dPCP PCP-q, PCPQ, destabilized tdPCP, d-td-PCP).

In one aspect, described herein is an engineered PCP protein comprising (e.g., from N-terminus to C-terminus): (a) AN engineered RNA-binding domain comprising (e.g., from N-terminus to C-terminus): (i) a C-terminal portion of a first PCP monomer; and (ii) an N-terminal portion of the first PCP monomer; and (b) a degron. Such an engineered PCP protein can be referred to herein as dmPCP (degron-equipped cpmPCP; cpmPCP-RRRG).

In one aspect, described herein is an engineered PP7 coat protein (PCP) comprising an engineered RNA-binding domain. In some embodiments, the engineered PCP protein is stable when the engineered RNA-binding domain is bound to a PP7 RNA hairpin loop. In some embodiments, when the engineered RNA-binding domain is not bound to the PP7 RNA hairpin loop, the engineered PCP protein is unstable and degradation of the engineered PCP protein increases. Such an engineered PCP protein can be referred to herein as cpmPCP.

In some embodiments, the engineered RNA-binding domain comprises: (a) a C-terminal portion of a first PCP monomer; and (b) an N-terminal portion of the first PCP monomer. In some embodiments, the engineered PCP protein comprises: (a) the engineered RNA-binding domain comprising from N-terminus to C-terminus: (i) a C-terminal portion of a first PCP monomer; and (ii) an N-terminal portion of the first PCP monomer. Non-limiting examples of the C-terminal and N-terminal portions of the first PCP monomer are provided herein.

In some embodiments, the engineered PCP protein does not comprise a degron. In some embodiments, the engineered PCP protein further comprises a degron, non-limiting examples of which are provided herein.

In some embodiments, the first or second PCP monomer, or the N-terminal or C-terminal portions thereof, comprise at least one mutation to decrease self-assembly of dimers into higher order aggregates. In some embodiments, the at least one mutation corresponds to S22R, L36A, and/or L71A in SEQ ID NO: 24.

Fusion Proteins

In multiple aspects, described herein are fusion proteins. In one aspect, described herein is fusion protein comprising an engineered MCP protein linked to at least one (e.g., 1, 2, 3, 4, 5, or more) effector protein(s), which can be the same or different effector proteins. In one aspect, described herein is fusion protein comprising an engineered PCP protein linked to at least one (e.g., 1, 2, 3, 4, 5, or more) effector protein(s), which can be the same or different effector proteins.

In some embodiments, the at least one effector protein is N-terminal of the engineered RNA-binding domain. In some embodiments, the at least one effector protein is linked to the N-terminus of the engineered RNA-binding domain.

In some embodiments, the at least one effector protein is located between: (a) the C-terminal portion of the first MCP monomer and the second MCP monomer. In some embodiments, the at least one effector protein is located between: (b) the C-terminal portion of the first MCP monomer and the N-terminal portion of the first MCP monomer. In some embodiments, the at least one effector protein is located between: (c) the second MCP monomer and the N-terminal portion of the first MCP monomer. In some embodiments, the at least one effector protein is located between: (d) the N-terminal portion of the first MCP monomer and the degron. Exemplary combinations with at least 2 effector proteins include: (a)(b), (a)(c), (a)(d), (b)(c), (b)(d), and (c)(d), as delineated above.

In some embodiments, the at least one effector protein is located between: (a) the C-terminal portion of the first PCP monomer and the second PCP monomer. In some embodiments, the at least one effector protein is located between: (b) the C-terminal portion of the first PCP monomer and the N-terminal portion of the first PCP monomer. In some embodiments, the at least one effector protein is located between: (c) the second PCP monomer and the N-terminal portion of the first PCP monomer. In some embodiments, the at least one effector protein is located between: (d) the N-terminal portion of the first PCP monomer and the degron. Exemplary combinations with at least 2 effector proteins include: (a)(b), (a)(c), (a)(d), (b)(c), (b)(d), and (c)(d), as delineated above.

Effector Proteins

In multiple embodiments, described herein are effector proteins, which can be included in the fusion proteins described herein. Such fusion proteins can comprise an engineered MCP protein or an engineered PCP protein linked to at least one (e.g., 1, 2, 3, 4, 5, or more) effector protein(s), which can be the same or different effector proteins.

In some embodiments, the at least one effector protein is selected from the group consisting of: (a) a detectable marker; (b) a trafficking domain and/or targeting sequence; (c) a Cas protein that binds to an RNA guide sequence; (d) an RNA-cleaving and/or RNA-modifying enzyme; (e) a translation-regulating and translation-associated domain; (f) a cell-cycle regulated degron; (g) a proximity-labeling and/or substrate-labeling enzyme; and (h) an antigen-binding domain, or any combinations thereof.

In some embodiments, the at least one effector protein is (a) a detectable marker, which can also be referred to interchangeably as a detectable label, a detection reagent, and the like. In some embodiments, the detectable marker is selected from the group consisting of: a luciferase, a fluorescent protein, and an ultrasound-mediated reporter. In some embodiments, the luciferase is selected from the group consisting of: NanoLuc®, RLuc, RLuc8, and Super RLuc8. In some embodiments, the fluorescent protein is an infrared fluorescent protein (iRFP). In some embodiments, the infrared fluorescent protein (iRFP) is selected from the group consisting of: iRFP-670 and miIRFP-670. In some embodiments, the fluorescent protein is fluorescent when bound to a substrate. In some embodiments, the fluorescent protein is HALOTAG. In some embodiments, the ultrasound-mediated reporter comprises a gas vesicle-based reporter protein.

In some embodiments of any of the aspects, detectable markers can include labels that can be detected by spectroscopic, photochemical, biochemical, immunochemical, electromagnetic, radiochemical, or chemical means, such as fluorescence, chemifluorescence, or chemiluminescence, or any other appropriate means. The detectable markers described herein can be primary labels (where the label comprises a moiety that is directly detectable or that produces a directly detectable moiety) or secondary labels (where the detectable marker binds to another moiety to produce a detectable signal, e.g., as is common in immunological labeling using secondary and tertiary antibodies). Detectable markers can include, but are not limited to radioisotopes, bioluminescent compounds, chromophores, antibodies, chemiluminescent compounds, fluorescent compounds, metal chelates, and enzymes.

In other embodiments, the detectable marker comprises a fluorescent compound. When the fluorescent detectable marker is exposed to light of the proper wavelength, its presence can then be detected due to fluorescence. In some embodiments of any of the aspects, a detectable marker can be a fluorescent dye molecule, or fluorophore including, but not limited to fluorescein, phycoerythrin, phycocyanin, o-phthalaldehyde, fluorescamine, Cy3™, Cy5™, allophyco-cyanin, Texas Red, peridinin chlorophyll, cyanine, tandem conjugates such as phycoerythrin-Cy5™, green fluorescent protein (GFP), rhodamine, fluorescein isothiocyanate (FITC) and Oregon Green™, rhodamine and derivatives (e.g., Texas red and tetramethylrhodamine isothiocyanate (TRITC)), biotin, phycoerythrin, AMCA, CyDyes™ 6-carboxyfluorescein (commonly known by the abbreviations FAM and F), 6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g., umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g., cyanine dyes such as Cy3, Cy5, etc.; BODIPY dyes and quinoline dyes. In some embodiments of any of the aspects, a detectable marker can be a radiolabel including, but not limited to $^{3}$H, $^{125}$I, $^{35}$S, $^{14}$C, $^{32}$P, and $^{33}$P. In some embodiments of any of the aspects, a detectable marker can be an enzyme including, but not limited to horseradish peroxidase and alkaline phosphatase. An enzymatic label can produce, for example, a chemiluminescent signal, a color signal, or a fluorescent signal. Enzymes contemplated for use to detectably label a fusion protein include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase, and acetylcholinesterase. In some embodiments of any of the aspects, a detectable marker is a chemiluminescent label, including, but not limited to lucigenin, luminol, luciferin, isoluminol, theromatic acridinium ester, imidazole, acridinium salt and oxalate ester. In some embodiments of any of the aspects, a detectable marker can be a spectral colorimetric label including, but not limited to colloidal gold or colored glass or plastic (e.g., polystyrene, polypropylene, and latex) beads.

In some embodiments of any of the aspects, the detectable marker comprises a detectable tag, such as c-Myc, HA, VSV-G, HSV, FLAG, V5, HIS, or biotin. Other detection systems can also be used, for example, a biotin-streptavidin system. In this system, the antibodies immunoreactive (i.e., specific for) with the biomarker of interest is biotinylated. Quantity of biotinylated antibody bound to the biomarker is determined using a streptavidin-peroxidase conjugate and a chromogenic substrate. Such streptavidin peroxidase detection kits are commercially available, e.g., from DAKO; Carpinteria, CA. A fusion protein can also be detectably labeled using fluorescence emitting metals such as $^{152}$Eu, or others of the lanthanide series. These metals can be attached to the fusion protein using such metal chelating groups as diethylenetriaminepentaacetic acid (DTPA) or ethylenediaminetetraacetic acid (EDTA).

In some embodiments of any of the aspects, the fusion protein does not comprise detectable markers that are immunogenic. In some embodiments of any of the aspects, the fusion protein does not comprise GFP, mCherry, HA1, or any other immunogenic markers. In some embodiments of any of the aspects, a fusion protein described herein that comprises a detectable marker can have the detectable marker removed at a later time, e.g., a removable (e.g., cleavable) detectable marker.

In some embodiments, the at least one effector protein is (b) a trafficking domain and/or targeting sequence. In some embodiments, the trafficking domain and/or targeting sequence is selected from the group consisting of: (a) a microtubule motor protein (e.g., a kinesin or dynein); (b) a mitochondrial surface targeting sequence; (c) a nuclear localization signal; (d) a nuclear exclusion signal; (e) a transmembrane domain; (f) a signaling receptor; (g) a lipid-modification substrate; (h) a Pleckstrin homology domain; and (i) a split pleckstrin homology domain. In some embodiments, the signaling receptor is selected from the group consisting of: (a) a GPCR; (b) a SynNotch; or (c) a CAR. In some embodiments, the lipid-modification substrate comprises a substrate for: (i) myristoylation, (ii) palmitoylation, (iii) myristoylation and palmitoylation, or (iv) prenylation.

In some embodiments, the at least one effector protein is (c) a Cas protein that binds to an RNA guide sequence. In some embodiments, the Cas protein is selected from the group consisting of: (a) an RNA-guided DNA binding Cas protein; and (b) an RNA-guided RNA binding Cas protein. In some embodiments, the RNA-guided DNA binding Cas protein comprises Cas9 or Cas12. In some embodiments, the RNA-guided RNA binding Cas protein comprises Cas13 or Cas CSM. In some embodiments, the Cas protein is catalytically inactive. In some embodiments, the Cas protein is catalytically active.

In some embodiments, the at least one effector protein is (d) an RNA-cleaving and/or RNA-modifying enzyme. In some embodiments, the RNA-cleaving and/or RNA-modifying enzyme is selected from the group consisting of: (a) an RNA-cleaving nuclease; (b) a de-adenylating enzyme; (c) a de-capping enzyme; (d) a capping enzyme; (e) an RNA base editor; (f) an enzyme that adds covalent attachments to RNA; and (g) an adduct-forming protein. In some embodiments, the RNA-cleaving nuclease is selected from the group consisting of: (i) a pre-crRNA-processing enzyme; (ii) an RNase; and (iii) a sequence comprising a SMG6 PIN domain. In some embodiments, the pre-crRNA-processing enzyme is selected from the group consisting of: Csy4 (Cas6f), Cas5d, Cas6e, and Cas6. In some embodiments, the RNase is selected from the group consisting of: RNase H, RNase III, RNase A, and RNase T1. In some embodiments, the de-adenylating enzyme is selected from the group consisting of: (i) CCR4-Not; and (ii) Poly(A)-specific ribonuclease (PARN). In some embodiments, the de-capping enzyme comprises Dcp1/Dcp2. In some embodiments, the capping enzyme is selected from the group consisting of: (i) a Faustovirus capping enzyme; (ii) a Vaccinia RNA capping enzyme; and (iii) an HIV capping enzyme. In some embodiments, the RNA base editor comprises Adenosine Deaminase Acting on RNA (ADAR). In some embodiments, the enzyme that adds covalent attachments to RNA is a poly-adenylating enzyme. In some embodiments, the poly-adenylating enzyme is selected from the group consisting of: (i) an *E. coli* Poly(A) polymerase; (ii) a yeast poly(A) polymerase; and (iii) a mammalian poly(A) polymerase. In some embodiments, the adduct-forming protein is selected from the group consisting of: (i) a tyrosyl-RNA phosphodiester bond-forming domain; and (ii) a VPg viral protein.

In some embodiments, the at least one effector protein is (e) a translation-regulating and translation-associated domain. In some embodiments, the translation-regulating and translation-associated domain is selected from the group consisting of: (a) a cap-independent initiation domain; (b) a translational downregulation domain; (c) an amino acyl tRNA synthetase (aaRS); and (d) a peptide-based sequence that facilitates translation modulation or RNA stability changes when recruited to an RNA molecule. In some embodiments, the cap-independent initiation domain comprises a caliciviral VPg protein. In some embodiments, the translational downregulation domain comprises eif4e-bp1, or the Eif4E binding domain from CUP, THOR, or 4E-T. In some embodiments, the translational downregulation domain blocks ribosome translocation. In some embodiments, the translational downregulation domain comprises a stable secondary structure that blocks ribosome translocation. In some embodiments, the amino acyl tRNA synthetase (aaRS) is selected from the group consisting of: (a) mutant *E. coli* amino aaRS; (b) mutant endogenous aaRS; (c) mutant *Methanocaldococcus jannaschii* aaRS; (d) mutant yeast aaRS; and (e) mutant pyrrolysine aaRS.

In some embodiments, the at least one effector protein is (f) a cell-cycle regulated degron. In some embodiments, the cell-cycle regulated degron is selected from the group consisting of: (a) a CdtI degron domain; (b) a Geminin degron domain; and (c) a FUCCI sensor.

In some embodiments, the at least one effector protein is (g) a proximity-labeling and/or substrate-labeling enzyme. In some embodiments, the proximity-labeling and/or substrate-labeling enzyme is selected from the group consisting of: (a) a biotin ligase in combination with a biotin ligase substrate; (b) a peroxidase-based enzyme; (c) miniSOG; (d) RNA methyltransferase (e.g., METTL16); (e) 'LITtag', an engineered flavin-mononucleotide-binding LOV domain; and (f) an RNA Transglycosylase. In some embodiments, the biotin ligase is *E. coli* biotin ligase (BirA). In some embodiments, the biotin ligase is derived from BirA and selected from the group consisting of BioID, BioID2, and TurboID. In some embodiments, the biotin ligase substrate is an acceptor peptide (AP), a biotinylated sequence from *Propionibacterium shermanii* transcarboxylase, or AviTag. In some embodiments, the peroxidase-based enzyme is selected from the group consisting of APEX, APEX2, and HRP. In some embodiments, the RNA Transglycosylase is *E. coli* tRNA guanine transglycosylase (TGT).

In some embodiments, the at least one effector protein is (h) an antigen-binding domain. In some embodiments, the antigen-binding domain is comprised by an antibody or nanobody. In some embodiments, the antigen-binding domain binds to an endogenous protein. In some embodiments, the antigen-binding domain binds to an intracellular protein. In some embodiments, the nanobody comprises a destabilized nanobody. In some embodiments, the at least one effector protein recruits at least one additional effector protein.

In some embodiments, the at least one effector protein comprises a (i) transmembrane domain. In some embodiments, a fusion protein described herein further comprises a transmembrane domain. The transmembrane domain can be from any known transmembrane protein or can be an engineered and/or synthetic transmembrane domain.

In some embodiments, a fusion protein comprises at least two effector domains, described herein. Table 10 below provides exemplary combinations of two effector domains, where the letter designations are as follows: (a) a detectable marker; (b) a trafficking domain and/or targeting sequence; (c) a Cas protein that binds to an RNA guide sequence; (d) an RNA-cleaving and/or RNA-modifying enzyme; (e) a translation-regulating and translation-associated domain; (f) a cell-cycle regulated degron; (g) a proximity-labeling and/or substrate-labeling enzyme; (h) an antigen-binding domain; and (i) a transmembrane domain.

TABLE 10

Exemplary combinations of two effector domains.

| 1st | 2nd |
| --- | --- |
| a | b |
| a | c |
| a | d |
| a | e |
| a | f |
| a | g |

TABLE 10-continued

Exemplary combinations of two effector domains.

| 1st | 2nd |
| --- | --- |
| a | h |
| a | i |
| b | c |
| b | d |
| b | e |
| b | f |
| b | g |
| b | h |
| b | i |
| c | d |
| c | e |
| c | f |
| c | g |
| c | h |
| c | i |
| d | e |
| d | f |
| d | g |
| d | h |
| d | i |
| e | f |
| e | g |
| e | h |
| e | i |
| f | g |
| f | h |
| f | i |
| g | h |
| g | i |
| h | i |

Linkers

In multiple embodiments, described herein are linkers, which can be included in the fusion proteins described herein. Such fusion proteins can comprise an engineered MCP protein or an engineered PCP protein with at least one (e.g., 1, 2, 3, 4, 5, or more) linker, e.g., at least one linker for each effector protein(s), which can be the same or different linkers. Linkers can also be referred to herein as linker domains, linkage domains, connecting domains, drug-inducible domains, or druggable domains, and the like.

In some embodiments, the fusion protein further comprises a linker between the engineered RNA-binding domain and the at least one effector protein. In some embodiments, the fusion protein further comprises a linker between the engineered RNA-binding domain and each effector protein.

In some embodiments, the linker is selected from the group consisting of: (a) drug-inducible heterodimerization domains; (b) drug-dissociable heterodimerization domains; (c) drug-preservable domains; (d) a gas-vesicle associated domain that is released by ultrasound; (e) light-regulated protein-protein interaction domains; and (f) protein-protein interaction domains dependent on an extracellular or intracellular signal; or combinations thereof.

In some embodiments, the linker comprises (a) drug-inducible heterodimerization domains. In some embodiments, the drug-inducible heterodimerization domains are selected from the group consisting of: (a) FKBP and FRB; (b) abscisic acid (ABA)-inducible heterodimeric protein binding domains; (c) gibberellin-inducible heterodimeric protein binding domains; (d) a drug-inducible reader domain that specifically binds to an NS3 protease inhibitor-bound NS3 protease; and (e) human antibody-based dimerizers (AbCIDs).

In some embodiments, the linker comprises (b) drug-dissociable heterodimerization domains. In some embodiments, the drug-dissociable heterodimerization domains are selected from the group consisting of: (a) Bcl-xL and BH3 proteins, the interaction of which can dissociated by small molecules (e.g., A-1155463); (b) NS3 protease complexed with an inhibitory peptide, the interaction of which can be dissociated using an NS3 protease inhibitor, optionally wherein the NS3 protease is catalytically inactive; and (c) a drug-dissociable reader domain that specifically binds to a first NS3 protease inhibitor-bound NS3 protease, the interaction of which can dissociated by a second NS3 protease inhibitor that binds to NS3 protease.

In some embodiments, the linker comprises (c) drug-preservable domains. In some embodiments, the drug-preservable domains comprise an active NS3 protease and a cognate cleavage site for the active NS3 protease, wherein the linker is preserved in the presence of an NS3 protease inhibitor, and the linkage is severed in the absence of the NS3 protease inhibitor.

In some embodiments, the linker comprises (d) a gas-vesicle associated domain that is released by ultrasound.

In some embodiments, the linker comprises (e) light-regulated protein-protein interaction domains. In some embodiments, the light-regulated protein-protein interaction domains are selected from the group consisting of (a) PhoCl; (b) mMaple3; (c) LOV domains; (d) luciferase-fused LOV domains; and (e) red light-inducible PPI domains (e.g., PhyB/Pif).

In some embodiments, the linker comprises (f) protein-protein interaction domains dependent on an extracellular or intracellular signal. In some embodiments, the protein-protein interaction domains dependent on an extracellular or intracellular signal are selected from the group consisting of (a) beta-arrestin, which bind to phosphorylated tails of GPCRs; (b) phosphorylated kinase substrates in combination with domains recognizing such phosphorylated sequences; (c) binding proteins that recognize and undergo protein interactions in response to secondary metabolites (e.g., cAMP) or ions (including Ca2+); and (d) a nanobody that binds the intracellular region of an activated GPCR.

In some embodiments, a fusion protein comprises at least two linkers, described herein. Table 11 below provides exemplary combinations of two linkers, where the letter designations are as follows: (a) drug-inducible heterodimerization domains; (b) drug-dissociable heterodimerization domains; (c) drug-preservable domains; (d) a gas-vesicle associated domain that is released by ultrasound; (e) light-regulated protein-protein interaction domains; and (f) protein-protein interaction domains dependent on an extracellular or intracellular signal.

TABLE 11

Exemplary combinations of two linkers

| 1st | 2nd |
| --- | --- |
| a | b |
| a | c |
| a | d |
| a | e |
| a | f |
| b | c |
| b | d |
| b | e |
| b | f |
| c | d |
| c | e |
| c | f |
| d | e |

TABLE 11-continued

| Exemplary combinations of two linkers | |
| --- | --- |
| 1st | 2nd |
| d | f |
| e | f |

Nucleic Acids and Vectors

Described herein are various nucleic acids. In one aspect, described herein is a nucleic acid encoding a fusion protein as described herein. In one aspect, described herein is a nucleic acid encoding a synthetic RNA molecule as described herein. In one aspect, described herein is a nucleic acid encoding a fusion protein and a synthetic RNA molecule as described herein.

In some embodiments, an RNA molecule described herein comprises at least one MS2 RNA hairpin loop, for example, 1, 2, 3, 4, 5, 6, 7, 8, 9, 10, 11, 12, 13, 14, 15, 16, 17, 18, 19, 20, 30, 40, 50, 60, 70, 80, 90, 100 or more MS2 RNA hairpin loops. In some embodiments, the MS2 RNA hairpin loop comprises one of SEQ ID NOs: 27, 29, 42-44, 47, 54, or a nucleic acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to one of SEQ ID NOs: 27, 29, 42-44, 47, 54, which maintains its function (e.g., binding to an engineered MCP protein as described herein).

In some embodiments, an RNA molecule described herein comprises at least one PP7 RNA hairpin loop, for example, 1, 2, 3, 4, 5, 6, 7, 8, 9, 10, 11, 12, 13, 14, 15, 16, 17, 18, 19, 20, 30, 40, 50, 60, 70, 80, 90, 100 or more PP7 RNA hairpin loops. In some embodiments, the PP7 RNA hairpin loop comprises SEQ ID NO: 53 (ggagcagacgatatggcgtcgctcc) or a nucleic acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to SEQ ID NO: 53, which maintains its function (e.g., binding to an engineered PCP protein as described herein).

In some embodiments, an RNA molecule described herein comprises at least one MS2 RNA hairpin loop and at least one PP7 RNA hairpin loop, for example, 1, 2, 3, 4, 5, 6, 7, 8, 9, 10, 11, 12, 13, 14, 15, 16, 17, 18, 19, 20, 30, 40, 50, 60, 70, 80, 90, 100 or more MS2 RNA hairpin loops, and 1, 2, 3, 4, 5, 6, 7, 8, 9, 10, 11, 12, 13, 14, 15, 16, 17, 18, 19, 20, 30, 40, 50, 60, 70, 80, 90, 100 or more PP7 RNA hairpin loops.

In some embodiments, the at least one MS2 RNA hairpin loop and/or the at least one PP7 RNA hairpin loop is located in a specific region of the RNA to recruit an engineered MCP protein and/or an engineered PCP protein, or fusion proteins thereof. For example, the at least one MS2 RNA hairpin loop and/or the at least one PP7 RNA hairpin loop can be in a 5' un-translated region, an open-reading frame, or a 3' un-translated region of the RNA molecule.

In some embodiments, the at least one hairpin loop does not comprise uridine. In some embodiments, the at least one hairpin loop does not comprise substituted synthetic nucleotides. In some embodiments, the at least one hairpin loop does not comprise pseudouridine (Ψ) or 5-methylcytosine (m5C).

In some embodiments, the RNA molecule comprises a circular RNA. In some embodiments, the RNA molecule comprises a capless linear RNA. In some embodiments, the RNA molecule comprises an IRES for cap-independent translation of the encoded gene of interest.

In some embodiments, the RNA molecule comprises substituted synthetic nucleotides. In some embodiments, the substituted synthetic nucleotides are pseudouridine (Ψ) and/or 5-methylcytosine (m5C). Further non-limiting examples of synthetic nucleotides are provided herein.

In some embodiments, the RNA molecule comprises at least one (e.g., 1, 2, 3, 4, 5, or more) open reading frame(s) (ORF). In some embodiments, at least one ORF encodes for a gene of interest. In some embodiments, at least one ORF encodes for a fusion protein. In some embodiments, at least one ORF encodes for a therapeutic protein, e.g., to treat a specific disease or disorder. In some embodiments, at least one ORF encodes for a fusion protein and at least one ORF encodes for a therapeutic protein.

In some embodiments, the nucleic acid encoding the fusion protein and the nucleic acid encoding the RNA molecule are operably linked to a single promoter. In some embodiments, the nucleic acid encoding the fusion protein and the nucleic acid encoding the RNA molecule are each operably linked to a separate promoter. The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. A variety of conditional promoters also can be used, such as promoters controlled by the presence or absence of a molecule. In some embodiments, the nucleic acid encoding the fusion protein is linked to and 5' of the nucleic acid encoding the RNA molecule. In some embodiments, the nucleic acid encoding the fusion protein is linked to and 3' of the nucleic acid encoding the RNA molecule.

In some embodiments, the nucleic acid comprises DNA. In some embodiments, the nucleic acid comprises RNA. In some embodiments, the nucleic acid comprises RNA and DNA.

In some embodiments, the nucleic acid is one of SEQ ID NOs: 7-9, 27-36, 40-44, 46-47, 53-54, 56, or a sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 7-9, 27-36, 40-44, 46-47, 53-54, 56, that maintains the same function, or a codon-optimized version thereof.

In some embodiments of any of the aspects, a nucleic acid (e.g. DNA, or RNA transcript disclosed herein) is chemically modified to enhance stability or other beneficial characteristics. The nucleic acids described herein may be synthesized and/or modified by methods well established in the art, such as those described in "Current protocols in nucleic acid chemistry," Beaucage, S. L. et al. (Edrs.), John Wiley & Sons, Inc., New York, NY, USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of nucleic acid compounds useful in the embodiments described herein include, but are not limited to nucleic acids containing modified backbones or no natural internucleoside linkages. nucleic acids having modified backbones include, among others, those that do not have a phosphorus atom in the backbone. For the purposes of this specification, and as sometimes referenced in the art, modified nucleic acids that do not have a phosphorus atom in their internucleoside backbone can also be considered to be oligonucleosides. In some embodiments of any of the aspects, the modified nucleic acid will have a phosphorus atom in its internucleoside backbone.

Modified nucleic acid backbones can include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included. Modified nucleic acid backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; others having mixed N, O, S and CH2 component parts, and oligonucleosides with heteroatom backbones, and in particular —CH2-NH—CH2-, —CH2-N(CH3)-O—CH2-[known as a methylene (methylimino) or MMI backbone], —CH2-O—N(CH3)-CH2-, —CH2-N(CH3)-N(CH3)-CH2- and —N(CH3)-CH2-CH2- [wherein the native phosphodiester backbone is represented as —O—P—O—CH2-].

In other nucleic acid mimetics, both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone.

The nucleic acid can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) Nucleic Acids Research 33(1):439-

447; Mook, OR. et al., (2007) Mol. Canc. Ther. 6(3):833-843; Grunweller, A. et al., (2003) Nucleic Acids Research 31(12):3185-3193).

Modified nucleic acids can also contain one or more substituted sugar moieties. The nucleic acids described herein can include one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10 alkyl or $C_2$ to C10 alkenyl and alkynyl. Exemplary suitable modifications include O[(CH2)nO]mCH3, O(CH2)nOCH3, O(CH2)nNH2, O(CH2) nCH3, O(CH2)nONH2, and O(CH2)nON[(CH2)nCH3)]2, where n and m are from 1 to about 10. In some embodiments of any of the aspects, nucleic acids include one of the following at the 2' position: C1 to C10 lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of a nucleic acid, or a group for improving the pharmacodynamic properties of a nucleic acid, and other substituents having similar properties. In some embodiments of any of the aspects, the modification includes a 2' methoxyethoxy (2'-O—$CH_2CH_2OCH_3$, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a O(CH2)2ON(CH3)2 group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH2-O—CH2-N(CH2)2, also described in examples herein below.

Other modifications include 2'-methoxy (2'-OCH3), 2'-aminopropoxy (2'-OCH2CH2CH2NH2) and 2'-fluoro (2'-F). Similar modifications can also be made at other positions on the nucleic acid, particularly the 3' position of the sugar on the 3' terminal nucleotide or in 2'-5' linked dsRNAs and the 5' position of 5' terminal nucleotide. Nucleic acids may also have sugar mimetics such as cyclobutyl moieties in place of the pentofuranosyl sugar.

A nucleic acid can also include nucleobase (often referred to in the art simply as "base") modifications or substitutions. As used herein, "unmodified" or "natural" or "canonical" nucleobases include the purine bases adenine (A) and guanine (G), and the pyrimidine bases thymine (T), cytosine (C) and uracil (U). Modified or "non-canonical" nucleobases can include other synthetic and natural nucleobases including but not limited to as inosine, isocytosine, isoguanine, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Certain of these nucleobases are particularly useful for increasing the binding affinity of the inhibitory nucleic acids featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications. In some embodiments of any of the aspects, modified nucleobases can include d5SICS and dNAM, which are a non-limiting example of unnatural nucleobases that can be used separately or together as base pairs (see e.g., Leconte et. al. J. Am. Chem. Soc. 2008, 130, 7, 2336-2343; Malyshev et. al. PNAS. 2012. 109 (30) 12005-12010). In some embodiments of any of the aspects, the nucleic acid comprises any modified nucleobases known in the art, i.e., any nucleobase that is modified from an unmodified and/or natural nucleobase.

The preparation of the modified nucleic acids, backbones, and nucleobases described above are well known in the art.

Another modification of a nucleic acid featured in the invention involves chemically linking to the nucleic acid to one or more ligands, moieties or conjugates that enhance the activity, cellular distribution, pharmacokinetic properties, or cellular uptake of the nucleic acid. Such moieties include but are not limited to lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylamino-carbonyloxycholesterol moiety (Crooke et al., J. Pharmacol. Exp. Ther., 1996, 277:923-937).

The fusion proteins and/or synthetic RNA molecules described herein can be encoded and/or expressed by nucleic acids and/or vectors. Accordingly, in one aspect, described herein is a vector encoding or comprising a fusion proteinas described herein. In another aspect described herein is a vector encoding or comprising a synthetic RNA molecule as described herein.

In some embodiments of any of the aspects, the nucleic acid comprises DNA. In some embodiments of any of the aspects, the nucleic acid consists essentially of DNA. In some embodiments of any of the aspects, the nucleic acid consists of DNA.

In some embodiments of any of the aspects, the nucleic acid comprises RNA. In some embodiments of any of the aspects, the nucleic acid consists essentially of RNA. In some embodiments of any of the aspects, the nucleic acid consists of RNA.

In some embodiments of any of the aspects, a DNA molecule encoding a gene of interest (e.g., a fusion protein, a therapeutic protein as described herein) comprises at least one regulatory sequence upstream of the encoded gene of interest. In some embodiments of any of the aspects, a DNA molecule encoding a gene of interest (e.g., a fusion protein, a therapeutic protein as described herein) comprises a promoter for transcription of the gene of interest using an RNA polymerase. In some embodiments of any of the aspects, a DNA molecule comprises a T7 promoter.

When the nucleic acid molecule that encodes any of the genes of interest described herein is expressed in a cell, a variety of transcription control sequences (e.g., promoter/enhancer sequences) can be used to direct its expression. The promoter can be a native promoter, e.g., the promoter of the at least one gene of interest in its endogenous context, which provides normal regulation of expression of the encoded protein. In some embodiments the promoter can be constitutive, i.e., the promoter is unregulated allowing for continual transcription. A variety of conditional promoters also can be used, such as promoters controlled by the presence or absence of a molecule.

The precise nature of the regulatory sequences needed for expression can vary between species or cell types, but in general can include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences can include a promoter region which includes a promoter sequence for transcriptional control of the encoded gene of interest. Regulatory sequences can also include enhancer sequences or upstream activator sequences as desired.

As used herein, an gene of interest-encoding sequence and regulatory sequences are said to be "operably" joined when they are covalently linked in such a way as to place the expression or transcription of the gene of interest-encoding sequence under the influence or control of the regulatory sequences. If it is desired that at least one gene of interest encoded in the nucleic acid be translated into a functional protein, two DNA sequences are said to be operably joined if induction of a promoter in the 5' regulatory sequences results in the transcription of the gene of interest and if the nature of the linkage between the two DNA sequences does not (1) result in the introduction of a frame-shift mutation, (2) interfere with the ability of the promoter region to direct the transcription of the gene of interest, or (3) interfere with the ability of the at least one gene of interest to be translated into a protein.

A nucleic acid molecule that encodes a gene of interest as described herein can be introduced into a cell or cells using methods and techniques that are standard in the art. For example, nucleic acid molecules can be introduced by standard protocols such as transformation including chemical transformation and electroporation, transduction, particle bombardment, etc. Expressing the nucleic acid molecule encoding a gene of interest as described herein can also be accomplished by integrating the nucleic acid molecule into the genome.

In some embodiments, one or more of the genes of interest described herein is expressed in a recombinant expression vector or plasmid. As used herein, the term "vector" refers to a polynucleotide sequence suitable for transferring nucleic acids into a host cell. The vector can encompass any genetic element that is capable of replication when associated with the proper control elements and that can transfer nucleic acid sequences to cells. The term "vector" includes a plasmid, a cloning vector, an expression vector, naked DNA, a mini-chromosome, a chromosome, a transposon, a cosmid, a virus, virion, phage, and the like. See, for example, U.S. Pat. Nos. 4,980,285; 5,631,150; 5,707,828; 5,759,828; 5,888,783 and, 5,919,670, and, Sambrook et al, Molecular Cloning: A Laboratory Manual, 2nd Ed., Cold Spring Harbor Press (1989). One type of vector is a "plasmid," which refers to a circular double stranded DNA loop into which additional DNA segments are ligated. Another type of vector is a viral vector, wherein additional DNA segments are ligated into the viral genome. Certain vectors are capable of autonomous replication in a host cell into which they are introduced (e.g., bacterial vectors having a bacterial origin of replication and episomal mammalian vectors). Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" are used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

In some embodiments of any of the aspects, the vector is recombinant, e.g., it comprises sequences originating from at least two different sources. In some embodiments of any of the aspects, the vector comprises sequences originating from at least two different species. In some embodiments of any of the aspects, the vector comprises sequences originating from at least two different genes, e.g., it comprises a fusion protein or a nucleic acid encoding an expression product which is operably linked to at least one non-native (e.g., heterologous) genetic control element (e.g., a promoter, suppressor, activator, enhancer, response element, or the like).

In some embodiments of any of the aspects, the vector or nucleic acid described herein is codon-optimized, e.g., the native or wild-type sequence of the nucleic acid sequence has been altered or engineered to include alternative codons such that altered or engineered nucleic acid encodes the same polypeptide expression product as the native/wild-type sequence, but will be transcribed and/or translated at an improved efficiency in a desired expression system. In some embodiments of any of the aspects, the expression system is an organism other than the source of the native/wild-type sequence (or a cell obtained from such organism). In some embodiments of any of the aspects, the vector and/or nucleic acid sequence described herein is codon-optimized for expression in a mammal or mammalian cell, e.g., a mouse, a murine cell, or a human cell. In some embodiments of any of the aspects, the vector and/or nucleic acid sequence described herein is codon-optimized for expression in a human cell. In some embodiments of any of the aspects, the vector and/or nucleic acid sequence described herein is codon-optimized for expression in a yeast or yeast cell. In some embodiments of any of the aspects, the vector and/or nucleic acid sequence described herein is codon-optimized for expression in a bacterial cell. In some embodiments of any of the aspects, the vector and/or nucleic acid sequence described herein is codon-optimized for expression in an E. coli cell.

A cloning vector is one which is able to replicate autonomously or integrated in the genome in a host cell, and which is further characterized by one or more endonuclease restriction sites at which the vector can be cut in a determinable fashion and into which a desired DNA sequence can be ligated such that the new recombinant vector retains its ability to replicate in the host cell. In the case of plasmids, replication of the desired sequence can occur many times as the plasmid increases in copy number within the host cell such as a host bacterium or just a single time per host before the host reproduces by mitosis. In the case of phage, replication can occur actively during a lytic phase or passively during a lysogenic phase.

An expression vector is one into which a desired DNA sequence can be inserted by restriction and ligation such that it is operably joined to regulatory sequences and can be expressed as a transcript. Vectors can further contain one or more marker sequences suitable for use in the identification of cells which have or have not been transformed or transformed or transfected with the vector. Markers include, for example, genes encoding proteins which increase or decrease either resistance or sensitivity to antibiotics or other compounds (e.g., ampicillin resistance), genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). In certain embodiments, the vectors used herein are capable of autonomous replication and expression of the genes of interest present in the DNA segments to which they are operably joined. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification.

Expression vectors containing all the necessary elements for expression are commercially available and known to those skilled in the art. See, e.g., Sambrook et al., Molecular Cloning: A Laboratory Manual, Second Edition, Cold Spring Harbor Laboratory Press, 1989. Cells are genetically engineered by the introduction into the cells of heterologous DNA (or RNA). That heterologous DNA (or RNA) is placed under operable control of transcriptional elements to permit the expression of the heterologous DNA in the host cell.

As used herein, the term "viral vector" refers to a nucleic acid vector construct that includes at least one element of viral origin and has the capacity to be packaged into a viral vector particle. The viral vector can contain the nucleic acid encoding a polypeptide as described herein in place of non-essential viral genes. The vector and/or particle may be utilized for the purpose of transferring any nucleic acids into cells either in vitro or in vivo. Numerous forms of viral vectors are known in the art. Non-limiting examples of a viral vector of this invention include an AAV vector, an adenovirus vector, a lentivirus vector, a retrovirus vector, a herpesvirus vector, an alphavirus vector, a poxvirus vector, a baculovirus vector, and a chimeric virus vector.

It should be understood that the vectors described herein can, in some embodiments, be combined with other suitable compositions and therapies. In some embodiments, the vector is episomal. The use of a suitable episomal vector provides a means of maintaining the nucleic acid of interest in the subject in high copy number extra chromosomal DNA thereby eliminating potential effects of chromosomal integration.

Complexes and Systems

In multiple aspects, described herein are complexes and/or systems comprising the fusion proteins and nucleic acids (e.g., RNA molecules) described herein. In one aspect, described herein is a complex comprising a fusion protein bound to an RNA molecule comprising at least one hairpin loop specifically bound by the engineered RNA-binding domain of the fusion protein. In one aspect, described herein is a complex comprising a fusion protein bound to an RNA molecule comprising at least one MS2 RNA hairpin loop or at least one PP7 RNA hairpin loop. In one aspect, described herein is a complex comprising an engineered MCP fusion protein bound to an RNA molecule comprising at least one MS2 RNA hairpin loop. In one aspect, described herein is a complex comprising an engineered PCP fusion protein bound to an RNA molecule comprising at least one PP7 RNA hairpin loop.

In one aspect, described herein is a system comprising a fusion protein and an RNA molecule comprising at least one hairpin loop specifically bound by the engineered RNA-binding domain of the fusion protein.

In one aspect, described herein is a system comprising a fusion protein and an RNA molecule comprising at least one MS2 RNA hairpin loop or at least one PP7 RNA hairpin loop.

In one aspect, described herein is a system comprising: (a) a fusion protein comprising an engineered MCP protein linked to at least one effector protein; and (b) an RNA molecule comprising at least one MS2 RNA hairpin loop.

In one aspect, system comprising: (a) a fusion protein comprising an engineered PCP protein linked to at least one effector protein; and (b) an RNA molecule comprising at least one PP7 RNA hairpin loop.

In one aspect, described herein is a system comprising: (a) a first fusion protein comprising an engineered MCP protein linked to at least one effector protein; (b) a second fusion protein comprising an engineered PCP protein linked to at least one effector protein; and (c) an RNA molecule comprising at least one MS2 RNA hairpin loop and at least one PP7 RNA hairpin loop.

In one aspect, described herein is a system comprising: (a) a first fusion protein comprising an engineered MCP protein linked to at least one effector protein; (b) a second fusion protein comprising an engineered PCP protein linked to at least one effector protein; (c) a first RNA molecule comprising at least one MS2 RNA hairpin loop; and (d) a second RNA molecule comprising at least one PP7 RNA hairpin loop.

In some embodiments, the engineered RNA-binding domain of the fusion protein is capable of binding to the at least one hairpin loop in the RNA molecule, thereby decreasing degradation of the bound fusion protein. In some embodiments, the engineered RNA-binding domain of the fusion protein is capable of binding to the at least one hairpin loop in the RNA molecule, thereby increasing stability of the bound fusion protein.

In some embodiments, the RNA molecule comprises at least one (e.g., 1, 2, 3, 4, 5, or more) open reading frame(s) (ORF). In some embodiments, at least one ORF encodes for a gene of interest. In some embodiments, the gene of interest encodes for a fusion protein described herein, which can be the same or different fusion protein that controls expression of the encoded fusion protein. In some embodiments, at least one ORF encodes for a fusion protein. In some embodiments, at least one ORF encodes for a therapeutic protein, e.g., to treat a specific disease or disorder. In some embodiments, at least one ORF encodes for a fusion protein and at least one ORF encodes for a therapeutic protein.

In some embodiments, the at least one hairpin loop is located in an untranslated region of the RNA molecule that is 5' or 3' from an encoded gene of interest.

In some embodiments, the fusion protein binds to the at least one hairpin loop in the RNA molecule and modulates (e.g., decreases or increase) expression (e.g., translation) of the encoded gene of interest. In some embodiments, the fusion protein binds to the at least one hairpin loop in the RNA molecule and decreases expression (e.g., translation) of the encoded fusion protein, thus resulting in auto-inhibition.

In some embodiments, the RNA molecule comprises a circular RNA. In some embodiments, the RNA molecule comprises a capless linear RNA. In some embodiments, the RNA molecule comprises an IRES for cap-independent translation of the encoded gene of interest.

In some embodiments, the RNA molecule comprises substituted synthetic nucleotides. In some embodiments, the substituted synthetic nucleotides are pseudouridine ($\Psi$) and/or 5-methylcytosine ($m^5C$). Further non-limiting examples of synthetic nucleotides are provided herein.

In some embodiments, the at least one hairpin loop does not comprise uridine. In some embodiments, the at least one hairpin loop does not comprise substituted synthetic nucleotides. In some embodiments, the at least one hairpin loop does not comprise pseudouridine ($\Psi$) or 5-methylcytosine ($m^5C$).

Methods and Uses

In multiple aspects, described herein are methods and uses for the engineered MCP proteins, engineered PCP proteins, and/or fusion proteins thereof, as described herein.

In one aspect, described herein is a method of detecting an RNA molecule. In some embodiments, the method comprises contacting an RNA molecule with an engineered MCP or PCP fusion protein comprising a detectable marker. In some embodiments, the RNA molecule comprises at least one hairpin loop specifically bound by the engineered RNA-binding domain of the fusion protein.

In one aspect, described herein is a method of detecting an RNA molecule in a cell. In some embodiments, the method comprises contacting a cell with an engineered MCP or PCP fusion protein comprising a detectable marker. In some embodiments, wherein the RNA molecule comprises at least one hairpin loop specifically bound by the engineered RNA-binding domain of the fusion protein.

In one aspect, described herein is a method of trafficking or targeting an RNA molecule to a specific location in a cell. In some embodiments, the method comprises contacting the cell with an engineered MCP or PCP fusion protein comprising a trafficking domain and/or targeting sequence. In some embodiments, the RNA molecule comprises at least one hairpin loop specifically bound by the engineered RNA-binding domain of the fusion protein.

In one aspect, described herein is a method of editing an RNA molecule. In some embodiments, the method comprises contacting an RNA molecule with an engineered MCP or PCP fusion protein comprising a Cas protein that binds to an RNA guide sequence. In some embodiments, the RNA molecule comprises at least one hairpin loop specifically bound by the engineered RNA-binding domain of the fusion protein.

In one aspect, described herein is a method of editing an RNA molecule in a cell. In some embodiments, the method comprises contacting the cell with an engineered MCP or PCP fusion protein comprising a Cas protein that binds to an RNA guide sequence. In some embodiments, the RNA molecule comprises at least one hairpin loop specifically bound by the engineered RNA-binding domain of the fusion protein.

In one aspect, described herein is a method of cleaving an RNA molecule. In some embodiments, the method comprises contacting the RNA molecule with an engineered MCP or PCP fusion protein comprising an RNA-cleaving enzyme. In some embodiments, the RNA molecule comprises at least one hairpin loop specifically bound by the engineered RNA-binding domain of the fusion protein.

In one aspect, described herein is a method of cleaving an RNA molecule in a cell. In some embodiments, the method comprises contacting a cell with an engineered MCP or PCP fusion protein comprising an RNA-cleaving enzyme. In some embodiments, the RNA molecule comprises at least one hairpin loop specifically bound by the engineered RNA-binding domain of the fusion protein.

In one aspect, described herein is a method of modifying an RNA molecule. In some embodiments, the method comprises contacting an RNA molecule with an engineered MCP or PCP fusion protein comprising an RNA-modifying enzyme. In some embodiments, the RNA molecule comprises at least one hairpin loop specifically bound by the engineered RNA-binding domain of the fusion protein.

In one aspect, described herein is a method of modifying an RNA molecule in a cell. In some embodiments, the method comprises contacting a cell with an engineered MCP or PCP fusion protein comprising an RNA-modifying enzyme. In some embodiments, the RNA molecule comprises at least one hairpin loop specifically bound by the engineered RNA-binding domain of the fusion protein.

In one aspect, described herein is a method of regulating translation of an RNA molecule. In some embodiments, the method comprises contacting an RNA molecule with an engineered MCP or PCP fusion protein comprising a translation-regulating and translation-associated domain. In some embodiments, the RNA molecule comprises at least one hairpin loop specifically bound by the engineered RNA-binding domain of the fusion protein.

In one aspect, described herein is a method of regulating translation of an RNA molecule in a cell. In some embodiments, the method comprises contacting a cell with an engineered MCP or PCP fusion protein comprising a translation-regulating and translation-associated domain. In some embodiments, the RNA molecule comprises at least one hairpin loop specifically bound by the engineered RNA-binding domain of the fusion protein.

In one aspect, described herein is a method of regulating an RNA molecule in a cell according to the cell cycle. In some embodiments, the method comprises contacting a cell with an engineered MCP or PCP fusion protein comprising a cell-cycle regulated degron. In some embodiments, the RNA molecule comprises at least one hairpin loop specifically bound by the engineered RNA-binding domain of the fusion protein.

In one aspect, described herein is a method of detecting the proximity of an RNA molecule to another molecule. In some embodiments, the method comprises contacting an RNA molecule with an engineered MCP or PCP fusion protein comprising a proximity-labeling and/or substrate-labeling enzyme. In some embodiments, the RNA molecule comprises at least one hairpin loop specifically bound by the engineered RNA-binding domain of the fusion protein.

In one aspect, described herein is a method of detecting the proximity of an RNA molecule to another molecule in a cell. In some embodiments, the method comprises contacting a cell with an engineered MCP or PCP fusion protein comprising a proximity-labeling and/or substrate-labeling enzyme. In some embodiments, the RNA molecule comprises at least one hairpin loop specifically bound by the engineered RNA-binding domain of the fusion protein.

In one aspect, described herein is a method of targeting an RNA molecule to an antigen. In some embodiments, the method comprises contacting an RNA molecule with an engineered MCP or PCP fusion protein comprising an antigen-binding domain. In some embodiments, the RNA molecule comprises at least one hairpin loop specifically bound by the engineered RNA-binding domain of the fusion protein.

In one aspect, described herein is a method of targeting an RNA molecule to an antigen in a cell. In some embodiments, the method comprises contacting a cell with an engineered MCP or PCP fusion protein comprising an antigen-binding domain. In some embodiments, the RNA molecule comprises at least one hairpin loop specifically bound by the engineered RNA-binding domain of the fusion protein.

In one aspect, described herein is a method of modulating a linker in a fusion protein. In some embodiments, the linker is between an engineered MCP protein and at least one effector protein. In some embodiments, the linker is between an engineered PCP protein and at least one effector protein. In some embodiments, the method comprises inducing a signal that modulates the linker.

In some embodiments, the linker is selected from the group consisting of: (a) drug-inducible heterodimerization domains; (b) drug-dissociable heterodimerization domains; (c) drug-preservable domains; (d) gas-vesicle associated domains that are released by ultrasound; (e) light-regulated protein-protein interaction domains; and (f) protein-protein interaction domains dependent on an extracellular or intracellular signal; or combinations thereof (see e.g., Table 11).

In some embodiments, the signal is selected from the group consisting of: (a) a drug that induces heterodimerization of drug-inducible heterodimerization domains; (b) a drug that induces dissociation of drug-dissociable heterodimerization domains; (c) a drug that induces preservation of drug-preservable domains; (d) ultrasound that releases gas-vesicle associated domains; (e) light that induces cleavage (e.g., PhoCL, mMaple3), dissociation (e.g., LOV, luciferase-LOV) or dimerization (e.g., PhyB/PIF); and (f) an extracellular or intracellular signal that induces interaction of protein-protein interaction domains.

In some embodiments, the linker comprises (a) drug-inducible heterodimerization domains, and the signal is (a) a drug that induces heterodimerization of drug-inducible heterodimerization domains. In some embodiments, the linker comprises (b) drug-dissociable heterodimerization domains, and the signal is (b) a drug that induces dissociation of drug-dissociable heterodimerization domains. In some embodiments, the linker comprises (c) drug-preservable domains, and the signal is (c) a drug that induces preservation of drug-preservable domains. In some embodiments, the linker comprises (d) gas-vesicle associated domains that are released by ultrasound, and the signal is (d) ultrasound that releases gas-vesicle associated domains. In some embodiments, the linker comprises (e) light-regulated protein-protein interaction domains, and the signal is (e) light that induces cleavage (e.g., PhoCL, mMaple3), dissociation (e.g., LOV, luciferase-LOV) or dimerization (e.g., PhyB/PIF). In some embodiments, the linker comprises (f) protein-protein interaction domains dependent on an extracellular or intracellular signal, and the signal is (f) an extracellular or intracellular signal that induces interaction of protein-protein interaction domains.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal, e.g., for an individual without a given disorder.

The terms "increased", "increase", "enhance", or "activate" are all used herein to mean an increase by a statistically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, the terms "protein" and "polypeptide" are used interchangeably to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested to confirm that a desired activity.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments, the polypeptide described herein (or a nucleic acid encoding such a polypeptide) can be a functional fragment of one of the amino acid sequences described herein. As used herein, a "functional fragment" or a "functional portion" is a fragment, portion, or segment of a polypeptide which retains at least 50% of the wild-type reference polypeptide's activity. A functional fragment can comprise conservative substitutions of the sequences disclosed herein.

In some embodiments, the polypeptide described herein can be a variant of a polypeptide sequence described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a protein or fragment thereof that retains activity of the native or reference polypeptide. A wide variety of, for example, PCR-based, site-specific mutagenesis approaches are known in the art and can be applied by the ordinarily skilled artisan to generate and test artificial variants.

A variant amino acid or DNA sequence can be at least 80%, at least 85%, at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

A variant amino acid sequence can be at least 50%, at least 60%, at least 70%, at least 80%, at least 90%, at least 91%, at least 92%, at least 93%, at least 94%, at least 95%, at least 96%, at least 97%, at least 98%, at least 99%, or more, similar to a native or reference sequence. As used herein, "similarity" refers to an identical amino acid or a conservatively substituted amino acid, as described herein. Accordingly, the percentage of "sequence similarity" is the percentage of amino acids which is either identical or conservatively changed; e.g., "sequence similarity"=(% sequence identity)+(% conservative changes). It should be understood that a sequence that has a specified percent similarity to a reference sequence necessarily encompasses a sequence with the same specified percent identity to that reference sequence. The skilled person will be aware of various computer programs, using different mathematical algorithms, that are available to determine the identity or similarity between two sequences. For instance, use can be made of a computer program employing the Needleman and Wunsch algorithm (Needleman et al. (1970)); the GAP program in the Accelrys GCG software package (Accelerys Inc., San Diego U.S.A.); the algorithm of E. Meyers and W. Miller (Meyers et al. (1989)) which has been incorporated into the ALIGN program (version 2.0); or more preferably the BLAST (Basic Local Alignment Tool using default parameters); see e.g., U.S. Pat. No. 10,023,890, the content of which is incorporated by reference herein in its entirety.

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. A wide variety of, site-specific mutagenesis approaches, e.g., Kunkel's method, cassette mutagenesis, PCR site-directed mutagenesis (e.g., traditional PCR, primer extension, or inverse PCR), whole plasmid mutagenesis, in vivo site-directed mutagenesis, CRISPR/Cas-guided mutagenesis, are known in the art and can be applied by the ordinarily skilled artisan to introduce mutations into specific nucleic acid loci. Techniques for making such alterations are very well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); Braman, Jeff, ed. (2002) In Vitro Mutagenesis Protocols, Methods in Molecular Biology, Vol. 182 (2nd ed.); Khudyakov and Fields (2002), Artificial DNA: Methods and Applications, CRC Press; Hsu et al. (2014), Cell 157 (6): 1262-78; Cerchione et al. (2020) PLOS ONE 15 (4): e0231716; and U.S. Pat. Nos. 4,518,584 and 4,737,462, which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA, vector DNA, or cDNA. Suitable RNA can include, e.g., mRNA.

The term "expression" refers to the cellular processes involved in producing RNA and proteins and as appropriate, secreting proteins, including where applicable, but not limited to, for example, transcription, transcript processing, translation and protein folding, modification and processing. Expression can refer to the transcription and stable accumulation of sense (e.g., mRNA) or antisense RNA derived from a nucleic acid fragment or fragments and/or to the translation of mRNA into a polypeptide.

"Expression products" include RNA transcribed from a gene, and polypeptides obtained by translation of mRNA transcribed from a gene. The term "gene" refers to the nucleic acid sequence which is transcribed (DNA) to RNA in vitro or in vivo when operably linked to appropriate regulatory sequences. The gene may or may not include regions preceding and following a coding region, e.g. 5' untranslated (5'UTR) or "leader" sequences and 3' UTR or "trailer" sequences, as well as intervening sequences (introns) between individual coding segments (exons).

In some embodiments, the methods described herein relate to measuring, detecting, or determining the level of at least one marker. As used herein, the term "detecting" or "measuring" refers to observing a signal from, e.g. a probe, label, or target molecule to indicate the presence of an analyte in a sample. Any method known in the art for detecting a particular label moiety can be used for detection. Exemplary detection methods include, but are not limited to, spectroscopic, fluorescent, photochemical, biochemical, immunochemical, electrical, optical or chemical methods. In some embodiments of any of the aspects, measuring can be a quantitative observation.

In some embodiments of any of the aspects, a polypeptide, nucleic acid, or cell as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

As used herein, "contacting" refers to any suitable means for delivering, or exposing, an agent to at least one cell or to at least one RNA molecule. Exemplary delivery methods include, but are not limited to, direct delivery to cell culture medium, transfection, transduction, perfusion, injection, or other delivery method known to one skilled in the art. In some embodiments, contacting comprises physical human activity, e.g., an injection; an act of dispensing, mixing, and/or decanting; and/or manipulation of a delivery device or machine. A cell in a subject can be contacted with any of the fusion proteins described herein. "Contacting" of a cell can be performed in vitro, ex vivo, or in vivo.

As used herein, the term "specific binding" refers to a chemical or physical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third non-target entity. A reagent specific for a given target is one that exhibits specific binding for that target under the conditions of the assay being utilized.

The term "statistically significant" or "significantly" refers to statistical significance and generally means a two standard deviation (2SD) or greater difference or a p-value of less than 0.05.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used herein, the term "corresponding to" refers to an amino acid or nucleotide at the enumerated position in a first polypeptide or nucleic acid, or an amino acid or nucleotide that is equivalent to an enumerated amino acid or nucleotide in a second polypeptide or nucleic acid. Equivalent enumerated amino acids or nucleotides can be determined by alignment of candidate sequences using degree of homology programs known in the art, e.g., BLAST.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in cell biology, immunology, and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Some embodiments of the technology described herein can be defined according to any of the following numbered paragraphs:

1. An engineered MS2 coat protein (MCP) comprising an engineered RNA-binding domain and a degron; wherein the degron is hidden upon binding of the engineered RNA-binding domain to an MS2 RNA hairpin loop; wherein when the engineered RNA-binding domain is not bound to the MS2 RNA hairpin loop, the degron is exposed and degradation of the engineered MCP protein increases.

2. The engineered MCP protein of paragraph 1, wherein the degron is C-terminal of the engineered RNA-binding domain.

3. The engineered MCP protein of paragraph 2, wherein the C-terminal degron comprises RRRG (SEQ ID NO: 10).

4. The engineered MCP protein of paragraph 1, wherein the degron is N-terminal of the engineered RNA-binding domain.

5. The engineered MCP protein of paragraph 4, wherein the N-terminal degron comprises RAS.

6. The engineered MCP protein of paragraph 1, wherein the engineered RNA-binding domain comprises a tandem dimer of MCP monomers.

7. The engineered MCP protein of paragraph 1, wherein the engineered RNA-binding domain comprises circular permutation of MCP monomers.

8. The engineered MCP protein of paragraph 1, wherein the engineered RNA-binding domain comprises:
   (a) a C-terminal portion of a first MCP monomer;
   (b) a second MCP monomer; and
   (c) an N-terminal portion of the first MCP monomer.

9. The engineered MCP protein of paragraph 1, wherein the engineered RNA-binding domain comprises:
   (a) a C-terminal portion of a first MCP monomer; and
   (b) an N-terminal portion of the first MCP monomer.

10. The engineered MCP protein of paragraph 8 or 9, wherein the first MCP monomer is split into the N-terminal portion and the C-terminal portion at a binding pocket for the MS2 RNA hairpin loop.

11. The engineered MCP protein of paragraph 8 or 9, wherein the first MCP monomer is split into the N-terminal portion and the C-terminal portion at residue 48, 49, 50, 51, 52, 53, 54, or 55 of an MCP monomer (SEQ ID NO: 22 or SEQ ID NO: 23).

12. The engineered MCP protein of paragraph 8 or 9, wherein:
   (a) the C-terminal portion of the first MCP monomer comprises at least residues 53-116 of an MCP monomer (SEQ ID NO: 22 or SEQ ID NO: 23); and/or
   (b) the N-terminal portion of the first MCP monomer comprises at least residues 3-50 of an MCP monomer (SEQ ID NO: 22 or SEQ ID NO: 23).

13. The engineered MCP protein of paragraph 8 or 9, wherein:
   (a) the C-terminal portion of the first MCP monomer comprises SEQ ID NO: 19 or an amino acid sequence that is at least 80% identical to SEQ ID NO: 19;
   (b) the second MCP monomer comprises SEQ ID NO: 20 or an amino acid sequence that is at least 80% identical to SEQ ID NO: 20; and/or
   (c) the N-terminal portion of the first MCP monomer comprises SEQ ID NO: 21 or an amino acid sequence that is at least 80% identical to SEQ ID NO: 21.

14. The engineered MCP protein of paragraph 1, wherein the MS2 RNA hairpin loop comprises one of SEQ ID NOs: 27, 29, 42-44, 47, 54 or a nucleic acid sequence that is at least 80% identical to one of SEQ ID NOs: 27, 29, 42-44, 47, 54.

15. The engineered MCP protein of paragraph 1 comprising SEQ ID NO: 4, SEQ ID NO: 50, or an amino acid sequence that is at least 80% identical to SEQ ID NO: 4 or SEQ ID NO: 50.

16. The engineered MCP protein of paragraph 1, comprising from N-terminus to C-terminus:
   (a) the engineered RNA-binding domain comprising from N-terminus to C-terminus:
      (i) a C-terminal portion of a first MCP monomer;
      (ii) a second MCP monomer; and
      (iii) an N-terminal portion of the first MCP monomer; and
   (b) the degron.

17. The engineered MCP protein of paragraph 1, comprising from N-terminus to C-terminus:
(a) the engineered RNA-binding domain comprising from N-terminus to C-terminus:
(i) a C-terminal portion of a first MCP monomer; and
(ii) an N-terminal portion of the first MCP monomer; and
(b) the degron.
18. An engineered MS2 coat protein (MCP; cpmMCP) comprising an engineered RNA-binding domain; wherein the engineered MCP protein is stable when the engineered RNA-binding domain is bound to an MS2 RNA hairpin loop; wherein when the engineered RNA-binding domain is not bound to the MS2 RNA hairpin loop, the engineered MCP protein is unstable and degradation of the engineered MCP protein increases.
19. The engineered MCP protein of paragraph 18, wherein the engineered RNA-binding domain comprises:
(a) a C-terminal portion of a first MCP monomer; and
(b) an N-terminal portion of the first MCP monomer.
20. The engineered MCP protein of paragraph 18, comprising:
(a) the engineered RNA-binding domain comprising from N-terminus to C-terminus:
(i) a C-terminal portion of a first MCP monomer; and
(ii) an N-terminal portion of the first MCP monomer.
21. The engineered MCP protein of paragraph 18, which does not comprise a degron.
22. The engineered MCP protein of paragraph 21 comprising SEQ ID NO: 49, or an amino acid sequence that is at least 80% identical to SEQ ID NO: 49.
23. The engineered MCP protein of paragraph 18, further comprising a degron.
24. An engineered PP7 coat protein (PCP) comprising an engineered RNA-binding domain and a degron; wherein the degron is hidden upon binding of the engineered RNA-binding domain to a PP7 RNA hairpin loop; wherein when the engineered RNA-binding domain is not bound to the PP7 RNA hairpin loop, the degron is exposed and degradation of the engineered PCP protein increases.
25. The engineered PCP protein of paragraph 24, wherein the degron is C-terminal of the engineered RNA-binding domain.
26. The engineered PCP protein of paragraph 25, wherein the C-terminal degron comprises RRRG (SEQ ID NO: 10).
27. The engineered PCP protein of paragraph 24, wherein the degron is N-terminal of the engineered RNA-binding domain.
28. The engineered PCP protein of paragraph 27, wherein the N-terminal degron comprises RAS.
29. The engineered PCP protein of paragraph 24, wherein the engineered RNA-binding domain comprises a tandem dimer of PCP monomers.
30. The engineered PCP protein of paragraph 24, wherein the engineered RNA-binding domain comprises circular permutation of PCP monomers.
31. The engineered PCP protein of paragraph 24, wherein the engineered RNA-binding domain comprises:
(a) a C-terminal portion of a first PCP monomer;
(b) a second PCP monomer; and
(c) an N-terminal portion of the first PCP monomer.
32. The engineered PCP protein of paragraph 24, wherein the engineered RNA-binding domain comprises:
(a) a C-terminal portion of a first PCP monomer; and
(b) an N-terminal portion of the first PCP monomer.

33. The engineered PCP protein of paragraph 31 or 32, wherein the first PCP monomer is split into the N-terminal portion and the C-terminal portion at a binding pocket for the PP7 RNA hairpin loop.
34. The engineered PCP protein of paragraph 31 or 32, wherein the first PCP monomer is split into the N-terminal portion and the C-terminal portion at residue 48, 49, 50, 51, 52, 53, 54, or 55 of a PCP monomer (SEQ ID NO: 24).
35. The engineered PCP protein of paragraph 31 or 32, wherein:
(a) the C-terminal portion of the first PCP monomer comprises at least residues 52-123 of a PCP monomer (SEQ ID NO: 24); and/or
(b) the N-terminal portion of the first PCP monomer comprises at least residues 3-48 of a PCP monomer (SEQ ID NO: 24).
36. The engineered PCP protein of paragraph 31 or 32, wherein:
(a) the C-terminal portion of the first PCP monomer comprises SEQ ID NO: 11, SEQ ID NO: 16, or an amino acid sequence that is at least 80% identical to SEQ ID NO: 11 or SEQ ID NO: 16;
(b) the second PCP monomer comprises SEQ ID NO: 12, SEQ ID NO: 17, or an amino acid sequence that is at least 80% identical to SEQ ID NO: 12 or SEQ ID NO: 17; and/or
(c) the N-terminal portion of the first PCP monomer comprises SEQ ID NO: 13, SEQ ID NO: 18, or an amino acid sequence that is at least 80% identical to SEQ ID NO: 13 or SEQ ID NO: 18.
37. The engineered PCP protein of paragraph 24, wherein the PP7 RNA hairpin loop comprises SEQ ID NO: 53 (ggagcagacgatatggcgtcgctcc) or a nucleic acid sequence that is at least 80% identical to SEQ ID NO: 53.
38. The engineered PCP protein of paragraph 24 comprising SEQ ID NO: 2, SEQ ID NO: 15, or an amino acid sequence that is at least 80% identical to SEQ ID NO: 2 or SEQ ID NO: 15.
39. The engineered PCP protein of paragraph 31 or 32, wherein the first or second PCP monomer, or the N-terminal or C-terminal portions thereof, comprises at least one mutation to decrease self-assembly of dimers into higher order aggregates.
40. The engineered PCP protein of paragraph 39, wherein the at least one mutation corresponds to S22R, L36A, and/or L71A in SEQ ID NO: 24.
41. The engineered PCP protein of any one of paragraphs 24, comprising from N-terminus to C-terminus:
(a) the engineered RNA-binding domain comprising from N-terminus to C-terminus:
(i) a C-terminal portion of a first PCP monomer;
(ii) a second PCP monomer; and
(iii) an N-terminal portion of the first PCP monomer; and
(b) the degron.
42. The engineered PCP protein of any one of paragraphs 24, comprising from N-terminus to C-terminus:
(a) the engineered RNA-binding domain comprising from N-terminus to C-terminus:
(i) a C-terminal portion of a first PCP monomer; and
(ii) an N-terminal portion of the first PCP monomer; and
(b) the degron.
43. An engineered PP7 coat protein (PCP) comprising an engineered RNA-binding domain; wherein the engineered PCP protein is stable when the engineered RNA-binding domain is bound to a PP7 RNA hairpin loop; wherein when the engineered RNA-binding domain is not bound to the PP7 RNA hairpin loop, the engineered PCP protein is unstable and degradation of the engineered PCP protein increases.

44. The engineered PCP protein of paragraph 43, wherein the engineered RNA-binding domain comprises:
(a) a C-terminal portion of a first PCP monomer; and
(b) an N-terminal portion of the first PCP monomer.

45. The engineered PCP protein of paragraph 43, comprising:
(a) the engineered RNA-binding domain comprising from N-terminus to C-terminus:
(i) a C-terminal portion of a first PCP monomer; and
(ii) an N-terminal portion of the first PCP monomer.

46. The engineered PCP protein of paragraph 43, which does not comprise a degron.

47. The engineered PCP protein of paragraph 43, further comprising a degron.

48. The engineered PCP protein of any one of paragraphs 44 or 45, wherein the first or second PCP monomer, or the N-terminal or C-terminal portions thereof, comprise at least one mutation to decrease self assembly of dimers into higher order aggregates.

49. The engineered PCP protein of paragraph 48, wherein the at least one mutation corresponds to S22R, L36A, and/or L71A in SEQ ID NO: 24.

50. A fusion protein comprising the engineered MCP protein of any one of paragraphs 1-23 linked to at least one effector protein.

51. A fusion protein comprising the engineered PCP protein of any one of paragraphs 24-49 linked to at least one effector protein.

52. The fusion protein of paragraph 50 or 51, wherein the at least one effector protein is selected from the group consisting of:
(a) a detectable marker;
(b) a trafficking domain and/or targeting sequence;
(c) a Cas protein that binds to an RNA guide sequence;
(d) an RNA-cleaving and/or RNA-modifying enzyme;
(e) a translation-regulating and translation-associated domain;
(f) a cell-cycle regulated degron;
(g) a proximity-labeling and/or substrate-labeling enzyme; and
(h) an antigen-binding domain.

53. The fusion protein of paragraph 52, wherein the detectable marker is selected from the group consisting of: a luciferase, a fluorescent protein, and an ultrasound-mediated reporter.

54. The fusion protein of paragraph 53, wherein the luciferase is selected from the group consisting of: NanoLuc®, RLuc, RLuc8, and Super RLuc8.

55. The fusion protein of paragraph 53, wherein the fluorescent protein is an infrared fluorescent protein (iRFP).

56. The fusion protein of paragraph 55, wherein the infrared fluorescent protein (iRFP) is selected from the group consisting of: iRFP-670 and miIRFP-670.

57. The fusion protein of paragraph 53, wherein the fluorescent protein is fluorescent when bound to a substrate.

58. The fusion protein of paragraph 53, wherein the fluorescent protein is HALOTAG.

59. The fusion protein of paragraph 53, wherein the ultrasound-mediated reporter comprises a gas vesicle-based reporter protein.

60. The fusion protein of paragraph 52, wherein the trafficking domain and/or targeting sequence is selected from the group consisting of:
(a) a microtubule motor protein (e.g., a kinesin or dynein);
(b) a mitochondrial surface targeting sequence;
(c) a nuclear localization signal;
(d) a nuclear exclusion signal;
(e) a transmembrane domain;
(f) a signaling receptor;
(g) a lipid-modification substrate;
(h) a Pleckstrin homology domain; and
(i) a split pleckstrin homology domain.

61. The fusion protein of paragraph 60, wherein the signaling receptor is selected from the group consisting of:
(a) a GPCR;
(b) a SynNotch; or
(c) a CAR.

62. The fusion protein of paragraph 60, wherein the lipid-modification substrate comprises a substrate for: (i) myristoylation, (ii) palmitoylation, (iii) myristoylation and palmitoylation, or (iv) prenylation.

63. The fusion protein of paragraph 52, wherein the Cas protein is selected from the group consisting of:
(a) an RNA-guided DNA binding Cas protein; and
(b) an RNA-guided RNA binding Cas protein.

64. The fusion protein of paragraph 63, wherein the RNA-guided DNA binding Cas protein comprises Cas9 or Cas12.

65. The fusion protein of paragraph 63, wherein the RNA-guided RNA binding Cas protein comprises Cas13 or Cas CSM.

66. The fusion protein of paragraph 63, wherein the Cas protein is catalytically inactive.

67. The fusion protein of paragraph 52, wherein the RNA-cleaving and/or RNA-modifying enzyme is selected from the group consisting of:
(a) an RNA-cleaving nuclease;
(b) a de-adenylating enzyme;
(c) a de-capping enzyme;
(d) a capping enzyme;
(e) an RNA base editor;
(f) an enzyme that adds covalent attachments to RNA; and
(g) an adduct-forming protein.

68. The fusion protein of paragraph 67, wherein the RNA-cleaving nuclease is selected from the group consisting of
(i) a pre-crRNA-processing enzyme;
(ii) an RNase; and
(iii) a sequence comprising a SMG6 PIN domain.

69. The fusion protein of paragraph 68, wherein the pre-crRNA-processing enzyme is selected from the group consisting of Csy4 (Cas6f), Cas5d, Cas6e, and Cas6.

70. The fusion protein of paragraph 68, wherein the RNase is selected from the group consisting of: RNase H, RNase III, RNase A, and RNase T1.

71. The fusion protein of paragraph 67, wherein the de-adenylating enzyme is selected from the group consisting of
(i) CCR4-Not; and
(ii) Poly(A)-specific ribonuclease (PARN).

72. The fusion protein of paragraph 67, wherein the de-capping enzyme comprises Dcp1/Dcp2.

73. The fusion protein of paragraph 67, wherein the capping enzyme is selected from the group consisting of
(i) a Faustovirus capping enzyme;
(ii) a Vaccinia RNA capping enzyme; and
(iii) an HIV capping enzyme.

74. The fusion protein of paragraph 67, wherein the RNA base editor comprises Adenosine Deaminase Acting on RNA (ADAR).

75. The fusion protein of paragraph 67, wherein the enzyme that adds covalent attachments to RNA is a poly-adenylating enzyme.

76. The fusion protein of paragraph 75, wherein the poly-adenylating enzyme is selected from the group consisting of
(i) an E. coli Poly(A) polymerase;
(ii) a yeast poly(A) polymerase; and
(iii) a mammalian poly(A) polymerase.

77. The fusion protein of paragraph 67, wherein the adduct-forming protein is selected from the group consisting of:
(i) a tyrosyl-RNA phosphodiester bond-forming domain; and
(ii) a VPg viral protein.

78. The fusion protein of paragraph 52, wherein the translation-regulating and translation-associated domain is selected from the group consisting of:
(a) a cap-independent initiation domain;
(b) a translational downregulation domain;
(c) an amino acyl tRNA synthetase (aaRS); and
(d) a peptide-based sequence that facilitates translation modulation or RNA stability changes when recruited to an RNA molecule.

79. The fusion protein of paragraph 78, wherein the cap-independent initiation domain comprises a caliciviral VPg protein.

80. The fusion protein of paragraph 78, wherein the translational downregulation domain comprises eif4e-bp1, or the Eif4E binding domain from CUP, THOR, or 4E-T.

81. The fusion protein of paragraph 78, wherein the translational downregulation domain blocks ribosome translocation.

82. The fusion protein of paragraph 78, wherein the translational downregulation domain comprises a stable secondary structure that blocks ribosome translocation.

83. The fusion protein of paragraph 78, wherein the amino acyl tRNA synthetase (aaRS) is selected from the group consisting of:
(a) mutant E. coli amino aaRS;
(b) mutant endogenous aaRS;
(c) mutant Methanocaldococcus jannaschii aaRS;
(d) mutant yeast aaRS; and
(e) mutant pyrrolysine aaRS.

84. The fusion protein of paragraph 52, wherein the cell-cycle regulated degron is selected from the group consisting of:
(a) a CdtI degron domain;
(b) a Geminin degron domain; and
(c) a FUCCI sensor.

85. The fusion protein of paragraph 52, wherein the proximity-labeling and/or substrate-labeling enzyme is selected from the group consisting of:

(a) a biotin ligase in combination with a biotin ligase substrate;
(b) a peroxidase-based enzyme;
(c) miniSOG;
(d) RNA methyltransferase (e.g., METTL16);
(e) 'LITtag', an engineered flavin-mononucleotide-binding LOV domain; and
(f) an RNA Transglycosylase.

86. The fusion protein of paragraph 85, wherein the biotin ligase is E. coli biotin ligase (BirA).

87. The fusion protein of paragraph 85, wherein the biotin ligase is derived from BirA and selected from the group consisting of BioID, BioID2, and TurboID.

88. The fusion protein of paragraph 85, wherein the biotin ligase substrate is an acceptor peptide (AP), a biotinylated sequence from Propionibacterium shermanii transcarboxylase, or AviTag.

89. The fusion protein of paragraph 85, wherein the peroxidase-based enzyme is selected from the group consisting of APEX, APEX2, and HRP.

90. The fusion protein of paragraph 85, wherein the RNA Transglycosylase is E. coli tRNA guanine transglycosylase (TGT).

91. The fusion protein of paragraph 52, wherein the antigen-binding domain is comprised by an antibody or nanobody.

92. The fusion protein of paragraph 52, wherein the antigen-binding domain binds to an endogenous protein.

93. The fusion protein of paragraph 52, wherein the antigen-binding domain binds to an intracellular protein.

94. The fusion protein of paragraph 91, wherein the nanobody comprises a destabilized nanobody.

95. The fusion protein of paragraph 50 or 51, wherein the at least one effector protein recruits at least one additional effector protein.

96. The fusion protein of paragraph 50 or 51, further comprising a linker between the engineered RNA-binding domain and the at least one effector protein.

97. The fusion protein of paragraph 96, wherein the linker is selected from the group consisting of:
(a) drug-inducible heterodimerization domains;
(b) drug-dissociable heterodimerization domains;
(c) drug-preservable domains;
(d) a gas-vesicle associated domain that is released by ultrasound;
(e) light-regulated protein-protein interaction domains; and
(f) protein-protein interaction domains dependent on an extracellular or intracellular signal.

98. The fusion protein of paragraph 97, wherein the drug-inducible heterodimerization domains are selected from the group consisting of:
(a) FKBP and FRB;
(b) abscisic acid (ABA)-inducible heterodimeric protein binding domains;
(c) gibberellin-inducible heterodimeric protein binding domains;
(d) a drug-inducible reader domain that specifically binds to an NS3 protease inhibitor-bound NS3 protease; and
(e) human antibody-based dimerizers (AbCIDs).

99. The fusion protein of paragraph 97, wherein the drug-dissociable heterodimerization domains are selected from the group consisting of:

(a) Bcl-xL and BH3 proteins, the interaction of which can dissociated by small molecules (e.g., A-1155463);

(b) NS3 protease complexed with an inhibitory peptide, the interaction of which can be dissociated using an NS3 protease inhibitor, optionally wherein the NS3 protease is catalytically inactive; and (c) a drug-dissociable reader domain that specifically binds to a first NS3 protease inhibitor-bound NS3 protease, the interaction of which can dissociated by a second NS3 protease inhibitor that binds to NS3 protease.

100. The fusion protein of paragraph 97, wherein the drug-preservable domains comprise an active NS3 protease and a cognate cleavage site for the active NS3 protease, wherein the linker is preserved in the presence of an NS3 protease inhibitor, and the linkage is severed in the absence of the NS3 protease inhibitor.

101. The fusion protein of paragraph 97, wherein the light-regulated protein-protein interaction domains are selected from the group consisting of:

(a) PhoCl;

(b) mMaple3;

(c) LOV domains;

(d) luciferase-fused LOV domains; and (e) red light-inducible PPI domains (e.g., PhyB/Pif).

102. The fusion protein of paragraph 97, wherein the protein-protein interaction domains dependent on an extracellular or intracellular signal are selected from the group consisting of:

(a) beta-arrestin, which bind to phosphorylated tails of GPCRs;

(b) phosphorylated kinase substrates in combination with domains recognizing such phosphorylated sequences;

(c) binding proteins that recognize and undergo protein interactions in response to secondary metabolites (e.g., cAMP) or ions (including Ca2+); and (d) a nanobody that binds the intracellular region of an activated GPCR.

103. The fusion protein of any one of paragraphs 50-102, further comprising a transmembrane domain.

104. The fusion protein of paragraph 50 or 51, wherein the at least one effector protein is N-terminal of the engineered RNA-binding domain.

105. The fusion protein of paragraph 50 or 51, wherein the at least one effector protein is linked to the N-terminus of the engineered RNA-binding domain.

106. The fusion protein of paragraph 50, wherein the at least one effector protein is located between:

(a) the C-terminal portion of the first MCP monomer and the second MCP monomer;

(b) the C-terminal portion of the first MCP monomer and the N-terminal portion of the first MCP monomer;

(c) the second MCP monomer and the N-terminal portion of the first MCP monomer; and/or (d) the N-terminal portion of the first MCP monomer and the degron.

107. The fusion protein of paragraph 51, wherein the at least one effector protein is located between:

(a) the C-terminal portion of the first PCP monomer and the second PCP monomer;

(b) the C-terminal portion of the first PCP monomer and the N-terminal portion of the first PCP monomer;

(c) the second PCP monomer and the N-terminal portion of the first PCP monomer; and/or (d) the N-terminal portion of the first PCP monomer and the degron.

108. A nucleic acid encoding the fusion protein of any one of paragraphs 50-107.

109. A vector comprising the nucleic acid of paragraph 108.

110. A complex comprising the fusion protein of any one of paragraphs 50-107 bound to an RNA molecule comprising at least one hairpin loop specifically bound by the engineered RNA-binding domain of the fusion protein.

111. A complex comprising the fusion protein of any one of paragraphs 50-107 bound to an RNA molecule comprising at least one MS2 RNA hairpin loop or at least one PP7 RNA hairpin loop.

112. A system comprising the fusion protein of any one of paragraphs 50-107 and an RNA molecule comprising at least one hairpin loop specifically bound by the engineered RNA-binding domain of the fusion protein.

113. A system comprising the fusion protein of any one of paragraphs 50-107 and an RNA molecule comprising at least one MS2 RNA hairpin loop or at least one PP7 RNA hairpin loop.

114. A system comprising:

(a) a fusion protein comprising the engineered MCP protein of any one of paragraphs 1-23 linked to at least one effector protein; and (b) an RNA molecule comprising at least one MS2 RNA hairpin loop.

115. A system comprising:

(a) a fusion protein comprising the engineered PCP protein of any one of paragraphs 24-49 linked to at least one effector protein; and (b) an RNA molecule comprising at least one PP7 RNA hairpin loop.

116. The system of any one of paragraphs 112-115, wherein the engineered RNA-binding domain of the fusion protein is capable of binding to the at least one hairpin loop in the RNA molecule, thereby decreasing degradation of the fusion protein.

117. The system of any one of paragraphs 112-116, wherein the at least one hairpin loop is located in an untranslated region of the RNA molecule that is 5' or 3' from an encoded gene of interest.

118. The system of any one of paragraphs 117, wherein the fusion protein binds to the at least one hairpin loop in the RNA molecule and modulates expression of the encoded gene of interest.

119. The system of paragraph 117 or 118, wherein the gene of interest encodes for the fusion protein.

120. The system of any paragraph 119, wherein the fusion protein binds to the at least one hairpin loop in the RNA molecule and decreases expression of the encoded fusion protein, thus resulting in auto-inhibition.

121. The system of any one of paragraphs 112-120, wherein the RNA molecule comprises a circular RNA.

122. The system of any one of paragraphs 112-120, wherein the RNA molecule comprises a capless linear RNA.

123. The system of any one of paragraphs 112-122, wherein the RNA molecule comprises an IRES for cap-independent translation of the encoded gene of interest.

124. The system of any one of paragraphs 112-123, wherein the RNA molecule comprises substituted synthetic nucleotides.

125. The system of any one of paragraphs 124, wherein the substituted synthetic nucleotides are pseudouridine (Ψ) and/or 5-methylcytosine (m⁵C).

126. The system of any one of paragraphs 112-125, wherein the at least one hairpin loop does not comprise uridine.

127. The system of any one of paragraphs 112-126, wherein the at least one hairpin loop does not comprise substituted synthetic nucleotides.

128. A system comprising:
(a) a first fusion protein comprising the engineered MCP protein of any one of paragraphs 1-23 linked to at least one effector protein;
(b) a second fusion protein comprising the engineered PCP protein of any one of paragraphs 24-49 linked to at least one effector protein; and
(c) an RNA molecule comprising at least one MS2 RNA hairpin loop and at least one PP7 RNA hairpin loop.

129. A system comprising:
(a) a first fusion protein comprising the engineered MCP protein of any one of paragraphs 1-23 linked to at least one effector protein;
(b) a second fusion protein comprising the engineered PCP protein of any one of paragraphs 24-49 linked to at least one effector protein;
(c) a first RNA molecule comprising at least one MS2 RNA hairpin loop; and
(d) a second RNA molecule comprising at least one PP7 RNA hairpin loop.

130. A method of detecting an RNA molecule, the method comprising contacting the RNA molecule with the fusion protein of any one of paragraphs 50-107; wherein the at least one effector protein comprises a detectable marker; wherein the RNA molecule comprises at least one hairpin loop specifically bound by the engineered RNA-binding domain of the fusion protein.

131. A method of detecting an RNA molecule in a cell, the method comprising contacting the cell with the fusion protein of any one of paragraphs 50-107; wherein the at least one effector protein comprises a detectable marker; wherein the RNA molecule comprises at least one hairpin loop specifically bound by the engineered RNA-binding domain of the fusion protein.

132. A method of trafficking or targeting an RNA molecule to a specific location in a cell, the method comprising contacting the cell with the fusion protein of any one of paragraphs 50-107; wherein the at least one effector protein comprises a trafficking domain and/or targeting sequence; wherein the RNA molecule comprises at least one hairpin loop specifically bound by the engineered RNA-binding domain of the fusion protein.

133. A method of editing an RNA molecule, the method comprising contacting the RNA molecule with the fusion protein of any one of paragraphs 50-107; wherein the at least one effector protein comprises a Cas protein that binds to an RNA guide sequence; wherein the RNA molecule comprises at least one hairpin loop specifically bound by the engineered RNA-binding domain of the fusion protein.

134. A method of editing an RNA molecule in a cell, the method comprising contacting the cell with the fusion protein of any one of paragraphs 50-107; wherein the at least one effector protein comprises a Cas protein that binds to an RNA guide sequence; wherein the RNA molecule comprises at least one hairpin loop specifically bound by the engineered RNA-binding domain of the fusion protein.

135. A method of cleaving an RNA molecule, the method comprising contacting the RNA molecule with the fusion protein of any one of paragraphs 50-107; wherein the at least one effector protein comprises an RNA-cleaving enzyme; wherein the RNA molecule comprises at least one hairpin loop specifically bound by the engineered RNA-binding domain of the fusion protein.

136. A method of cleaving an RNA molecule in a cell, the method comprising contacting the cell with the fusion protein of any one of paragraphs 50-107; wherein the at least one effector protein comprises an RNA-cleaving enzyme; wherein the RNA molecule comprises at least one hairpin loop specifically bound by the engineered RNA-binding domain of the fusion protein.

137. A method of modifying an RNA molecule, the method comprising contacting the RNA molecule with the fusion protein of any one of paragraphs 50-107; wherein the at least one effector protein comprises an RNA-modifying enzyme; wherein the RNA molecule comprises at least one hairpin loop specifically bound by the engineered RNA-binding domain of the fusion protein.

138. A method of modifying an RNA molecule in a cell, the method comprising contacting the cell with the fusion protein of any one of paragraphs 50-107; wherein the at least one effector protein comprises an RNA-modifying enzyme; wherein the RNA molecule comprises at least one hairpin loop specifically bound by the engineered RNA-binding domain of the fusion protein.

139. A method of regulating translation of an RNA molecule, the method comprising contacting the RNA molecule with the fusion protein of any one of paragraphs 50-107; wherein the at least one effector protein comprises a translation-regulating and translation-associated domain; wherein the RNA molecule comprises at least one hairpin loop specifically bound by the engineered RNA-binding domain of the fusion protein.

140. A method of regulating translation of an RNA molecule in a cell, the method comprising contacting the cell with the fusion protein of any one of paragraphs 50-107; wherein the at least one effector protein comprises a translation-regulating and translation-associated domain; wherein the RNA molecule comprises at least one hairpin loop specifically bound by the engineered RNA-binding domain of the fusion protein.

141. A method of regulating an RNA molecule in a cell according to the cell cycle, the method comprising contacting the cell with the fusion protein of any one of paragraphs 50-107; wherein the at least one effector protein comprises a cell-cycle regulated degron; wherein the RNA molecule comprises at least one hairpin loop specifically bound by the engineered RNA-binding domain of the fusion protein.

142. A method of detecting the proximity of an RNA molecule to another molecule, the method comprising contacting the RNA molecule with the fusion protein of any one of paragraphs 50-107; wherein the at least one effector protein comprises a proximity-labeling and/or substrate-labeling enzyme; wherein the RNA molecule comprises at least one hairpin loop specifically bound by the engineered RNA-binding domain of the fusion protein.

143. A method of detecting the proximity of an RNA molecule to another molecule in a cell, the method comprising contacting the cell with the fusion protein of any one of paragraphs 50-107; wherein the at least one effector protein comprises a proximity-labeling and/or substrate-labeling enzyme; wherein the RNA molecule comprises at least one hairpin loop specifically bound by the engineered RNA-binding domain of the fusion protein.

144. A method of targeting an RNA molecule to an antigen, the method comprising contacting the RNA molecule with the fusion protein of any one of paragraphs 50-107; wherein the at least one effector protein comprises an antigen-binding domain; wherein the RNA molecule comprises at least one hairpin loop specifically bound by the engineered RNA-binding domain of the fusion protein.

145. A method of targeting an RNA molecule to an antigen in a cell, the method comprising contacting the cell with the fusion protein of any one of paragraphs 50-107; wherein the at least one effector protein comprises an antigen-binding domain; wherein the RNA molecule comprises at least one hairpin loop specifically bound by the engineered RNA-binding domain of the fusion protein.

146. A method of modulating the linker in the fusion protein of any one of paragraphs 50-107, the method comprising inducing a signal that modulates the linker.

147. The method of paragraph 146, wherein the linker is between the engineered MCP protein and the at least one effector protein.

148. The method of paragraph 146, wherein the linker is between the engineered PCP protein and the at least one effector protein.

149. The method of paragraph 146, wherein the linker is selected from the group consisting of:
(a) drug-inducible heterodimerization domains;
(b) drug-dissociable heterodimerization domains;
(c) drug-preservable domains;
(d) gas-vesicle associated domains that are released by ultrasound;
(e) light-regulated protein-protein interaction domains; and
(f) protein-protein interaction domains dependent on an extracellular or intracellular signal.

150. The method of paragraph 146, wherein the signal is selected from the group consisting of:
(a) a drug that induces heterodimerization of drug-inducible heterodimerization domains;
(b) a drug that induces dissociation of drug-dissociable heterodimerization domains;
(c) a drug that induces preservation of drug-preservable domains;
(d) ultrasound that releases gas-vesicle associated domains;
(e) light that induces cleavage (e.g., PhoCL, mMaple3), dissociation (e.g., LOV, luciferase-LOV) or dimerization (e.g., PhyB/PIF); and
(f) an extracellular or intracellular signal that induces interaction of protein-protein interaction domains.

Some embodiments of the technology described herein can be defined according to any of the following numbered paragraphs:

1. An engineered MS2 coat protein (MCP) comprising an engineered RNA-binding domain and a degron; wherein the degron is hidden upon binding of the engineered RNA-binding domain to an MS2 RNA hairpin loop; wherein when the engineered RNA-binding domain is not bound to the MS2 RNA hairpin loop, the degron is exposed and degradation of the engineered MCP protein increases.

2. The engineered MCP protein of paragraph 1, wherein the degron is C-terminal of the engineered RNA-binding domain.

3. The engineered MCP protein of paragraph 2, wherein the C-terminal degron comprises RRRG (SEQ ID NO: 10).

4. The engineered MCP protein of paragraph 1, wherein the degron is N-terminal of the engineered RNA-binding domain.

5. The engineered MCP protein of paragraph 4, wherein the N-terminal degron comprises RAS.

6. The engineered MCP protein of paragraph 1, wherein the engineered RNA-binding domain comprises a tandem dimer of MCP monomers.

7. The engineered MCP protein of paragraph 1, wherein the engineered RNA-binding domain comprises circular permutation of MCP monomers.

8. The engineered MCP protein of paragraph 1, wherein the engineered RNA-binding domain comprises:
(a) a C-terminal portion of a first MCP monomer;
(b) a second MCP monomer; and
(c) an N-terminal portion of the first MCP monomer.

9. The engineered MCP protein of paragraph 1, wherein the engineered RNA-binding domain comprises:
(a) a C-terminal portion of a first MCP monomer; and
(b) an N-terminal portion of the first MCP monomer.

10. The engineered MCP protein of paragraph 1, wherein the first MCP monomer is split into the N-terminal portion and the C-terminal portion at a binding pocket for the MS2 RNA hairpin loop.

11. The engineered MCP protein of paragraph 1, wherein the first MCP monomer is split into the N-terminal portion and the C-terminal portion at residue 48, 49, 50, 51, 52, 53, 54, or 55 of an MCP monomer (SEQ ID NO: 22 or SEQ ID NO: 23).

12. The engineered MCP protein of paragraph 1, wherein:
(a) the C-terminal portion of the first MCP monomer comprises at least residues 53-116 of an MCP monomer (SEQ ID NO: 22 or SEQ ID NO: 23); and/or
(b) the N-terminal portion of the first MCP monomer comprises at least residues 3-50 of an MCP monomer (SEQ ID NO: 22 or SEQ ID NO: 23).

13. The engineered MCP protein of paragraph 1, wherein:
(a) the C-terminal portion of the first MCP monomer comprises SEQ ID NO: 19 or an amino acid sequence that is at least 80% identical to SEQ ID NO: 19;
(b) the second MCP monomer comprises SEQ ID NO: 20 or an amino acid sequence that is at least 80% identical to SEQ ID NO: 20; and/or
(c) the N-terminal portion of the first MCP monomer comprises SEQ ID NO: 21 or an amino acid sequence that is at least 80% identical to SEQ ID NO: 21.

14. The engineered MCP protein of paragraph 1, wherein the MS2 RNA hairpin loop comprises one of SEQ ID NOs: 27, 29, 42-44, 47, 54 or a nucleic acid sequence that is at least 80% identical to one of SEQ ID NOs: 27, 29, 42-44, 47, 54.

15. The engineered MCP protein of paragraph 1 comprising SEQ ID NO: 4, SEQ ID NO: 50, or an amino acid sequence that is at least 80% identical to SEQ ID NO: 4 or SEQ ID NO: 50.

16. The engineered MCP protein of any one of paragraphs 1, comprising from N-terminus to C-terminus:
    (a) the engineered RNA-binding domain comprising from N-terminus to C-terminus:
        (i) a C-terminal portion of a first MCP monomer;
        (ii) a second MCP monomer; and
        (iii) an N-terminal portion of the first MCP monomer; and
    (b) the degron.

17. The engineered MCP protein of any one of paragraphs 1, comprising from N-terminus to C-terminus:
    (a) the engineered RNA-binding domain comprising from N-terminus to C-terminus:
        (i) a C-terminal portion of a first MCP monomer; and
        (ii) an N-terminal portion of the first MCP monomer; and
    (b) the degron.

18. An engineered MS2 coat protein (MCP; cpmMCP) comprising an engineered RNA-binding domain; wherein the engineered MCP protein is stable when the engineered RNA-binding domain is bound to an MS2 RNA hairpin loop; wherein when the engineered RNA-binding domain is not bound to the MS2 RNA hairpin loop, the engineered MCP protein is unstable and degradation of the engineered MCP protein increases.

19. An engineered PP7 coat protein (PCP) comprising an engineered RNA-binding domain and a degron; wherein the degron is hidden upon binding of the engineered RNA-binding domain to a PP7 RNA hairpin loop; wherein when the engineered RNA-binding domain is not bound to the PP7 RNA hairpin loop, the degron is exposed and degradation of the engineered PCP protein increases.

20. An engineered PP7 coat protein (PCP) comprising an engineered RNA-binding domain; wherein the engineered PCP protein is stable when the engineered RNA-binding domain is bound to a PP7 RNA hairpin loop; wherein when the engineered RNA-binding domain is not bound to the PP7 RNA hairpin loop, the engineered PCP protein is unstable and degradation of the engineered PCP protein increases.

21. A fusion protein comprising the engineered MCP protein of paragraph 1 linked to at least one effector protein.

22. A fusion protein comprising the engineered PCP protein of paragraph 19 linked to at least one effector protein.

23. The fusion protein of paragraph 21, wherein the at least one effector protein is selected from the group consisting of:
    (a) a detectable marker;
    (b) a trafficking domain and/or targeting sequence;
    (c) a Cas protein that binds to an RNA guide sequence;
    (d) an RNA-cleaving and/or RNA-modifying enzyme;
    (e) a translation-regulating and translation-associated domain;
    (f) a cell-cycle regulated degron;
    (g) a proximity-labeling and/or substrate-labeling enzyme; and
    (h) an antigen-binding domain.

24. The fusion protein of paragraph 21, further comprising a linker between the engineered RNA-binding domain and the at least one effector protein; wherein the linker is selected from the group consisting of:
    (a) drug-inducible heterodimerization domains;
    (b) drug-dissociable heterodimerization domains;
    (c) drug-preservable domains;

(d) a gas-vesicle associated domain that is released by ultrasound;
    (e) light-regulated protein-protein interaction domains; and
    (f) protein-protein interaction domains dependent on an extracellular or intracellular signal.

25. The fusion protein of paragraph 21, further comprising a transmembrane domain.

26. A nucleic acid encoding the fusion protein of paragraph 21.

27. A vector comprising the nucleic acid of paragraph 26.

28. A complex comprising the fusion protein of paragraph 21 bound to an RNA molecule comprising at least one hairpin loop specifically bound by the engineered RNA-binding domain of the fusion protein.

29. A system comprising:
    (a) a fusion protein comprising the engineered MCP protein of paragraph 1 linked to at least one effector protein; and
    (b) an RNA molecule comprising at least one MS2 RNA hairpin loop.

30. A system comprising:
    (a) a fusion protein comprising the engineered PCP protein of paragraph 19 linked to at least one effector protein; and
    (b) an RNA molecule comprising at least one PP7 RNA hairpin loop.

The technology described herein is further illustrated by the following examples which in no way should be construed as being further limiting.

EXAMPLES

Example 1: Protein-RNA and Protein-Protein Stoichiometries for Increased Labeling and Signaling/Effector Specificities The technology described herein is directed to compositions and methods related to engineered RNA binding domains (RBD) and other protein-based interaction domains that exhibit conditional stability via designed degron shielding. The conditional stability dependent on RNA binding permits real-time titration of the RBDs in living cells, such that a 1-to-1 stoichiometry exists between protein and RNA in cells, and excess RBD-fusion proteins are rapidly destroyed. The RNA binding protein can also be fused to effector domains and/or peptides capable of modulating RNA properties, including modification, cleavage/degradation, localization, degradation, stability, or translation. In this context, destabilized RNA-binding proteins provide multiple advantageous utilities. For example, degradation of RNA-unbound effector-binder units limit the "off target" effects due to expression of excess effector copies, which can compete for endogenous factors, and as a result sequester them from executing normal activities. By using a destabilized RNA binding protein, the effector-binder fusion protein is preserved only in the desired context—in the presence of the target mRNA. This feature thus has the dual utility of confining effectors to desired RNAs while simultaneously eliminating undesired outcomes due to excess effector sequence expression.

As it relates to the inducible ADAR (iADAR) system, a useful therapeutic composition combines the iADAR deaminase domains with the engineered RBDs to minimize potential off-target ADAR editing from non-target localized RBDs. This helps with ensuring efficacy by reducing any off-target effects of an iADAR-based mRNA therapeutic.

More specifically, such an mRNA-based therapeutic can, for example, comprise an open reading frame composed of a cancer-antigen activated iADAR domain fused to the conditionally stable MS2 or PCP coat proteins (dMCP or dPCP) upstream of an editable stop codon and downstream effector protein. In this case, the dMCP/dPCP limits the concentration of free iADAR, thus limiting a toxic or undesirable response due to high levels of intracellular iADAR.

Described herein is a conditionally stable RNA binding protein based on the MS2 Coat Protein (MCP). MCP selectively binds and recognizes MS2 hairpin RNA. The MCP-MS2 system has been used in the imaging of RNA sequences tagged with repeating sequences of MS2; in these applications, localization of the mRNA is visualized via the formation of fluorescent punctae due to the association of MCP-fluorescent protein fusions to the RNA tag (e.g., 12×MS2, 24×MS2, etc.). In synthetic biology applications, MCP can be used to localize proteins to tagged mRNAs, including RNA editing enzymes, or regulatory factors such as translation, localization, or degradation mediators.

While the MCP/MS2 system has been used in biological studies and synthetic applications, a limitation of the current components is that MCP is an independently stable protein, meaning MCP fusions can persist inside cells in the absence of the cognate MS2 hairpin RNA. Such persistence can be problematic in several ways. (1) In imaging applications, fluorescence from free-floating (unbound) MCP-FP can overwhelm signals corresponding to transcript-associated/bound protein units. (2) In synthetic applications, persistence of excess (unbound) MCP proteins can result in undesired effector function on non-targeted RNAs. For example, although MCP-ADAR is able to edit MS2-tagged RNA, the presence of excess (non-RNA bound) MCP-ADAR can lead to off-target editing of untagged and/or endogenous transcripts, which can be problematic in synthetic biology applications.

To overcome the limitations above, described herein is a "destabilized MCP," which is rapidly degraded in mammalian cells but is preserved upon MS2 hairpin binding. In imaging applications, this reduces the background signal due to RNA-unbound MCP-FP fusion proteins, and in synthetic biology applications this approach selectively localizes effector proteins to targeted RNAs of interest (and as a result, lowers/eliminates off-target events). The destabilized MCP, and the design strategy, has multiple applications in RNA imaging and synthetic RNA regulation, detection, delivery, and control.

Additionally, a similar design strategy can be used to develop destabilized protein interaction pairs based on coiled-coil domains (also known as leucine zippers) and ALFAtag—ALFA nanobody respectively. In this scheme, an unbound protein domain is rapidly degraded but is protected by specific binding to another protein domain. Synthetic biology applications of such destabilized protein interaction pairs include controlling and titrating protein-complex stoichiometry.

In addition to MCP and PCP RNA binding proteins, this strategy can be used to design many other proteins whose stabilities depend on RNA binding, including Cas13, dCas1.3, or other related proteins.

SEQ ID NOs: 1-2 show the dPCP nucleic and amino acid sequences; annotations are as follows: C half PCP shown in bolded text (for amino acid sequence of C half PCP, see e.g., SEQ ID NO: 11), PCP monomer shown in italicized text (for amino acid sequence of PCP monomer, see e.g., SEQ ID NO: 12), N half PCP shown in bold italicized text (for amino acid sequence of N half PCP, see e.g., SEQ ID NO: 13), Degron show in dashed underline (for amino acid sequence of Degron, see e.g., SEQ ID NO: 10), S>R mutations shown with double-underlined text, and L>A mutations shown with zigzag-underlined text.

```
dPCP nucleic acid sequence:
                                                          SEQ ID NO: 1

TCCAAGACTGCGTATAGAGTAAACCTGAAACTGGATCAAGCCGATGTCGTAGATAGTG

GGGCTCCTAAAGTGAGGTATACTCAAGTCTGGTCACATGACGTAACGATAGTCGCTAA

CTCTACGGAAGCGAGCCGAAAAAGCCTCTACGATCTCACGAAGTCCCTCGTGGCTACT

TCTCAAGTCGAGGATCTCGTAGTCAATCTTGTCCCGCTTGGGCGCgcggatccgctagccTCAAA

GACAATAGTGTTGAGTGTGGGGGAAGCTACGCGGACCTTGACTGAAATACAACGCACCGCAGATC

GGCAGATTTTCGAGGAGAAGGTGGGGCCTGCTGTCGGCCGCTTGAGGCTTACCGCTTCACTGCGA

CAGAACGGAGCTAAAACCGCCTATAGGGTCAACTTGAAATTGGATCAGGCAGACGTCGTTGATTCT

GGGGCGCCAAAGGTAAGGTATACCCAAGTATGGTCCCACGACGTTACGATTGTAGCCAATTCTACT

GAGGCTTCACGAAAGTCACTCTACGACTTGACCAAATCTCTTGTTGCAACATCACAGGTGGAGGAC

CTTGTCGTCAATTTGGTGCCACTCGGGCGAgcgGGCGCCctagccAGTAAGACCATTGTGCTTAGCG

TAGGGGAAGCCACACGGACGCTTACCGAAATACAGAGAACGGCCGACCGGCAGATTTTTGAA

GAAAAAGTAGGCCCCGCAGTTGGACGCCTGAGGCTTACGGCTTCCCTTCGACAGAGGCGTCG

Aggataa
```

-continued dPCP amino acid sequence:

SEQ ID NO: 2

SKTAYRVNLKLDQADVVDSGAPKVRYTQVWSHDVTIVANSTEASRKSLYDLTKSLVATSQV

EDLVVNLVPLGRADPLASKTIVLSVGEATRTLTEIQRTADRQIFEEKVGPAVGRLRLTASLRQNGAKT

AYRVNLKLDQADVVDSGAPKVRYTQVWSHDVTIVANSTEASRKSLYDLTKSLVATSQVEDLVVNLVPLG

RAGALASKTIVLSVGEATRTLTEIQRTADRQIFEEKVGPAVGRLRLTASLRQRRRG*

SEQ ID NOs: 14-15 show the dPCP nucleic and amino acid sequences, without S>R mutations or L>A mutations; annotations are as follows: C half PCP shown in bolded text (for amino acid sequence of C half PCP, see e.g., SEQ ID NO: 16), PCP monomer shown in italicized text (for amino acid sequence of PCP monomer, see e.g., SEQ ID NO: 17), N half PCP shown in bold italicized text (for amino acid sequence of N half PCP, see e.g., SEQ ID NO: 18), Degron show in dashed underline (for amino acid sequence of Degron, see e.g., SEQ ID NO: 10).

dPCP nucleic acid sequence, without S > R mutations or L > A mutations:

SEQ ID NO: 14

TCCAAGACTGCGTATAGAGTAAACCTGAAACTGGATCAAGCCGATGTCGTAGATAGTG

GGCTTCCTAAAGTGAGGTATACTCAAGTCTGGTCACATGACGTAACGATAGTCGCTAA

CTCTACGGAAGCGAGCCGAAAAAGCCTCTACGATCTCACGAAGTCCCTCGTGGCTACT

TCTCAAGTCGAGGATCTCGTAGTCAATCTTGTCCCGCTTGGGCGCgcggatccgctagccTCAAA

GACAATAGTGTTGAGTGTGGGGGAAGCTACGCGGACCTTGACTGAAATACAAAGCACCGCAGATC

GGCAGATTTTCGAGGAGAAGGTGGGGCCTCTTGTCGGCCGCTTGAGGCTTACCGCTTCACTGCGA

CAGAACGGAGCTAAAACCGCCTATAGGGTCAACTTGAAATTGGATCAGGCAGACGTCGTTGATTCT

GGGCTGCCAAAGGTAAGGTATACCCAAGTATGGTCCCACGACGTTACGATTGTAGCCAATTCTACT

GAGGCTTCACGAAAGTCACTCTACGACTTGACCAAATCTCTTGTTGCAACATCACAGGTGGAGGAC

CTTGTCGTCAATTTGGTGCCACTCGGGCGAgcgGGCGCCctagccAGTAAGACCATTGTGCTTAGCG

TAGGGGAAGCCACACGGACGCTTACCGAAATACAGAGTACGGCCGACCGGCAGATTTTTGAAG

AAAAAGTAGGCCCCCTAGTTGGACGCCTGAGGCTTACGGCTTCCCTTCGACAGAGGCGTCGAg gataa dPCP amino acid sequence, without S > R mutations or L > A mutations:

SEQ ID NO: 15

SKTAYRVNLKLDQADVVDSGLPKVRYTQVWSHDVTIVANSTEASRKSLYDLTKSLVATSQV

EDLVVNLVPLGRADPLASKTIVLSVGEATRTLTEIQSTADRQIFEEKVGPLVGRLRLTASLRONGAKT

AYRVNLKLDQADVVDSGLPKVRYTQVWSHDVTIVANSTEASRKSLYDLTKSLVATSQVEDLVVNLVPLG

RAGALASKTIVLSVGEATRTLTEIQSTADRQIFEEKVGPLVGRLRLTASLRQRRRG

SEQ ID NOs: 3-4 show the dMCP nucleic and amino acid sequences; annotations are as follows: C half MCP shown in bolded text (for amino acid sequence of C half MCP, see e.g., SEQ ID NO: 19), MCP monomer shown in italicized text (for amino acid sequence of MCP monomer, see e.g., SEQ ID NO: 20), N half MCP shown in bold italicized text (for amino acid sequence of N half MCP, see e.g., SEQ ID NO: 21), and Degron show in dashed underline (for amino acid sequence of Degron, see e.g., SEQ ID NO: 10).

dMCP nucleic acid sequence:

SEQ ID NO: 3

GCCCAAAACAGGAAATACACCATCAAAGTGGAGGTGCCCAAAGGGTGCCTGGCGGAGCT

ACCTGAACATGGAGCTGACTATTCCAATCTTCGCTACTAATTCCGATTGCGAACTGATA

GTAAAAGCGATGCAAGGTTTGCTGAAAGACGGCAACCCAATTCCCAGCGCAATCGCCG

CCAATAGCGGCATCTACGCTAATTTCACACAGTTCGTGCTGGTCGACAACGGCGGCACCGGCG

ACGTTACGGTGGCCCCCTCAAACTTTGCCAACGGGATTGCCGAGTGGATAAGCAGCAATAGCAGG

TCCCAGGCCTACAAGGTTACCTGTAGCGTAAGGCAGAGCAGCGCCCAGAACCGAAAGTACACGAT

TAAGGTGGAAGTCCCCAAAGGCGCATGGAGGAGCTATCTTAATATGGAACTGACCATCCCCATATT

CGCGACAAACAGCGACTGTGAGCTGATCGTGAAGGCTATGCAGGGCCTCCTCAAGGATGGGAACC

CGATCCCGTCTGCCATCGCTGCTAACTCCGGCATTTATGCAAACTTCACTCAATTTGTTCTGGTG

GACAATGGTGGGACCGGGGATGTTACCGTGGCTCCCAGCAATTTTGCTAACGGTATCGCAGAA

TGGATCAGTAGTAACAGCAGGAGCCAAGCCTATAAAGTGACGTGCAGCGTACGGCAG<u>AGGAG</u>

<u>AAGAGGC</u> dMCP amino acid sequence:

SEQ ID NO: 4

AQNRKYTIKVEVPKGAWRSYLNMELTIPIFATNSDCELIVKAMQGLLKDGNPIPSAIAANSG

*IYANFTQFVLVDNGGTGDVTVAPSNFANGIAEWISSNSRSQAYKVTCSVRQSSAQNRKYTIKVEVPKGA*

*WRSYLNMELTIPIFATNSDCELIVKAMQGLLKDGNPIPSAIAANSGIYANFTQFVLVDNGGTGDVTVA*

*PSNFANGIAEWISSNSRSQAYKVTCSVRQ*<u>RRRG</u>*

TABLE 1

| Amino Acid Sequences from which dMCP and dPCP were derived. | |
| --- | --- |
| Protein Name | Amino Acid Sequence |
| SEQ ID NO: 5, tdMCP (MCP monomer 1 in bolded text - SEQ ID NO: 22; MCP monomer 2 in italicized text - SEQ ID NO: 23) | ASNFTQFVLVDNGGTGDVTVAPSNFANGI AEWISSNSRSQAYKVTCSVRQSSAQNRKY TIKVEVPKGAWRSYLNMELTIPIFATNSD CELIVKAMQGLLKDGNPIPSAIAANSGIYA *MASNFTQFVLVDNGGTGDVTVAPSNFANGIAE* *WISSNSRSQAYKVTCSVRQSSAQNRKYTIKVEVP* *KGAWRSYLNMELTIPIFATNSDCELIVKAMQGL* *LKDGNPIPSAIAANSGIYA* |
| SEQ ID NO: 6, tdPCP (PCP monomer 1 in bolded text, PCP monomer 2 in italicized text; for amino acid sequence of PCP monomer 1 or 2, see e.g., SEQ ID NO: 24) | LASKTIVLSVGEATRTLTEIQSTADRQIFE EKVGPLVGRLRLTASLRQNGAKTAYRVN LKLDQADVVDSGLPKVRYTQVWSHDVTI VANSTEASRKSLYDLTKSLVATSQVEDLV VNLVPLGRADP*LASKTIVLSVGEATRTLTEIQS* *TADRQIFEEKVGPLVGRLRLTASLRONGAKTAY* *RVNLKLDQADVVDSGLPKVRYTQVWSHDVTIV* *ANSTEASRKSLYDLTKSLVATSQVEDLVVNLVPL* *GR* |

TABLE 2

| Ribonucleotide sequence from which MS2-tornado and PP7-tornado were derived | |
|---|---|
| Transcript Name | Ribonucleotide Sequence |
| SEQ ID NO: 7, Tornado- F30-TAR_variant_1(pepper); F30 is shown in bolded text; TAR_variant_1(pepper) is shown in double-underlined text | cggtcccaagcccggataaaatgggaggggggggaaaccgccta accatgccgagtgcggccgcttgccatgtgtatgtgggacgcgttg ccacgtttcccacatactctgatgatccgctagcaaa<u>ggctcgtctg</u> <u>agctcattagctccgagccc</u>gaggtaccggatcattcatggcaagc ggccgcggtcggcgtggactgtagaacactgccaatgccggtccca agcccggataaaagtggagggtacagtccacgc |

TABLE 3

| Ribonucleotide sequences for MS2-tornado and PP7-tornado | |
|---|---|
| Transcript Name | Ribonucleotide Sequence |
| SEQ ID NO: 8, Tornado- F30 -MS2; F30 is shown in bolded text; MS2 is shown in double-underlined text | cggtcccaagcccggataaaatgggaggggggggaaaccgccta accatgccgagtgcggccgcttgccatgtgtatgtgggacgcgttg ccacgtttcccacatactctgatgatccgctagcaaa<u>gcacgagcat</u> <u>cagccgtgcc</u>gaggtaccggatcattcatggcaagcggccgcggt cggcgtggactgtagaacactgccaatgccggtcccaagcccggat aaaagtggagggtacagtccacgc |
| SEQ ID NO: 9, Tornado- F30-PP7; F30 is shown in bolded text; PP7 is shown in double-underlined text | cggtcccaagcccggataaaatgggaggggggggaaaccgccta accatgccgagtgcggccgcttgccatgtgtatgtgggacgcgttg ccacgtttcccacatactctgatgatccgctagcaaa<u>ggagcagac</u> <u>gatatggcgtcgctccc</u>gaggtaccggatcattcatggcaagcggc cgcggtcggcgtggactgtagaacactgccaatgccggtcccaagc ccggataaaagtggagggtacagtccacgc |
| MS2 - SEQ ID NO: 54 | gcacgagcatcagccgtgc |
| PP7 - SEQ ID NO: 53 | ggagcagacgatatggcgtcgctcc |

Example 2: Conditionally Stable Proteins for Single-Molecule RNA Imaging and Protein Interaction Control In Live Cells Many multi-protein complexes in the cell, such as the ribosome, consist of proteins that degrade if they do not form a complex, so excess protein is eliminated if more is produced than needed for complex assembly. This work describes methods for artificial design of proteins that degrade unless they form a specific complex, which can be applied to produce a conditionally stable RNA binding protein for live-cell single-molecule mRNA imaging with low background signal. Additionally, targeted protein degraders can be made to remove excess protein subunits during the formation of multi-protein complexes, replicating cellular function. Degradation-sensitive transcriptional and translational feedback mechanisms can be built to regulate expression of conditionally stable proteins for consistent behavior in multiple cell types. These efforts produce a toolbox of degradation-based methods for precise observation and manipulation of protein interactions.

Introduction

The Ubiquitin Proteasome System

A major research focus in biology is how cells control expression of specific genes at specific times. This is often studied at the stages of gene transcription into mRNA, and mRNA translation into protein. However, the dynamics of gene expression are also tightly controlled by proteasomal degradation. Proteasomes have been referred to as the "evil twin" of ribosomes, and their degradation mechanism involves unraveling proteins into linear peptides, which enter the proteasome to be shredded bit-by-bit, reaching a depolymerization rate comparable to the ribosome's polymerization rate.

In eukaryotes, degradation of specific proteins is carried out by the ubiquitin-proteasome system, in which ubiquitination of a target protein leads to its recognition and degradation by the 26s proteasome. In brief, the function of this system begins with expression of poly-ubiquitin chains that are cleaved into single ubiquitin proteins, then activated by E1 ligases which form a thioester bond with ubiquitin. Activated ubiquitin is transferred from a handful of E1s to tens of different E2 ligases. Next, hundreds of unique E3 ligases catalyze ubiquitin transfer from E2s to a lysine on proteins targeted for degradation.

E3 Ligases Target Proteins Based on Highly Specific Criteria

Ubiquitination occurs in three stages because each additional stage increases the cell's ability to control ubiquitin targeting by an order of magnitude. Over 600 distinct E3 ligases are encoded within the human genome, and each one is capable of targeting a specific set of proteins. E3 ligases can discriminate among various proteins emerging from the same mRNA transcript. They can degrade proteins with specific post-translational modifications, in specific subcellular compartments, and at specific stages in the cell life cycle. They can also selectively degrade proteins based on changes in the accessibility of an E3 recognition-site (also known as a "degron") caused by the protein interacting with other molecules. This allows types of protein level control through regulation of degradation that are not possible through transcriptional and translational regulation.

This work focuses on "degron masking": a mechanism where protein-protein interactions conceal a degron which would otherwise be recognized by E3 ligases and trigger protein degradation. This mechanism is involved in removing excess subunits during the assembly of multi-protein complexes, from simple hemoglobin tetramers, to massive protein-RNA complexes like the ribosome. Proteins subject to degron masking can be identified by their non-exponential degradation rates, where the majority of protein degrades rapidly, and the fraction that integrates into a degron-masking complex exhibits an extended half-life equal to that of other proteins in the complex (see e.g., McShane et al. Cell 167, 803-815.e21 (2016)).

Applying Principles of Degron Masking for Sensitive Assays

Degron masking has been used to engineer conditionally stable proteins. Some of these conceal degrons until a heat, chemical or light stimulus exposes them, triggering protein degradation (see e.g., Bonger et al. Nat. Chem. Biol. 7, 531-537 (2011); Bonger et al. ACS Chem. Biol. 9, 111-115 (2014); Dohmen et al. Science 263, 1273-1276 (1994); Deng et al. Nat. Commun. 11, 304 (2020)). Others leave degrons unconcealed until a target protein binds its ligand, leading to clearance of unbound proteins through degradation and preservation of ligand-bound protein (see e.g., Wu et al. Nat. Methods 16, 862-865 (2019); Tang et al. eLife 5, e15312 (2016)). Clearance of unbound protein is also used for in-vitro assays that permit highly sensitive detection of proteins, including western blot and immunofluorescence. In these assays, a protein of interest is stained with an antibody, then subsequent wash steps remove excess antibody to eliminate background signal. Thus, engineered proteins that are conditionally stable through degron masking upon binding of a ligand can permit highly sensitive in-vivo detection of the ligand.

Significance of Work

Although several methods have been developed to apply degron masking for conditional protein degradation based on intramolecular interactions, their performance for sensitive in-vivo detection of molecules like RNA (see e.g., Wu et al. Nat. Methods 16, 862-865 (2019) remains far from the capabilities of in-vitro methods (see e.g., Choi et al. Dev. Camb. Engl. 145, dev165753 (2018)). Both methods work by binding a target molecule with a protein, then clearing excess protein that does not bind the target, so the issues that prevent the degron-masking approach from matching in-vitro approaches are based on performance and time restrictions more than functional principles. Described in this work are methods to raise the performance and reliability of conditionally stable proteins until their molecular sensitivities approach those of in-vitro methods. Successful implementation of these methods can achieve sensitive detection and imaging of molecules, with the added capability of observing real-time molecular dynamics in living systems.

Additionally, although methods to harness the unique degrading capabilities of E3 ligases have been developed to target specific protein variants emerging from a single transcript (see e.g., Stephens et al. ACS Synth. Biol. 10, 2396-2408 (2021); Bery et al. Nat. Commun. 11, 3233 (2020); Lim et al. ACS Cent. Sci. 7, 274-291 (2021)), they have not yet been applied to replicate the protein complex assembly quality control mechanisms used by the cell for construction of multi-subunit assemblies. Described herein are methods to harness an E3 ligase for robust quality control during the assembly of engineered protein complexes. Successful implementation of these methods permit artificial replication of cellular quality control mechanisms and manipulation of these mechanisms for modification of multi-protein complexes. These methods have uses in engineering supramolecular complexes with capabilities approaching those of complexes made through similar mechanisms in the cell.

This work is divided into three sections:

Section 1: MS2 Cap Protein That is Conditionally Stabilized Upon RNA Binding Permits Low Background Single Molecule RNA Imaging in Live Cells. Degron masking is integrated into an RNA binding protein for improved single-molecule imaging in live cells that approaches the image quality of in-vitro methods.

Section 2: Feedback Systems for Robust Conditional Degradation. Cell-cell variability in protein expression, which negatively impacts the performance of degron masking systems, can be reduced through the use of negative feedback systems.

Section 1: MS2 Cap Protein that is Conditionally Stabilized Upon RNA Binding Permits Low Background Single Molecule RNA Imaging in Live Cells

Background

Subcellular localization of mRNA is necessary for many processes in the cell. For example, localization of beta-actin mRNA enables fibroblast movement through concentrated actin translation at a defined end of the cell, and localization of arc mRNA in neurons allows protein translation at specific dendrites, which can play a role in memory storage. Imaging the subcellular distribution of single mRNA molecules is possible for fixed cells with single-molecule fluorescence in-situ hybridization (smFISH). smFISH stains specific RNAs in fixed cells with a concentrated solution of fluorescent oligo probes, and then excess probes are washed away to reveal punctae where multiple probes have tagged a single RNA target. This approach has yielded insights into RNA translation, splicing, transport, and degradation, with some FISH methods capable of imaging thousands of transcripts in parallel. However, it cannot reveal real-time dynamics of mRNA behavior in live cells.

Single-molecule live cell RNA imaging can be achieved with the MS2-MCP system, in which a bacteriophage MS2 coat protein fused to a fluorophore tags its cognate 'MS2' RNA aptamers attached to an RNA of interest. This specific protein-RNA pair has been used for live cell RNA imaging; see e.g., Bertrand et al. Mol Cell. 1998 October; 2(4):437-45. Its temporal precision has produced insights into dynamic phenomena like transcriptional bursting and translation. The key weakness of MS2-MCP is that excess MCP cannot be washed away when all MS2 has been labeled, so it lingers in the cell and produces high background fluorescence that obscures images.

Single-molecule live RNA imaging systems that overcome this weakness include fluorogenic dyes that fluoresce only upon binding specific RNA aptamers, like the mango II system. However, Mango II is limited to one color and requires exogenous dye addition. This system also lacks the flexibility of genetically encoded systems like MS2-MCP, whose functionality can be customized by mutation and fusion of various protein domains. One genetically encoded "fluorogenic" live-cell single-RNA imaging system is tDeg, a peptide that is stable when bound to TAR RNA aptamers, but degraded when not. tDeg is capable of imaging single mRNA transcripts tagged with an array TAR aptamers in live cells.

It is contemplated herein that the principle behind tDeg can be integrated into MCP so that it would degrade when not bound to MS2 RNA loops. A conditionally stable MCP would be readily compatible with many MS2 systems. Additionally, MCP-MS2 dissociates on the order of hours, while the binding pair used for tDeg, tat-TAR, dissociates on the order of minutes. Despite having similar affinity to the tat-TAR interaction, the stabilizing "fluorogenic" effect of MS2-MCP interaction could be stronger because slower dissociation would protect MCP from degradation for an extended amount of time. See e.g., Bertrand et al. Mol. Cell 2, 437-445 (1998); Hu et al. "Enhanced Single RNA Imaging Reveals Dynamic Gene Expression in Live Animals". 2022.07.26.501631 Preprint at doi 10.1101/2022.07.26.501631 (2022); Li et al. "An improved MS2-MCP imaging system with minimal perturbation of mRNA stability." 2022.02.05.479257 Preprint at doi 10.1101/2022.02.05.479257 (2022); Chubb et al. Curr. Biol. CB 16, 1018-1025 (2006); Halstead et al. Science 347, 1367-1671 (2015); Cawte et al. Nat. Commun. 11, 1283 (2020); Wu et al. Nat. Methods 16, 862-865 (2019); Lowary et al. Nucleic Acids Res. 15, 10483-10493 (1987); Long et al. Biochemistry 34, 8885-8895 (1995).

Section 1.1 Design and Testing of Conditionally Stable MCP

MCP forms an obligate homodimer with a stable clasp-like structure. A fused dimer version (tdMCP), has been described, which not only improved MS2 labeling efficiency but stabilized the protein's structure, making it more accommodating to insertions; see e.g., Wu et al. Biophys. J. 102, 2936-2944 (2012); Peabody et al. Nucleic Acids Res. 24, 2352-2359 (1996).

As described herein, tdMCP was circularly permuted to relocate its N and C termini to the unstructured loop adjacent to the binding site (see e.g., FIG. 1). Circular permutation made S52 on the original tdMCP the new C-terminus, and it was hypothesized that a C-terminal -RRRG degron could be introduced to induce conditional stability. This degron has been applied to create conditionally stable proteins in which the degron was hidden until exposed by a chemical or light inducible conformational change; see e.g., Bonger et al. Nat. Chem. Biol. 7, 531-537 (2011); Bonger et al. ACS Chem. Biol. 9, 111-115 (2014). Upon exposure, the degron is recognized by endogenous E3 ligases, including several ubiquitin ligase complex adaptors for cullin 2 and cullin 4, which rapidly degrade the protein. By placing this degron in the binding pocket of MCP, it was hypothesized that it would be hidden when MCP binds RNA, but be exposed in unbound MCP, leading to removal of the excess MCP that would otherwise generate background fluorescence.

Figure 2A:
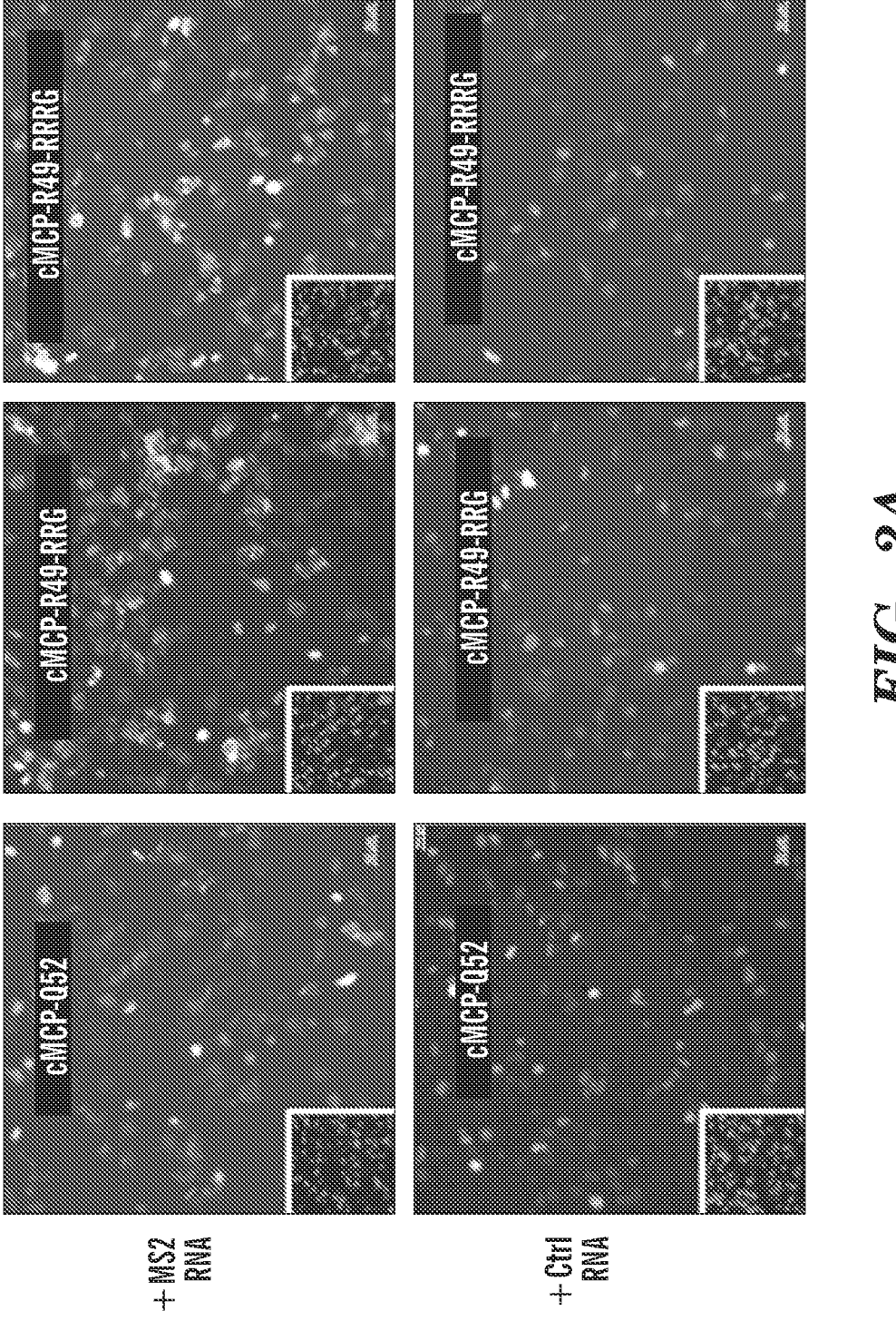
FIG. 2A-2C is a series of images showing initial characterization of an RNA-stabilized circularly permuted MCP.
Figure 2A:
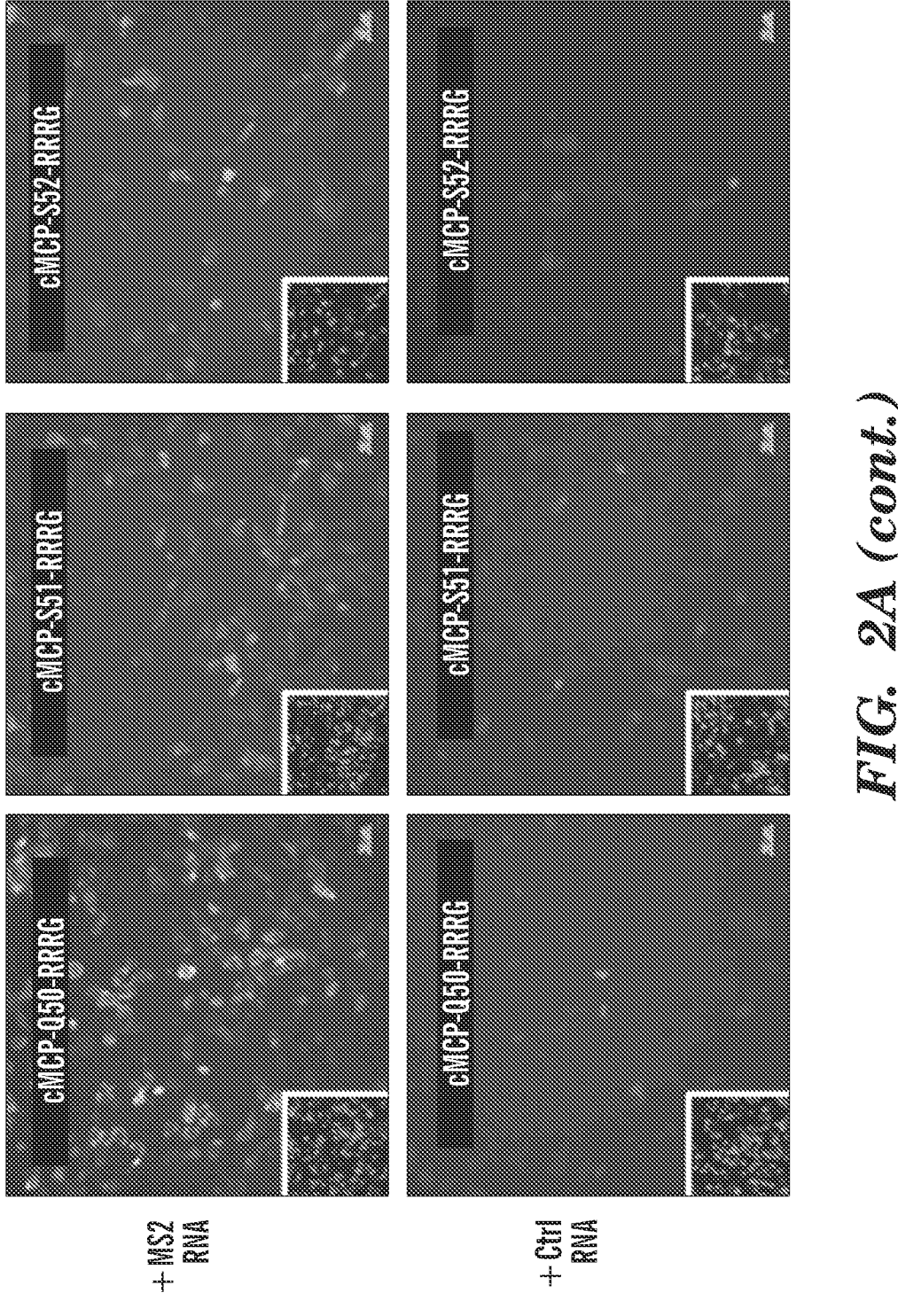

In order to create an RNA-stabilized MCP, several variants of circularly permuted mVenus-tagged MCP were screened with the -RRRG degron inserted at various positions. When transfected into HEK293FT cells, permuted MCP variants with the degron inserted after Q50 degraded and were stabilized by MS2 containing RNA, but variants with the degron inserted before Q50 did not degrade, indicating that the permuted MCP was structurally intact, but the degron was concealed too deep within its structure (see e.g., FIG. 2A). These results show that conditional stability of permuted MCP with the -RRRG degron is caused by the degron being exposed to E3 ligases, and then concealed upon MS2 binding. It is not a result of MCP's structure being disordered in the absence of MS2 ligand, which is the mechanism of several other conditionally stable proteins (see e.g., Dohmen et al. Science 263, 1273-1276 (1994); Tang et al. eLife 5, e15312 (2016)). In the following work, the best performing variant was used with the RRRG degron placed immediately after Q50, which I refer to as "MCPQ".

Figure 2B:
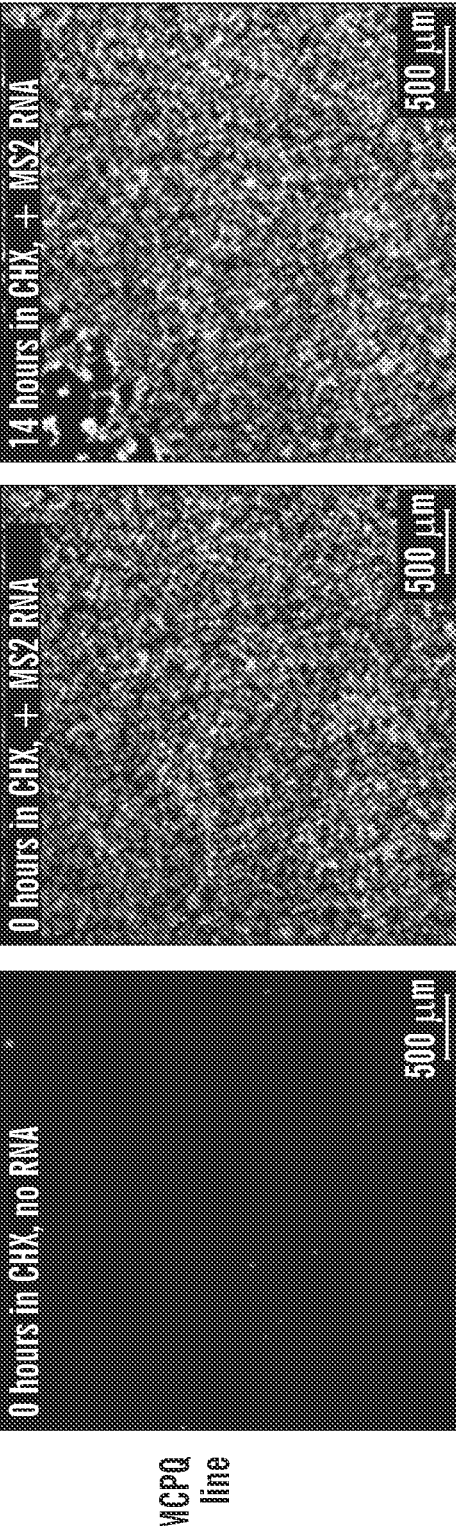
Figure 2C:
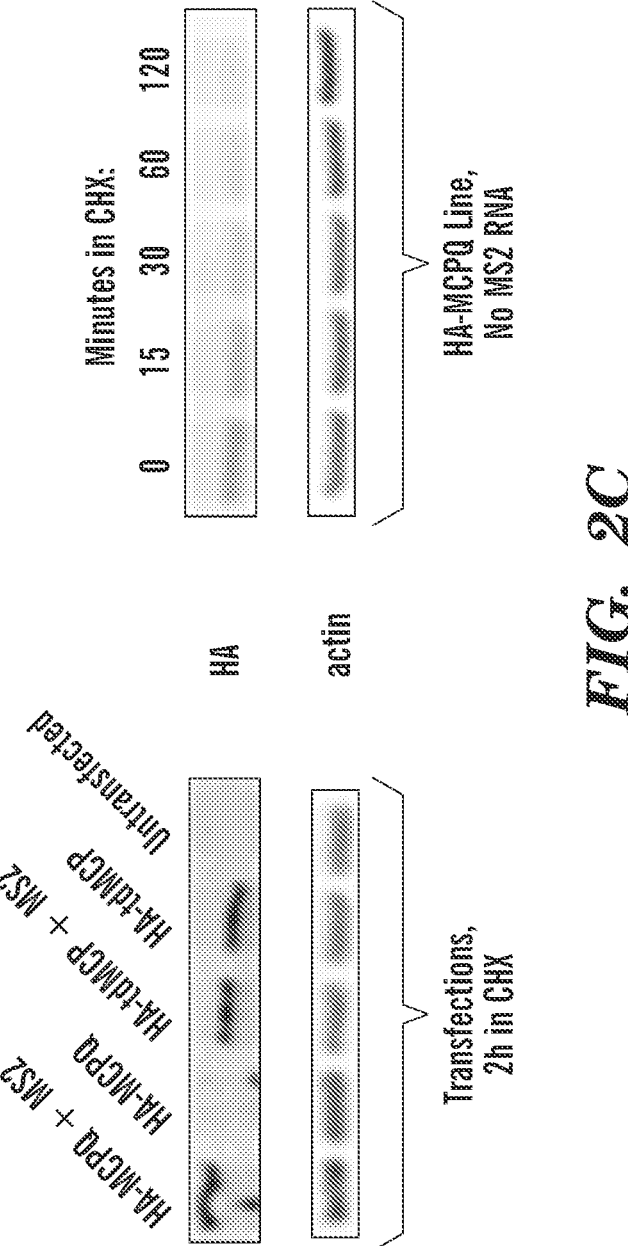

A stable HEK293FT cell line was generated that constitutively expressed a hemagglutinin (HA) tagged 4×mNeon-Green-HA-MCPQ on a UBC promoter for characterization of its dynamic range and half-life. These cells were transfected with and without a plasmid overexpressing tornado-MS2, a circular mRNA with a long half-life so as not to influence the measure of MCPQ stability when in complex with mRNA. 15 mM cycloheximide was added to these cells to halt protein translation and observe the rate of fluorescence decay as a result of protein degradation. While the tornado-MS2 transfected cells showed no noticeable degradation over several hours (see e.g., FIG. 2B for 2 hours; no significant degradation of stabilized MCPQ has been detected after 14 hours (data not shown)), the non-transfected cell line had such weak signal that half-life could not be measured by microscopy. Anti-HA Western blot revealed that this half-life appeared to be on the order of 15-30 minutes (see e.g., FIG. 2C). A transfection in HEK293FT comparing tdMCP and MCPQ stability was conducted with cycloheximide chase (see e.g., FIG. 2C). This revealed that MCPQ stabilized by tornado-MS2 appears to be as stable over two hours as the naturally stable tdMCP, showing that the RRRG degron is well shielded from E3 recognition in the MCPQ-RNA complex.

Section 1.2

Rationale: The binding kinetics and temporal dynamics of MCPQ can be measured to understand what minimal rate of expression can be used to effectively label all MS2-tagged transcripts in a cell, how long it takes for MS2-containing RNA to be labeled at this expression rate, and how long a single MCPQ protein can remain attached once bound to MS2 RNA. Tests of imaging an MS2-tagged RNA with MCPQ yielded suboptimal results when the RNA lacked a polyadenylation signal. Without 3' polyadenylation, eukaryotic mRNAs are rapidly degraded. It was hypothesized that the poly-A-tail-less transcript was degrading before it could be fully labeled by MCPQ, and a strong mRNA signal was recovered upon addition of an SV40 polyadenylation signal (data not shown). It is expected that specific MCPQ expression rates are optimal for labeling different RNA depending on RNA half-life, and thorough characterization of the MCPQ-RNA interaction can help determine these levels.

Results: MCPQ's increased stability when bound to mRNA is in part dependent on binding strength. It must bind strong enough to outcompete E3 ligase binding to its degron, and it must remain bound for a long period of time to avoid degradation. To better characterize the binding properties of MCPQ, it was expressed it in BP10a *E. coli* with an N-terminal HIS tag, and it was successfully purified it with native affinity chromatography (data not shown). Affinity of this purified protein can be determined using electrophoretic mobility shift assay (EMSA). The dissociation rate can also be determined, which reveals the maximum length of time that MCPQ can be stabilized upon binding MS2. MCPQ's structure in complex with MS2 RNA can also be obtained. A structure allows for better understanding of the mechanism through which the degron is masked, and specifically to what degree the positively charged C-terminal RRRG degron is interacting with mRNA.

Next, optimal MCPQ expression schemes can be determined for various mRNA half-lives. An array of mRNAs with distinct half-lives can be assembled using various stabilizing elements, such as polyadenylation signals, and destabilizing elements, such as an AU-rich 3' UTR. Actinomycin D chase followed by q-rtPCR can be used to determine half-lives of the mRNAs. A tet-inducible MCPQ cell line (described in Section 2.1) can then be used to determine the rate of MCPQ expression that produces maximum signal-to-noise for each respective mRNA. mRNAs with half-lives below 15 minutes degrade faster than MCPQ, so it is expected that MCPQ binding to these mRNAs will not effectively stabilize it. Through this mRNA screen, a minimal RNA half-life can be determined where MCPQ labeling is significantly more effective than MCP labeling.

In order to image mRNAs whose half-life falls below this threshold, it can be possible to shorten the half-life of unbound MCPQ through the replacement of amino acids near the degron with lysine. Data presented below indicates that if additional lysines are introduced near the active site of E3 ligases (near the degron), then degradation rates will increase. Addition of one lysine to the C-terminus of the RRRG degron can accelerate ubiquitination rates, and addition of several lysines near an N-degron can strongly accelerate degradation. Addition of unstructured domains can accelerate 26S proteasomal degradation of a protein, which could further reduce half-life of MCPQ. Finally, addition of an N-terminal degron into the binding pocket, such that it would be masked upon RNA binding, could shorten the half-life of unbound MCPQ but not RNA-bound MCPQ. Masked N-degrons have been used to generate conditionally stable proteins, such as a dihydrofolate reductase that undergoes heat-induced degradation (see e.g., Dohmen et al. Science 263, 1273-1276 (1994)). The effect of these modifications on MCPQ half-life can be analyzed with western blot. So long as MCPQ-RNA half-life remains more than an order of magnitude longer than that of unbound MCPQ, background will be reduced, therefore these modifications can permit MCPQ to work with shorter-lived transcripts.

Section 1.3 Single Molecule Live Imaging in Mammalian Cell Lines with MCPQ

Rationale: The results from section 1.1 show that MCPQ was stabilized in the presence of saturating concentrations of overexpressed MS2-containing RNA. From this data, it is to be determined if MCPQ maintains the nanomolar binding affinity that makes MCP suitable for single-molecule imaging. It is hypothesized that if MCPQ has maintained this binding affinity, it can saturate MS2 sites on RNA molecules to resolve them as a single fluorescent puncta, and MCPQ degradation when not binding RNA will lead to low image background. If this is the case, the increased imaging quality can be used to uncover previously unseen mRNA dynamics.

MCPQ can be used for visualizing differences in the movement of mRNA transcripts at a single-molecule level. Exemplary transcripts to be analyzed include H2B, Lysozyme Secretion Signal (LSS), and TOM20. H2B is a nuclear protein that is synthesized in the cytosol prior to transport into the nucleus, so its transcript is expected to be found in the cytosol. Transcripts encoding proteins that span the plasma membrane, are secreted, or are ER-targeted produce a signal peptide during translation that is recognized by the signal recognition particle (SRP). The SRP halts translation and transports the nascent peptide, together with ribosome and mRNA, to the endoplasmic reticulum, where it is anchored so that the protein can be cotranslationally threaded into the ER membrane. Thus, transcripts for these proteins are static when anchored to the ER. TOM20 spans the mitochondrial outer membrane, but unlike proteins spanning the plasma membrane, it does not rely on cotranslational mechanisms for insertion, as revealed by in-vitro TOM20 membrane insertion in the absence of RNA. Most mitochondrial membrane proteins can be post-translationally imported like TOM20, but this does not exclude the possibility of cotranslational import for mitochondrial membrane proteins. Electron cryo-tomography has shown ribosomes associate with the mitochondrial surface, and when translation is halted with cycloheximide, ribosome-mRNA complexes can be found anchored to the mitochondria, e.g., by the nascent peptide emerging from the ribosome. It is hypothesized that transcripts encoding the N-terminal signal peptide from TOM20 can begin inserting said peptide into the mitochondrial membrane before translation is completed, which would be observed as brief interactions between TOM20 mRNA and mitochondria.

Figure 3A:
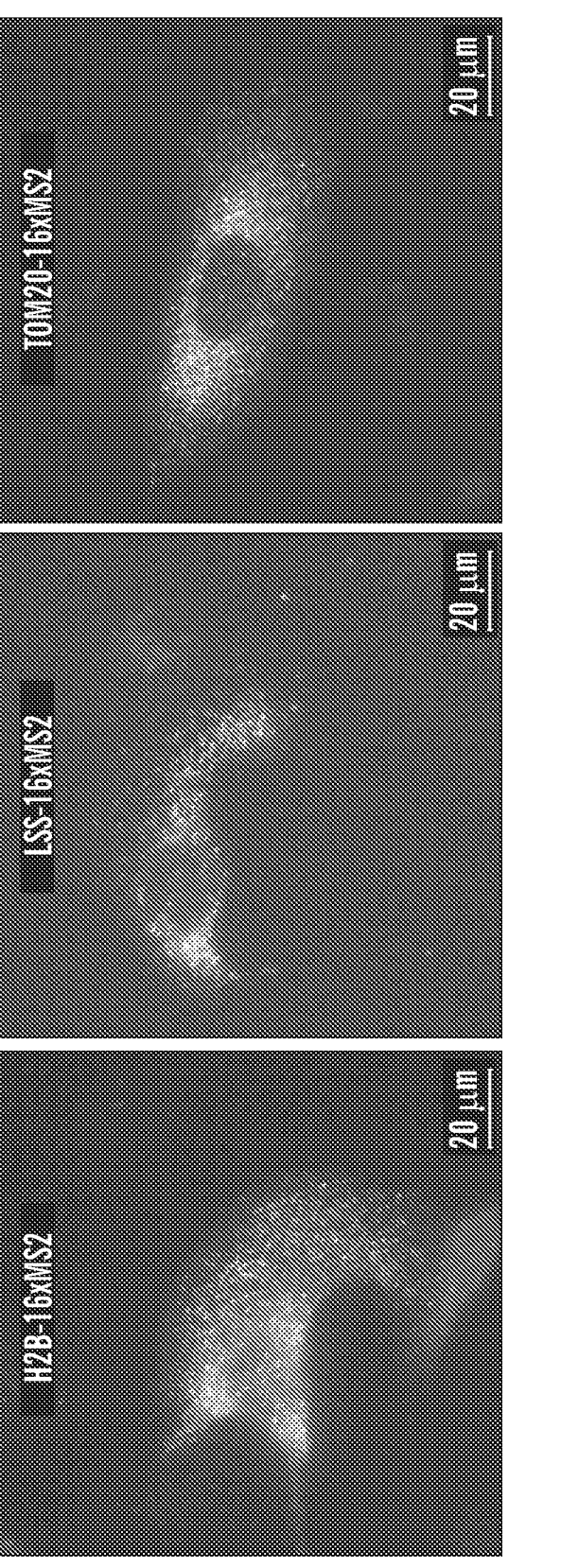
FIG. 3A-3D show single molecule imaging with MCPQ.
Figure 3B:
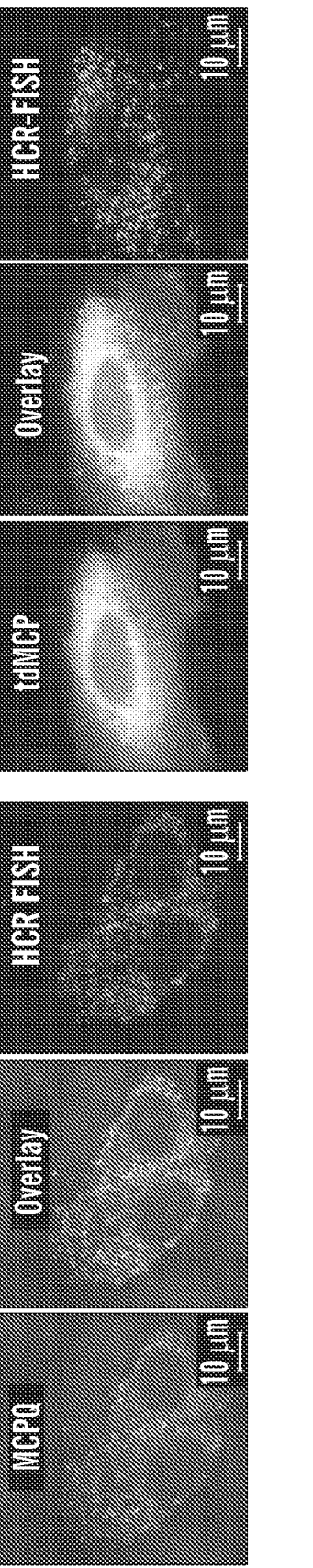
Figure 3C:
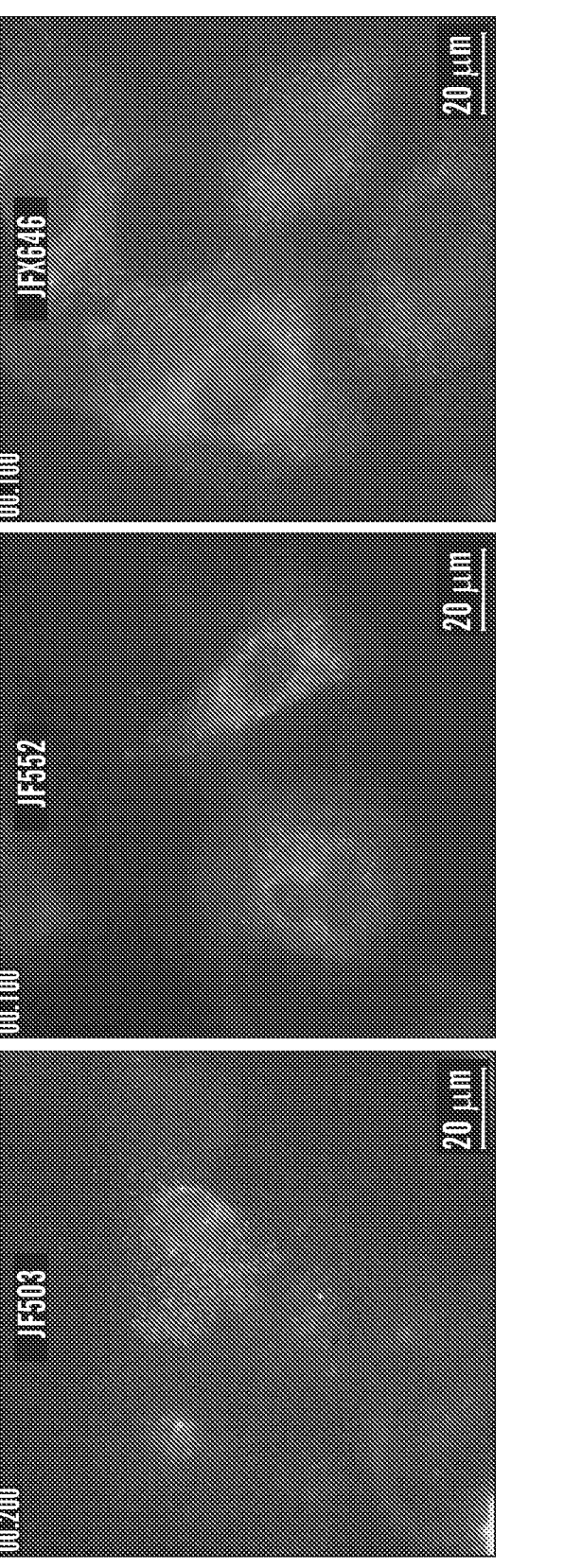
Figure 3D:
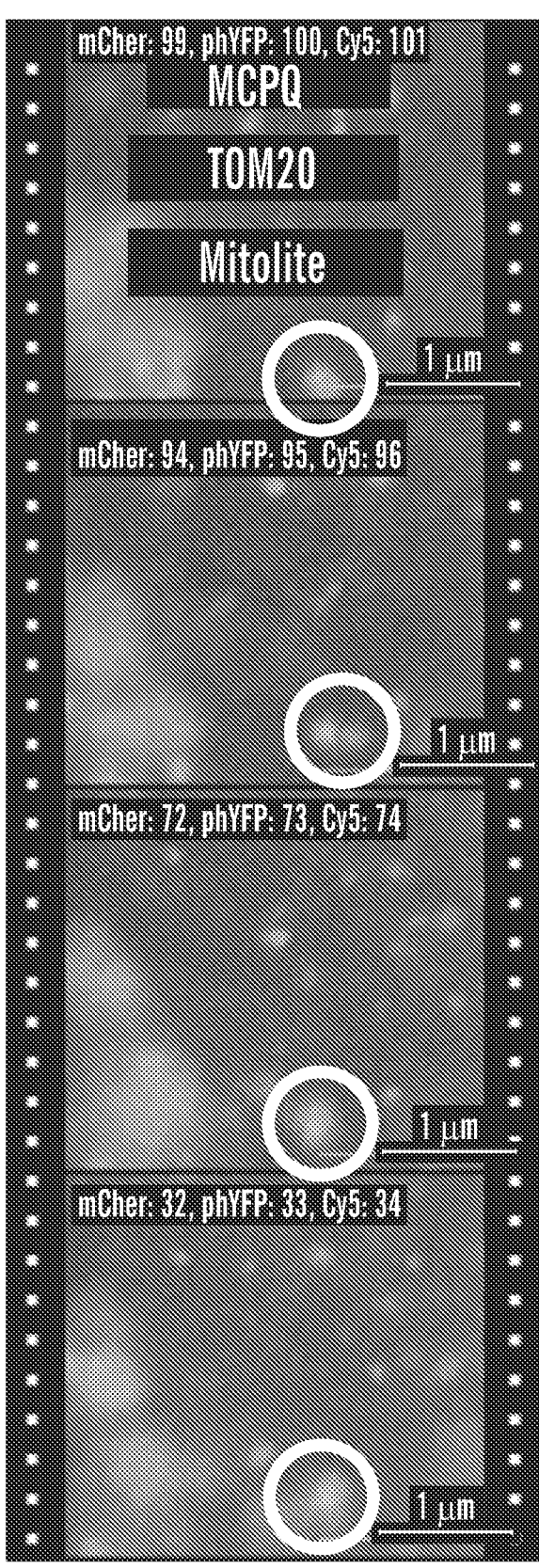
Figure 3D:
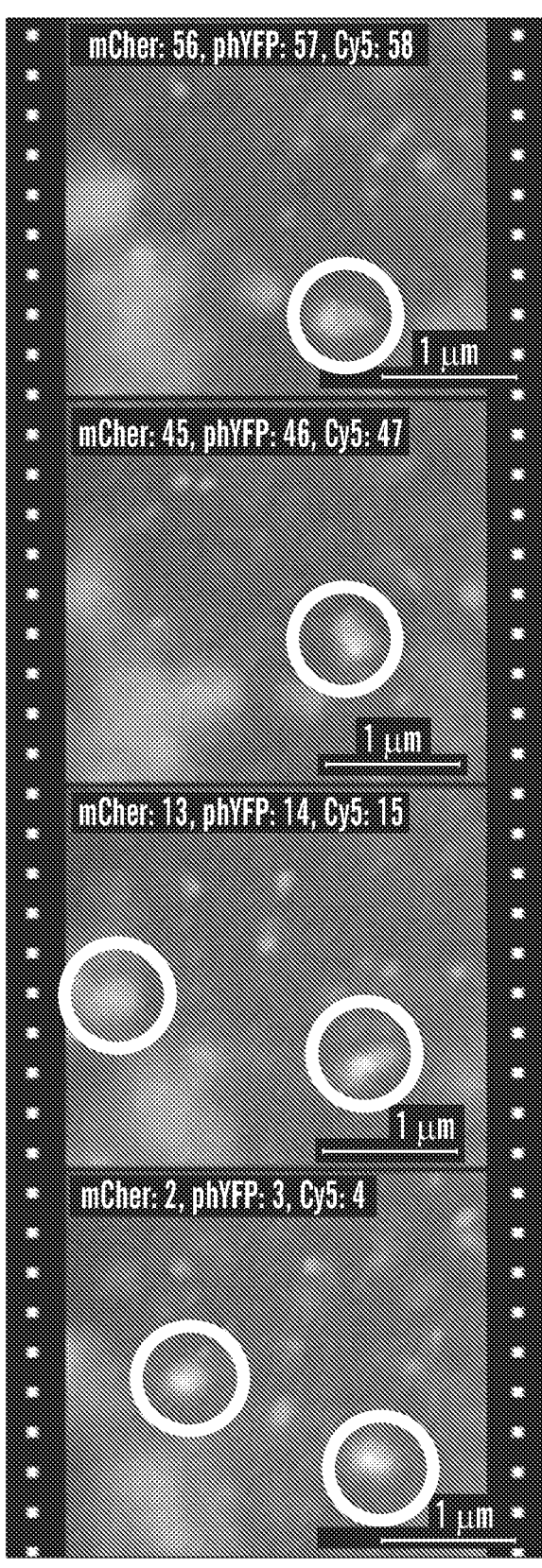

Results: Several mRNA variants with different subcellular localization patterns were transfected into U2OS cells along with MCPQ to test its single-molecule imaging capabilities. MCPQ resolved single H2B-mCherry-16×MS2 transcripts with sufficient clarity to record their movements in real time (50 ms exposure/20 frames per second) on a conventional fluorescence microscope, and these mRNAs moved freely throughout the cytosol as expected (see e.g., FIG. 3A). Lysozyme secretion signal-mTurq-16×MS2 transcripts were imaged by MCPQ and, as expected, were anchored in place at the ER (see e.g., FIG. 3A). For confirmation that the punctae observed were mRNA transcripts, HCR-FISH was performed to label MS2-containing transcripts on cells transfected with MS2-tagged H2B mRNA. Overlap between MCPQ and HCR signal confirmed transcript labeling, with much lower background than the stable tdMCP (see e.g., FIG. 3B). However, paraformaldehyde fixation appeared to increase the background fluorescence in these images, likely due to induction of autofluorescence. Further FISH experiments can be performed using immunostaining on the HA tag in MCPQ for improved image quality. Upon imaging TOM20 transcripts with MCPQ, a range of movement patterns were noted from free to fixed, with fixed transcripts accumulating in the center of the cell outside of the nucleus, where mitochondria are concentrated (see e.g., FIG. 3A). To ensure that this pattern was not an artifact of TOM20 overexpression, MCPQ was used to image a cell line with mcherry-8×MS2 knocked into the endogenous TOM20 gene via CRISPR. The 8×MS2 yielded weakened MCPQ signals relative to 16×MS2, but transcripts could be seen moving together with mitochondria as tagged by both mCherry and MITOTRACKER (see e.g., FIG. 3D). In further work, a knock-in line with more than 8 MS2 loops can exhibit brighter mRNA spots that stand out more clearly from background, and live stains for lysosomes and stress granules can help further confirm that the moving spots with TOM20, MITOLITE, and MCPQ signal are indeed mitochondria.

In further work, neuronal transcripts can be imaged. Many neuronal transcripts exhibit distinct subcellular localization, and even undergo localized translation to synthesize proteins at specific dendrites, which is thought to play a role in memory formation, among other functions. For example, Arc mRNA accumulates only at dendrites receiving stimulus, while it is degraded in inactive dendrites. Many of these transcripts have been studied at the single-molecule level, but it is expected that MCPQ can yield significantly clearer images and/or videos of single molecule dynamics than before, and is expected to unveil previously unseen behaviors as with TOM20.

Section 1.4 Application of MCPQ for Single-Molecule RNA Pulse-Chase Experiments Rationale: A different method from cycloheximide chase is needed to measure the half-life of MCPQ when bound to long-lived RNA. Although cycloheximide chase showed the half-life of MCPQ in the presence of tornado-MS2 is significantly longer than two hours, this assay is not suitable for determining the exact half-life because cycloheximide causes ubiquitin depletion after two hours, which interferes with protein degradation. A method that cuts off MCPQ production at a specific time point without affecting production of other proteins can be used for determining MCPQ-RNA half-life. This can be tested with a fusion of HALOTAG and MCPQ. HALOTAG is a haloalkane dehalogenase that covalently and irreversibly bonds to cell-permeant haloalkane dyes and other ligands, allowing live staining of proteins in the cell at specific timepoints. HALOTAG is a multifunctional protein that can be fluorescent. Specifically, HALOTAG is a self-labeling enzyme that conjugates to chloroalkane substrates, which can be fluorescent dyes, photosensitizing dyes, or any other HALOTAG ligand.

Results: A 2×HaloTag®-MCPQ fusion yielded clear single-molecule images in yellow, red, and far-red channels upon staining with various JANELIAFLUOR HALOTAG dyes, all of which had a low rate of photobleaching (see e.g., FIG. 3B). 2×Halotag®-MCPQ can be suitable for measuring the half-life of RNA-bound MCPQ using pulse-chase. Specifically, an initial stain can be performed with either yellow, red, or far-red dyes, and a chase ligand can be added after a set period. Any nascent HALOTAG-MCPQ that binds MS2 before the addition of the chase stain can be tagged with the original stain, while any binding afterwards can be tagged with the chase stain, which outcompetes the original stain for HALOTAG labeling. MCPQ that does not bind MS2 during staining is quickly cleared by degradation during the stains, so lingering MCPQ labeled with the original stain does not tag additional RNAs after the chase stain is added. This allows for determination of half-life of MCPQ in complex with long-lived RNA by measuring the decay rate of signal from the original stain after the chase has been added. The change in fluorescent signal over time can be measured with flow cytometry, and the results can be analyzed on western blot as well due to HALOTAG's covalent tagging mechanism. Pulse chase is also useful for imaging mRNA transport by tracking changes in subcellular distribution for mRNA produced within a narrow time frame. In this application, the JFX646 dye can be useful as a chase stain because it only fluoresces upon HALOTAG labeling, so data collection can proceed immediately after JFX646 chase addition, with no wash step.

Section 1.5 Multi-Cell Single-Molecule RNA Tracking In-Vivo within *Drosophila* Using Conditionally Stable MCP Rationale: Transport of mRNA to specific subcellular sites is critical for proper tissue development in multicellular organisms, as is intracellular mRNA transport of transcripts, like bicoid in the fruit fly *Drosophila*. Although the phenomenon of subcellular and intracellular mRNA transport has been explored in vivo within fly embryos, it has not yet been conducted at a single-molecule level in live organisms. This is partially because a method for imaging single-RNAs in with stable MCP is not easily extendable to multicellular settings. To image single molecules with stable MCP, background fluorescence in the cytosol is lowered by equipping MCP with a nuclear localization signal (NLS) that moves MCP not bound to RNA to the nucleus. This can produce bright nuclear signal that obscures images with nuclei in the imaging field. Thus, for live in-vivo images, MCP struggles to resolve single RNA molecules outside of supramolecular clusters. On the other hand, MCPQ, with its degrading mechanism that decreases background fluorescence in all subcellular regions, can permit single-molecule imaging when the nuclei of multiple cells are in the imaging field. This section can include use of the MS2-MCPQ system for gene-transcription analysis.

Results: The degron used to destabilize MCPQ produces robust protein degradation in *Drosophila* embryos. MCPQ can maintain single-RNA imaging capability in *Drosophila*. Testing can be conducted with *Drosophila* S2 cells. Degron and lysine positions can be adjusted as described in sections 1.1 and 1.3 for optimal MCPQ performance. When the system is working in S2 cells, RNAs can be analyzed in *Drosophila*, where the in-vivo dynamics of such RNAs have been invisible outside of oligomers containing many RNAs. These include RNAs like Bicoid mRNA, whose transport is necessary for development of apical-basal polarity. It is expected that MCPQ can uncover previously unseen RNA-transport phenomena critical for development in *Drosophila*.

Section 1 Outcomes and Alternative Strategies

A genetically encoded low-background single-molecule live-cell imaging system using conditionally stable MCP, 'MCPQ' is described herein. MCPQ can unveil previously unseen TOM20 mRNA dynamics. Due to short MCPQ half-life when not bound to RNA, pulse-chase using HALOTAG-MCPQ can permit highly time-sensitive imaging of RNA dynamics. MCPQ appears to be completely stabilized by RNA binding, so the half-life of RNA-bound MCPQ is expected to be either that of its bound RNA, or the amount of time it takes for half of it to dissociate from RNA. This time is roughly 5 hours for MCP, and experiments with purified protein can determine if the time is similar for MCPQ. For imaging of very short-lived RNAs, MCPQ can be modified to shorten its half-life; an alternative strategy would be to use tDeg, whose minutes-long dissociation time can make it equally sensitive to short and long-lived mRNAs at the cost of reduced labeling for long-lived RNA. MCPQ can be used for RNA imaging in many cell types, including neurons and *drosophila*; variations in endogenous E3 ligase activity might alter its performance. If this occurs, an alternative strategy can used involving screening several of the C-terminal degrons for one that is strongly degraded in the cells of interest; see e.g., Koren et al. Cell 173, 1622-1635.e14 (2018).

Section 2: Feedback Systems for Robust Conditional Degradation

Background

MCPQ can be expressed at a sufficiently high level to bind and tag MS2 RNA. Expression can also be kept below levels where endogenous E3 ligases cannot degrade MCPQ fast enough to remove background signal. Even strong E3 ligases cannot completely degrade target proteins when they are overexpressed on strong promoters. At these 'runaway' expression levels, stabilization has a reduced effect because it does not substantially raise protein concentration over background. Most experiments involving these proteins have contained several runaway cells due to variability in expression levels. This can be problematic for in vivo *Drosophila* experiments where several cell types can express and degrade MCPQ at different rates. Solutions to this issue are described herein.

Most conditionally stable proteins expressed in a cell are not completely degraded. Instead, expression level is regulated so that the majority of protein is bound and stabilized by a partner, leaving a small excess to be degraded. Other conditionally stable proteins, like P53, must be constitutively degraded and kept at low concentrations. Aberrant overexpression of wild-type P53 (beyond degradation rate) triggers apoptosis. However, P53 expression must be maintained at a high enough level for stabilization to trigger a rapid rise in P53 concentration for antitumor response. To keep expression levels under tight control, P53 activates expression of its own degrader, MDM2, in an autoregulatory feedback loop.

These natural processes show that conditional degradation in nature is often accompanied by regulation of expression to ensure consistent function. Engineered degradation-sensitive negative feedback systems can be helpful for achieving optimal expression levels of conditionally stable proteins. In these systems, a regulator can detect when conditionally stable protein reaches runaway expression rates and can then repress expression of the conditionally stable protein to ensure expression remains beneath these levels.

Section 2.1 Dual-Expression Systems to Track Degradation Efficiency

Rationale: In addition to a negative feedback system, an approach to evaluate performance of the system can be developed. The performance of MCPQ can be quantified by comparing the brightness of mRNA punctae to background fluorescence. However, this approach only works for conditionally stable proteins that form spatially distinct complexes when stabilized, and it is not suitable for high-throughput analysis with flow cytometry. To permit high-throughput evaluation of MCPQ performance, a second reporter protein that is tagged with the same degron as MCPQ, such that it degrades by the same mechanisms but is not stabilized by MS2, can serve as a proxy for the level of unbound MCPQ that has not been degraded. Flow cytometry can be used to measure whole-cell fluorescence of both MCPQ signal and the reporter signal for high-throughput characterization of MCPQ signal-to-noise and determination of optimal MCPQ expression levels.

Figure 4A:
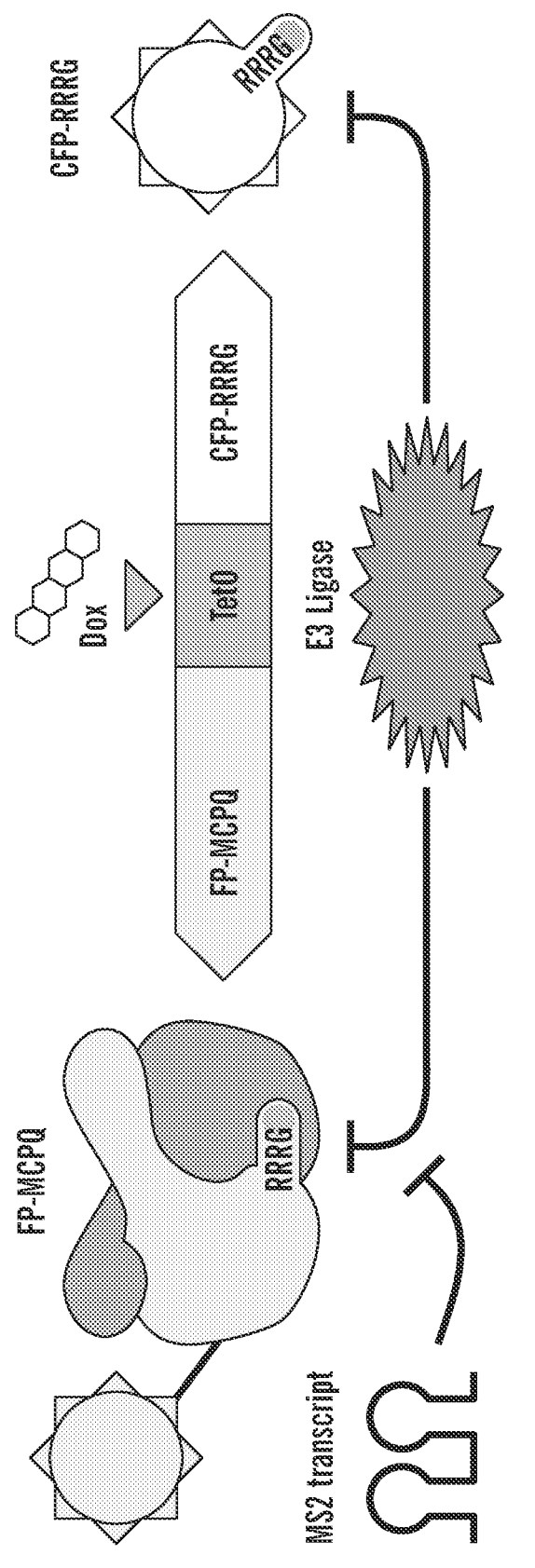
FIG. 4A-4C show systems for MCPQ performance analysis and negative feedback.

Results: A bidirectional tet-inducible expression vector can be assembled in order to transcribe two genes at the same rate, which can be adjusted with doxycycline. In one direction, mVenus-MCPQ can be expressed. In the other, cyan fluorescent protein CFP can be expressed with the RRRG degron fused to its C-terminus (see e.g., FIG. 4A). As expression is induced to high levels, protein production can begin to outcompete degradation. When this system is applied in cells, CFP signal can serve as a readout for whether mVenus signal is a result of MCPQ stabilization or of MCPQ production exceeding degradation capacity. Flow cytometry can be performed on cells containing the dual expression system with and without MS2 present, and CFP signal can be used to determine what level of background yields optimal signal-to noise.

Section 2.2 Transcriptional Negative Feedback for Robust Degradation

Rationale: The bidirectional expression vector described in section 2.1 is not only useful for measuring performance, but also for robust regulation of gene transcription. In nature, the tet repressor (tetR) represses a bidirectional promoter that transcribes tetR itself and tetA, the tetracycline resistance gene. In this system, tetR represses its own transcription, which both linearizes the dose response curve to its inducer and reduces heterogeneity of tetR regulated gene expression among cells. This negative feedback scheme has been applied in mammalian cells and the stabilizing effect has yielded at least 4.5 fold reduction in cell-cell variability of tetR regulated gene expression. If this system is applied to regulate expression of a conditionally stable protein, expression levels can more reliably be maintained within a window that produces low enough concentrations for the protein to be thoroughly degraded when not stabilized, but high enough concentrations for a rapid increase in protein concentration upon stabilization. Additionally, tetR itself can be targeted for degradation so that autorepression does not occur until expression approaches levels exceeding the cell's ability to degrade the target.

Results: A bidirectional tetR repressible promoter can be used to express tetR in one direction and MCPQ in the other. MCP has an affinity of kD=1 nM for the MS2 loops used in imaging experiments, and tetR's affinity for the tetO operating site is lower at roughly kD=5 nM. If basal expression of MCPQ under tetR repression is too high, it can be lowered by using a weaker tet-repressible promoter for MCPQ, but a strong one for tetR. If basal MCPQ expression is beneath optimal levels for imaging, doxycycline can be used to de-repress the system until MCPQ expression is within an optimal window. Both of these approaches can yield a predicted 4.5-fold reduction in expression noise relative to non-autorepressed systems, ensuring that a smaller number of cells express MCPQ at non-optimal levels.

Figure 4B:
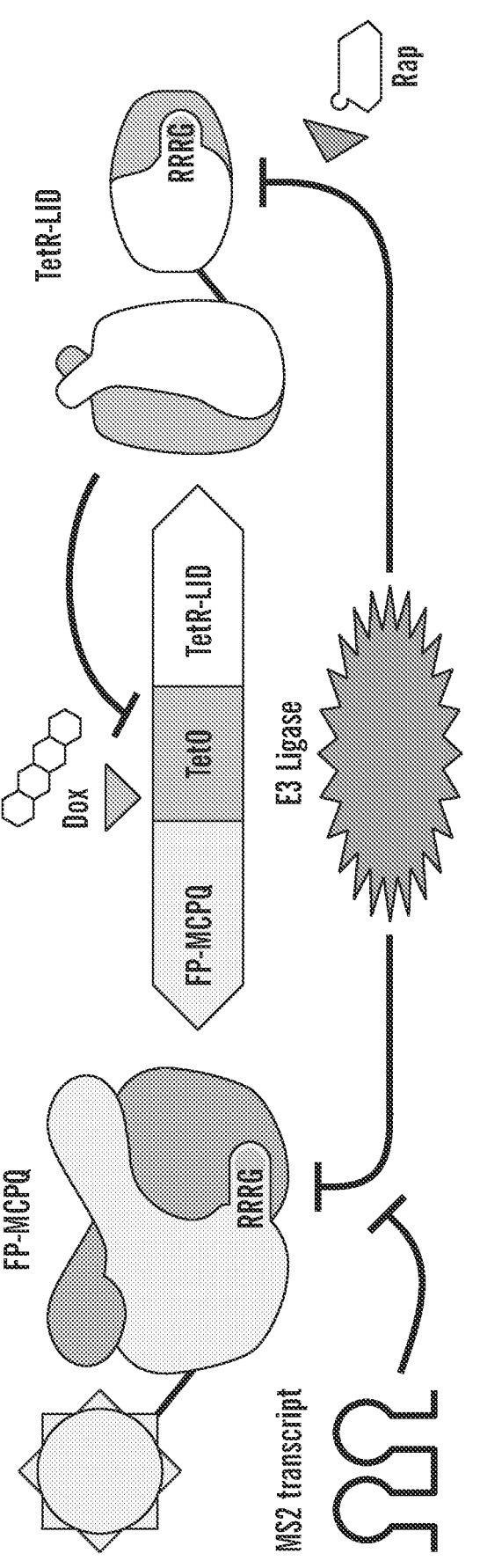

Adding the C-terminal RRRG degron to tetR can ensure that tetR-RRRG repression can only occur when runaway expression overpowers degradation, at which point tetR-RRRG concentration rises to autoinhibitory levels. Again, doxycycline can be used to reduce repression if basal expression of MCPQ is too low, although efficient tetR-RRRG degradation and subsequent de-repression at low expression levels can prevent this. If basal expression under tetR-RRRG repression is too high, tetR repression can be reinforced by lowering degradation rate with tunable degron systems. These systems are the rapamycin-controlled LID and its blue-light controlled counterpart, B-LID. B-LID has been shown to be effective for light-inducible degradation when fused to tetR, and has been applied to a negative feedback system where it reduced gene expression noise. It is expected that this tetR-B-LID fusion can maintain optimal MCPQ expression levels when its degradation is regulated by a specific intensity of blue light. If this is achieved with tetR-B-LID, the light controlled B-lid can be exchanged for the rapamycin-controlled LID. Using both doxycycline controlled tetR-LID affinity and rapamycin-controlled tetR-LID degradation, it is expected that repression can be adjusted for consistent, optimal MCPQ expression that is not only buffered against transcriptional variations, but also against variations in degradation rate among cells (see e.g., FIG. 4B).

Figure 4C:
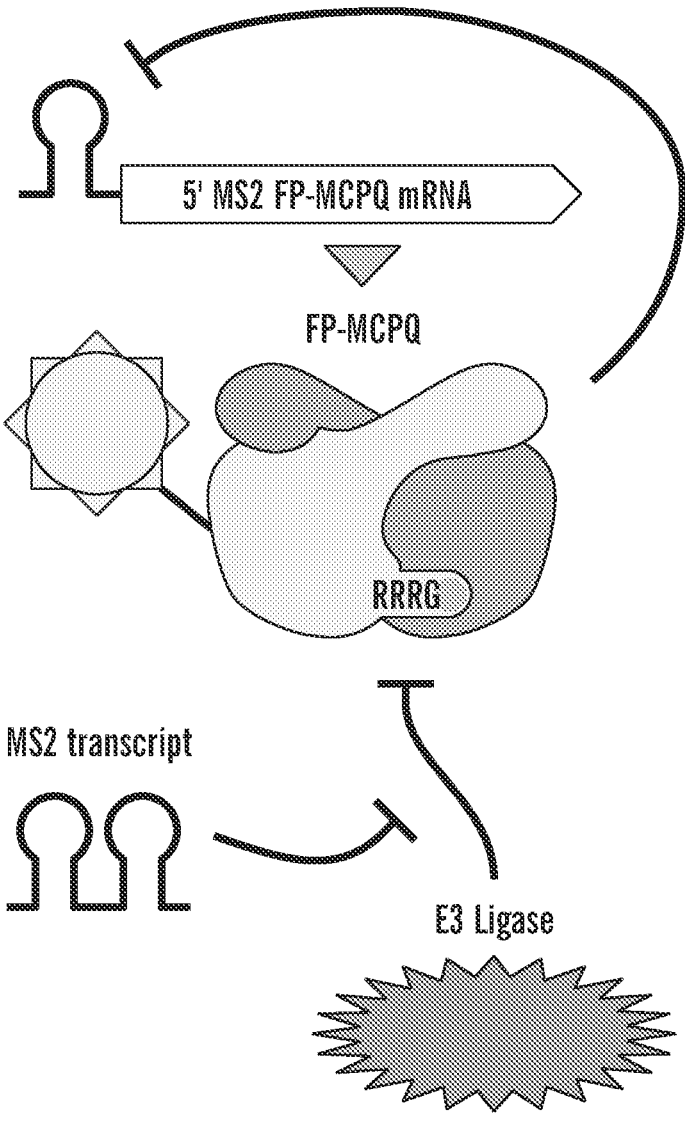

Section 2.3 MCPQ Translational Negative Feedback System for Robust MCPQ Imaging Rationale: One of MCP's functions in nature is gene suppression in the MS2 bacteriophage. When a c-variant MS2 loop is placed in the 5' UTR of a mammalian mRNA, MCP can suppress translation up to 20-fold without impacting RNA half-life. It is expected that, through negative feedback where MCPQ represses its own transcript, MCPQ expression can be autorepressed to prevent runaway expression (see e.g., FIG. 4C). MCPQ-encoding RNAs with 5' MS2 does not create false-positive punctae because only one MCPQ can bind them, so local MCPQ concentration does not rise like when several copies of MCP bind MS2 loops on a single RNA. Instead, 5' MS2 MCPQ transcripts can generate a low amount of background fluorescence proportional to their quantity, a tradeoff that can be justified by a reduced number of runaway cells.

MCPQ autorepression is more compact than the approach proposed in section 2.2, as it only requires the addition of one MS2 loop in the 5' UTR of MCPQ's transcript. Also, MCP translational repression of mRNAs with MS2 in the 5' UTR can be attenuated when mRNA containing multiple unoccupied MS2 loops is introduced. Thus, this repression can be tuned so that it only takes effect after transcripts have been sufficiently labeled for imaging, and it quickly lifts if many unlabeled transcripts suddenly appear. This approach can also be applied for improved imaging with stable MCP; the effect of 5' MS2 MCP autorepression on stable MCP can be modelled to assess feasibility.

Results: Assuming MCP-MS2 binding repression is a function of binding site saturation, it can be modeled relative to MS2 labeling for mRNA imaging. Peabody et al. showed that, when purified and tested in-vivo, the fused dimer 'tdMCP' version of MCP appeared to have the same binding profile as monomeric MCP, with a hill coefficient of two; see e.g., Peabody et al. Nucleic Acids Res. 24, 2352-2359 (1996). However, the monomeric MCP in this study was purified with a size-exclusion chromatography method that was able to separate capsids from lower-order oligomers, but not monomers from dimers. Thus, the binding curve observed could have been produced by pre-assembled MCP dimers, whose structure is roughly identical to tdMCP. MCP and tdMCP have distinct binding profiles in live cells due to the need for MCP to dimerize before binding MS2. Since tdMCP is "monomeric", its in-vivo binding profile is expected to match the in-vitro profile from Peabody, and that profile can be used to predict repression effects. In the following model, 'MCP' refers to the fused tdMCP version:

The kD of MCP for the C-variant of MS2, at which site occupancy is 50%, is one nanomolar. With a hill coefficient of 2, the hill equation for MS2 site occupancy ($MS2_{occ}$) is a function of MCP concentration (MCP) and kD. The relationship between MCP concentration and MS2 occupancy is the same regardless of whether or not MCP autorepression is in play:

$$MS2_{occ} = \frac{MCP^2}{\left(10^{-9}\right)^2 + MCP^2} \qquad \text{Formula I}$$

If MCP autorepression is directly proportional to the fraction of transcripts bound by MCP, and maximum repression is 20-fold, then the repressed MCP concentration ($MCP_{inh}$) can be expressed as a function of a maximum unrepressed concentration ($MCP_{max}$,) and occupancy of the 5' inhibitory MS2 site ($MS2_{occ}$):

$$MCP_{inh} = MCP_{max}\left(1 - \frac{19}{20}MS2_{occ}\right) \qquad \text{Formula II}$$

If MCP is not autorepressed, then MCP=$MCP_{max}$. Since transcript concentration can be used to approximate relative protein concentrations in the cell, $MCP_{max}$ can be used as an approximation for relative MCP transcript concentration. Note that this model is for stable MCP, so the effect of degradation on the transcript-to-protein relationship is not included here. With $MCP_{max}$ as a proxy for transcription, MCP concentration and MS2 occupancy can be plotted for various concentrations of repressed or unrepressed transcript.

MS2 occupancy can be converted to RNA-localized MCP concentration based on the length of the MS2 repeat cassette and how many MS2 loops it contains. An exemplary cassette contains 16 MS2 loops and is roughly as long as a 560 bp linear mRNA when accounting for reduction in length caused by MS2 secondary structure. When 16 MCP molecules are contained within a sphere with a diameter equal to the length of a 560 bp RNA (187 nm), the local concentration is 7.8 micromolar. This number multiplied by fraction of MS2 occupancy grants MS2-localized concentration of MCP on a single RNA.

Figure 5:
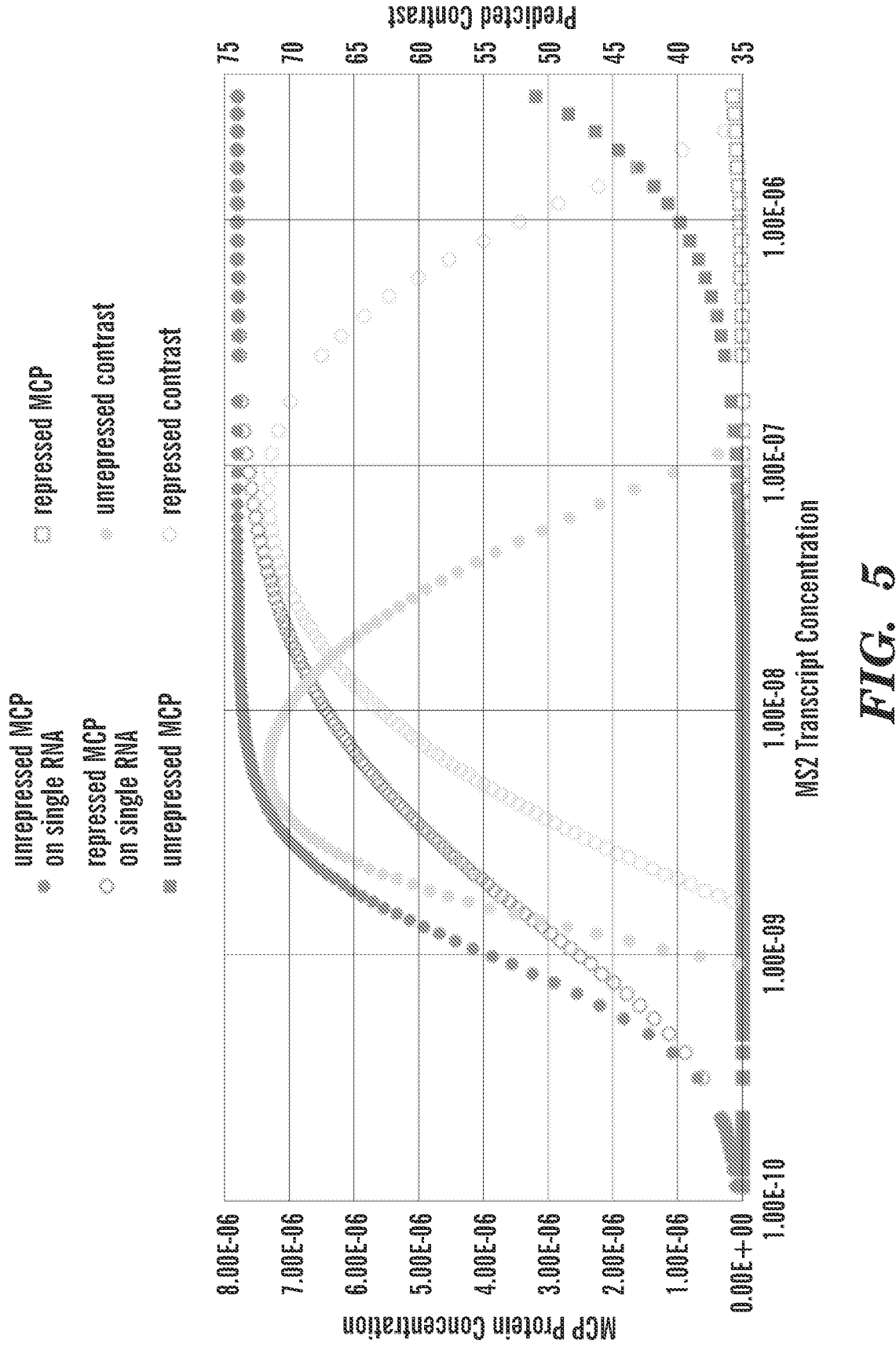
FIG. 5 is a graph showing the predicted relationship between MCP transcript concentration and MCP protein concentration with or without autorepression via 5' MS2. Autorepression can broaden the range of MCPQ transcription rates that can yield increased imaging contrast.

Finally, since brightness of a fluorescent protein is proportional to its concentration, signal-to-noise can be estimated by dividing concentration of MCP on RNA by cellular MCP concentration plus a small constant for autofluorescence. Autofluorescence was arbitrarily set at a value where maximum predicted contrast would be 75-fold. Concentrations and predicted contrasts for repressed and unrepressed MCP are plotted in FIG. 5.

Based on the model, autorepressed MCP is expected be less sensitive to changes in transcript concentration. For example, if optimal imaging is achieved at MCP concentrations when contrast is higher than 60-fold, this range of concentration is spanned by a roughly 15-fold change in unrepressed transcription, and a 77-fold change in repressed transcription, so the range of optimal induction levels in the repressed system is 5 times that of the unrepressed system. This increase in range can significantly lower the number of suboptimal cells in an imaging experiment. Note that autorepression has a decreased effect at low transcript concentration, so the lower-bound of the optimal transcription window is similar for repressed and unrepressed MCP, while the upper bounds are farther apart.

The above model is for stable MCP, but since MCPQ is stabilized upon MS2 binding, this mechanism is expected to perform similarly for MCP and MCPQ at steady state. Outside of steady state, degradation of unbound MCPQ can yield faster response to perturbation, because excess MCPQ is rapidly degraded if there are any sudden spikes in MCPQ expression or dips in MS2 availability. This response speed can be particularly useful for RNA imaging due to the unsteady, bursting nature of transcription. Since the mechanism of MCP autorepression is contained within a single RNA-protein pair, it can be combined with the tetR-LID system described in section 2.2. This combined system is expected to have reduced noise and enhanced sensitivity to degradation relative to either feedback system on its own.

Section 2 Outcomes and Alternative Strategies

Feedback mechanisms are predicted to yield more consistent performance of conditionally stable proteins based on results in published literature and predictions from modeling. However, targeting autorepressors for degradation can excessively weaken the negative feedback effect. Degradation could be repressed by LID as described in section 2.2, but this would reduce degradation sensitivity of the system. In an alternative design, tetR autorepression can be strengthened with an engineered cooperative mechanism. Similarly, if degradation weakens the effects of MCPQ autorepression too much, then addition of a second MS2 loop in the 5' UTR can strengthen autorepression. If background fluorescence from MCPQ stabilized by this transcript is too high, the 5' MS2 stem loop can be replaced with PP7 loops, whose cognate binding protein, PCP, has a nearly identical repressing effect. A non-fluorescent PCP can be co-expressed with MCPQ on the same transcript using a T2A peptide, ensuring feedback can be attained without background fluorescence. PCP is not conditionally stable like MCPQ, but it can be equipped with a C-terminal RRRG to sustain degradation-sensitivity.

Conclusion

Results of the work introduce a versatile and robust toolbox for the use and application of degron masking systems in live cells. Applications of these tools include single-molecule imaging and protein assembly.

Figure 6A:
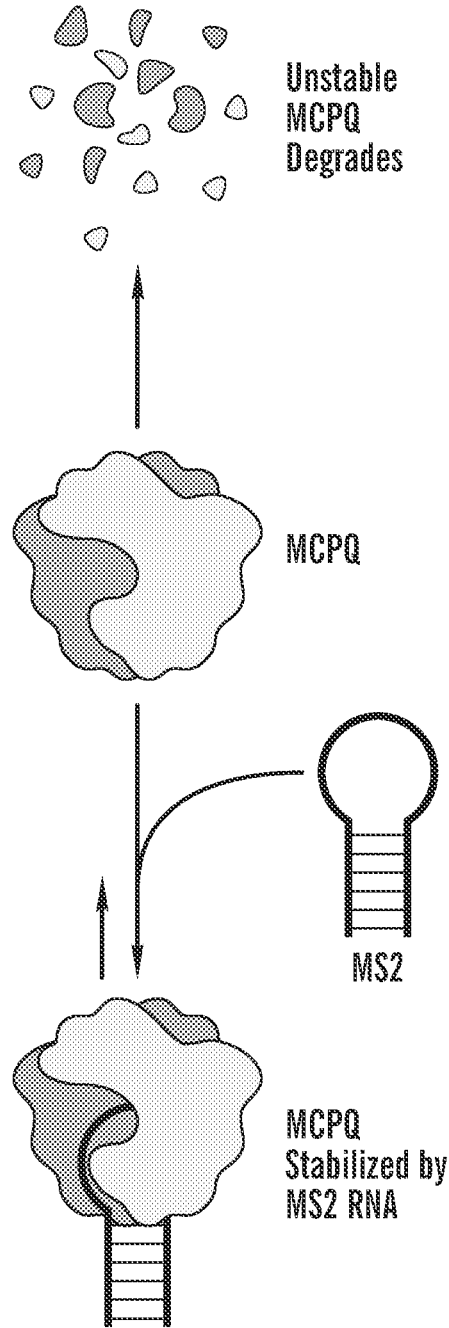
FIG. 6A-6D.
Figure 6B:
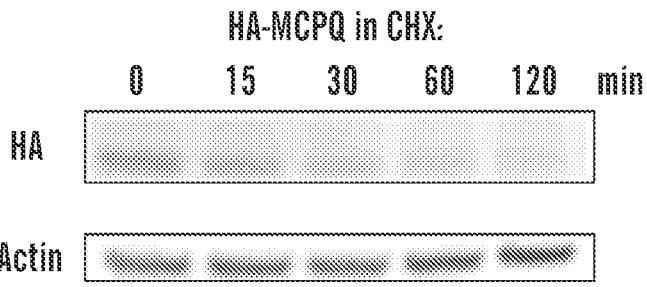
Figure 6C:
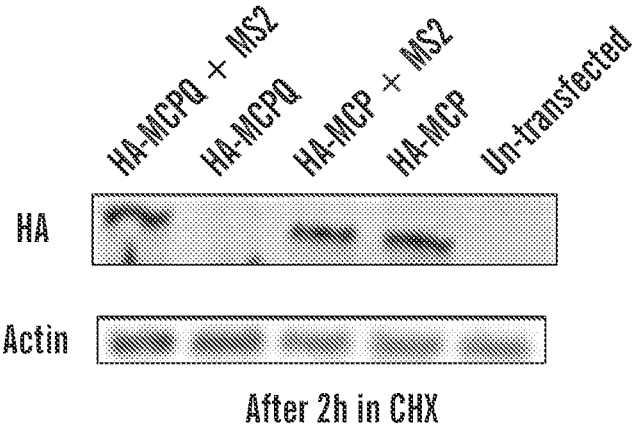
Figure 6D:
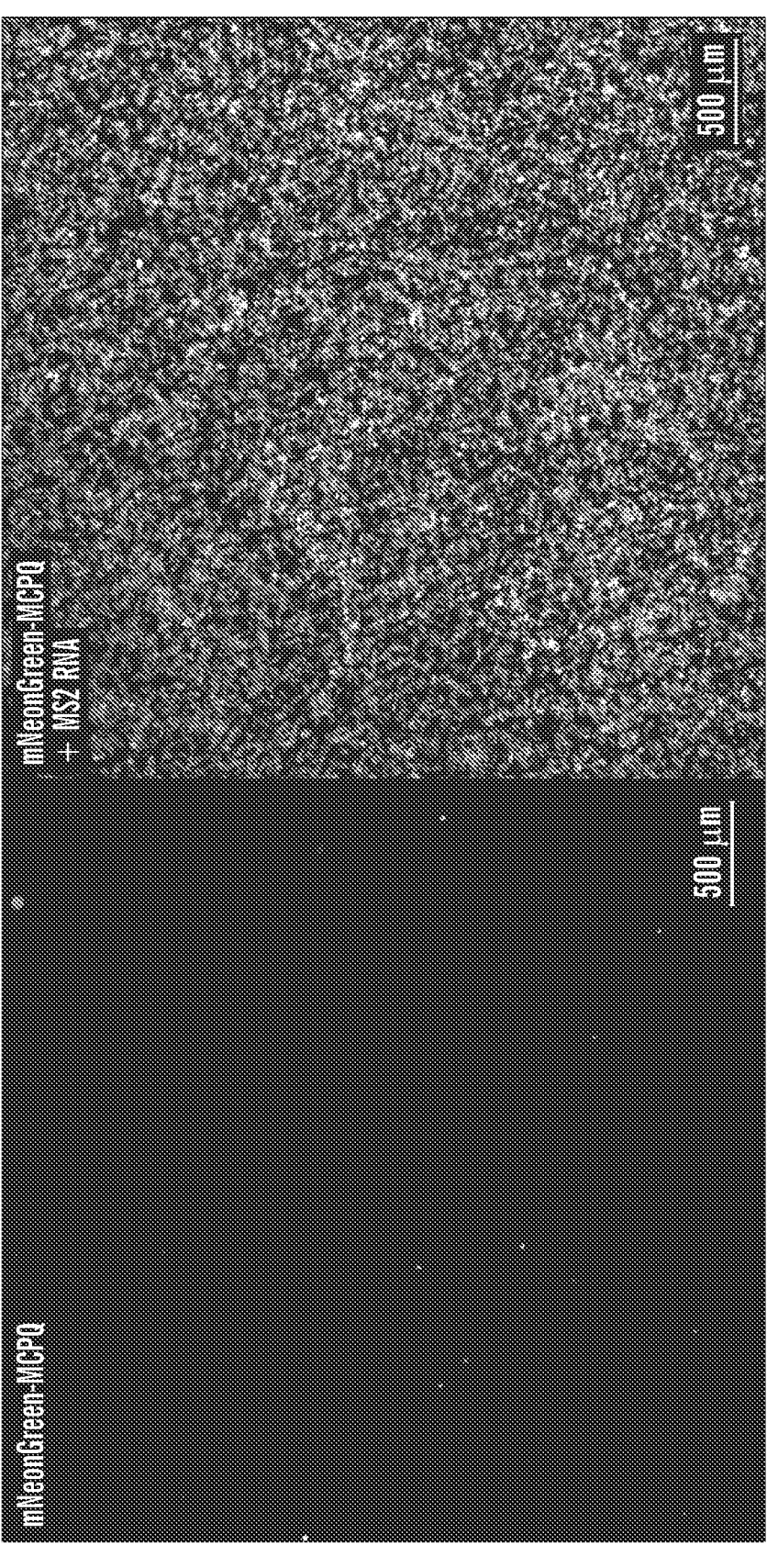
Figure 16A:
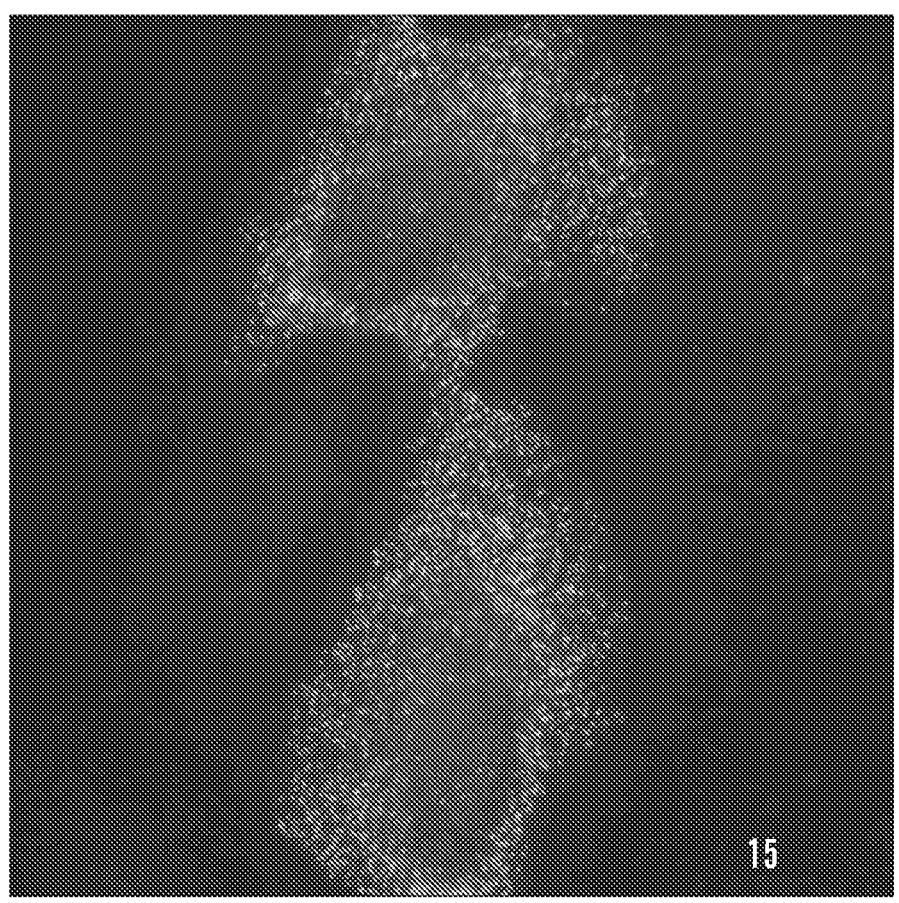
FIG. 16A-16B show exemplary fluorescent images produced using MCPQ imaging.
Figure 16B:
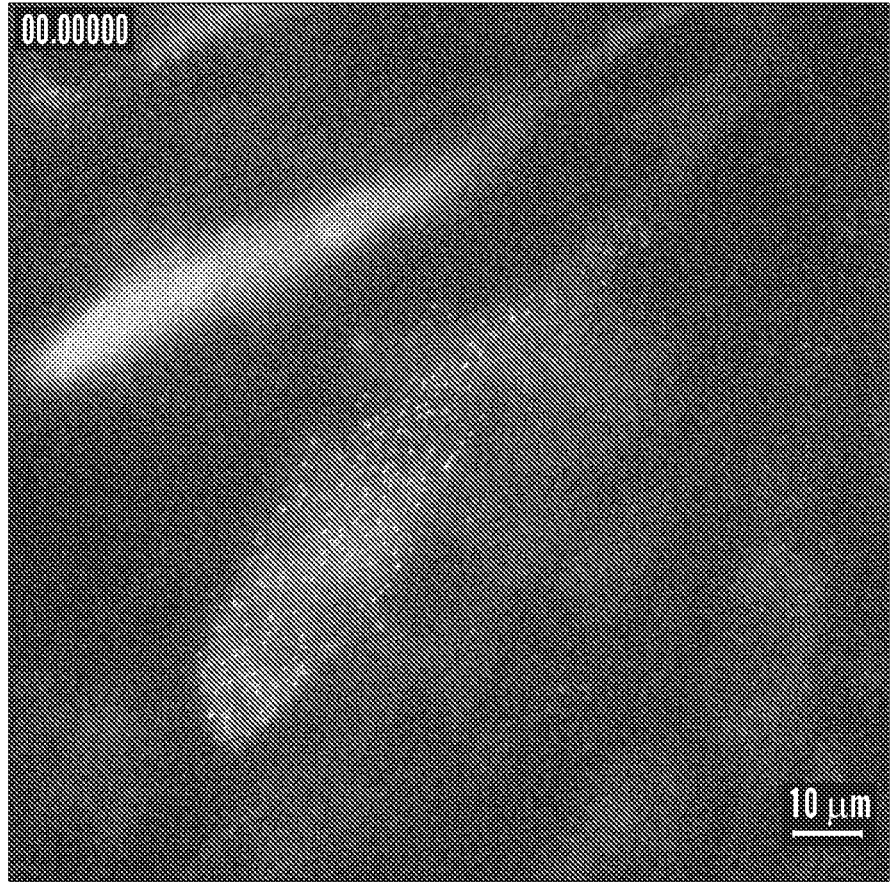
Figure 17A:
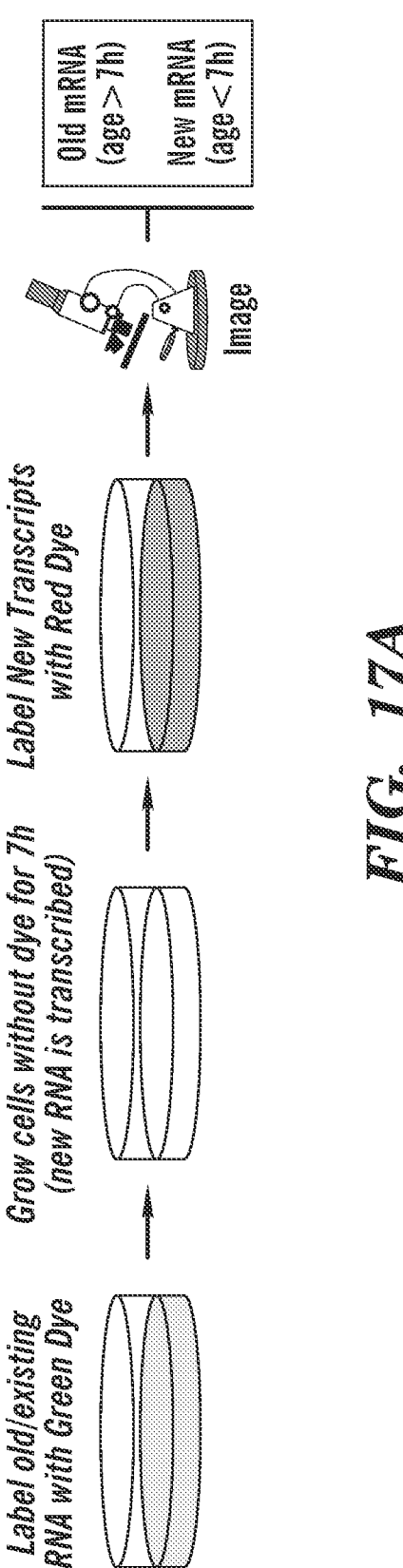
FIG. 17A-17B shows labeling of old versus new RNAs.
Figure 17B:
Figure 17B:
Figure 17B:
Figure 18:
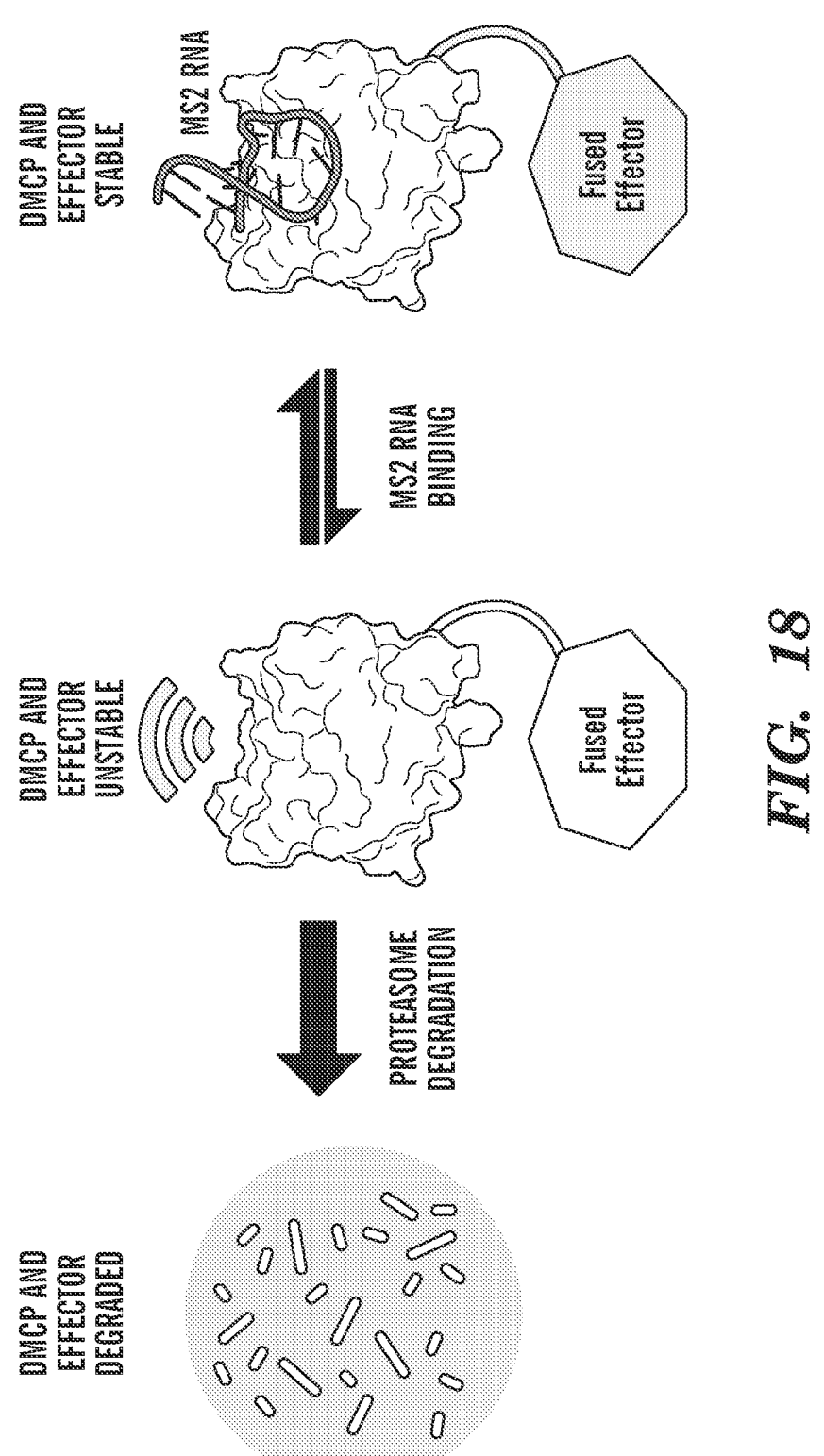
FIG. 18: Schematic of dMCP's RNA-dependant stability function, which can be extended to fused effector proteins.

Example 3: Conditionally Stable RNA Binding Protein for Improved Contrast in Live-Cell Single-Molecule RNA Imaging Conditionally Stable MCP: Cells employ intricate degradation schemes to regulate protein complex assembly within narrow space-time windows. Inspired by these mechanisms, an MS2 coat protein (MCP) was engineered that degrades when not bound to its cognate MS2 RNA stem loop but becomes stable when bound (see e.g., FIG. 16A-6C). This system maintains concentrations of MCP bound to RNA, while reducing concentrations of excess MCP not bound to RNA. Thus, when the conditionally stable MCP ("MCPQ") is fused to a fluorophore, the degradation scheme reduces background fluorescence in RNA imaging applications (see e.g., FIG. 6D) when compared to conventional MCP-MS2 RNA imaging. High-contrast live-cell single-molecule RNA imaging reveals real-time transport phenomena of RNA in clear detail.

Figure 7A:
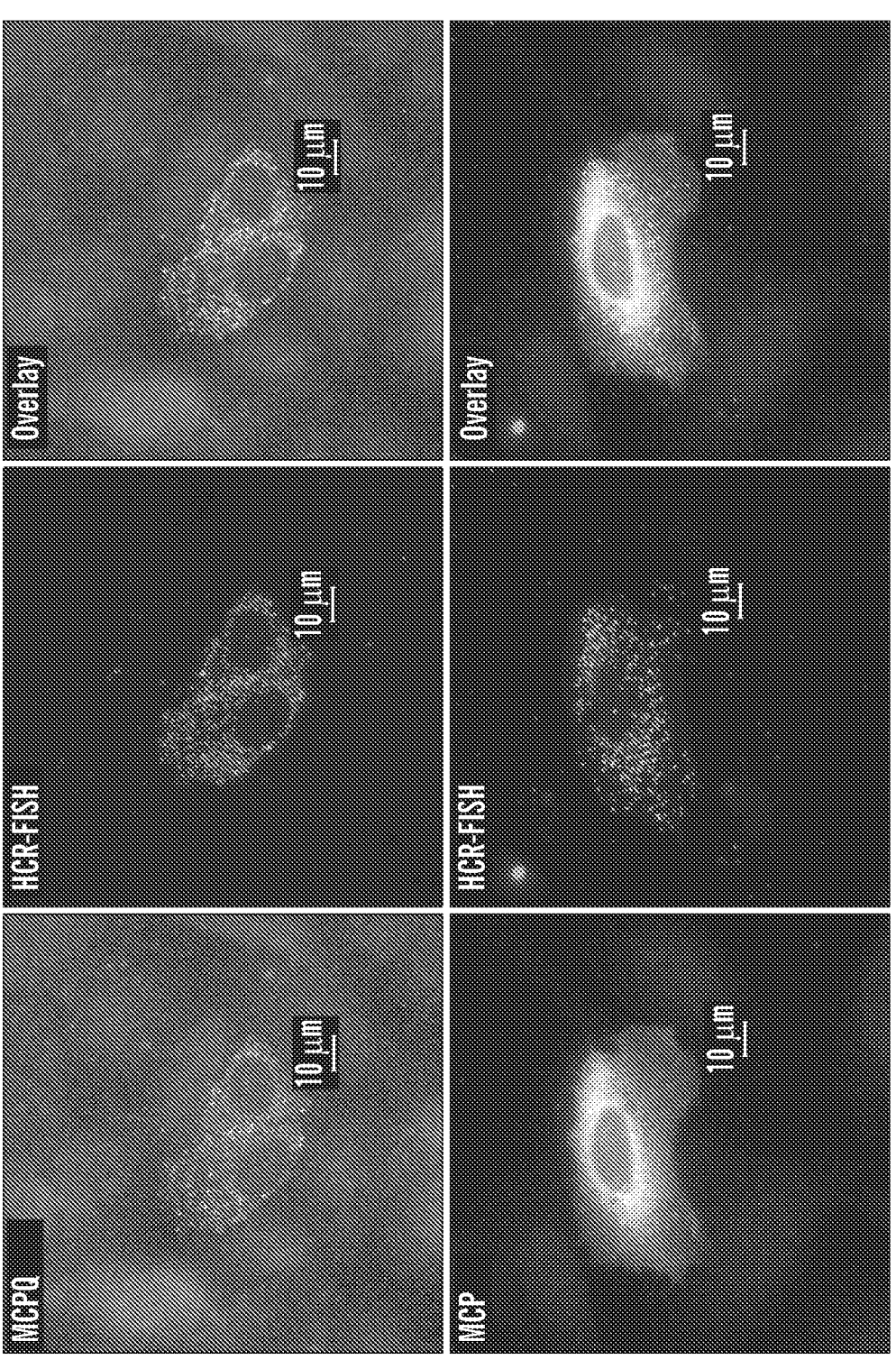
FIG. 7A-7C: Single RNA imaging using MCPQ. All images were captured on a 63× objective using widefield fluorescence microscopy.
Figure 7B:
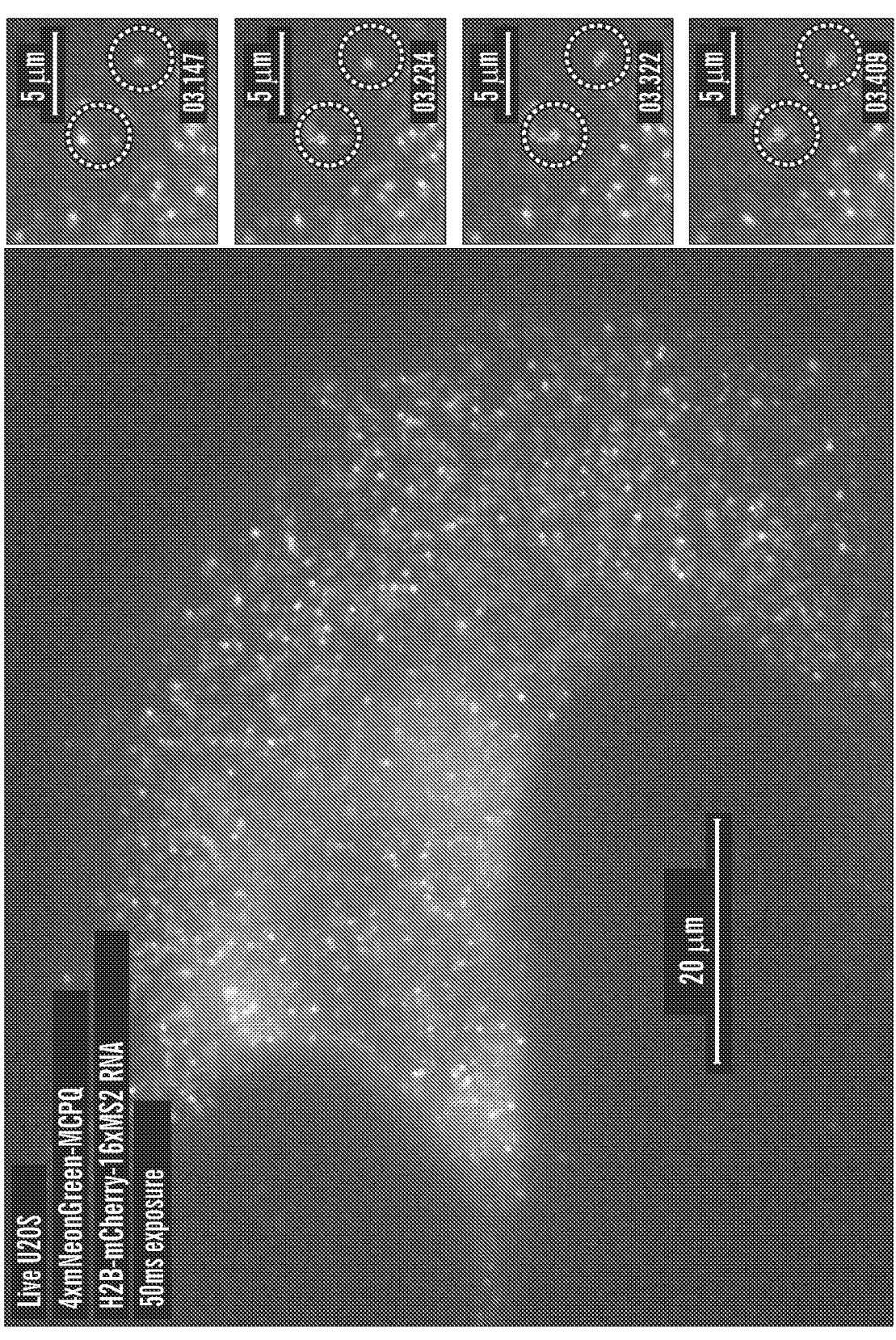

Single-RNA Imaging With MCPQ: Decreased background fluorescence from degradation of MCPQ that has not bound MS2 RNA yields high-contrast images of single RNAs containing MS2 repeats. Fluorescent punctae produced by RNAs tagged with MCPQ are more distinct than they are for normal MCP, and these punctae overlap with signal from Fluorescence In Situ Hybridization (FISH) staining of the same RNA (see e.g., FIG. 7A). Single-RNA imaging with MCP typically uses a nuclear localization signal (NLS) to reduce cytosolic background fluorescence by porting MCP not bound to RNA to the nucleus, but this is not necessary with MCPQ. The high signal-to-noise of MCPQ permitted recording of fast RNA movements in live cells using short (50 ms) exposure times (see e.g., FIG. 7B).

Figure 7C:
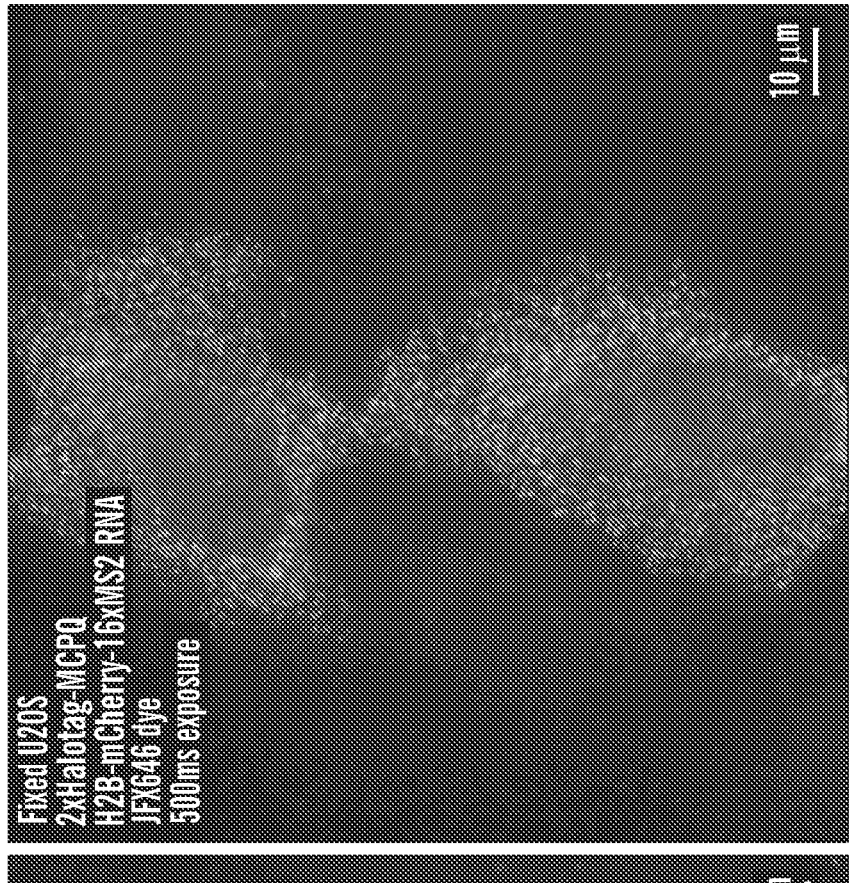
Figure 7C:
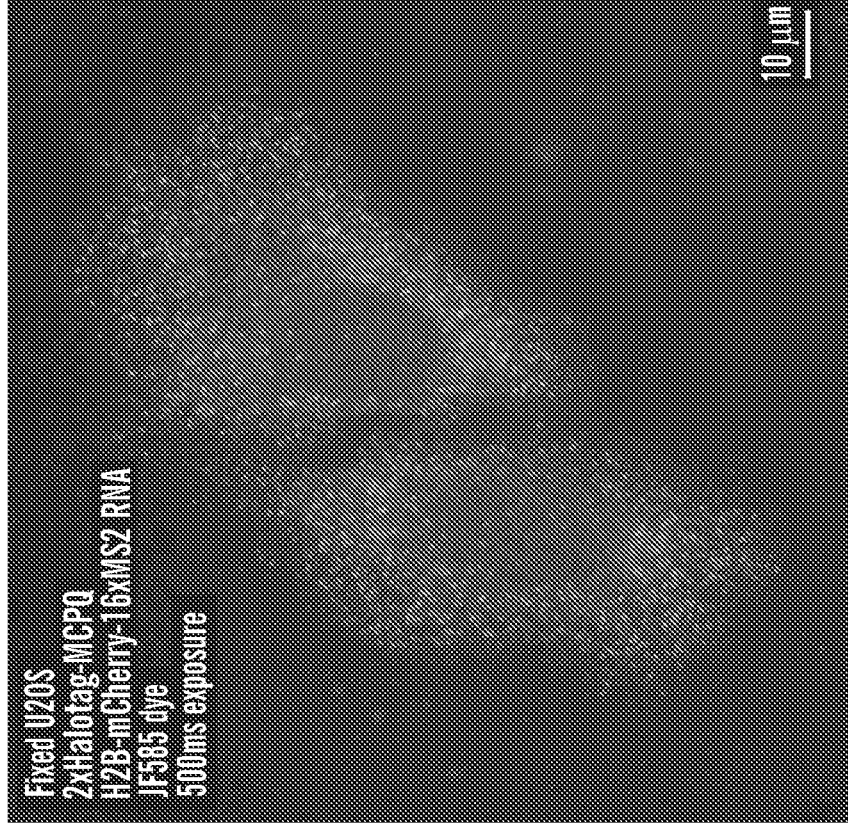
Figure 7D:
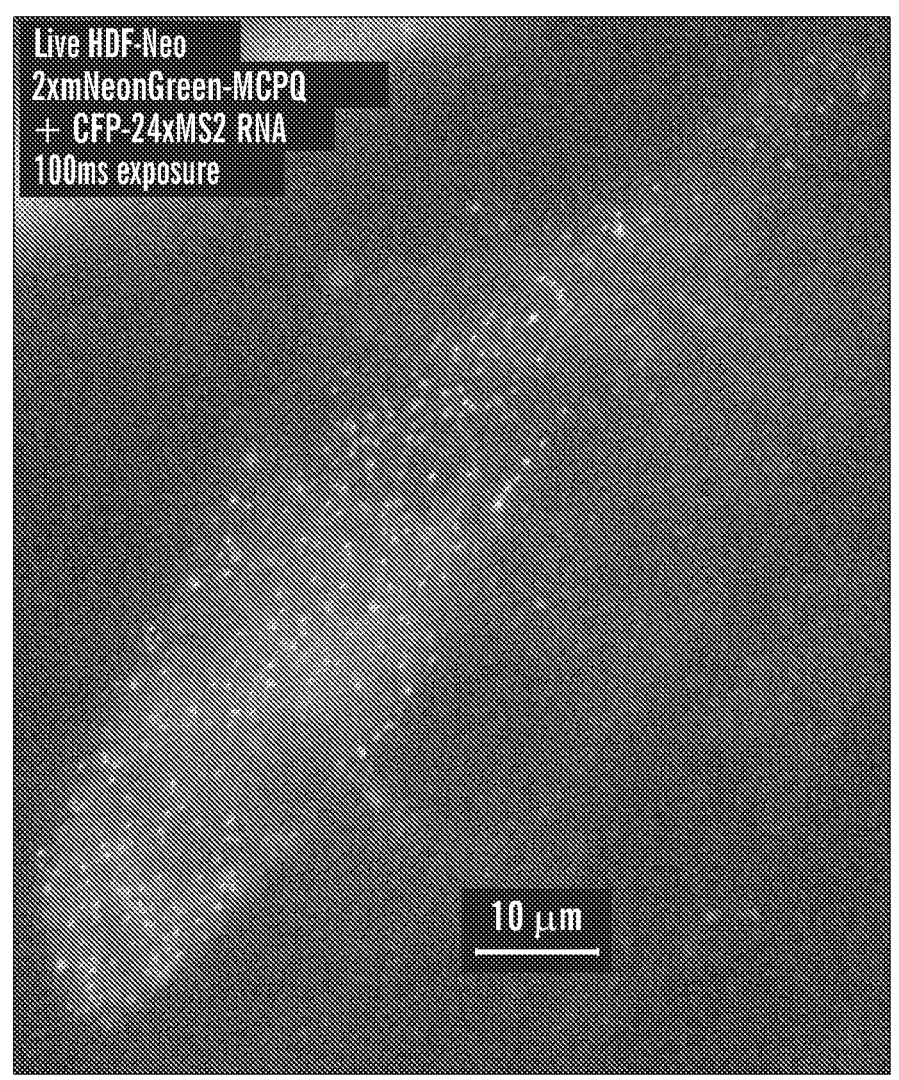
(FIG. 7D) A live Neonatal Human Dermal Fibroblast transduced with lentivirus to express CFP-24×MS2 RNA and 2×mNeonGreen-MCPQ.
Figure 8A:
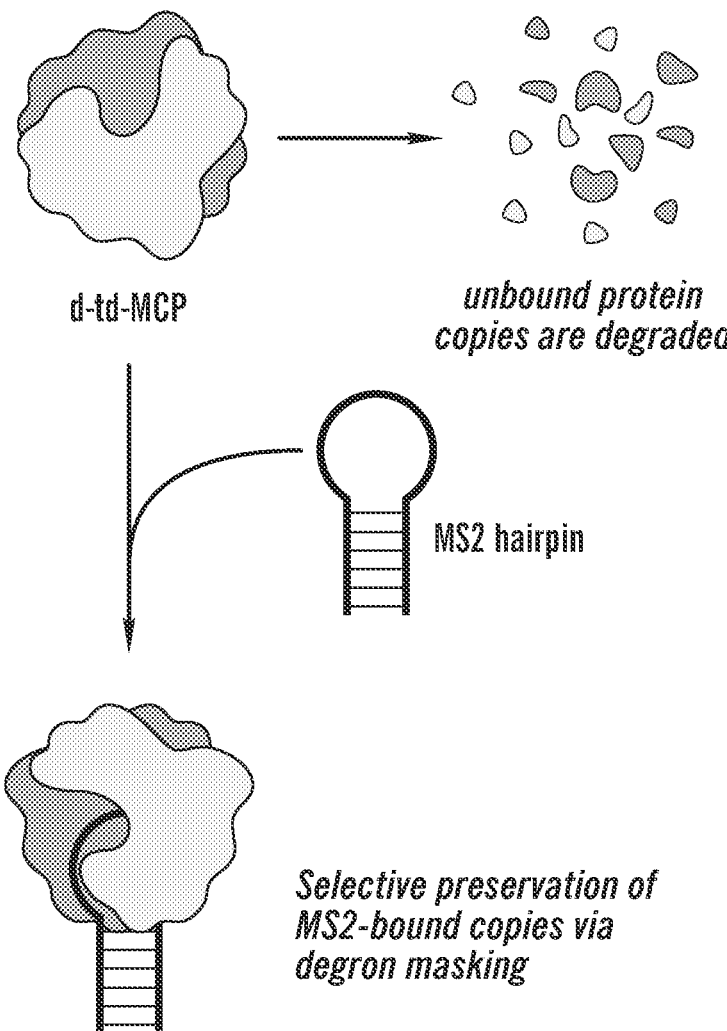
FIG. 8A-8C show a series of schematics and microscopy images.
Figure 8B:
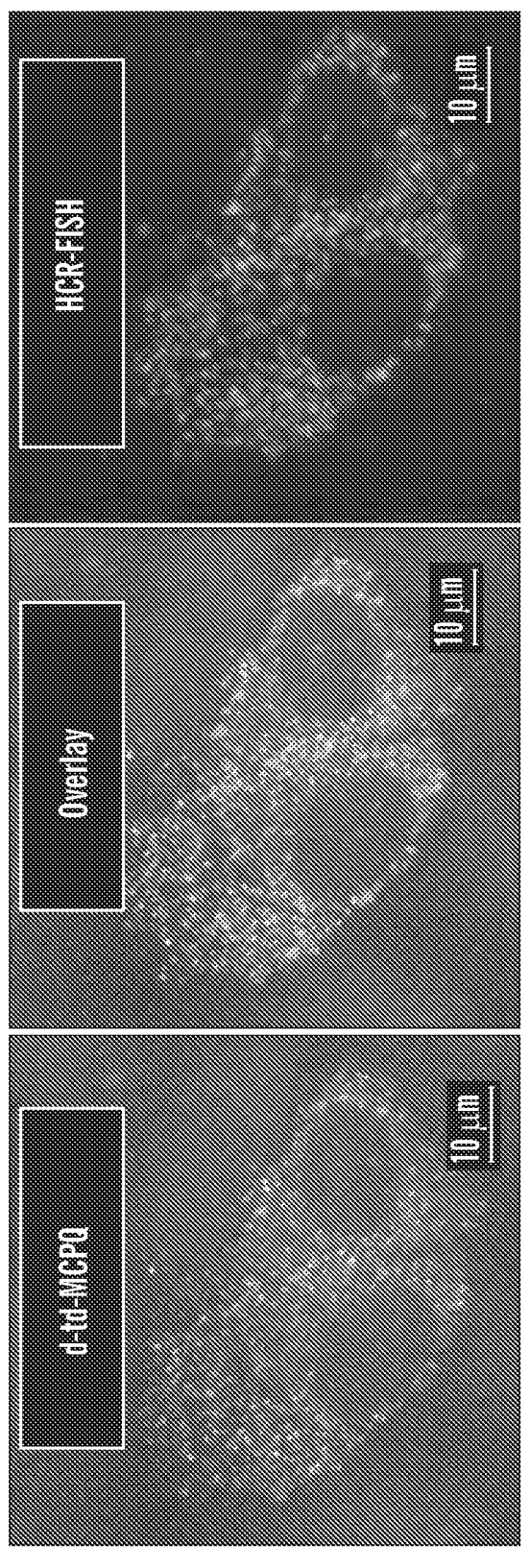
Figure 8C:
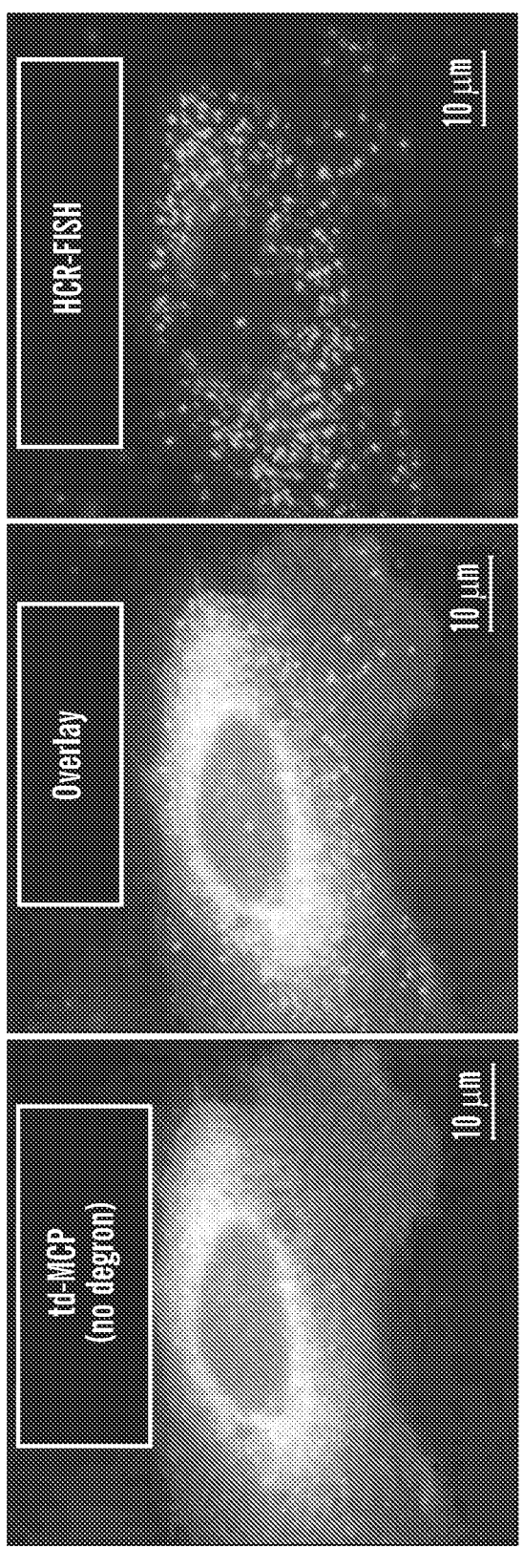
Figure 9A:
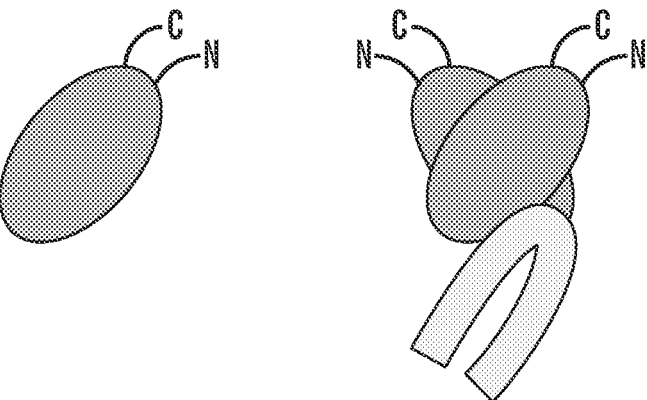
FIG. 9A-9C are a series of schematics showing design of tdMCP.
Figure 9B:
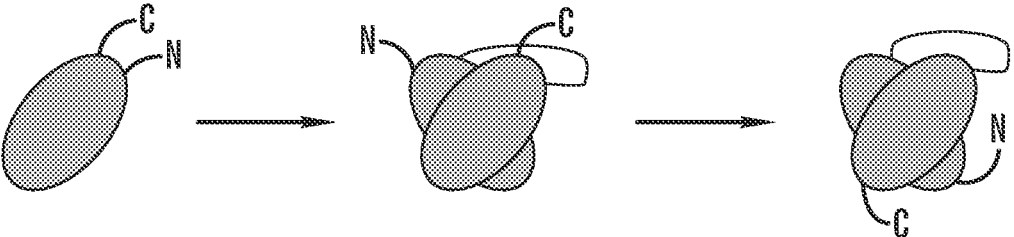
Figure 9C:
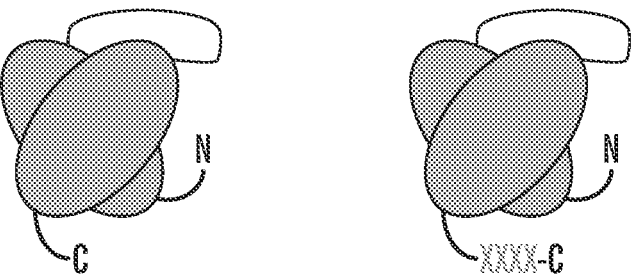
Figure 9D:
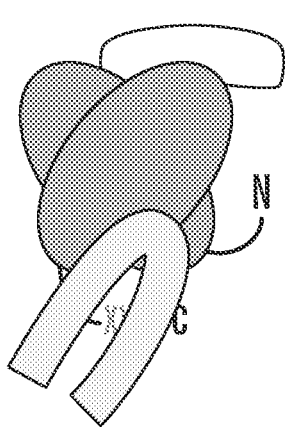
FIG. 9D: This degron is hidden within RNA-tdMCP interface upon hairpin binding.
Figure 9E:
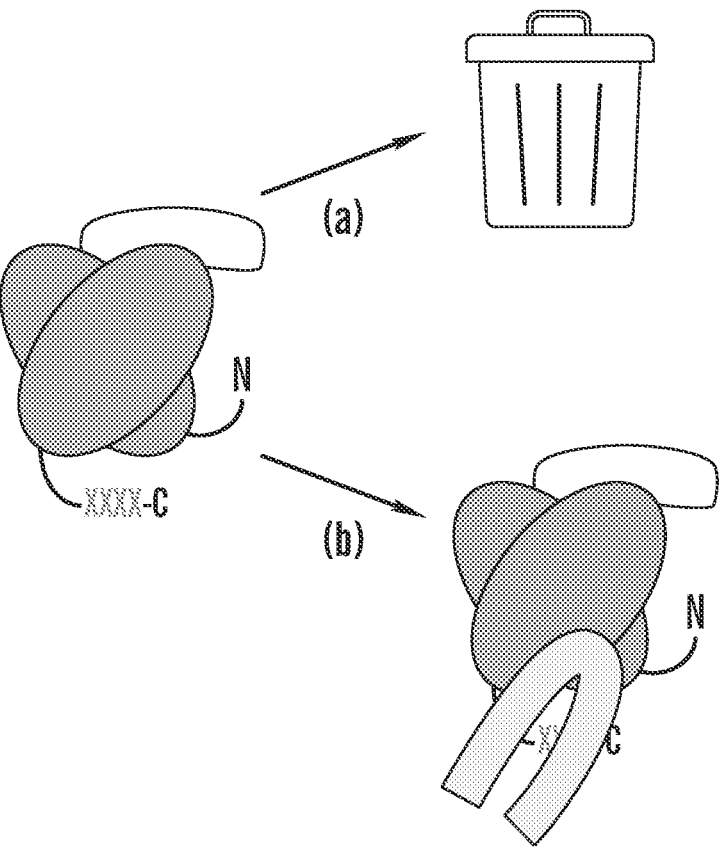
FIG. 9E: When the destabilized MCP is expressed without MS2 RNA, it is degraded rapidly due to the exposed degron (a). MS2 binding blocks the degron from access from ubiqutinylating enzymes, resulting in preservation of tdMCP (b).
Figure 10A:
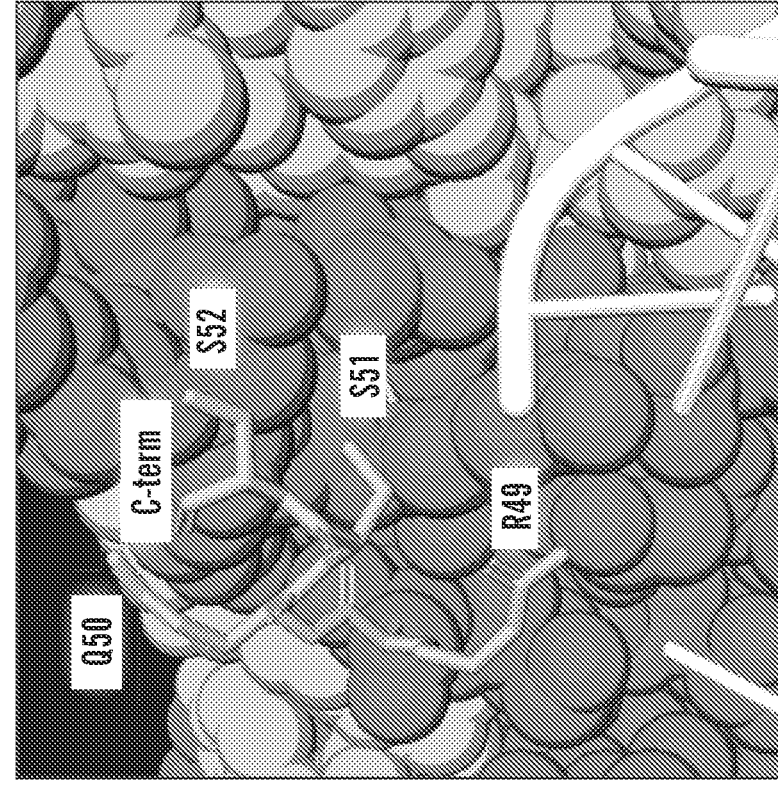
FIG. 10A-10C are a series of schematics showing the new C-terminus on permuted tdMCP. Structure is 2iz8. Q50, S51, S52 can be replaceable with a -RRRG C-terminal degron. Positively charged arginine can interact with backbone like R49. The goal was to insert a C-terminal degron that is masked upon MS2 binding.
Figure 10A:
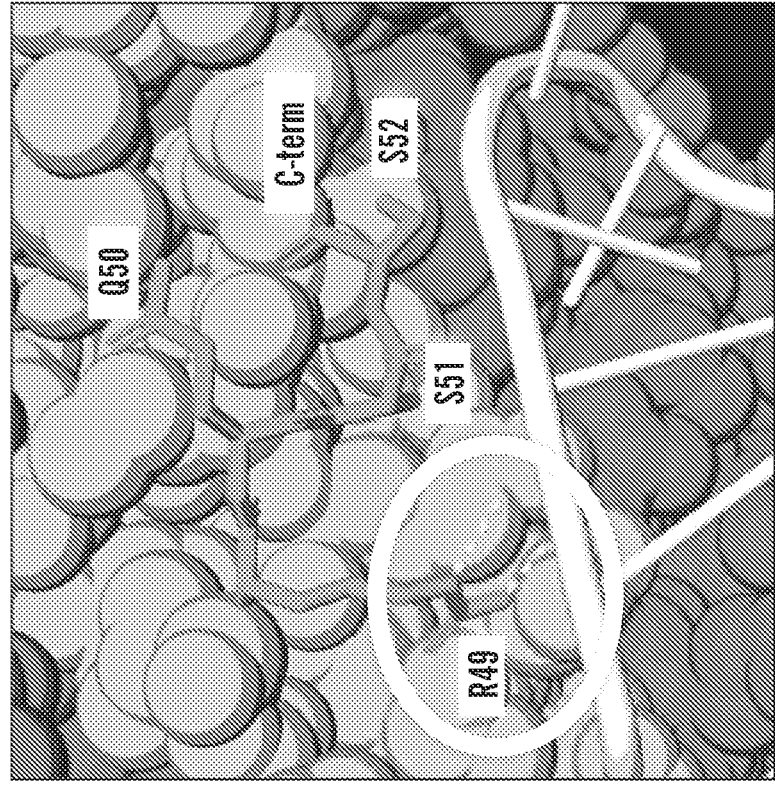
Figure 10B:
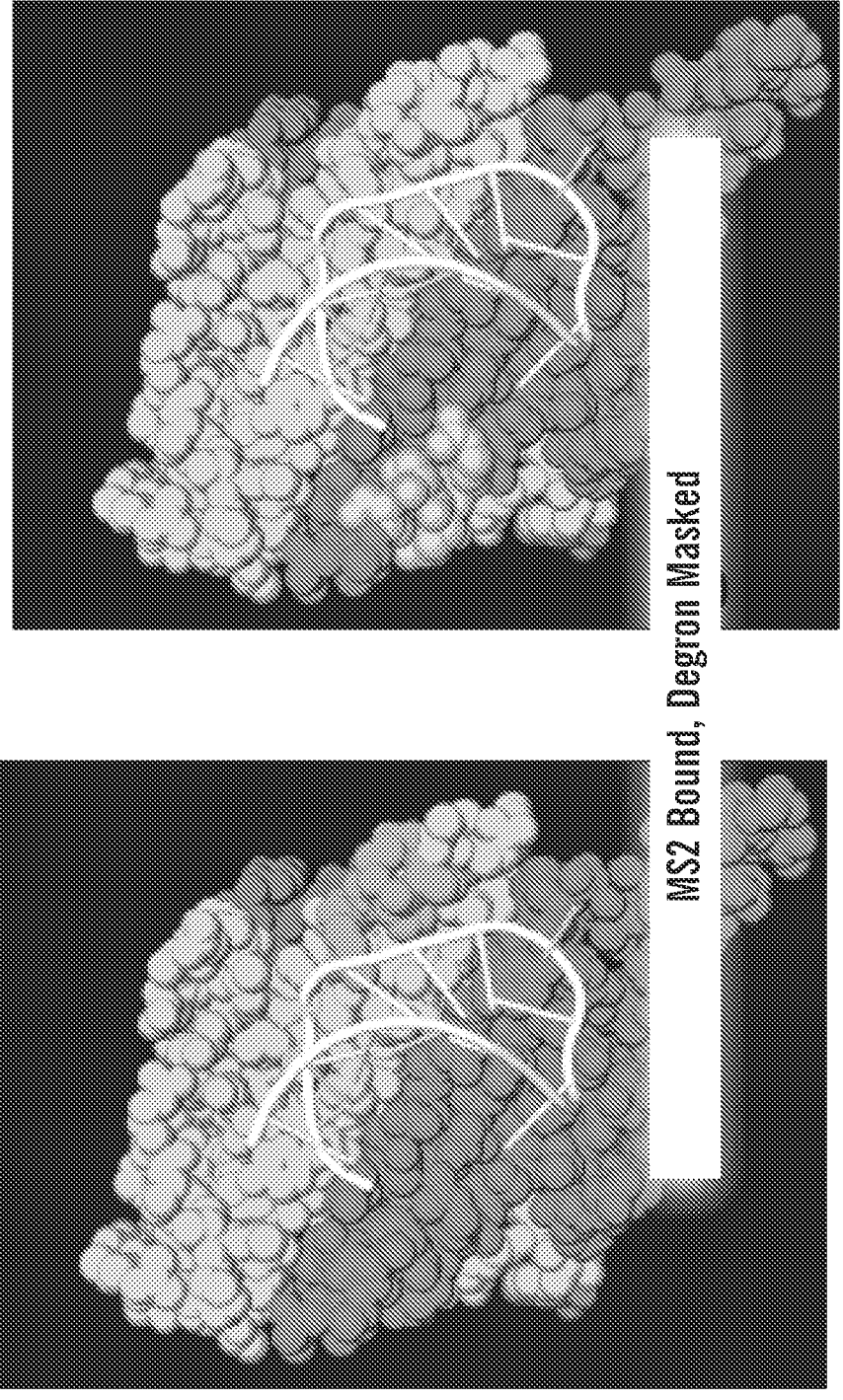
Figure 10C:
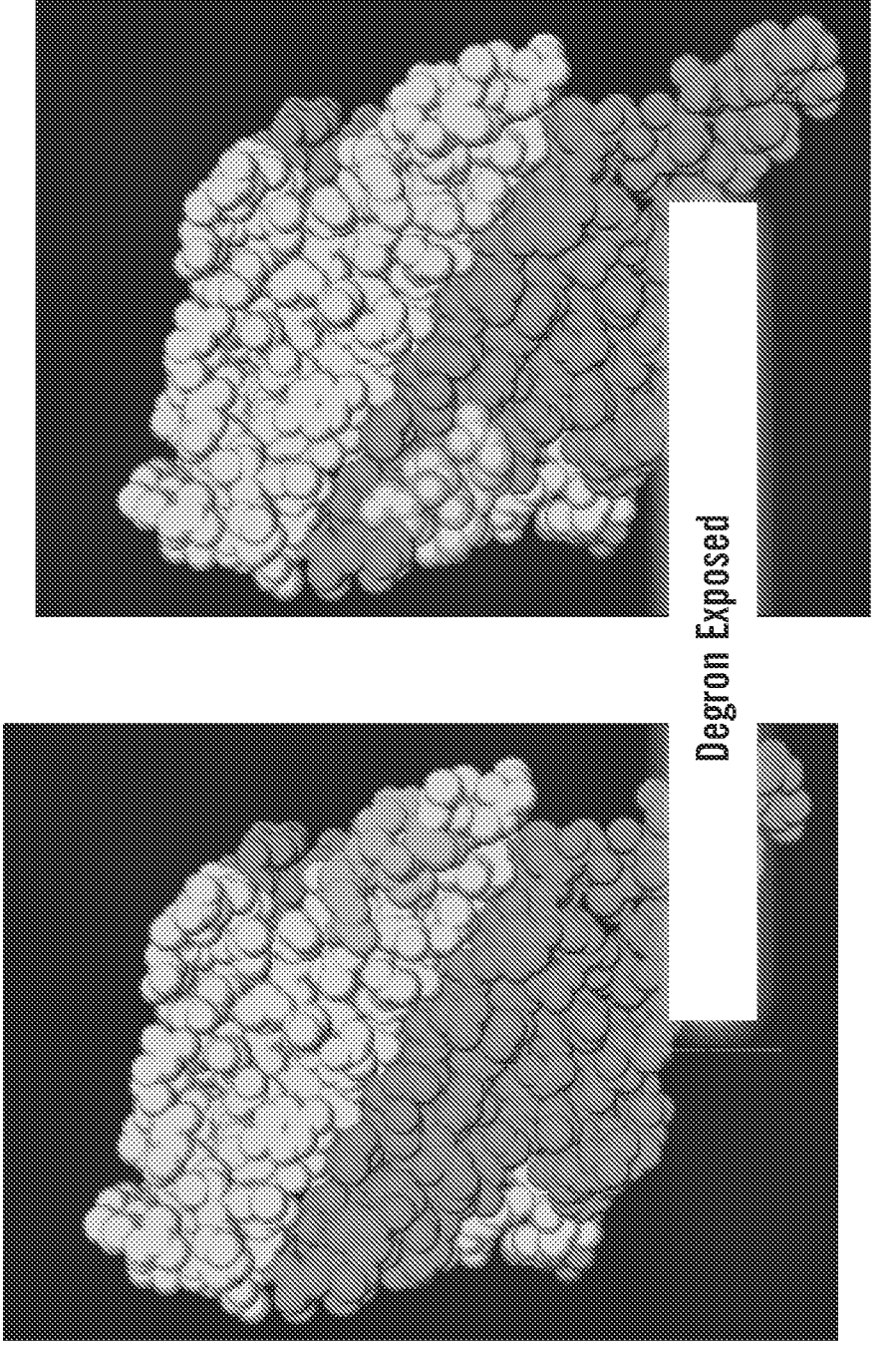
Figure 11:
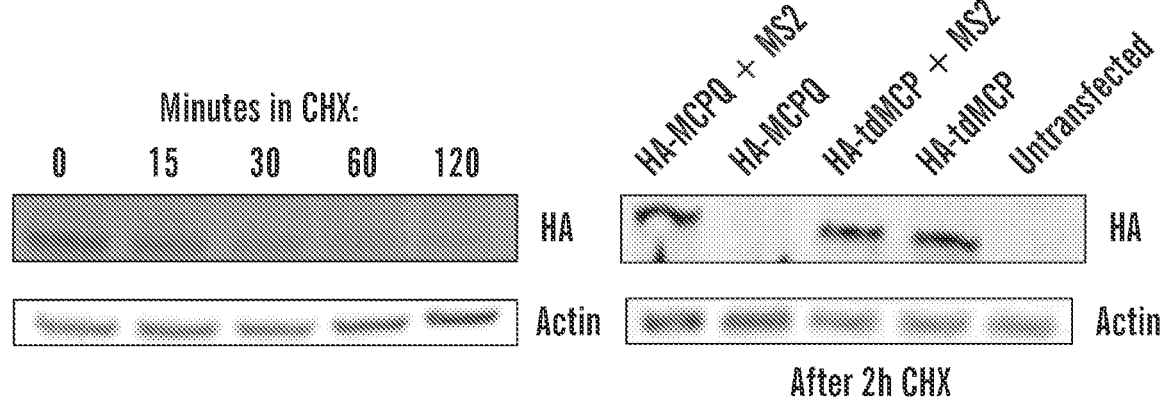
FIG. 11 shows Half-Life measurement of destabilized/tagged tdMCP (aka MCPQ, aka dMCP) by western blot and imaging. Cycloheximide (CHX) halts translation. Half-life of MCPQ was 15-30 min when not bound to MS2. In the presence of excess MS2 RNA, HA-tagged MCPQ was as stable over 2 h as tdMCP. Half-life shift generated contrast between conditions with/without MS2. Probes can introduce MS2 loop upon binding an endogenous mRNA.
Figure 11:
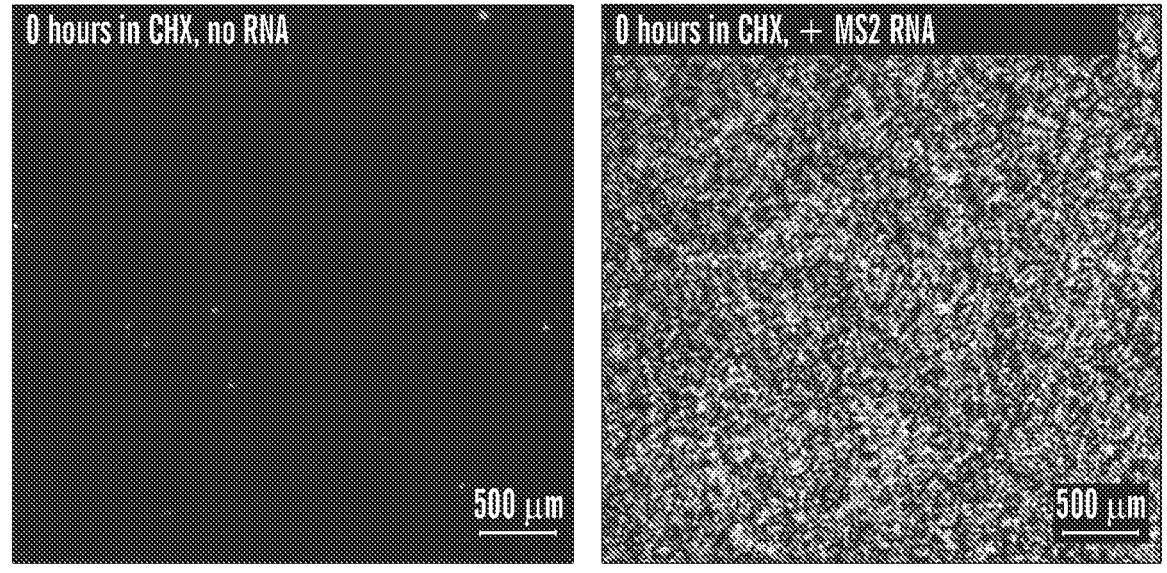
Figure 12:
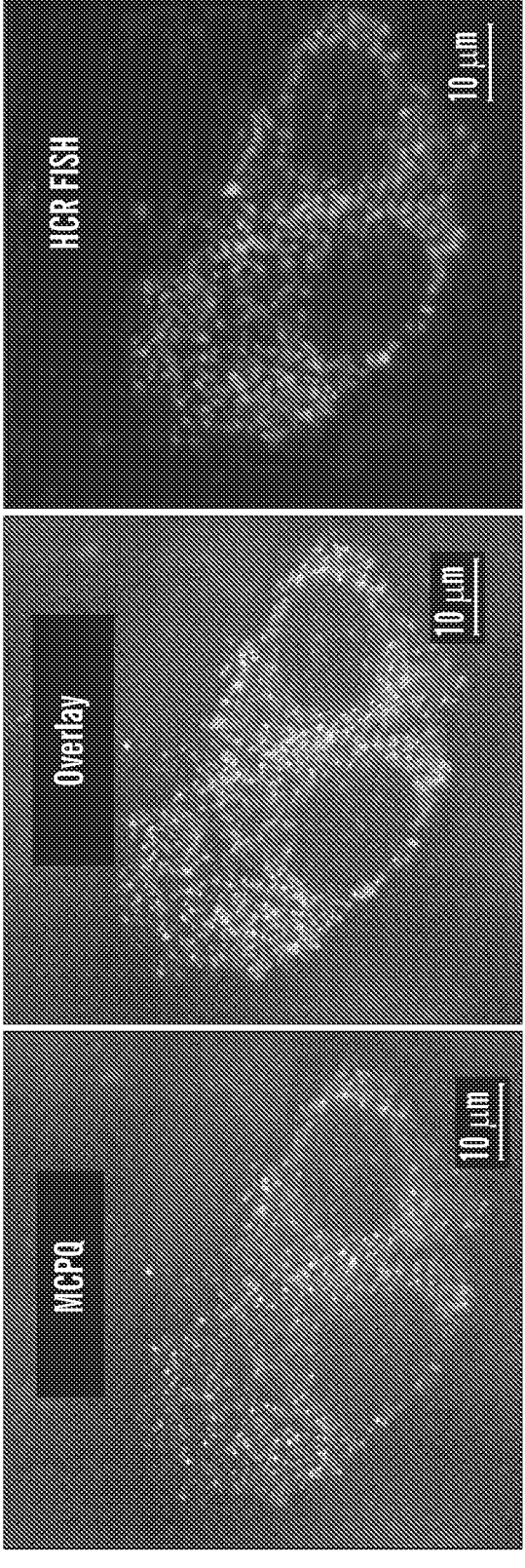
FIG. 12 shows expression of destabilized tdMCP enables background free single molecule detection of tagged RNAs in live cells. The detected MCP signals overlapped with direct detection of tag RNAs. 4×mNeonGreen was added to MCPQ for single-molecule imaging. HCR Fish uses an amplification technique to enhance signal. There was some heterogeneity in HCR FISH. Fixation reduced MCPQ image quality. MCPQ resolved single transcripts that overlap with HCR-FISH. tdMCP without an NLS was not effective at resolving single RNA molecules.
Figure 12:
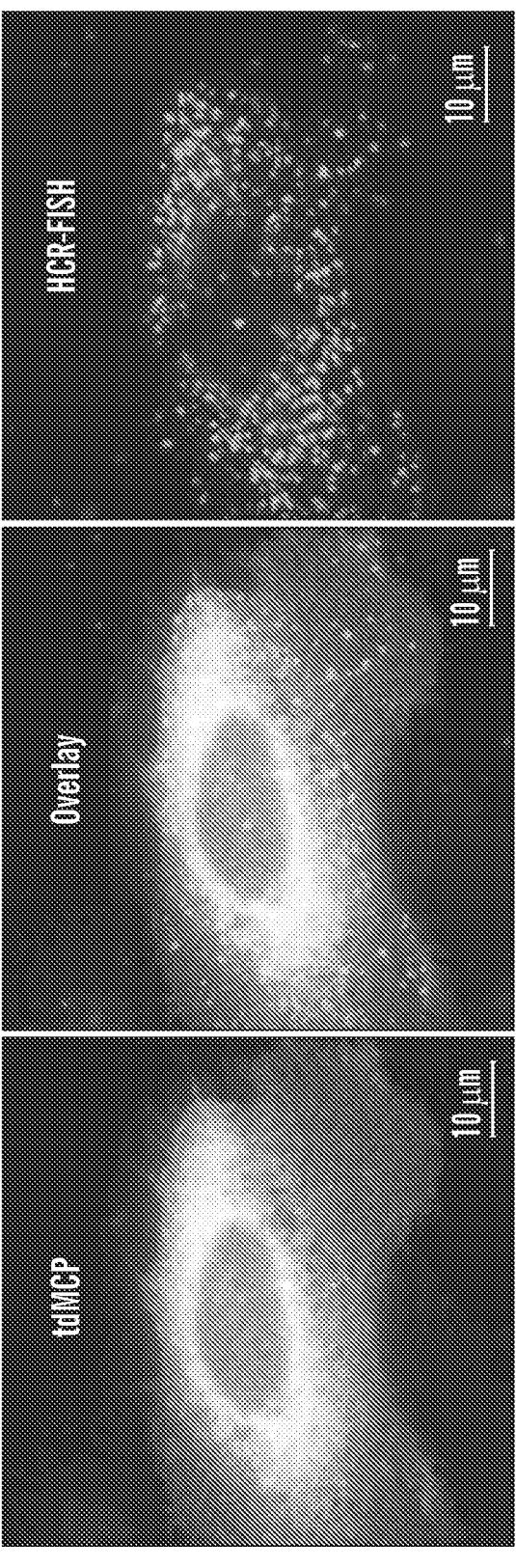
Figure 13:
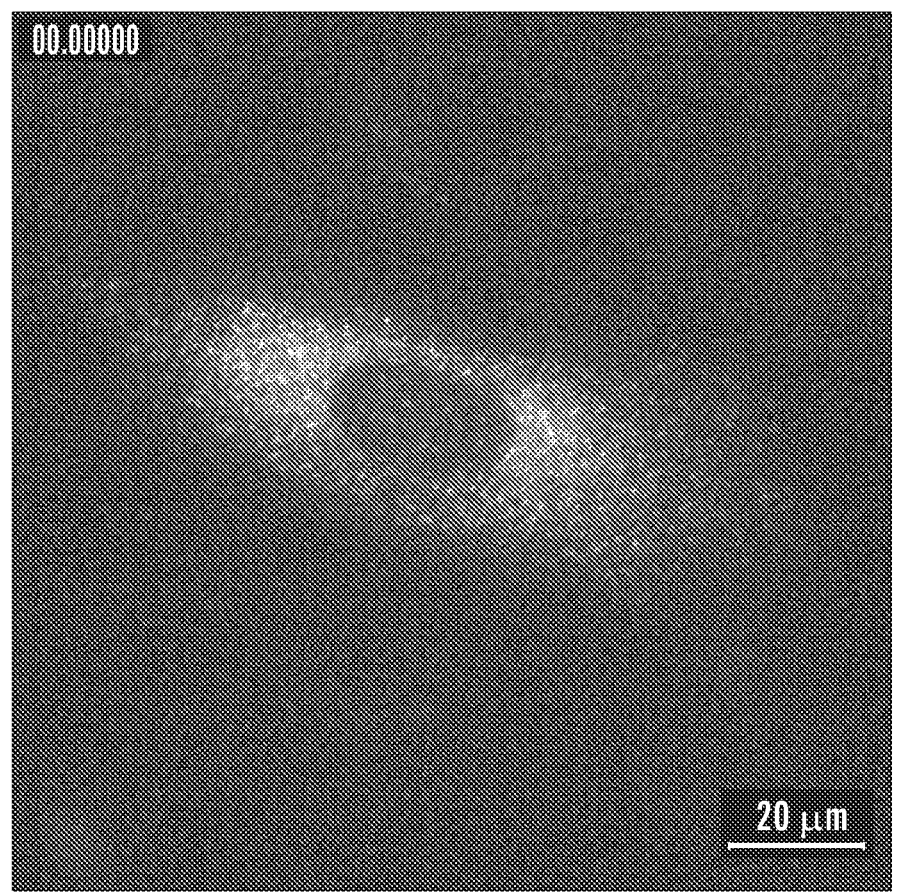
FIG. 13 shows Real-Time Live Imaging: TOM20-16× MS2 RNA. MCPQ imaging revealed an increase in static TOM20 mRNA in areas of high mitochondrial density.
Figure 14:
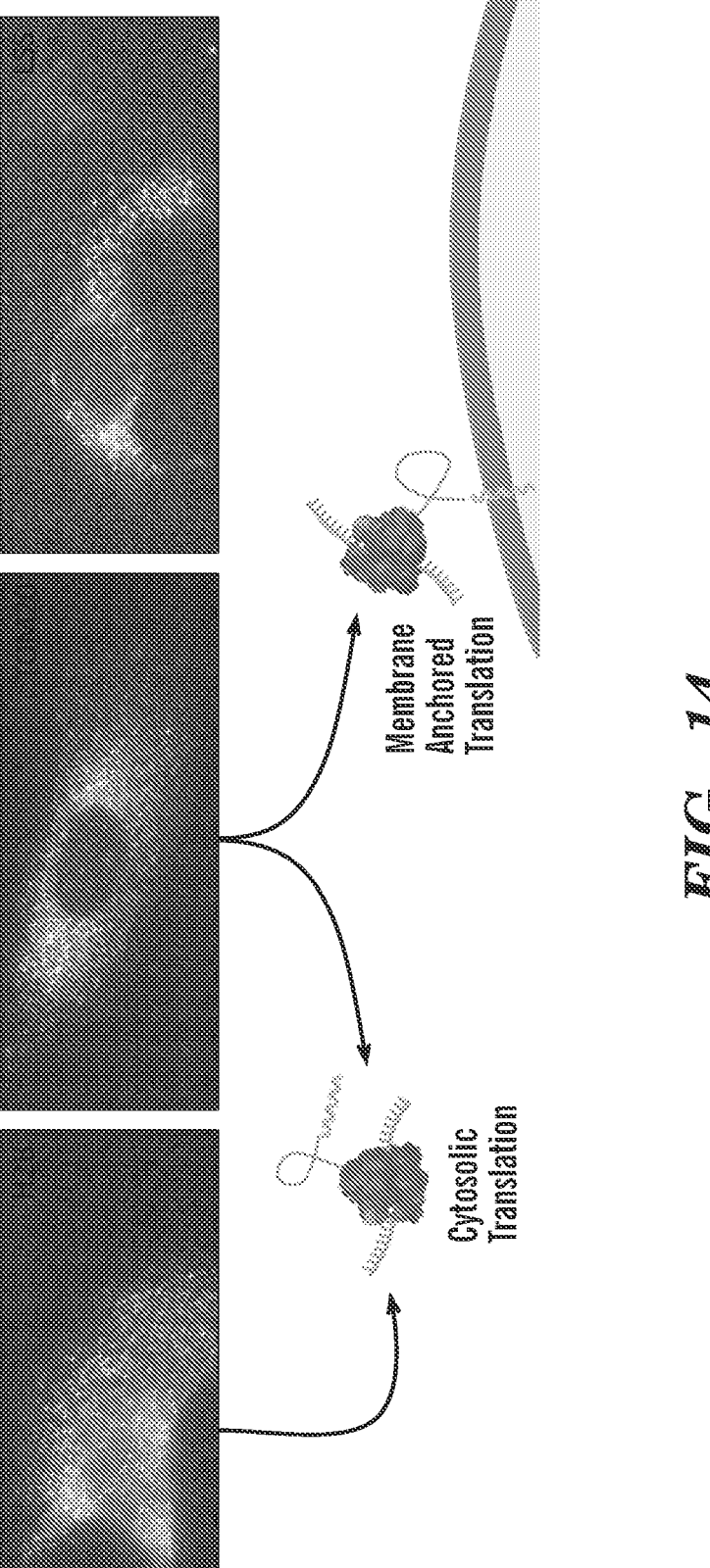
FIG. 14 shows an exemplary embodiment for detecting cytosolic translation and membrane anchored translation.
Figure 15:
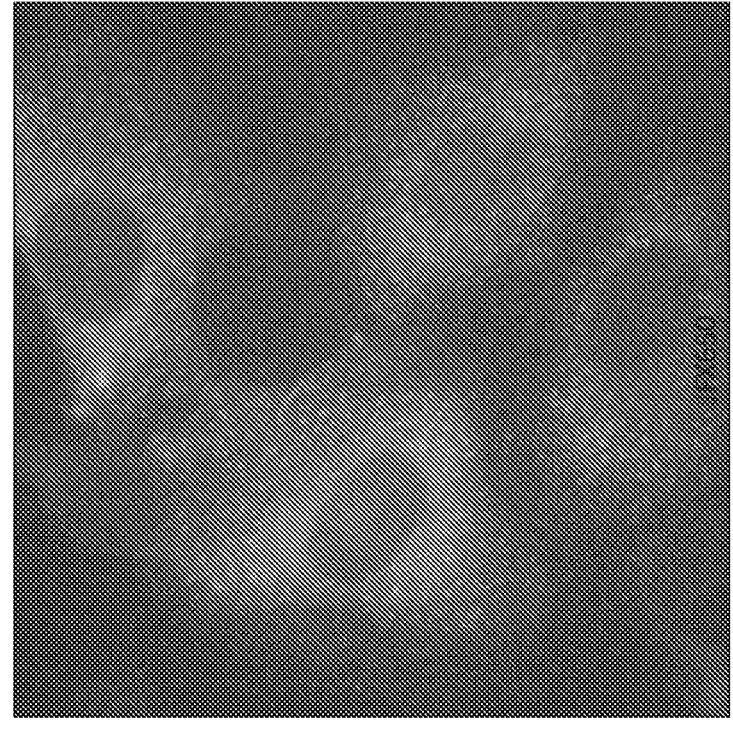
FIG. 15 shows 2×Halo-MCPQ With Far Red JFX Dyes.
Figure 15:
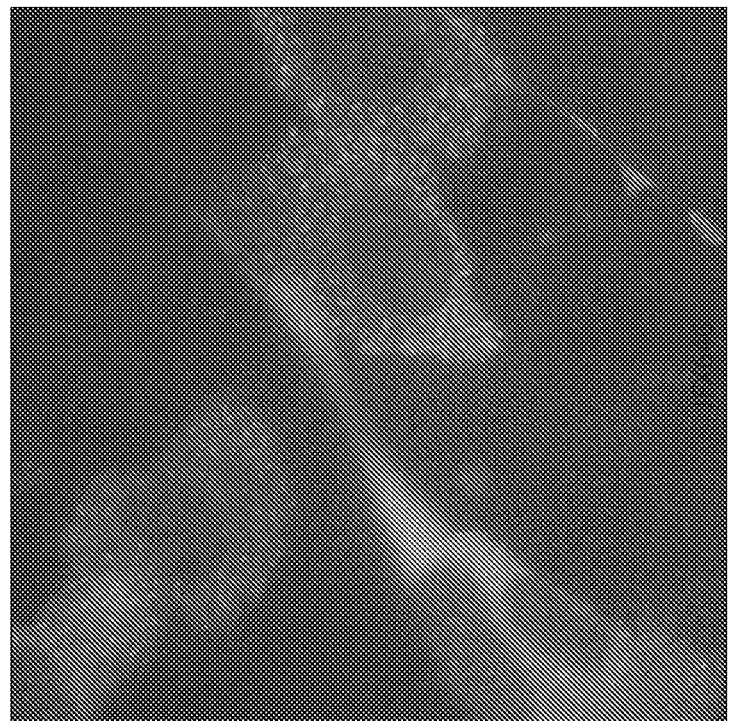

MCPQ fused to HALOTAG and stained with JANEL-IAFLUOR dyes yielded clear single-RNA imaging on red and far-red fluorescent channels (see e.g., FIG. 7C). In addition to HEK293FT and U20S cells, MCPQ performed well for RNA imaging in Human Dermal Fibroblast (HDF) primary cells (see e.g., FIG. 2D)

Example 4

The ubiquitin proteasome system degrades proteins from cells in a regulated way. Some proteins have degrons that are recognized by enzyme that attach ubiquitin to them, thus signaling their degradation. For certain proteins, attached degrons can be made "conditionally available" or "conditionally hidden." This mechanism is used to regulate when proteins are degraded or when they are preserved. In this project, a conditional C terminal degron was exploited to engineer an "MCP" protein (MS2 coat protein) that was stabilized in cells only upon binding a specific RNA tag (MS2 hairpin loop).

In cells, the "destabilized MCP" (also referred herein as d-MCP, MCP-q, destabilized tdMCP) confined signals from fused fluorescent tags only to sites where the RNA exists. In synthetic biology, an effector-fused MCP can be used to confine effector activity (such as translational control, localization, modification, or degradation of RNA, etc.) to only desired transcripts. The approach involved tandem dimerization followed by circular permutation of MCP. This allow attachment a C-degron to MCP in a manner such that is hidden from access only upon MS2 binding. This strategy is generalizable and was performed, e.g., with another protein-RNA pair based on PCP/PP7.

MCPQ revealed real-time single-RNA dynamics in live cells. MCPQ yielded high quality footage of known H2B and LSS mRNA dynamics. MCPQ revealed instances of TOM20 mRNA anchoring to mitochondria.

Alternative embodiments include: (A) HALOTAG work: (1) imaging RNA with red and far-red dyes; (2) Pulse chase experiments for protein and RNA half-life; (3) Electron microscopy using photosensitizer dyes; and (B) Primary cell work: Image cytoskeletal RNA during wound healing; Image RNA in *Drosophila*; Image RNA in neurons.

Example 5

The present disclosure describes work done to create a destabilized MCP, which is an RNA-binding component protein/device. MCP recognizes MS2 hairpins with high affinity and dissociates on the order of hours. The stable MS2-MCP complex has a much longer lifetime than the tDeg-TAR complex, and this stronger stabilization effect permits very sensitive and very selective detection/labeling of single mRNA transcripts.

The strategy used to develop the destabilized MCP involved the addition of a "C-degron" near the RNA-binding interface of the MCP protein. To do so, a tandem MCP fusion was created (MCP binds MS2 RNA as a dimer). In the normal/wild-type complex, the C-terminus of the dimeric MCP is positioned far away from the RNA-binding interface, and in this orientation RNA binding was not expected to result in protein stabilization. To create a version where the degron can be blocked via RNA binding, a circular permutation of the construct was generated in which the C-terminus of the tandem MCP fusion was repositioned to MCP's RNA binding pocket. In this way, the degron becomes masked upon RNA-recognition.

In addition to a destabilized MCP, also describe herein is a destabilized PCP, which is a distinct and orthogonal RNA hairpin binding protein. Such design also involved circular permutation and degron fusion.

There are several conceivable applications, including, but not limited, to the below examples.

1. Cellular RNA imaging by EM (e.g., via fusion with APEX, miniSOG, or other EM tags).
2. Cellular RNA imaging by fluorescence via fusion with fluorescent proteins, or other labels including HALOTAG, SNAP tag, etc.
3. In vivo imaging of RNA via fusion with luciferases with appropriate chemiluminescence emissions, or via fusion with other detectable labels in the near-IR range, or via MRI, etc.
4. Synthetic biology application in the regulation of expressed and delivered tagged mRNAs, including processes such as editing, translation, degradation, localization, etc.
5. Time-dependent labeling of RNA transcripts by multicolor pulse-chase labeling of the destabilized MCP construct though labels like HALOTAG and SNAP. When MCP is stained with different color dyes at different time points, RNA tagged by MCP appear as the color of the stain that was being administered to MCP at the time of the RNA's production
6. Synthetic biology application in the formation of multi-protein component complexes.

Example 6 dMCP is an engineered variant of a naturally occurring bacteriophage-derived protein (MS2 Coat Protein, or 'MCP') that binds a specific MS2 RNA aptamer with high affinity. It is derived from an engineered variant 'tdMCP'. Two modifications distinguish dMCP from its parent tdMCP. First, dMCP features a circular permutation that relocates its N and C-terminus to the binding pocket, where dMCP comes into contact with its MS2 RNA binding partner. Second, a degron is inserted at dMCP's C-terminus in such a position that it is concealed when dMCP binds its MS2 RNA binding partner, but is otherwise detectable.

Together, these modifications produce the function of dMCP, which is that it is only stable when bound to MS2 RNA, and is destroyed when not bound to the RNA. When dMCP is fused to another protein, its MS2 RNA-dependent stability is extended to that protein. dMCP-fusible effector proteins include RNA nucleases, DNA nucleases, RNA base editors, DNA base editors, translation initiators, translation inhibitors, transcription initiators, transcription inhibitors, peroxidases, transport domains, and more. By fusing these effector proteins to dMCP, their existence in a cell becomes dependent on their contact with specific MS2-containing RNA. As described herein. this function is valuable in a therapeutic context, as it can grant improved sensitivity and specificity to the effector proteins described above.
Therapeutic Applications An exemplary therapeutic application of this system is in treatments that use conventional MCP to bring effector proteins in contact with targeting RNAs. Direct replacement of MCP in these systems with dMCP can 1) reduce off-target effector protein activity in cells that do not receive targeting RNA, and 2) reduce off-target activity from effector proteins not bound to targeting RNA.

For example, dMCP can be used in ADAR-based therapies; see e.g., Katrekar et al. Nat. Methods 16, 239-242 (2019); Gayet et al. Nat. Commun. 14, 1339 (2023);

Kaseniit et al. Nat. Biotechnol. 41, 482-487 (2023). dMCP can improve the accuracy of the ADAR-based RNA-editing therapies. ADAR-based systems have been shown to have substantial levels of off-target effects (see e.g., Vallecillo-Viejo et al. RNA Biol. 15, 104-114 (2017)).; such effects can be reduced by using dMCP. dMCP can also be used in DNA base-editing systems in place of MCP to improve base editing fidelity; see e.g., International Patent Publications, WO2021072328A1, WO2019217943A1, WO2020191248A1.

Results

Figure 19:
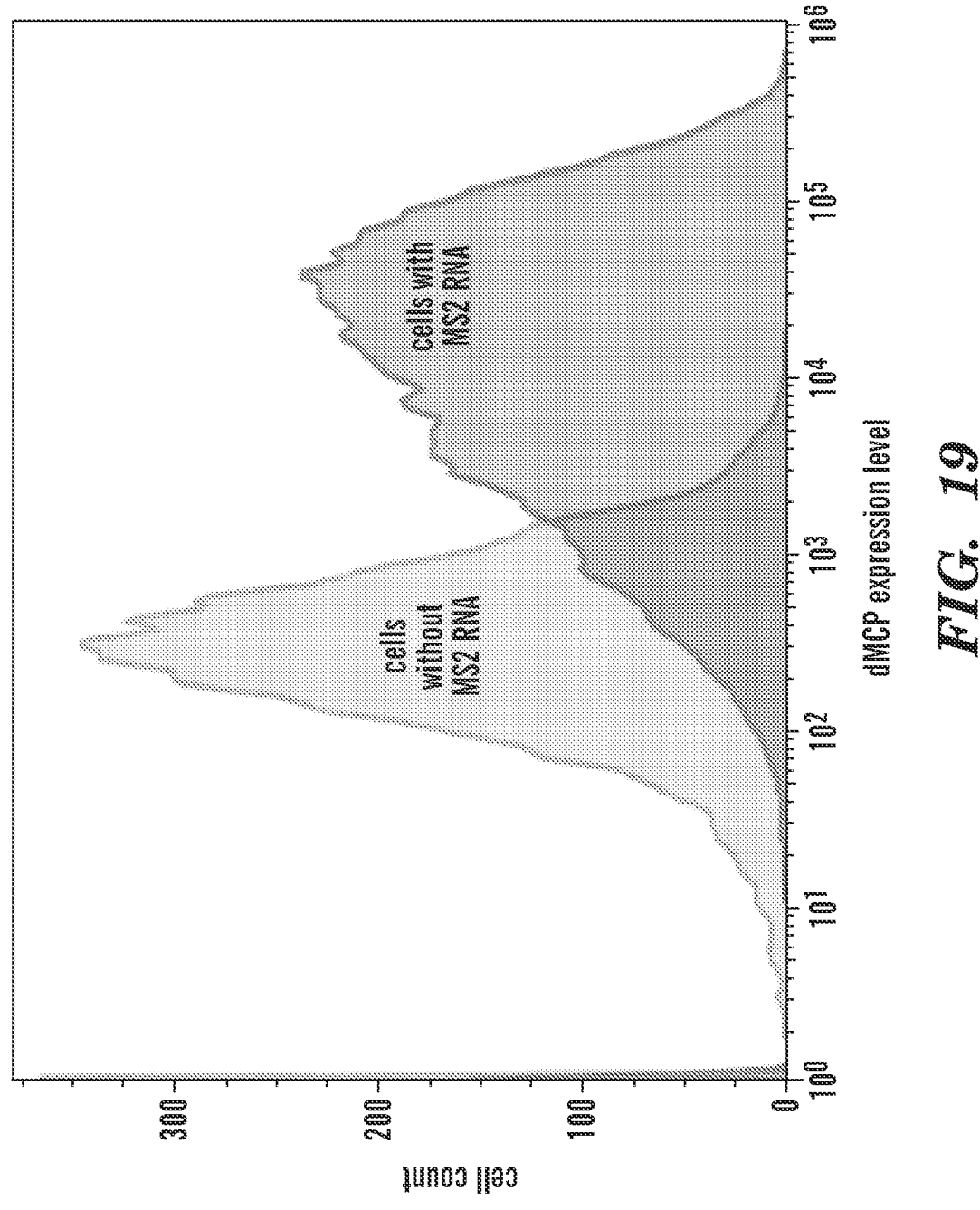
FIG. 19: Flow cytometry data of dMCP expression in cells with or without MS2 RNA. dMCP is fused to a fluorescent protein for expression measurement.

1: CELLULAR LEVEL RNA DEPENDENT PROTEIN ACTIVITY: dMCP undergoes a 50-fold increase in cellular concentration when MS2 RNA is present (see e.g., FIG. 19). This function is useful for therapeutics that involve delivery of both protein and RNA components, such as CRISPR or ADAR-based systems. These use RNA to direct activity of their effector proteins. Without targeting RNA, the effector protein can act on off-target sites and introduce effects that hurt patients. dMCP can disable effector activity in cells that did not receive targeting RNA during treatment, reducing the likelihood of an off-target event in these cells.

2: MOLECULAR LEVEL RNA DEPENDENT PROTEIN ACTIVITY: The protein-RNA therapeutics described above involve an effector protein and a targeting RNA binding one another within a cell. However, many cells will not receive enough targeting RNA to bind all received effector proteins. This is especially true for systems in which the protein is generated from the targeting RNA, because often hundreds of proteins are produced from a single RNA.

Figure 20:
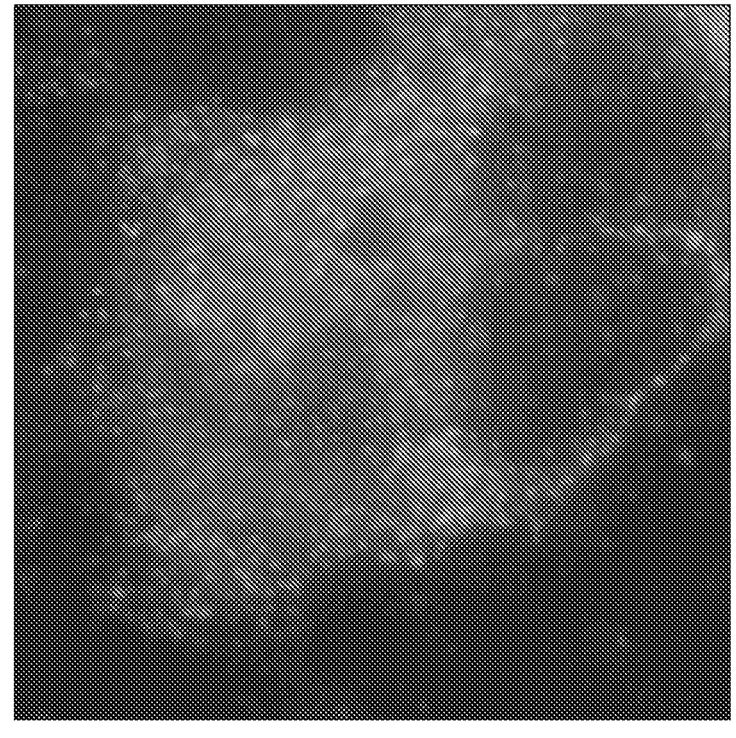
FIG. 20: Fluorescent microscopy images of a U2OS cell expressing a JF570-HaloTag® dMCP (red dye, left) or expressing a fluorescently labeled APEX2 dMCP (purple dye, right) targeted to an MS2-containing RNA. The pattern revealed increased JF570-HaloTag® and APEX2 concentration at the sites of MS2-containing RNA and reduced concentration outside of those sites.
Figure 20:
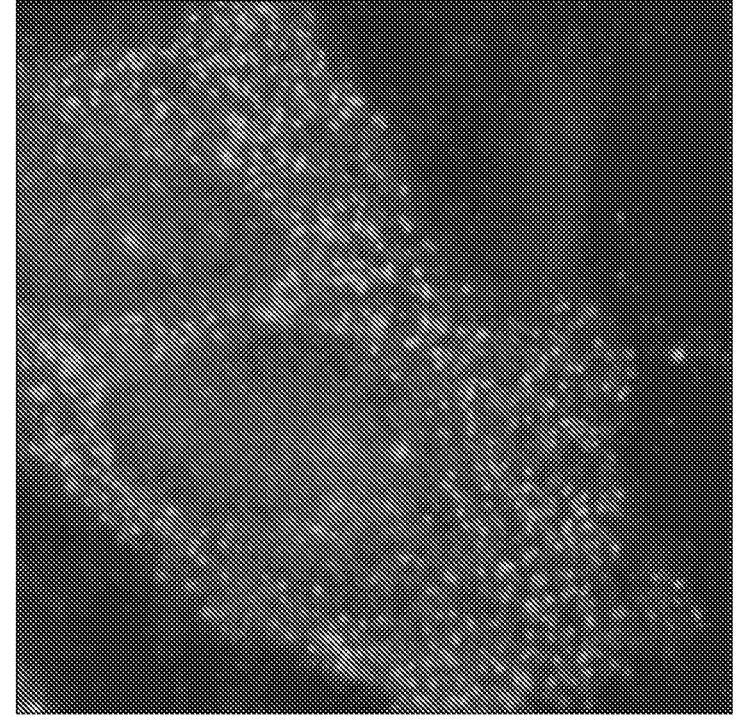

Within a cell containing both effector protein and targeting RNA, excess protein that does not bind targeting RNA introduces an increased risk of off-target effects. dMCP triggers the destruction of effectors not bound to a target RNA, reducing the risk of off-target activity within cells containing both effector protein and targeting RNA. Multiple effectors fused to dMCP, including a photo-oxidizing protein, JF570-HALOTAG, and a fluorescently tagged APEX2 peroxidase, were shown to be highly concentrated in regions proximal to MS2-containing targeting RNA while maintaining minimal concentration outside of these regions (see e.g., FIG. 20). Both JF570 and APEX2 can be used to target oxidative damage to viral RNAs without damaging off-target endogenous RNAs. MCP-fused APEX2 can be used to modify targeted RNA with a variety of chemical groups, and dMCP can increase the precision of this modification.

Figure 21A:
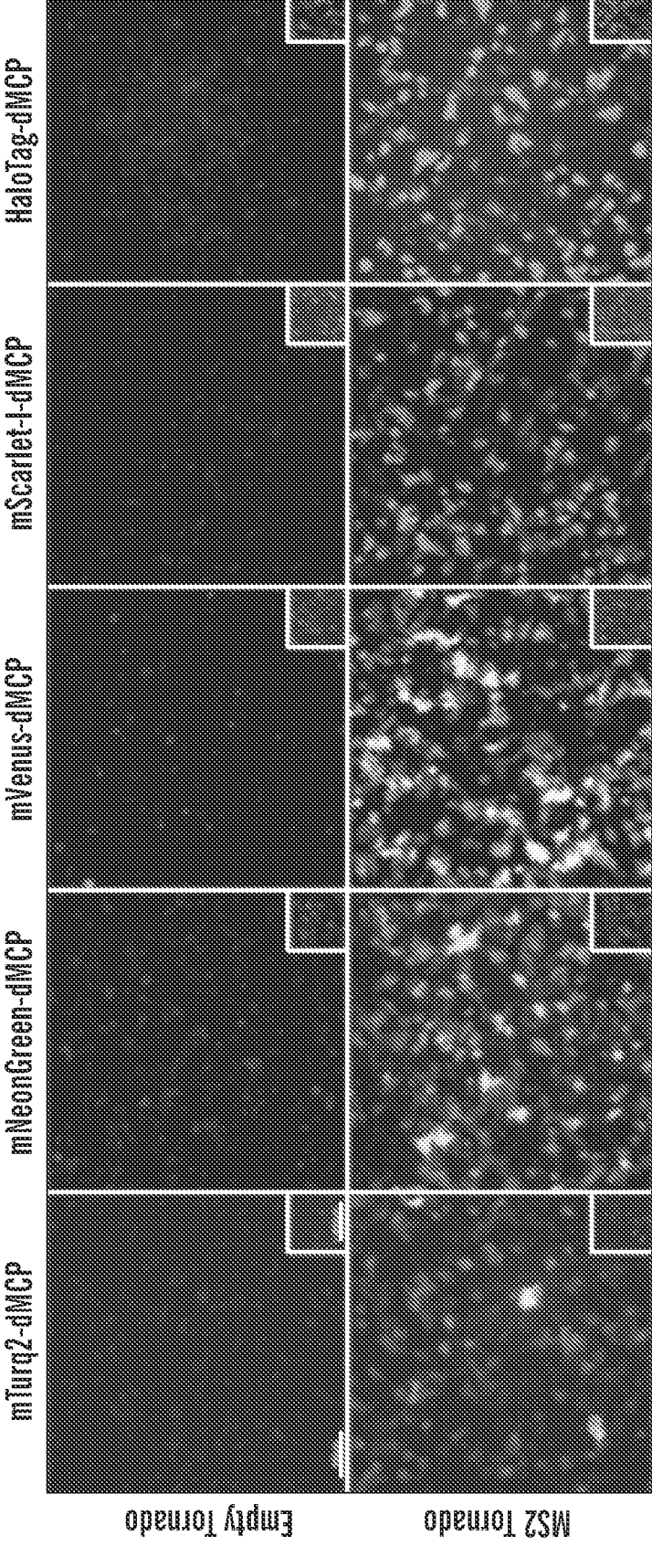
FIG. 21A-21B: dMCP retained strong RNA-dependent stability for multiple RNA types while used to multiple proteins.
Figure 21B:
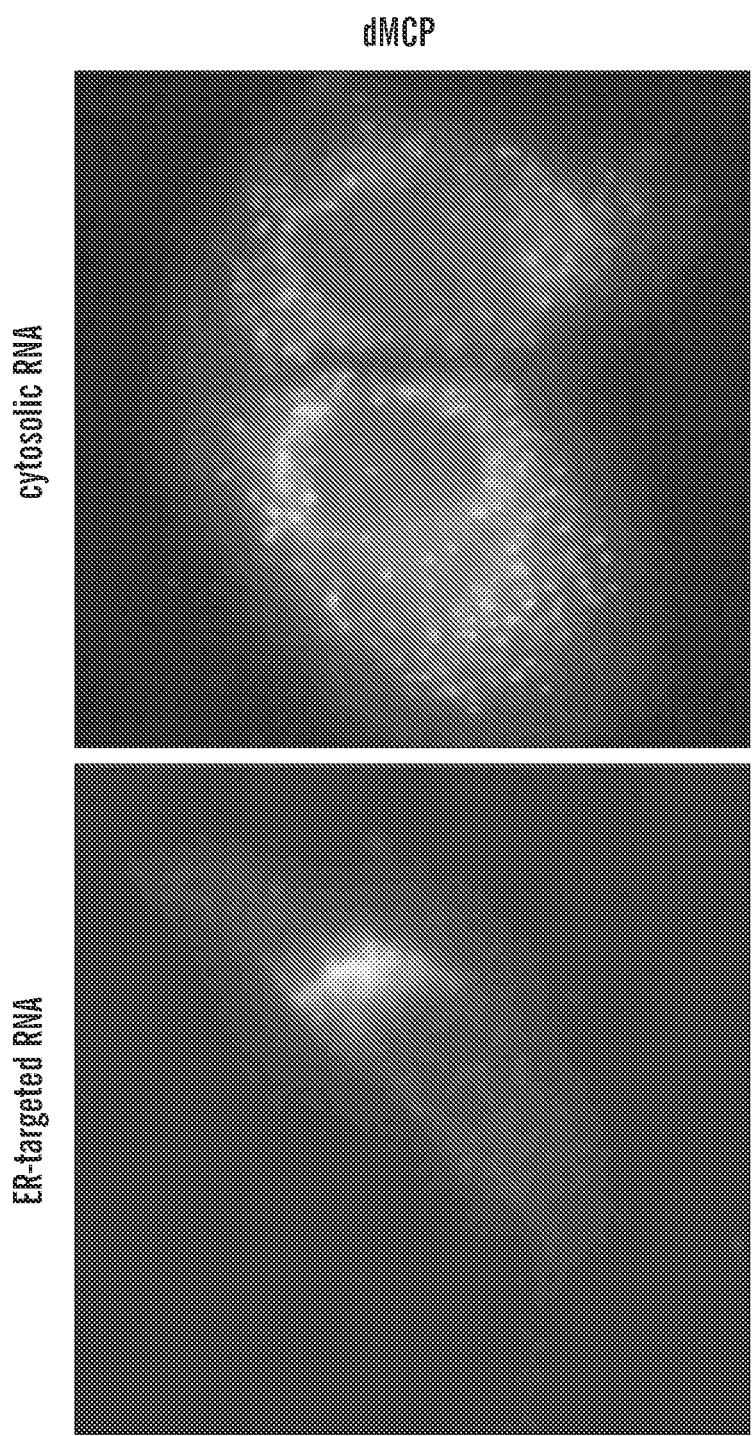
Figure 22:
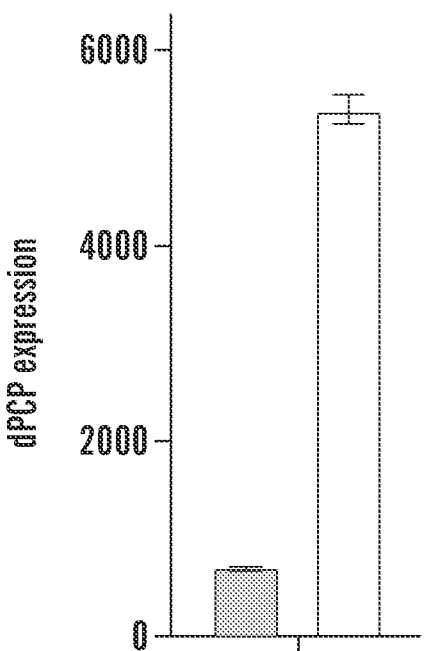
FIG. 22: Flow cytometry data of dPCP expression in cells with or without PP7 RNA. dPCP was fused to a fluorescent protein for expression measurement.

3: COMPATIBILITY WITH SEVERAL RNA TYPES AND COMPATIBILITY WITH SEVERAL FUSED PROTEIN DOMAINS: dMCP is sensitive to circular RNA as well as linear RNA and can also respond to a variety of subcellular targeted RNA, including endoplasmic-reticulum targeted RNA (see e.g., FIG. 21). Different RNA therapeutics can contain several combinations of these features, so this data demonstrates the flexibility of dMCP and its ability to be applied to a wide range of RNA-based therapeutics 4: GENERALIZABILITY OF APPROACH TO RELATED PROTEINS: The methods used to engineer dMCP were applied to a related RNA-binding protein, PCP, that binds an orthogonal aptamer, PP7. The resulting protein, dPCP, is stable only when bound to PP7 aptamer (see e.g., FIG. 22). This data introduces a second protein-RNA pair that maintains the functionality of dMCP while working independently such that dPCP and dMCP can work in parallel within the same cell. The data also indicates that the technique can be extended to generate further additional protein-RNA pairs in which the stability of the protein is RNA-dependent.

Figure 23:
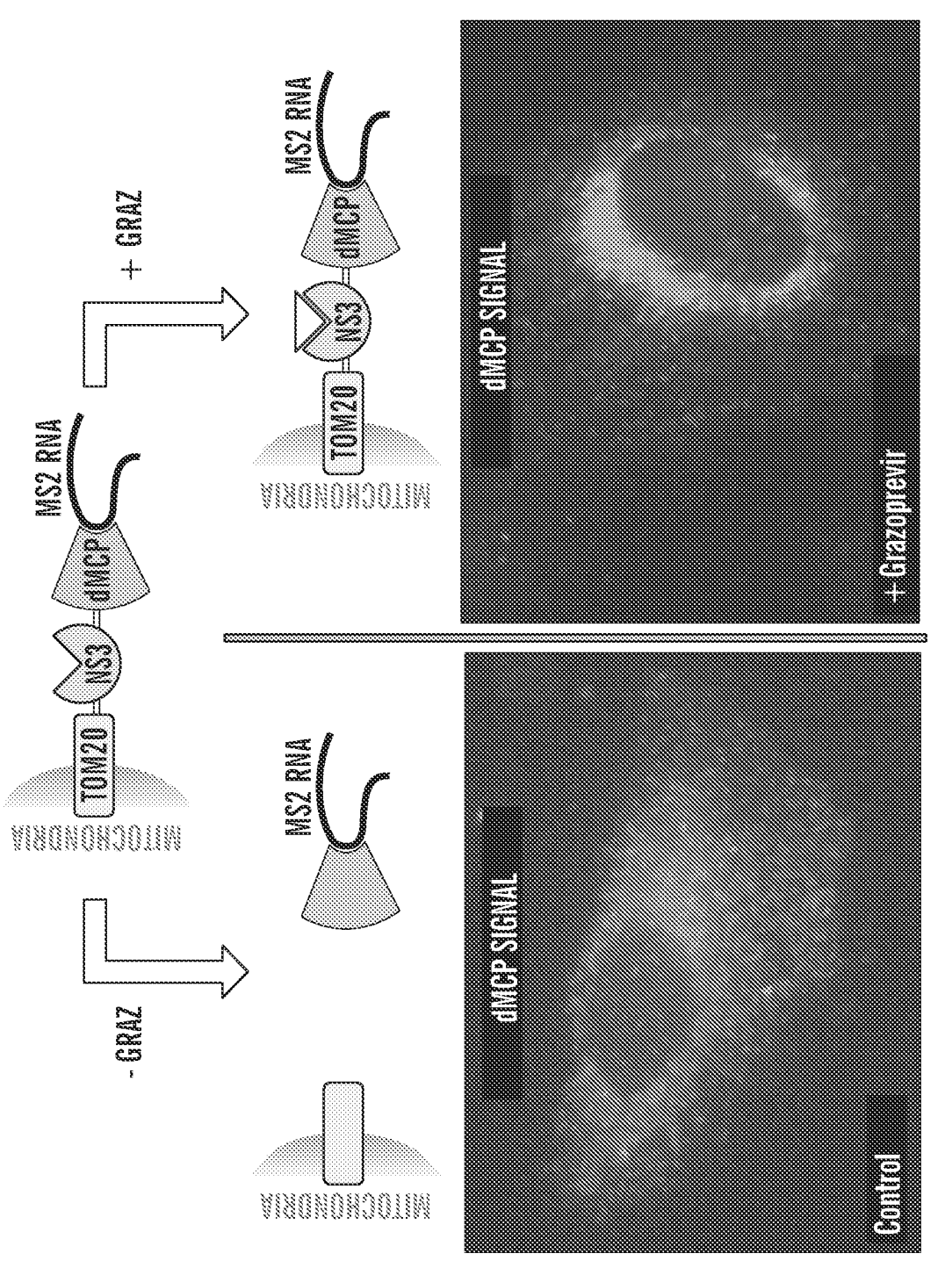
FIG. 23: dMCP can be fused to drug inducible domains. Here, fusion to TOM20-NS3 grants dMCP capability to transport RNA to mitochondrial regions in response to grazoprevir drug addition.

5: COMPATIBILITY WITH DRUG-REGULATED PROTEIN DOMAINS AND CONTROL OF RNA TRANSPORT: dMCP retains its function when fused to drug-regulated domains, allowing for the development of drug-dependent systems. For example, dMCP fused to NS3 protease can be used to bring a protein into contact with a specific RNA when the approved antiviral compound Grazoprevir is administered. NS3 was used to control the interaction between dMCP and a mitochondria-targeting TOM20 protein. Upon the addition of grazoprevir, dMCP and its bound RNA were brought into contact with mitochondria (see e.g., FIG. 23). Dynamic transport is necessary for the function of certain RNAs involved in tissue development such as beta actin, so a system like this can be applicable to tissue engineering.

Additional Therapeutic Applications

MCP has been used as a genetically-encoded protein-RNA adaptor to perform therapeutically useful functions. Lipid-nanoparticle and viral vector technology have permitted scalable delivery of genetically-encoded drugs. Therefore, several therapeutic functions of MCP that previously had not been used in patients due to delivery constraints are now eligible for translation using dMCP. dMCP, being a system that increases the specificity of MCP, can enhance the function of many therapeutics based on MCP.

Among systems that make use of MCP, gRNA-targeted effectors such as Cas9, dCas9, Cas13, dCas13, and others have therapeutic relevance as gene editors. Conventional MCP has been used to enhance these systems for therapeutic applications such as prime editing by recruiting effectors directly to the gRNA. dMCP can improve the specificity of such systems by eliminating effectors that have not bound the gRNA, thus preventing their off-target activity. Studies that use the RNA-binding protein tDeg in combination with Cas9 permitted more precise imaging of genomic loci (see e.g., Zhang et al. Nat. Commun. 15, 934 (2024); Chen et al. Adv. Sci. e2402534 (2024)), indicating the ability for improved precision of gene-editing effector protein activity when said proteins are targeted to these loci by RNA-stabilized domains like tDeg and dMCP.

An additional therapeutically relevant system is MCP-controlled cap-independent translation. These systems use MCP to recruit translation-initiating factors to mRNA. They are therapeutically relevant because circular RNA therapeutics rely on cap-independent translation and therefore require systems such as these to function. dMCP can reduce the risk of off-target cap-independent translation initiation events by eliminating any initiating factors which are not bound to a specific target RNA.

Example 7

The human body comprises over 200 distinct cell types, all arising from a single fertilized zygote. How does this occur? Furthermore, throughout development and adulthood, stem cells divide to give rise to daughter cells of distinct cellular fates—a process required for proper tissue formation and renewal. Can this process be engineered? The dMCP fusion proteins described herein can be used to help understand, detect, and/or control subcellular RNA localization.

Stem cells can divide into daughter cells committed to distinct lineage-specific fates. One mechanism underlying this capacity includes the ability to undergo asymmetric cell division (ACD), which can be facilitated through the direct transport of cellular components or contact-dependent mechanisms dependent on specific cellular niches. Synthetic versions of these mechanisms can mediate mRNA-based asymmetries in polarized mammalian cells, to facilitate a deeper understanding of ACD and to permit its engineering for multicellular and tissue design applications.

(1) Developing tools for inducible and bidirectional transport of synthetic mRNAs. Methods described herein can regulate the bi-directional transport of mRNAs along microtubules in polarized cells.

(2) Programing cell cycle-mediated regulation of mRNA stability. Cell cycle-regulated degrons can be exploited to control the trafficking and stability of engineered mRNAs within cells.

1. Developing tools for controlling synthetic and bidirectional mRNA transport. Tight regulation over mRNA localization is essential during development and adulthood, regulating processes from body axes determination in *Drosophila* to the synaptic plasticity exhibited by adult neurons. Described herein are tools to control mRNA localization using microtubule (MT)-associated motors fused with "destabilized" RNA binding proteins. The destabilized versions of phage-derived coat proteins MCP and PCP (dMCP and dPCP) described herein are rapidly degraded in cells—except when bound to their cognate RNA hairpins. Synthetic machinery using dMCP and dPCP, can control plus-end and minus-end direct transport mRNA transcripts tagged with MS2 or PP7 hairpin sequences. Described herein are fusion constructs in which the RNA-binding proteins are linked with MT-associated transport machinery (including kinesins and dyneins). In addition, light-inducible transport systems include fusions of kinesin and dMCP tagged with photoinducible heterodimerizing proteins. Tests involve using cultured polarized cells (including epithelial cell lines such as Caco2 and in iPSC-derived neurons generated via doxycycline-induced Ngn2). The localization of the targeted mRNAs can be confirmed in fixed specimens via in situ hybridization, and labeling technologies can be used to visualize the active transport of tagged mRNAs in real time. In addition to live-cell imaging, probes can be used for highly specific proximity labeling to identify components of natural RNA-protein complexes. To demonstrate the utility of these tools within an in vivo system, inducible localization experiments can be performed using a model based on the fly embryos. These studies demonstrate sensitive, selective, and foundational tools to permit new avenues of RNA investigation and synthetic engineering.

2. Programing cell cycle-mediated regulation over mRNA stability. The targeting and asymmetric inheritance of cellular components is intrinsically linked to the cell cycle. As described herein, cell cycle-regulated degrons can be used. Degrons from the licensing factor Cdt1 or its inhibitor Geminin can be used to generate cell-cycle dependent proteins linked to dMCP or dPCP, and their activities can be tested against corresponding mRNA targets in transduced HeLa cells, fly-derived S2 cells, and in the multipotent mouse embryonic fibroblast line C3H10T1/2. Since proteins tagged with the Cdt1 degron are stable only during G1, we expect Cdt1 fusions to bind mRNA only during G1 phase. Similarly, since Geminin is stable during S and G2, Geminin fusions are expected to bind its RNA target only during non-G1 stages of interphase (S and G2). In situ hybridization and live-cell RNA imaging can be used to validate these components. Phase-specific analyses can be done using synchronized cell populations (following treatment and release from cell cycle inhibitors, such as nocodazole or thymidine, etc.), and time-specific metabolic RNA labeling can be done, e.g., using the clickable ribonucleotide ethynyl-uridine (EU). Live RNA imaging using tools such as dye-aptamer-based systems and RNA visualization can be conducted in cells co-expressing Fluorescence Ubiquitin Cell Cycle Indicator (FUCCI) proteins.

Example 8: dMCP Utility: Recruitment of Translation Regulators to Synthetic MS2-Containing Linear and Circular mRNAs Recruitment of the Caliciviral VPg-based Translational activator (CaVT) to mRNAs can facilitate their translation. This is useful for mediating the translation of mRNAs lacking a canonical 5' cap, which typically needed to recruit ribosomes and translation machinery to mRNAs. CaVT can facilitate ribosome/translation machinery recruitment to RNA lacking such caps. MCP-CaVT fusions have been used to recruit translation machinery to MS2-containing mRNAs (see e.g., Nakanishi et al. Nat Commun. 2020, 11(1): 1297).

A dMCP-CaVT fusion can be used in similar applications. The advantage of using dMCP (instead of MCP) is that expression levels of CaVT-dMCP can be minimized and confined to the targeted (MS2-containing) RNA of interest (this occurs because excess unbound copies dMCP-CaVT copies are degraded).

(a) Inducible translation of MS2-containing mRNAs involve using systems to control the formation CaVT-dMCP complexes. For example, by using drug-sensitive systems such as: (1) dMCP and CaVT can be separately fused to drug-inducible heterodimerizing domains (e.g., FKBP/FRB, or domains that interact in response to gibberellin, abscisic acid, etc.), and chemically induced interaction complexes can be used to activate translation from MS2-containing mRNAs. (2) A separate drug-regulatable system can use a CaVT-NS3-dMCP fusion, where NS3 is the cis-protease from the Hepatitis C Virus (HCV). Upon translation of CaVT-NS3-dMCP, newly made copies would be destroyed by the self-cleaving activity of NS3. However, upon inhi-bition of the protease with a selective NS3 inhibitor (e.g., grazoprevir, asunaprevir, etc.), the fusion remains intact and thus facilitates CaVT recruitment to MS2 containing RNAs. (see e.g., Tague et al. Nat Methods, 2018, 15(7): 519-522)

(b) Cell-cycle dependent translation of MS2-containing mRNAs.

A system to mediate the cell-cycle-dependent translation of MS2-containing mRNAs involves fusing CaVT-dMCP to a cell-cycle-dependent degron, such as those used in design-ing FUCCI cell cycle indicators. Such degrons include those of cell cycle-regulated proteins such as Cdt1 and Geminin, etc. (see e.g., Grant et al. Cell Cycle, 2018, 17(21-22): 2496-2516; Lyons et al. Wiley Interdiscip Rev Dev Biol. 2012, 1(2): 231-52).

Using such a system, one can limit the translation of an mRNA to cells during only specific cell cycle stages. Such a system can also limit the translation of synthetic/delivered RNAs only to proliferating cells.

(c) Translation linear and MS2-circular mRNAs. Both linear and circular mRNAs can be combined with the CaVT-dMCP regulators.

Circular RNAs: Circular RNAs are intrinsically cap-less, and synthetic circ-RNAs rely on IRES sequences to facili-tate protein translation. A circ-mRNA can contain an MS2 loop 3' to an ORF. CaVT-dMCP binding to the MS2 loop can then facilitate the translation of the downstream ORF.

In a circular RNA construct, CaVT-dMCP can be expressed via an IRES, and the produced CaVT-dMCP can then activate the translation of the MS2-regulated ORF.

Circ-RNAs offer the advantage of prolonged lifetimes in cells. However, a recognized limitation of IRES-containing circ-RNAs is that the IRES-regulated protein is often expressed at relatively low levels. Using an IRES-driven CaVT-dMCP with an MS2-regulated effector-encoding ORF, CaVT-dMCP can drive amplified expression of the second ORF.

Cap-less linear RNAs: 5' caps typically recruit translation machinery to mRNAs and protect them from 5' to 3' exo-nuclease activity (e.g., Xml, etc.).

Cap-less linear mRNAs can be regulated by MS2/CaVT-dMCP as noted above. To prevent degradation of the capless linear RNAs, one can employ Xm-resistant RNA loops to create a nuclease-resistant capless linear sequence. When positioned at the 5' end, these loops protect linear/capless RNAs from degradation by 5'-to-3' exonucleases. (For a review of such sequences see e.g., Akiyama et al. Curr Opin Struct Biol. 2016, 36: 40-7)

A prototypical cap-less/linear sequence can contain from 5' to 3': (1) One or more Xm-resistant loops; (2) One or more MS2 hairpins; (3) An open reading frame encoding a protein of interest; (4) A polyadenylated tail.

Alternatively, from 5' to 3': (1) One or more Xrn-resistant loops. (2) One or more MS2 hairpins. (3) An open reading frame encoding a protein of interest. (4) An IRES sequence. (5) An IRES-regulated ORF that encodes CaVT-dMCP. (6) A polyadenylated tail.

(d) Translation of nucleotide-substitute MS2-containing mRNAs MCP/dMCP can bind and recognize mutated MS2 hairpins in nucleotide-substituted mRNAs. Thus, these can be used to control and regulate translation of synthetic MS2-containing mRNAs. In one approach, two separate nucleotide-substituted mRNAs can be employed:

Such a system is based on two separate nucleotide-modified RNAs:

(a) A linear, cap-containing, nucleotide-substituted mRNA encoding CaVT-dMCP. A prototypical sequence can contain, in order from 5' to 3': (1) A natural or synthetic 5' cap; (2) An AUG start codon at the beginning of an ORF, preceded by a Kozak sequence or without a preceding Kozak sequence; (3) An ORF encoding CaVT-dMCP, as initiated by the AUG codon above; (4) A polyadenylation sequence.

(b) The cap-containing linear mRNA encoding CaVT-dMCP can be combined with a second nucleotide-substitute mRNA in either a circular RNA, or a capless linear RNA containing a 5' Xrn-resistant loop. This second RNA can contain: (i) A modified MS2 hairpin with retained binding activity against MCP/dMCP can be positioned upstream of an ORF of interest; (ii) The ORF of interest can encode an effector sequence, or an effector sequence can follow CaVT-dMCP. The C-terminally positioned CaVT-dMCP can be preceded by one or more 2A "skipping" peptides (for example, Effector-T2A-P2A-CaVT-dMCP).

In this approach, the cap-containing RNA encoding CaVT-dMCP can facilitate initial CaVT-dMCP expression. The initially produced CaVT-dMCP can then activate the translation of the MS2-containing nucleotide-substituted RNA sequence. Upon such activation, the second (MS2-regulated) ORF can then facilitate the translation of an intended effector protein in combination with additional CaVT-dMCP copies. These additional copies can drive the further translation of the second (MS2-regulated) ORF sequence. This approach can be advantageous in the context of circular RNA. A limitation of circular RNA is that it relies on IRES to mediate encoded protein translation. However, given the complex 3D structures of IRES sequences, nucleotide-substituted IRES are often non-functional. Thus, circular RNAs are limited to natural nucleotides. Since a functional MS2 is described herein that can work in nucleotide-substituted RNA, this system can permit the use of substituted circ-RNA, where the prolonged life of circ-RNA can be combined with the immune-evading features of nucleotide-substituted sequences via MS2-mediated translation (in place of an IRES).

Summary for section "d": An initial trigger based on linear CaVT-dMCP encoding RNA can "jump start" translation of an MS2-containing nucleotide-modified circular RNA. By encoding an ORF of interest in combination with a second CaVT-dMCP in the circular sequence, prolonged expression from the circ-RNA can be achieved beyond the lifetime of the short-lived linear RNA. A variation of this approach can involve drug-inducible control over the initial CaVT-dMCP, the second (circ-RNA encoded) CaVT-dMCP, or both.

Example 9: NanoLuc®-Coat Protein Fusions

Imaging agents/dMCP fusions (i.e., an imaging agent fused to dMCP) can be used for body imaging.

Figure 24A:
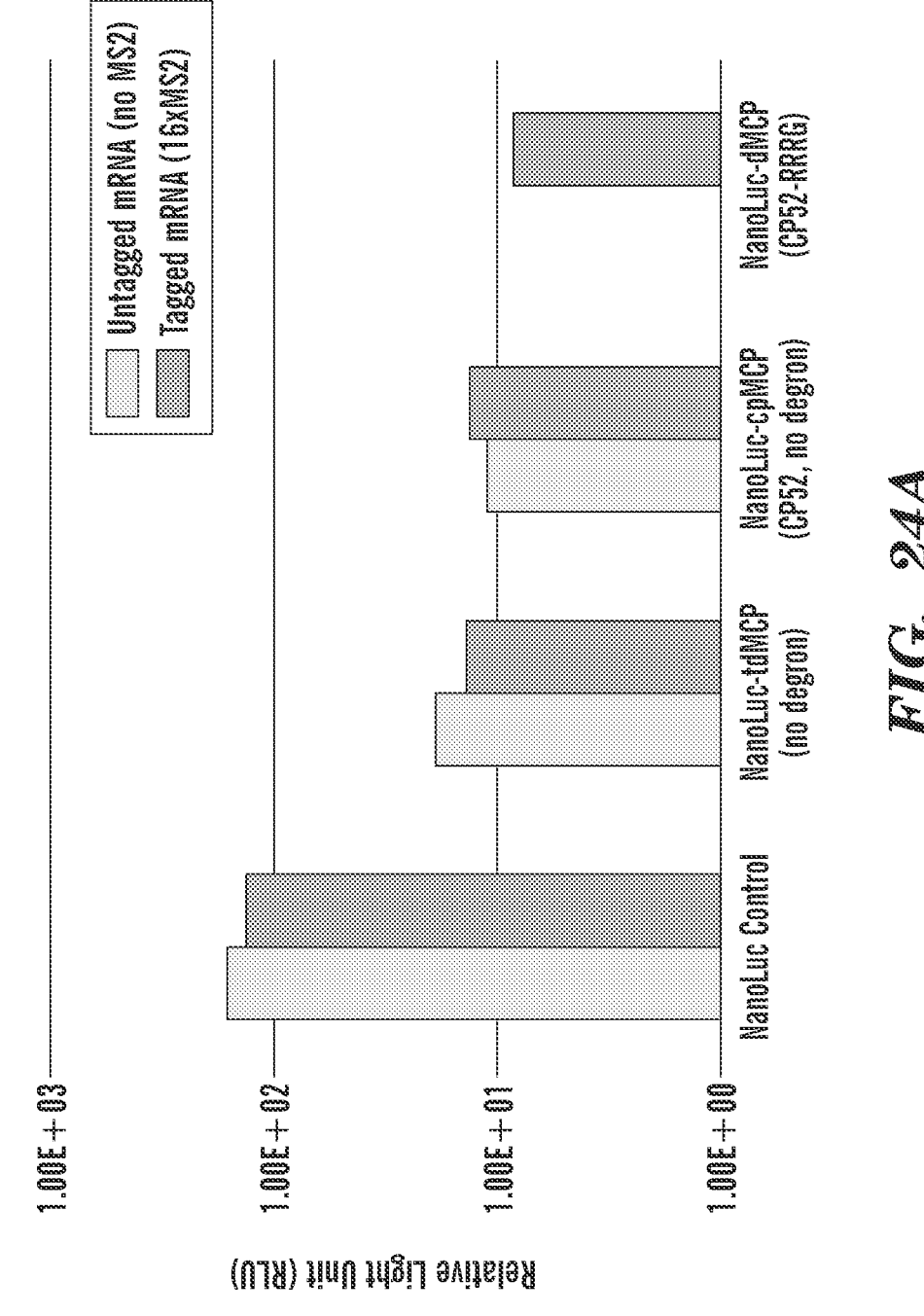
FIG. 24A-24B: Stability of NanoLuc®-coat protein fusions in cells with and without MS2-tagged mRNA. Cells were transfected with DNA constructs encoding the indicated NanoLuciferase (NanoLuc®) fusions containing C-terminal coat protein fusions (tdMCP—tandem dimer MCP; cpMCP—circularly permutated MCP; dMCP—destabilized MCP) in combination with a second plasmid encoding an untagged mRNA ("Untagged mRNA" as a control), or an mRNA sequence containing a cassette ("tagged mRNA"). Luminescence values were measured using Nano-Luc® substrate the next day.
Figure 24B:
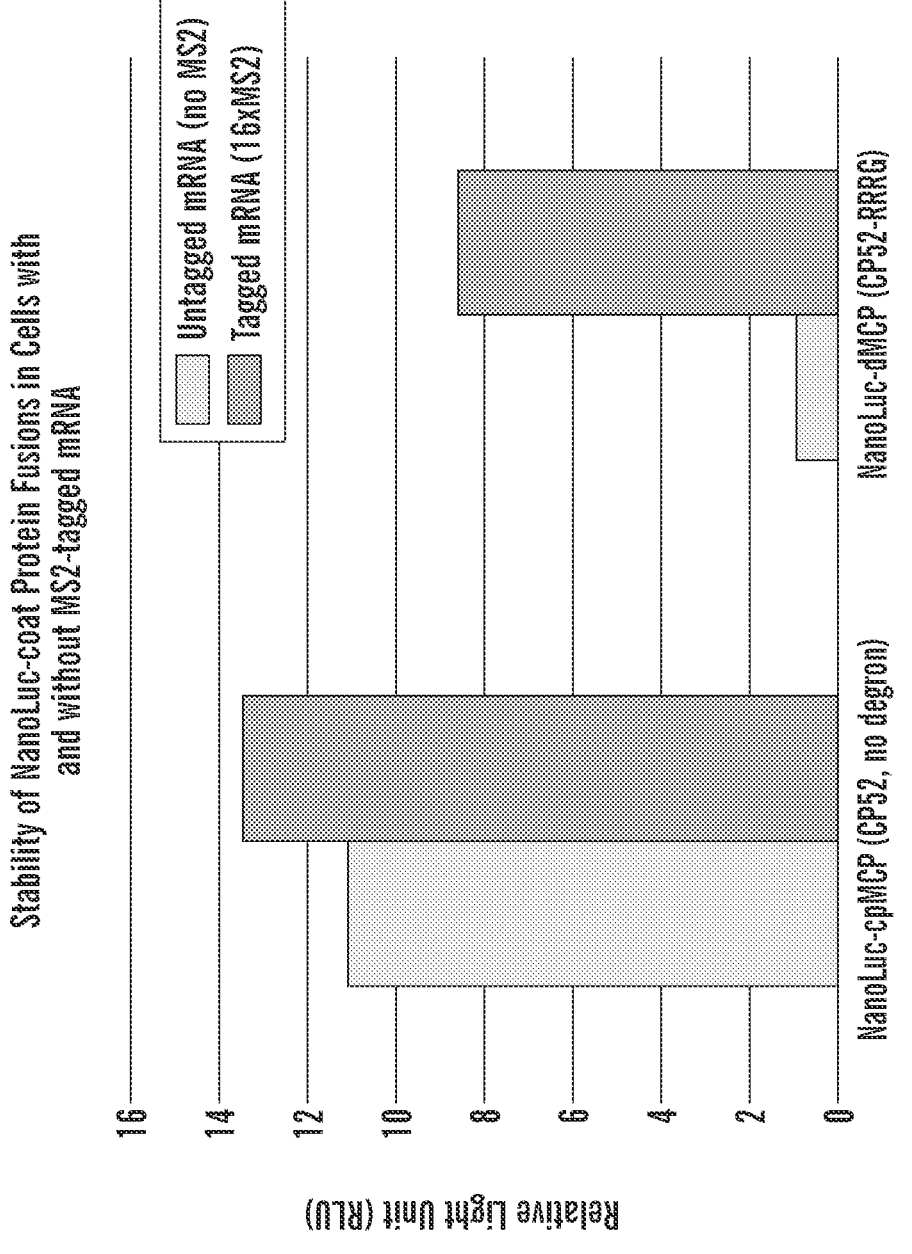

Luciferases and other bioluminescent reporters can be used, including but not limited to NanoLuc® (see e.g., FIG. 24A-24B).

Of interest are luciferases with red emissions for body imaging, including *Renilla luciferase* (RLuc) and sequences derived from it (RLuc8, Super RLuc8, etc.).

Infrared fluorescent proteins (iRFPs) can be for body imaging, including iRFP-670, miIRFP-670, and related sequences.

Gas vesicle-based reporter proteins can be for ultrasound-mediated detection/control.

HaloTag® can be used for detection, visualization, and degradation using chloroalkane-containing substrates, including those with red and far-red emissions and those with fluorogenic properties.

Example 10

(1) Alternative insertion sites within dMCP: Data demonstrates that effectors could be fused at internal sites within the dMCP sequence, in addition to the N-terminus.

(2) IRES expression of dMCP for cap-independent translation of dMCP: Data shows that IRES-mediated expression of dMCP (via cap-independent translation) efficiently facilitated dMCP:MS2 complex formation.

(3) MCP binds Uridine-free MS2 RNA aptamers: Data shows the binding of dMCP to uridine-free MS2 RNA hairpin sequence. Given this result, dMCP can be combined and used in nucleotide-modified (e.g., N1-methyl-pseudouridine-containing, etc.) RNAs tagged with this specific U-free MS2 sequence.

Figure 25:
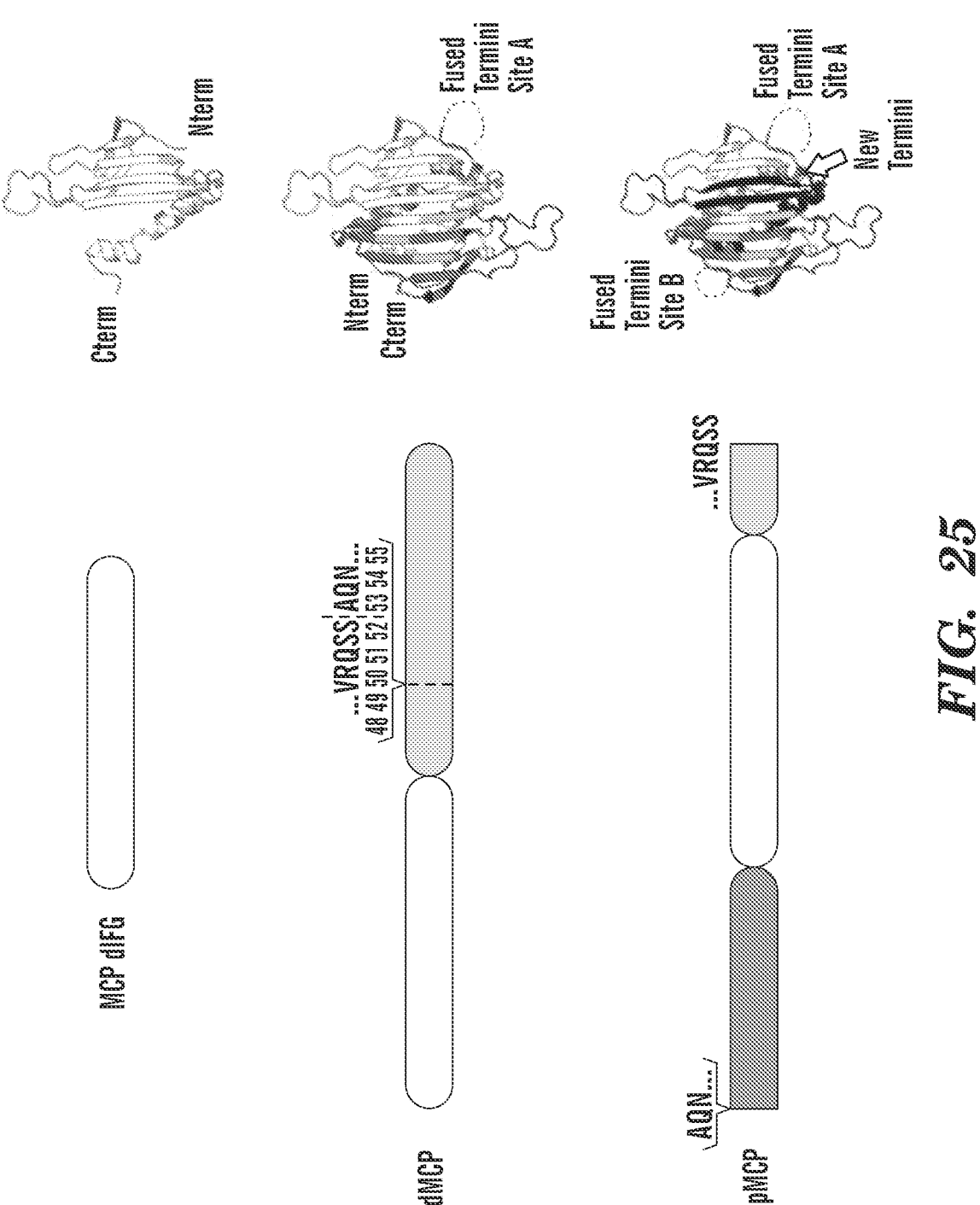
FIG. 25: Schematic indicating locations of termini fusions made to cpMCP from wild type MCP (MCP dlFP).

(1) Alternative Insertion Sites within dMCP dMCP is a circular permutant of a fused dimer, so in the process of converting wildtype MCP to cpMCP, two sets of termini were fused together (see e.g., FIG. 25). datain some embodiments, additional protein domains are fused to dMCP at the new N-terminus.

Figure 26:
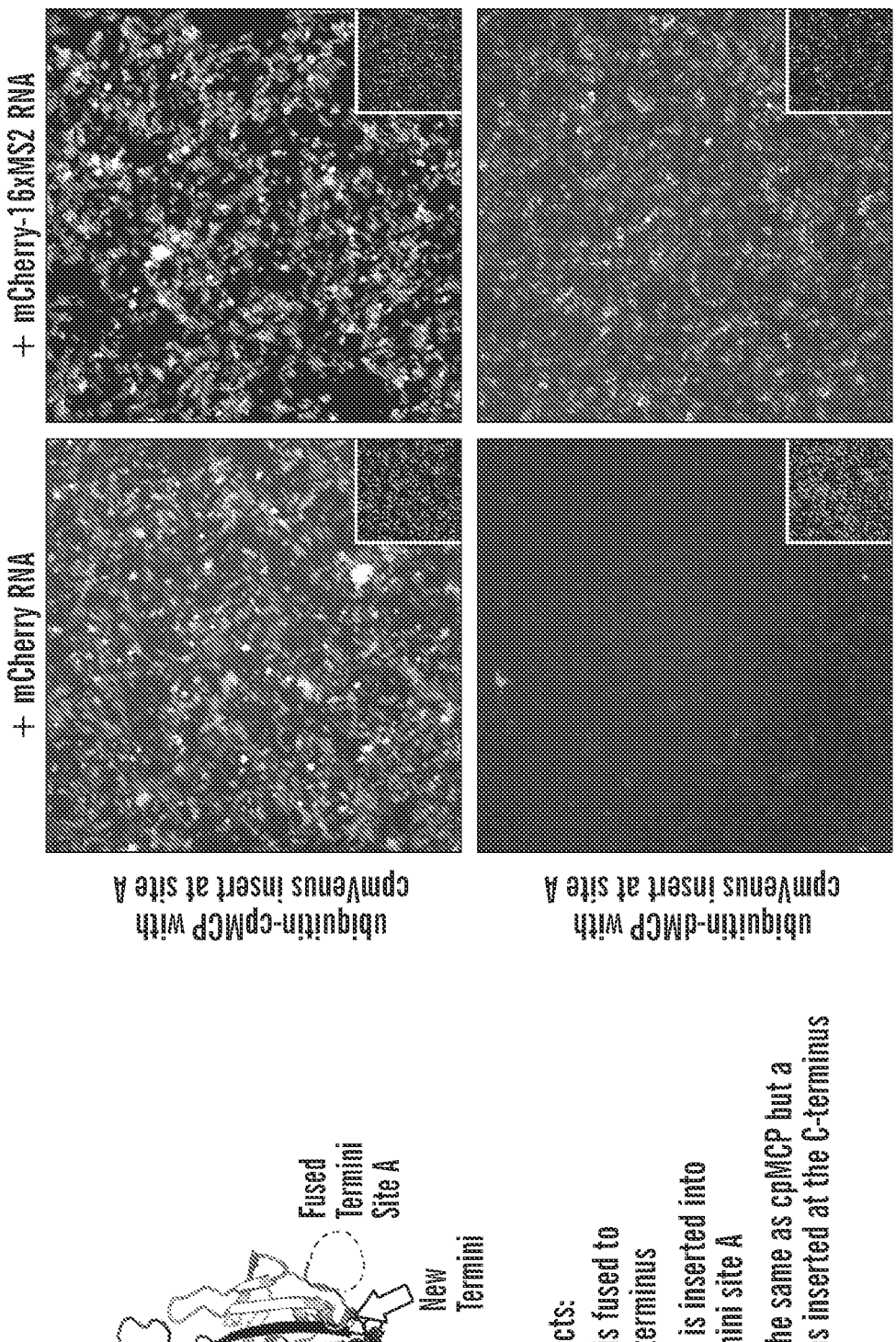
FIG. 26: RNA-binding behavior of cpMCP with cpmVenus inserted at a fused termini site and RNA-dependent stability of a dMCP variant with the same cpmVenus insertion. cpmVenus expression from MCP proteins shown in main images, and mCherry expression shown within insert images.

Additional protein domains can be inserted in at least the two sites on dMCP corresponding to the locations of the original termini from wild-type MCP, without losing dMCP's RNA binding functionality or its RNA-dependent stability. A fluorescent cpmVenus protein was inserted into cpMCP (no degron) and dMCP (with degron) at the site where the original termini of MCP were fused. The data for cpMCP shows nuclear exclusion of cpmVenus only when cpMCP with this cpmVenus insertion was co-expressed with MS2 RNA. This indicates that the protein is binding MS2 RNA and following it out of the nucleus. Additionally, dMCP with the cpmVenus insert retains MS2-dependent stability, as cpmVenus expression was only seen when this dMCP variant was expressed with MS2 RNA present (see e.g., FIG. 26)

(2) IRES Expression of dMCP for Cap-Independent Translation of dMCP

Figure 27:
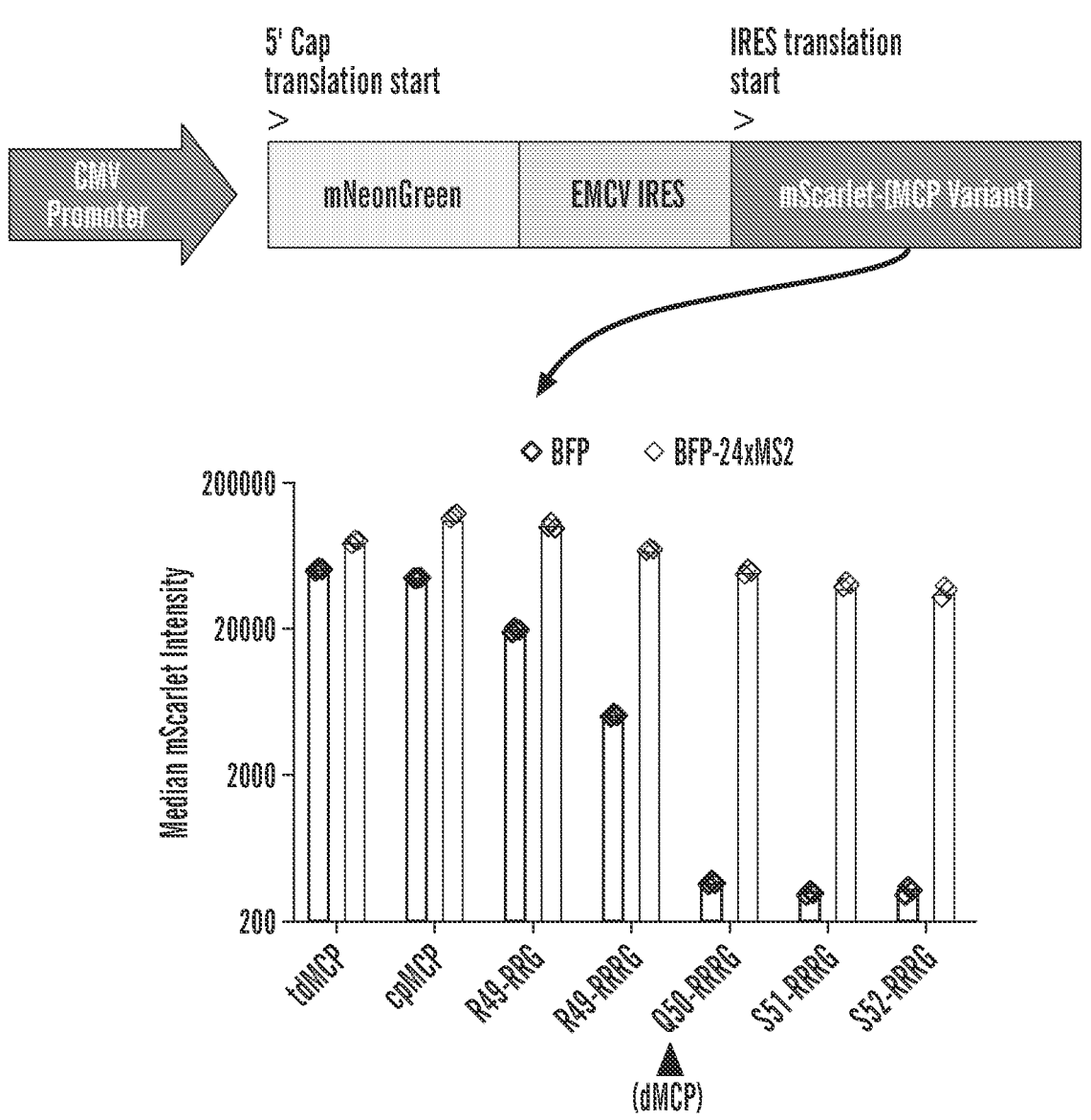
FIG. 27: Flow cytometry data showing that an mScarlet-dMCP fusion, and several other variants, were translated from an EMCV IRES on an mRNA expressed from a CMV promoter. dMCP-mScarlet and several other variants maintained MS2-dependent stability when expressed from this IRES.

Like other proteins, dMCP and its variants can be translated from an RNA transcript in a cap-independent manner though an IRES. FIG. 27 shows that dMCP and several additional MCP variants were translated and several continued to show MS2-RNA dependent stability when expressed from an EMCV IRES. This capability allows for expression of dMCP from circular RNAs, for which cap-independent translation is required.

(3) MCP binds Uridine-free MS2 RNA aptamers

Figure 28:
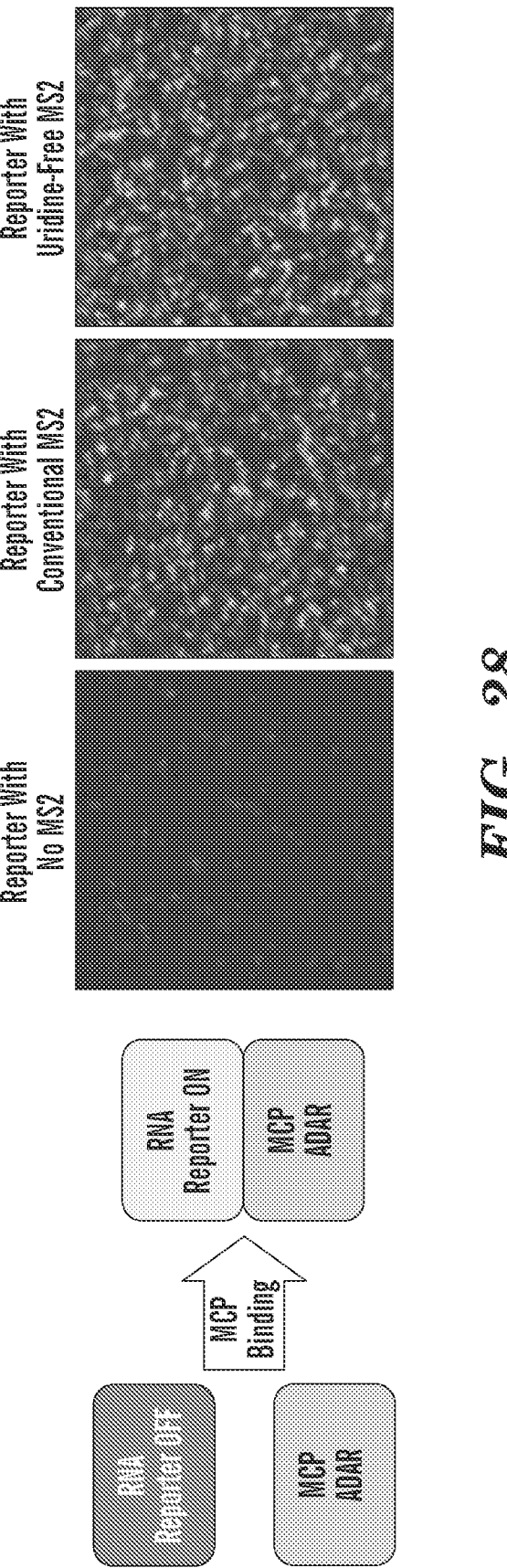
FIG. 28: Microscopy data from a reporter assay where expression of a green fluorescent protein was dependent on MCP binding an MS2 loop on an RNA reporter. The assay indicates that an MCP-ADAR fusion protein bound RNA reporters containing conventional MS2 loops as well as uridine-free MS2 loops.

Several different RNA sequences can form into MS2 aptamers that are bound by MCP and, by extension, dMCP. FIG. 28 demonstrates MCP binding to a uridine-free MS2 aptamer, as reported by a fluorescent readout that was triggered only when an ADAR-fused MCP protein bound to a reporter transcript containing an MS2 aptamer. It is expected that dMCP, whose RNA-binding pocket is identical to MCP, can also bind this uridine-free aptamer.

Therapeutic mRNAs used in vaccines (e.g., COVID vaccines) use a modified form of uridine, which can interfere with MCP binding to uridine-containing MS2 loops, but is not expected to affect MCP binding to uridine-free loops.

Relevant Annotated Amino Acid, DNA, RNA Sequences

Table 4: SEQ ID NO: 45; from N to C terminus: Ubiquitin is shown in dotted underlined text; C_half_MCP is shown in bolded text; MCP is shown in italicized text; cpmVenus is show with double-underlined text; N_half_MCP is shown in bolded italicized text; Degron is shown in zigzag underlined text.

TABLE 4

SEQ ID NO: 45; from N to C terminus: Ubiquitin is shown in dotted underlined text; C_half_MCP is shown in bolded text; MCP is shown in italicized text; cpm Venus is show with double-underlined text; N_half_MCP is shown in bolded italicized text; Degron is shown in zigzag underlined text.

| Construct | Sequence (Amino Acid) |
|---|---|
| Ubiquitin-dMCP with cpm Venus Inserted at Fused Termini Site A (Ubiquitin-C_half_MCP- MCP-cpm Venus- | MQIFVKTLTGKTITLEVEPSDTIENVKAKIQDKEGIPPDQQRLIFAG KQLEDGRTLSDYNIQKESTLHLVLRLRGGSAQNRKYTIKVEVPK GAWRSYLNMELTIPIFATNSDCELIVKAMQGLLKDGNPIPSAI AANSGIY_ANFTQFVLVDNGGTGDVTVAPSNFANGIAEWISSNSRSQA_ _YKVTCSVRQSSAQNRKYTIKVEVPKGAWRSYLNMELTIPIFATNSDCEL_ |

TABLE 4-continued

SEQ ID NO: 45; from N to C terminus: Ubiquitin is shown in dotted underlined
text; C_half_MCP is shown in bolded text; MCP is shown in italicized text; cpm Venus is show with
double-underlined text; N_half_MCP is shown in bolded italicized text; Degron is shown in zigzag
underlined text.

| Construct | Sequence (Amino Acid) |
|---|---|
| N_half_MCP-Degron:<br>SEQ ID NO: 45 | *IVKAMQGLLKDGNPIPSAIAANSGIYGS*VQLADHYQQNTPIGDGPV<br>LLPDNHYLSYQSKLSKDPNEKRDHMVLLEFVTAAGITLGMDELY<br>KGGTGGSMVSKGEELFTGVVPILVELDGDVNGHKESVSGEGEGD<br>ATYGKLTLKLICTTGKLPVPWPTLVTTLGYGLQCFARYPDHMKQ<br>HDFFKSAMPEGYVQERTIFFKDDGNYKTRAEVKFEGDTLVNRIE<br>LKGIDFKEDGNILGHKLEYNYNSHNVYITADKQKNGIKANFKIRH<br>NTS*ANFTQFVLVDNGGTGDVTVAPSNFANGIAEWISSNSRSQAYK*<br>*VTCSRQ*RRRG |

TABLE 5

SEQ ID NO: 26, *Note that this DNA produces an IRES-containing RNA which
translates the proteins mNeonGreen and mScarlet-dMCP as two separate polypeptides; from 5' to 3'
terminus: mNeonGreen is indicated by bolded text; IRES is indicated by italicized text; mScarlet is
indicated by bolded italicized text; dMCP is indicated by double-underlined text.

| Construct | Sequence (DNA) |
|---|---|
| mNeonGreen-IRES-<br>mScarlet-dMCP: SEQ ID<br>NO: 46 | atggtgagcaagggcgaggaggataacatggcctctctcccagcgacacatgagttacacatct<br>ttggctccatcaacggtgtggactttgacatggtgggtcagggcaccggcaatccaaatgatggt<br>tatgaggagttaaacctgaagtccaccaagggtgacctccagttctccccctggattctggtccct<br>catatcgggtatggcttccatcagtacctgccctaccctgacgggatgtcgcctttccaggccgcc<br>atggtagatggctccggataccaagtccatcgcacaatgcagtttgaagatggtgcctcccttact<br>gttaactaccgctacacctacgagggaagccacatcaaaggagaggcccaggtgaaggggact<br>ggtttccctgctgacggtcctgtgatgaccaactcgctgaccgctgcggactggtgcaggtcgaa<br>gaagacttaccccaacgacaaaaccatcatcagtacctttaagtggagttacaccactggaaat<br>ggcaagcgctaccggagcactgcgcggaccacctacacctttgccaagccaatggcggctaact<br>atctgaagaaccagccgatgtacgtgttccgtaagacggagctcaagcactccaagaccgagct<br>caacttcaaggagtggcaaaaggcctttaccgatgtgatgggcatggacgagctgtacaagtaa<br>CGGCTCTAGATCGCGAAC*gcgtgaattcctcgagggcggccgctctagagtcgacg*<br>*ggccgcggtaacaattgttaactaacttaagctagcaacggtttccctctagcgggatcaattccgcc*<br>*ccccccccctaacgttactggccgaagccgcttggaataaggccggtgtgcgtttgtctatatgttattt*<br>*tccaccatattgccgtcttttggcaatgtgagggcccggaaacctggccctgtcttcttgacgagcatt*<br>*cctaggggtctttcccctctcgccaaaggaatgcaaggtctgttgaatgtcgtgaaggaagcagttc*<br>*ctctggaagcttcttgaagacaaacaacgtctgtagcgacccctttgcaggcagcggaaccccccac*<br>*ctggcgacaggtgcctctgcggccaaaagccacgtgtataagatacacctgcaaaggcggcaca*<br>*acccccagtgccacgttgtgagttggatagttgtggaaagagtcaaatggctctcctcaagcgtattca*<br>*acaaggggctgaaggatgcccagaaggtaccccattgtatgggatctgatctggggcctcggtgc*<br>*acatgctttacatgtgtgtttagtcgaggttaaaaaaaacgtctaggccccccgaaccacggggacgtg*<br>*gttttcctttgaaaaacacgataatacc*atggTGAGCAAGGGCGAGGCAGTGATC<br>AAGGAGTTCATGCGGTTCAAGGTGCACATGGAGGGCTCCATGA<br>ACGGCCACGAGTTCGAGATCGAGGGCGAGGGCGAGGGCCGCC<br>CCTACGAGGGCACCCAGACCGCCAAGCTGAAGGTGACCAAGGG<br>TGGCCCCCTGCCCTTCTCCTGGGACATCCTGTCCCCTCAGTTCA<br>TGTACGGCTCCAGGGCCTTCATCAAGCACCCCGCCGACATCCC<br>CGACTACTATAAGCAGTCCTTCCCCGAGGGCTTCAAGTGGGAG<br>CGCGTGATGAACTTCGAGGACGGCGGCGCCGTGACCGTGACCC<br>AGGACACCTCCCTGGAGGACGGCACCCTGATCTACAAGGTGAA<br>GCTCCGCGGCACCAACTTCCCTCCTGACGGCCCCGTAATGCAG<br>AAGAAGACAATGGGCTGGGAAGCGTCCACCGAGCGGTTGTACC<br>CCGAGGACGGCGTGCTGAAGGGCGACATTAAGATGGCCCTGCG<br>CCTGAAGGACGGCGGCCGCTACCTGGCGGACTTCAAGACCACC<br>TACAAGGCCAAGAAGCCCGTGCAGATGCCCGGCGCCTACAACG<br>TCGACCGCAAGTTGGACATCACCTCCCACAACGAGGACTACAC<br>CGTGGTGGAACAGTACGAACGCTCCGAGGGCCGCCACTCCACC<br>GGCGGCATGGACGAGCTGTACAa*ggg*cGGGAGTtaccccctacgacgtgccc<br>gactacgccGGTACCGGCGGGAGTGGCGGTAGTGCCCAAAACAGG<br>AAATACACCATCAAAGTGGAGGTGCCAAAGGGTGCCTGGCGG<br>AGCTACCTGAACATGGAGCTGACTATTCCAATCTTCGCTACTAA<br>TTCCGATTGCGAACTGATAGTAAAAGCGATGCAAGGTTTGCTG<br>AAAGACGGCAACCCAATTCCCAGCGCAATCGCCGCCAATAGC<br>GGCATCTACGCTAATTTCACACAGTTCGTGCTGGTCGACAACG<br>GCGGCACCGGCGACGTTACGGTGGCCCCCTCAAACTTTGCCA<br>ACGGGATTGCCGAGTGGATAAGCAGCAATAGCAGGTCCCAGG<br>CCTACAAGGTTACCTGTAGCGTAAGGCAGAGCAGCGCCCAGA<br>ACCGAAAGTACACGATTAAGGTGGAAGTCCCCAAAGGCGCAT<br>GGAGGAGCTATCTTAATATGGAACTGACCATCCCCATATTCGCG<br>ACAAACAGCGACTGTGAGCTGATCGTGAAGGCTATGCAGGGC<br>CTCCTCAAGGATGGGAACCCGATCCCGTCTGCCATCGCTGCTA<br>ACTCCGGCATTTATGCAAACTTCACTCAATTTGTTCTGGTGGAC |

TABLE 5-continued

SEQ ID NO: 26, *Note that this DNA produces an IRES-containing RNA which
translates the proteins mNeonGreen and mScarlet-dMCP as two separate polypeptides; from 5' to 3'
terminus: mNeonGreen is indicated by bolded text; IRES is indicated by italicized text; mScarlet is
indicated by bolded italicized text; dMCP is indicated by double-underlined text.

| Construct | Sequence (DNA) |
|---|---|
| | AATGGTGGGACCGGGGATGTTACCGTGGCTCCCAGCAATTTTG CTAACGGTATCGCAGAATGGATCAGTAGTAACAGCAGGAGCCA AGCCTATAAAGTGACGTGCAGCGTACGGCAGAGGAGAAGAGG C |

TABLE 6

Exemplary MS2 Sequences

| Construct | Sequence (RNA) |
|---|---|
| Conventional MS2 | GCACGAGCAUCAGCCGUGC (SEQ ID NO: 47) |
| Uridine-Free MS2 Loop | GCGCGAGGAACACCCGCGC (SEQ ID NO: 29) |

Example 11: Effector Categories

Described herein are exemplary effector proteins that can be linked to an engineered MCP or an engineered PCP, as described herein, as well as exemplary linkers: (1) Inducible protein interactions or protein complex dissociation domains; (2) Trafficking domains and/or targeting sequence; (3) Cas-like proteins containing RINA-based guide sequences; (4) Enzymes that cleave or modify RINA, including by covalent attachment or new chemical groups and bases or via the formation of new bonds; (5) Translation-regulating and translation-associated domains; (6) Cell cycle-regulated degrons; (7) Proximity labeling and substrate labeling enzymes; or (8) Nanobodies/antibodies against endogenous proteins.

(1) Inducible Protein Interactions or Protein Complex Dissociation Domains

These domains serve as adaptors to control whether an effector domain (various effector domains are listed in subsequent sections) is brought into contact with dMCP and the MS2-containing RNA that it binds. Generally, this induced contact leads to an increase in effector domain activity towards the MS2 RNA that dMCP binds. Non-limiting examples include the following.

(a) Drug-INDUCIBLE heterodimerization domains (for inducing dimeric effector complexes in response to drug treatment) (i) FKBP and FRB and mutants thereof; (ii) Abscisic acid (ABA)-inducible heterodimeric protein binding domains; (iii) Gibberellin-inducible heterodimeric protein binding domains; (iv) "Reader" domains that recognize drug-bound NS3-units (see e.g., Foight et al. Nat Biotechnol. 2019 October; 37(10): 1209-1216); (v) Human antibody-based dimerizers (AbCIDs), including the humanized scFab "scAz1" which binds BCL-xL upon formation of the BCL-xL-ABT-737 complex (see e.g., Hill et al. Nat Chem Biol 14, 112-117 (2018)).

(b) Drug-DISSOCIABLE heterodimeric domains: (i) Including units based on Bcl-xL and BH3 proteins/peptides (and mutants thereof), which can be dissociated by small molecules such as A-1155463 (and related); (ii) NS3 or its catalytically inactive mutants ("dNS3") complexed with inhibitory peptides, the interactions of which can be dissociated using NS3 inhibitors; (iii) Grazoprevir-dissociable "Reader" domains that recognize danoprevir-bound NS3-units.

(c) Drug-PRESERVABLE domains (for inducing preservation/maintenance of effector fusions): (i) Fusion "poly-protein" constructs containing active NS3 protease, combined with NS3-inhibitors to inhibit cleavage and preserve poly-protein in intact uncleaved states (for example, X-NS3-dMCP, where NS3 is the active protease flanked by corresponding cleavage sites; X is an effector unit; and dMCP or dPCP is positioned C-terminally). (ii) Systems similar to (i) above but involving humanized NS3 sequences. (iii) Systems containing X-NS3-dMCP, where X=a transmembrane protein, including those loaded into extracellular vesicles.

(d) Ultrasound inducible/regulatable domains: Gas vesicle proteins can sequester and then subsequently release a domain in response to ultrasound stimulation.

(e) Light-regulated protein-protein interaction domains: (i) The light-cleavable PhoCl and its related mutants/derivatives (see e.g., Zhang et al. Nat Methods 14, 391-394 (2017)), e.g., Systems containing X-PhoCl-dMCP, where X=a transmembrane protein, including those that are loaded into extracellular vesicles; (ii) The light-cleavable mMaple3 (see e.g., Han et al. Sci Transl Med. 2024 Aug. 7; 16(759): eadi4830)); (iii) LOV domains; (iv) Luciferase-fused LOV domains, which can be activated in a drug-inducible manner via "BRET" (bioluminescence resonance energy transfer; see e.g., Kim Kelvin et al. (2019) eLife 8: e43826); (v) Red light-inducible PPI domains, including PhyB/Pif units. PhoCL and mMaple3 are light inducible cleavage domains. LOV and luciferase fused LOV are light inducible dissociation domains. PhyB/PIF is a light inducible dimerization system.

(f) Domains that undergo protein-protein interactions upon signaling due to extracellular or intracellular signals: (i) Beta-arrestin binding to phosphorylated tails of GPCRs; (ii) Phosphorylated kinase substrates in combination with domains recognizing such phosphorylated sequences; (iii) Binding proteins that recognize and undergo protein interactions in response to secondary metabolites (including cAMP) or ions (including Ca2+, etc.); (iv) a nanobody that binds the intracellular region of an activated GPCR, e.g., Nb81 which binds human ADBR2.

(2) Trafficking Domains and/or Targeting Sequences

These domains can be used to direct the location of dMCP and the MS2 RNA that it binds to various organelles and subcellular regions. Generally, targeting of an RNA to a specific subcellular region can increase local concentrations of protein expressed from that RNA. Non-limiting examples include the following.

(a) Microtubule motor proteins (plus end and minus end); (b) Mitochondrial surface targeting sequence; (c) Nuclear localization signal and exclusion signals; (d) Transmembrane domains; (e) Signaling receptors, including fusions of GPCRs, SynNotch, CARs, and other engineered receptor sequences; (f) Lipid-modification substrates, including peptide/protein substrates for: (i) Myristoylation, (ii) Palmitoylation, (iii) Myristoylation and palmitoylation, or (iv) Prenylation (via CaaX motif); (g) Membrane-binding protein domains: (i) Pleckstrin homology domains and split pleckstrin homology domains.

(3) Cas-Like Proteins Containing RNA-Based Guide Sequences

Here, RNA guides containing hairpin loops could be used with dMCP and dPCP fused proteins. Examples of such guide and guide-binding proteins include:

(a) RNA-guided DNA binding proteins and enzymes: (i) Cas9, Cas12, etc.; (ii) dCas9, dCas12, etc.

(b) RNA-guided RNA-binding proteins: (i) Cas13; (ii) Cas CSM (see e.g., Xia et al, Single-molecule live-cell RNA imaging with CRISPR-Csm, bioRxiv 2024 doi 10.1101/2024.07.14.603457).

(4) Enzymes that Cleave or Modify RNA, Including by Covalent Attachment or New Chemical Groups and Bases or Via the Formation of New Bonds (a) RNA cleaving nucleases: These domains have been fused to conventional MCP in order to target MS2-containing transcripts for proximity-dependent repression of translation and degradation of RNA transcripts. If overexpressed, these domains can come into proximity of off-target transcripts not containing MS2 and cause off-target downregulation of these transcripts.

Here, dMCP-fused enzymes can be used to recruit nuclease activity to MS2 or PP7-tagged RNAs. In this approach, targeted cleavage can be more specific due to eliminating excess (RNA unbound) nuclease-coat protein fusions, which would be active even without RNA hairpin binding. Selective localization of the nuclease to the targeted transcript can result in reduced off-target cleavages.

(i) Csy4 (Cas6f), which cleaves at the 3' end of a short RNA hairpin (csy4), (see e.g., Chen et al. Symbolic recording of signalling and cis-regulatory element activity to DNA. Nature (2024); Borchardt et al. RNA. 2015 November; 21(11):1921-30).

(ii) Other pre-crRNA processing enzymes, including: (1) Cas5d (from *Bacillus halodurans*); (2) Cas6e (CasE/Cse3; from *E. coli*); (3) Cas6 (from *Pyrococcus furiosus*); (4) see e.g., Brouns et al. Science. 2008 Aug. 15; 321(5891):960-4; Carte et al. Genes Dev. 2008 Dec. 15; 22(24):3489-96; Nam et al. Structure. 2012 Sep. 5; 20(9):1574-84; (5) Human SMG6 and sequences containing the PIN domain derived from human SMG6; (6) Generally, crRNA processing have evolved cleavage mechanisms that are highly specific for their cognate RNA loop target to avoid off-target cleavage in their hosts (see e.g., Sternberg et al. RNA. 2012 April; 18(4):661-72); however, these enzymes may not be as specific in human cells, and their specificity can be increased by fusing the domain to dMCP. By doing so, the domain can be made to be stable only when bound to an MS2-labeled target RNA, lowering the probability of cleaving non-target RNA; (7) Alternatively, stability and activity of these proteins can be made dependent on the presence of any other MS2-labeled RNA.

(iii) Human and mammalian-derived RNases, including RNase H, enzymes from the RNase III family, RNase A, RNase T1.

(iv) SMG6 PIN domain (b) De-adenylating enzymes (to remove 3' pA tails): (i) CCR4-Not; (ii) Poly(A)-specific ribonuclease (PARN), also referred to as polyadenylate-specific ribonuclease or deadenylating nuclease (DAN), encoded by the PARN gene. (iii)

See e.g., Skeparnias et al. RNA Biol. 2017 Oct. 3; 14(10):1320-1325). (iv) These specifically remove the polyA tail of mRNAs. Similar to the RNases above, these can be targeted to MS2-containing transcripts for proximity dependent removal of polyA tails, triggering repression of translation and degradation of the transcripts, and can receive the same benefits from fusion to dMCP.

(c) De-capping enzymes (to remove 5' caps from mRNAs): (i) Dcp1/Dcp2, See e.g., Borbolis et al. FEBS J. 2022 March; 289(6):1457-1475. These remove the 5' methyl cap of mRNAs. Similar to the RNases above, these can be targeted to MS2-containing transcripts for proximity-dependent removal of 5' caps, which directly causes repression of translation and degradation of the transcripts, and they can receive the same benefits from fusion to dMCP.

(d) Capping enzymes (to add 5' caps, including a 7-methylguanylate (7mG) caps): By adding 5' caps to non-capped RNA, cap-dependent translation of the RNA can be induced. Additionally, adding a 5' cap to a non-capped RNA can protect the transcript from degradation and stabilize it. There are several endogenous RNAs within human cells that are uncapped, so by fusing capping enzymes to dMCP it can lead to capping of MS2-containing RNAs while reducing the likelihood of off-target capping of non MS2-containing capless transcripts. (i) Faustovirus capping enzymes; (ii) Vaccinia RNA capping enzymes; (iii) Other viral capping enzymes, including those from HIV and other human infectious viruses, and viral capping enzymes for which there are drug-based inhibitors.

(e) RNA Base editors: Adenosine Deaminase Acting on RNA (ADAR) can modify nucleotides of a target RNA and has been used to turn specific RNAs on or off in response to varying stimuli. It can be directed to MS2-containing RNA for improved editing efficiency, but in this context, ADAR exhibits significant off-target editing of RNA without MS2. Fusing ADAR to dMCP can thus reduce off-target editing of RNA.

(f) Enzymes that add covalent attachments to RNAs: By recruiting poly-adenylating enzymes, pA tails can be added to mRNAs to induce their translation or to prolong their half-lives/stabilities. Such modifications can be added to RNAs based on native or modified nucleotides. Poly-adenylating enzymes: (1) *E. coli* Poly(A) Polymerase; (2) Yeast poly(a) polymerase; (3) Other eukaryotic and mammalian nuclear and cytoplasmic poly-adenylating enzymes; (4) Polyadenylation of transcripts stabilizes them and upregulates their translation. By fusing dMCP to polyadenylating domains, MS2-containing transcripts can be targeted for proximity-dependent stabilization and upregulation.

(h) Adduct-forming proteins (proteins that become directly linked to RNA): Upon forming direct covalent bonds with their target RNAs, these proteins are strongly attached, and they remain attached under denaturing conditions which is useful for purification of protein-RNA complexes. dMCP can help reduce the occurrence of covalent attachment to off-target RNA. (i) tyrosyl-RNA phosphodiester bond-forming domains; (ii) VPg viral proteins.

(5) Translation-Regulating and Translation-Associated Domains (a) Cap-independent initiation through anchoring of initiation factors: dMCP can be used to create a destabilized "Caliciviral VPg-based Translational activator (CaVT)", which permits the direct translational activation of synthetic mRNAs in RNA circuits. CaVT is composed of MS2 coat protein (MS2CP), which is a motif-specific RBP, and a caliciviral VPg protein, which acts as a substitute 5'-cap structure. CaVT binds to its target RNA motif in the 5' UTRs of mRNAs without a canonical 5'-cap to directly activate their translation. See e.g., Shao et al. Cell Res. 2024 January; 34(1):31-46.

(b) Translational downregulation: (i) Through initiation factor inhibitors (eif4e bp1 or the Eif4E binding domain from CUP, THOR, or 4E-T); (ii) Through the formation of stable secondary structure or blocking of ribosome translocation.

(c) Amino acyl tRNA synthetases—for targeting non-natural amino acid incorporation only into a specific protein encoded by and MS2-tagged mRNA: (i) Mutant *E. coli* amino aaRS; (ii) Mutant versions of endogenous aaRS; (iii) mutant *Methanocaldococcus jannaschii* aaRS; (iv) mutant yeast aaRS; (v) Mutants of pyrrolysine aaRS.

(d) Peptide-based sequences that can facilitate translation modulation or RNA stability changes when recruited to RNAs: see e.g., Thurm et al, High-throughput discovery of regulatory effector domains in human RNA-binding proteins, bioRxiv doi 10.1101/2024.07.19.604317; Reynaud et al. Nat Struct Mol Biol 30, 740-752 (2023).

(6) Cell Cycle-Regulated Degrons

These can be used to restrict expression of dMCP to specific phases of the cell cycle. Restricting protein expression to specific phases of the cell cycle can improve intended effects. For example, cell-cycle regulated Cas9 shows improved gene editing accuracy. (a) CdtI degron domain (Degraded in all phases besides G1); (b) Geminin degron domain (degraded during G1 phase); (c) FUCCI sensors, see e.g., Zielke et al. Wiley Interdiscip Rev Dev Biol. 2015 September-October; 4(5): 469-87.

(7) Proximity Labeling and Substrate Labeling Enzymes (a) Biotin ligase with biotin ligase substrate: These ligases can be used to detect RNA-binding proteins via proximity biotin labeling: (i) *E. coli* biotin ligase (BirA), with substrates including the "acceptor peptide" (AP; e.g., GLN-DIFEAQKIEWHE, SEQ ID NO: 52), a 75-amino acid sequence from a *Propionibacterium shermanii* transcarboxylase that is biotinylated in mammalian cells (see e.g., Negi et al. J Biol Chem. 2023 August; 299(8):104948), and AviTag; (ii) Promiscuous labeling enzymes derived from BirA, including BioID, BioID2, and TurboID, for identifying RNA-protein complex components.

(b) Peroxidase-based enzymes: These peroxidases can be used to discover RNA-binding proteins via proximity oxidative labeling: (i) including APEX and APEX2 (for intracellular labeling) and HRP (for extracellular labeling); (ii) Use APEX, APEX2, and HRP in imaging via electron microscopy.

(c) miniSOG: For imaging RNAs by electron microscopy. For generating localized reactive oxygen in live cells in response to light. Here, local reactive oxygen can facilitate inactivation/damage of specific RNA complexes.

(d) RNA methyltransferases (e.g., METTL16).

(e) 'LITtag', an engineered flavin-mononucleotide-binding LOV domain.

(d) RNA Transglycosylase: RNA glycosylases can be used for proximity-dependent glycosylation labeling of RNA, useful for detection of RNA-binding proteins and for covalent modification of RNA with functional chemical groups. A non-limiting example is *E. coli* tRNA guanine transglycosylase (TGT).

(8) Nanobodies/Antibodies Against Endogenous Proteins

These can serve as adaptors to bring endogenous proteins into contact with dMCP and the MS2 RNA that it binds. This can be used to control the location of MS2 RNA bound by dMCP, or to bring MS2 RNA into contact with endogenous effectors that will act upon the RNA when the nanobody brings them into contact. (a) Nanobodies binding intracellular target proteins; (b) Destabilized nanobodies (binding stabilized; see e.g., Tang et al. (2016) eLife 5:e15312).

Example 12

(1) RNA-induced proximity between two binding proteins: Data demonstrates that an RNA containing multiple protein binding sites can be used as an adaptor to bring various proteins into contact.

(2) Monomeric 'dmMCP' Versions of dMCP: Data demonstrates that dMCP can be split down the middle such that the half-dMCP retains MS2 RNA dependent stability.

(3) Additional Data for dPCP: More detailed flow cytometry data quantified the PP7 RNA dependent stability of dPCP.

(4) Data showing dPCP and dMCP functioning in parallel.

(1) RNA-Induced Proximity Between Two Binding Proteins

Figure 29:
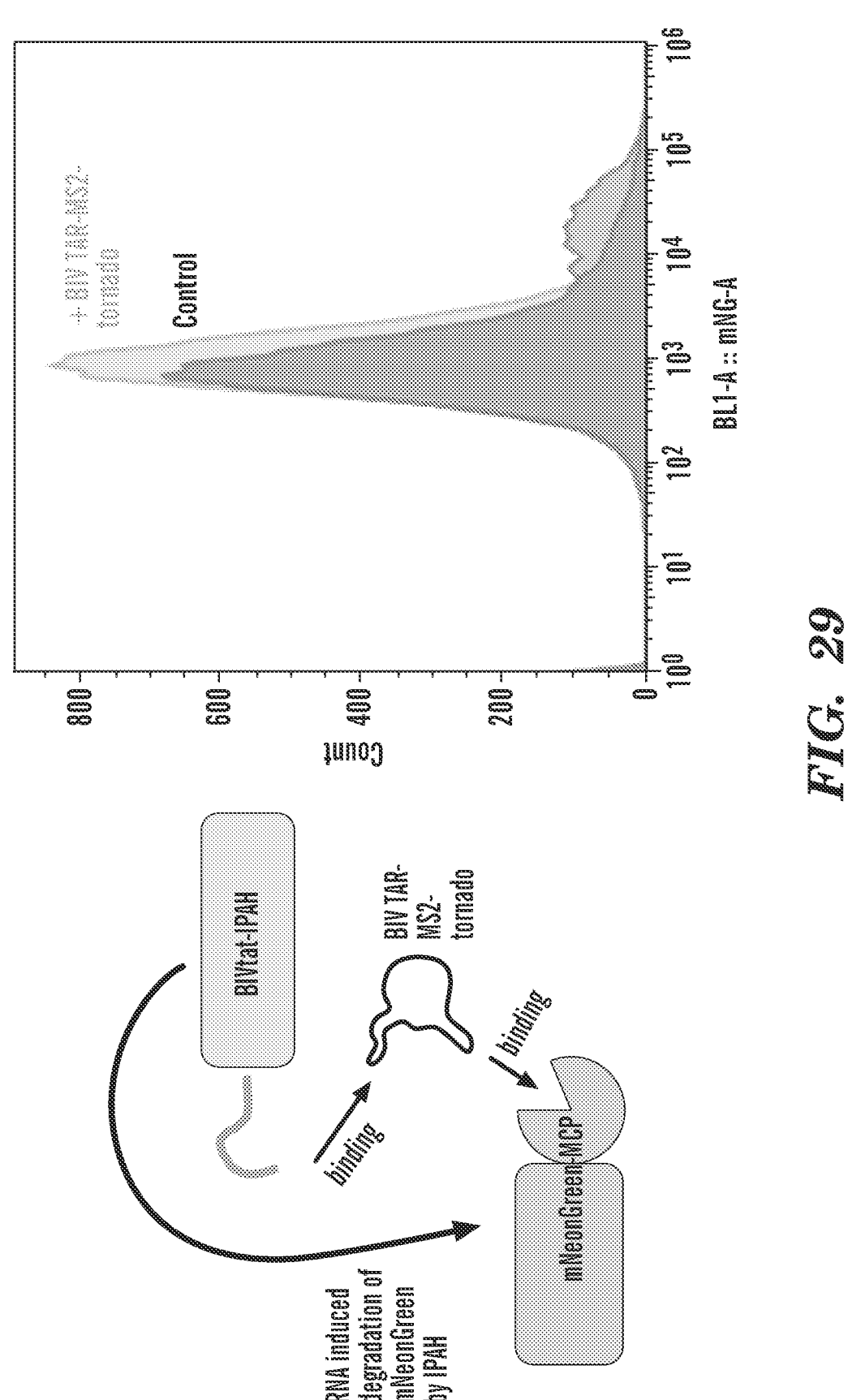
FIG. 29: Example of an adaptor RNA containing multiple protein-binding sites used to bring multiple proteins into contact. Here, BIVtat-IPAH is an E3 ligase (IPAH) fused to the BIV TAT domain, which binds BIV TAR RNA. mNeon-Green-MCP has green fluorescence and binds MS2. A circular RNA containing both MS2 and BIV TAR (BIV TAR-MS2-Tornado) brings these two proteins into contact, at which point the E3 ligase (IPAH) degrades mNeonGreen-MCP. The flow cytometry data on the right shows the reduction in green fluorescence triggered by RNA-induced contact.

RNA containing several distinct protein binding sites may be used as an adaptor to bring multiple proteins into contact. In FIG. 29, a circular adaptor RNA was expressed containing two RNA binding sites-BIV TAR, which binds the BIV TAR protein, and MS2, which binds the MCP protein. An E3 ligase was fused to BIV TAR and a fluorescent protein (mNeonGreen) was fused to MCP, such that when the adaptor RNA is expressed, the E3 ligase and mNeonGreen were brought into contact with one another. This triggered degradation of mNeonGreen by the E3 ligase, seen in flow cytometry data as a loss in mNeonGreen signal.

(2) Monomeric 'dmMCP' Versions of dMCP dMCP is derived from a tandem dimer that was created by the covalent fusion of two monomeric MCP halves. This covalent 'tdMCP' tandem dimer and the non-covalent dimer formed by two MCP monomers have the same overall shapes and RNA binding properties. It was reasoned that if the circular permutant of tdMCP that was used to make dMCP, cpMCP, were cut in half, the resultant half-protein could be able to reassemble into a dimeric form that matches the shape of the original cpMCP in the same way that monomeric MCP assembles into the same dimeric form as its fused dimeric version tdMCP (see e.g., FIG. 30, left).

Two versions were created of this monomeric cpMCP -cpmMCP, which has no degron, and dmMCP, which has the same degron as dMCP. Both variants showed RNA-dependent stability (see e.g., FIG. 30, right). The fact that cpmMCP appears to be unstable in the absence of MS2 RNA, despite having no degron, indicate that cpmMCP can misfold in the absence of MS2 RNA in such a way as to be targeted for degradation.

(3) Additional Data for dPCP

Figure 31:
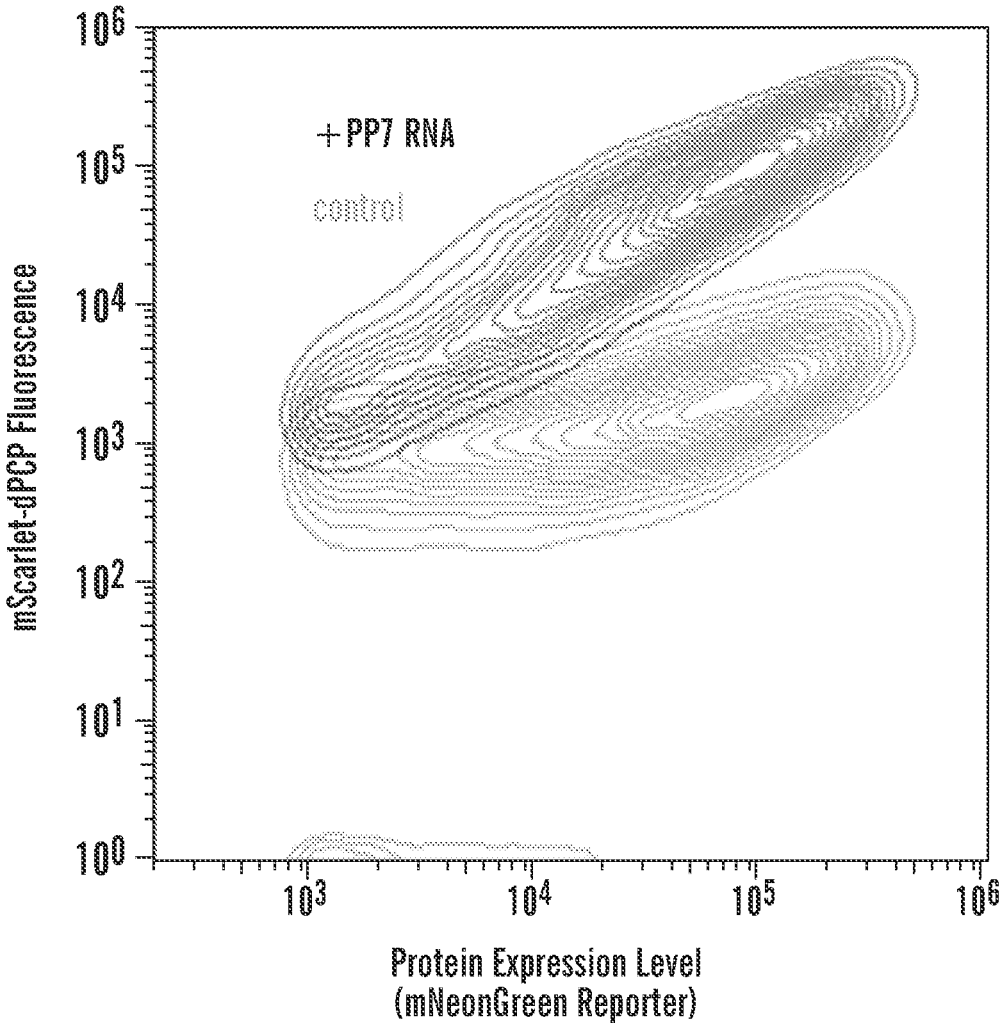
FIG. 31: Flow cytometry data showing upregulation in mScarlet-dPCP signal in response to PP7 RNA. mScarlet-dPCP fluorescence increased 25-fold in response to PP7-RNA. mNeonGreen coexpression reporter is shown on the X axis.

As previously described, dPCP is a protein that was generated from PP7-coat protein (PCP) through the same technique that was used to generate dMCP from MCP. Flow cytometry data demonstrates the RNA-dependent stability of dPCP in higher detail (see e.g., FIG. 31). In this data, mScarlet-dPCP undergoes a 25-fold increase in fluorescence in response to PP7 RNA.

Figure 32:
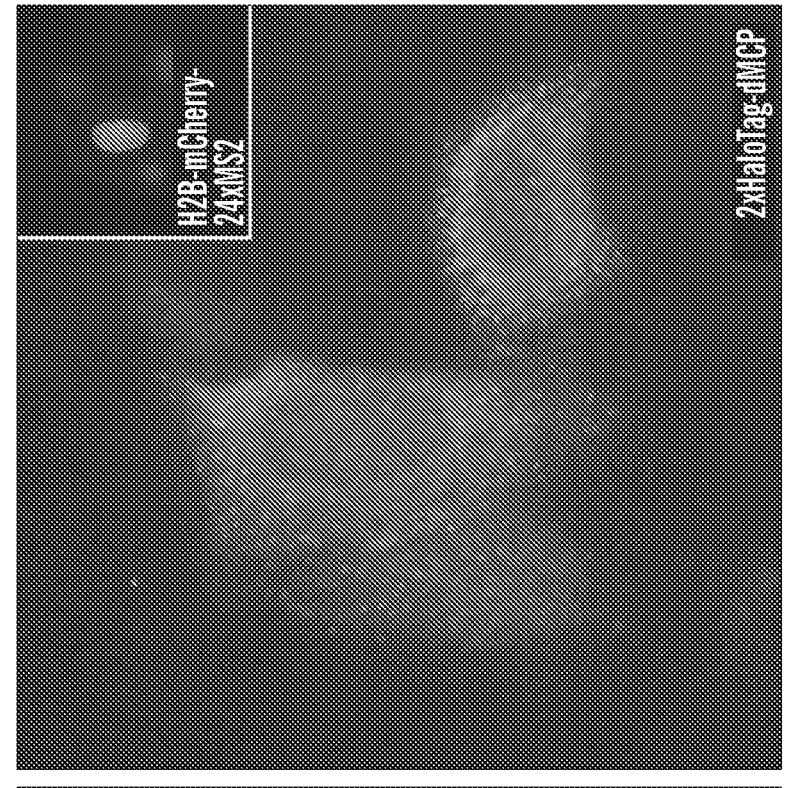
FIG. 32: Microscopy data showing 4×mNeonGreen-dPCP tagging an LSS-mTurq-24×PP7 RNA, while 2×Ha-loTag®-dMCP (stained with JFX646 dye) was simultaneously tagging an H2B-mCherry-24×MS2 RNA.
Figure 32:
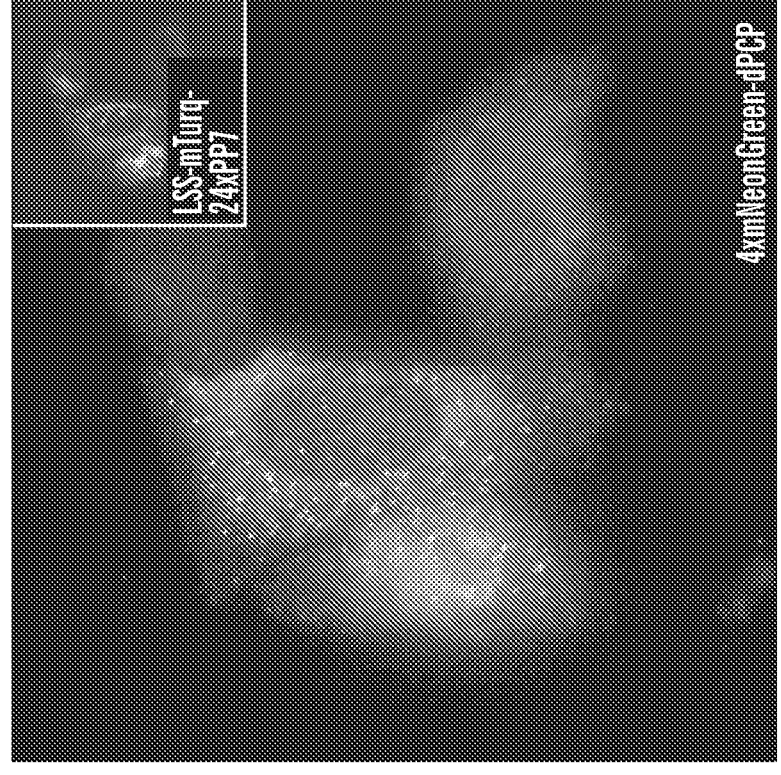

(4) Data for dPCP and dMCP Functioning in Parallel dMCP and dPCP can function simultaneously in the same cell. 4×mNeonGreen-dPCP was used for tagging an LSS-mTurq-24×PP7 RNA, while 2×HaloTag®-dMCP (stained with JFX646 dye) was used for tagging an H2B-mCherry-24×MS2 RNA (see e.g., FIG. 32).

Relevant Annotated Amino Acid and RNA Sequences ylcytosine (m⁵C) triphosphates were obtained from TRI-LINK, and IVT of the self-editing circuits was performed with either no modified nucleotides (NM), pseudouridine

TABLE 7

| Construct | Sequence (Amino Acid) |
|---|---|
| BIV TAT shown in bolded text - IPAH (254-545 fragment) shown in italicized text; SEQ ID NO: 48 | MVSSGPRPRGTRGKGRR IRRGGGLADAVTA *WFPENKQSDVSQIWHAFEHEEHANTFSAFLDR LSDTVSARNTSGFREQVAAWLEKLSASAELRQQ SFAVAADATESCEDRVALTWNNLRKTLLVHQAS EGLFDNDTGALLSLGREMFRLEILEDIARDKVR TLHFVDEIEVYLAFQTMLAEKLQLSTAVKEMRF YGVSGVTANDLRTAEAMVRSREENEFTDWFSL WGPWHAVLKRTEADRWAQAEEQKYEMLENEY PQRVADRLKASGLSGDADAEREAGAQVMRETE QQIYROLTDEVLALRLPENGSQLHHS** |
| cpmMCP; SEQ ID NO: 49 | SAQNRKYTIKVEVPKGAWRSYLNMELTIPIF ATNSDCELIVKAMQGLLKDGNPIPSAIAANS GIYANFTQFVLVDNGGTGDVTVAPSNFANGI AEWISSNSRSQAYKVTCSVRQSS* |
| dmMCP (cpmMCP-RRRG); SEQ ID NO: 50 | SAQNRKYTIKVEVPKGAWRSYLNMELTIPIF ATNSDCELIVKAMQGLLKDGNPIPSAIAANS GIYANFTQFVLVDNGGTGDVTVAPSNFANGI AEWISSNSRSQAYKVTCSVRQRRRG* |

TABLE 8

| Construct | Sequence (RNA) |
|---|---|
| BIV TAR (Pepper Variant); SEQ ID NO: 56 | ggcucgucugagcucauuagcuccgagcc |

Example 13

(1) Modified Nucleotide Substitution in In Vitro Transcribed mRNA Lead to Active iDAR Self-Editing Circuits Described herein is testing of the MS2 directed self-editing ADAR circuits using modified nucleotides (as is standard in mRNA therapeutics to reduce innate immune responses). For more details, see e.g., International Patent Publication WO2024137990A2.

Figure 33A:
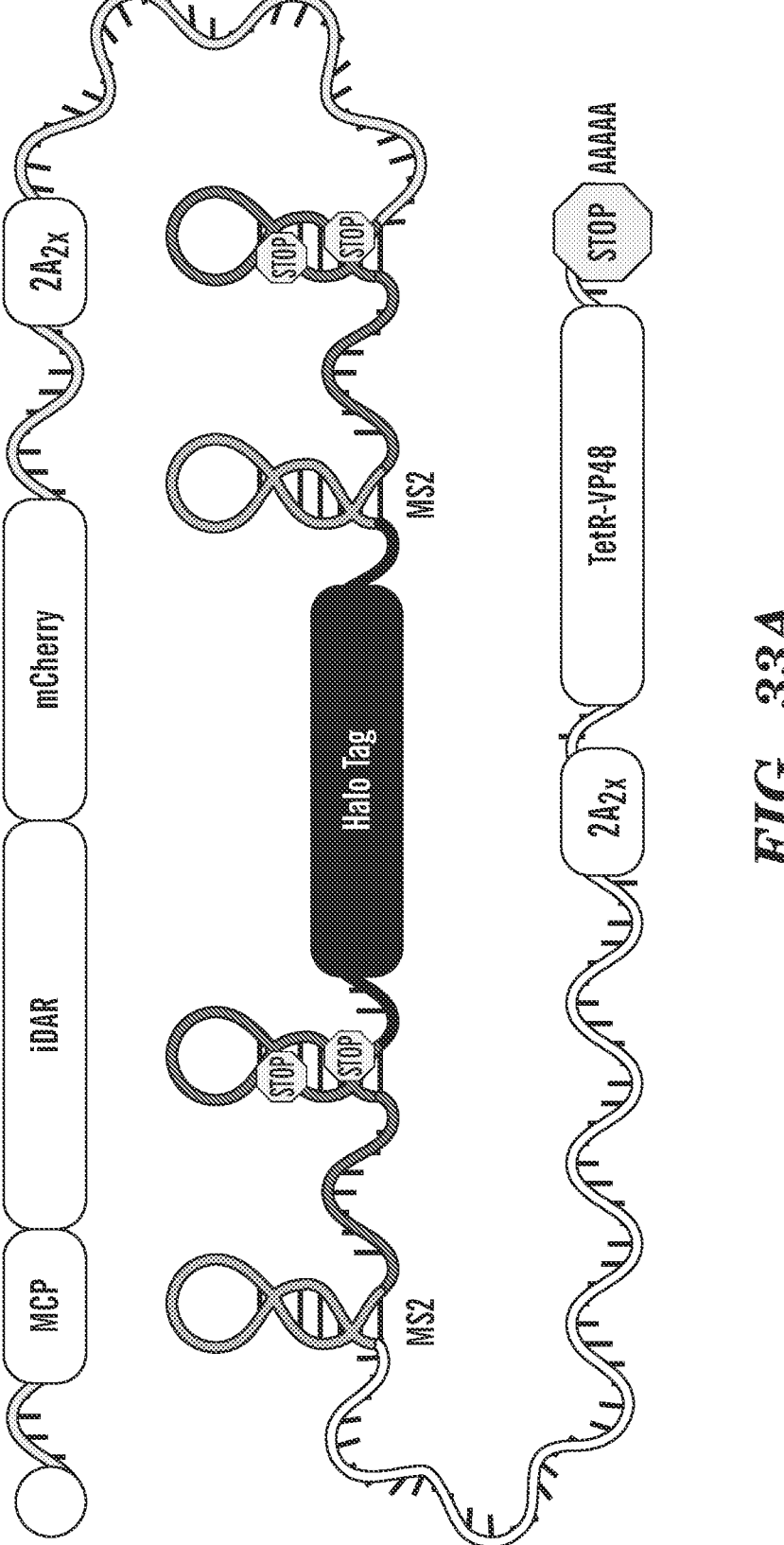
FIG. 33A-33D are a series of schematics and graphs.
Figure 33B:
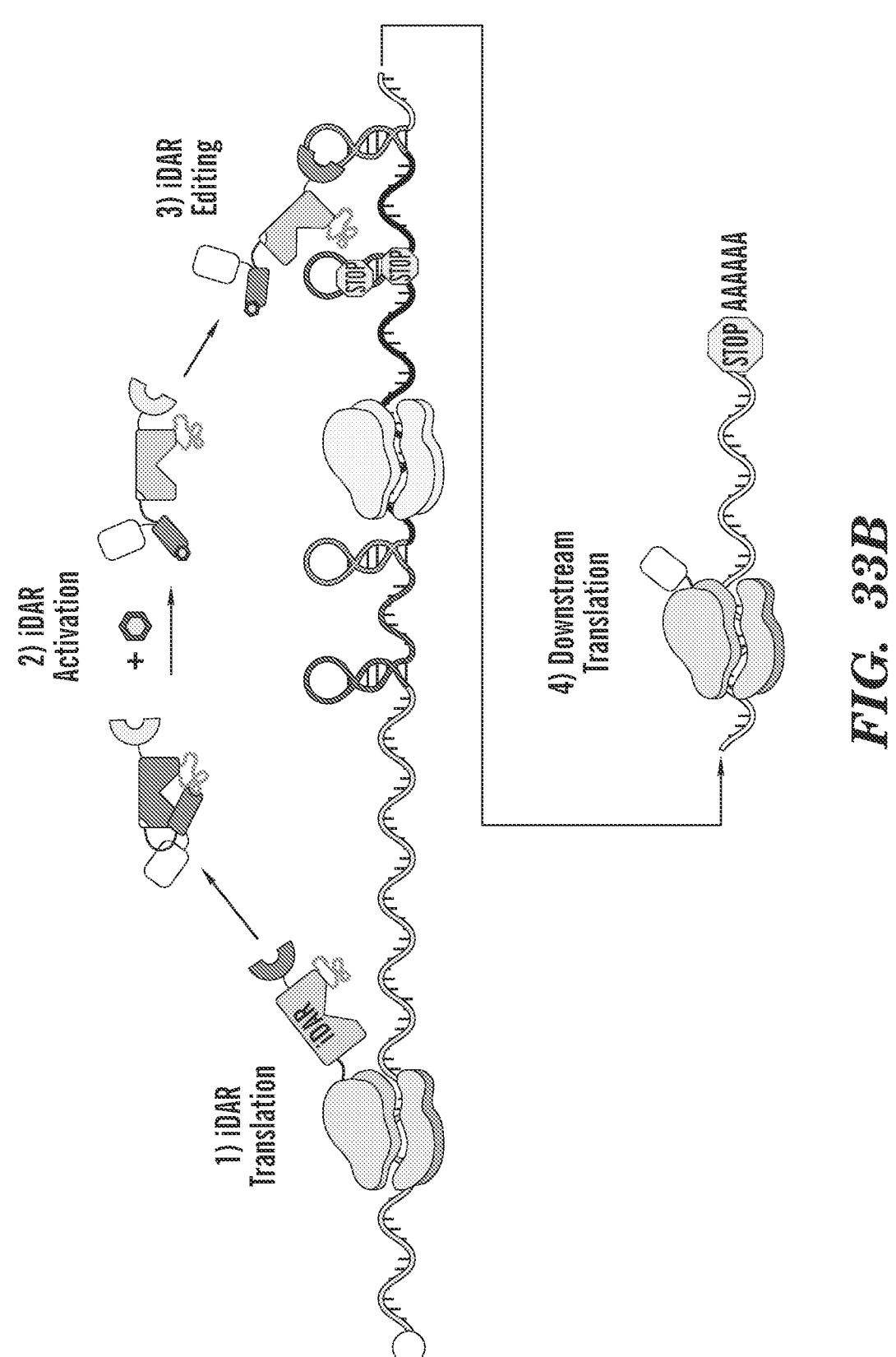

These circuits comprise MS2 coat protein (MCP) fused to the deaminase domain of ADAR2 (iDAR) and mCherry fluorescent protein (see e.g., FIG. 33A). The amber stop codons (UAG) present in the transcript are contained within a dsRNA substrate for ADAR editing and in local proximity to an MS2 RNA-binding motif. MCP-ADAR is therefore directed to the mRNA, where the catalytic domain leads to selective deamination of the adenosine present within the stop codon to inosine, leading to the conversion of a UAG codon to UIG. This codon is preferentially interpreted by the host cell's translation machinery as a sense codon (tryptophan, which has UGG) due to the altered hydrogen bonding of inosine. When editing occurs, translation continues to the downstream protein product (see e.g., FIG. 33B).

Figure 33C:
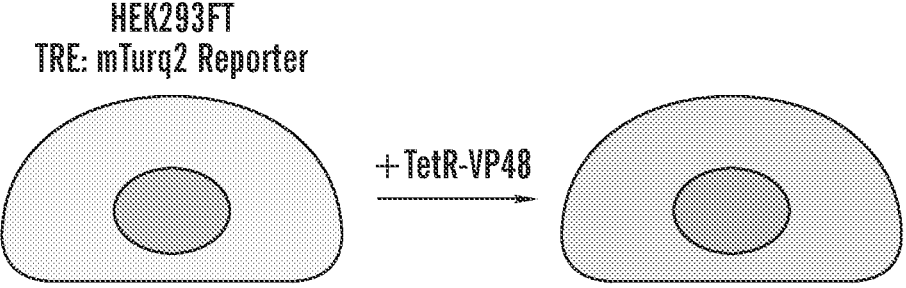

As a test to see if modified nucleotides can retain the ability to be edited by synthetic iDAR constructs, mRNA circuits were used containing constitutively active (ADAR) or constitutively inactive (dADAR, with an E396A mutation) ADAR variants upstream of a TetR-VP48 transcription factor. in vitro transcription (IVT) was then performed using NEB's HiScribe® T7 ARCA mRNA Kit (with tailing) and their mRNA Synthesis with Modified Nucleotides (E2060) protocol, which is expected to lead to ~50% modified nucleotide substitution rates. Pseudouridine (Ψ) and 5-meth- (Ψ), 5-methylcytosine (m⁵C), or both (Ψ & m⁵C). A clonal HEK293FT reporter cell line that contains an integrated mTurq2 under a TRE promoter was then transiently transfected with 100 ng of the each of the different IVT mRNAs (see e.g., FIG. 33C). 24-hours after transfection, cells were lifted and analyzed by flow cytometry, and median mTurq2 expression levels were quantified.

Figure 33D:
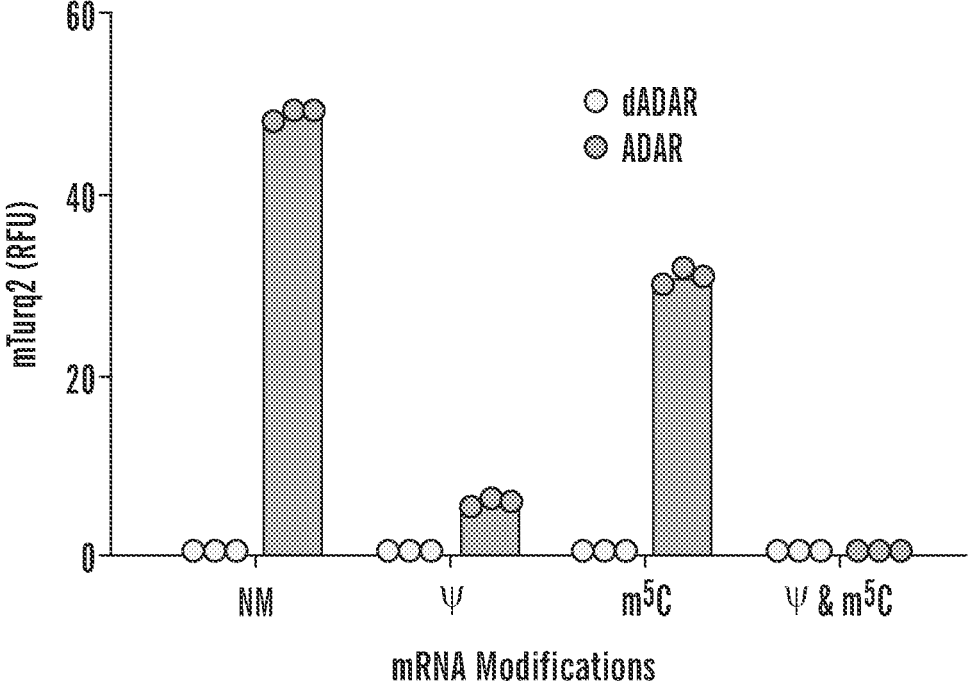

These experiments showed that partial substitution with the modified nucleotides retained self-editing and TetR-VP48 expression, but that the efficiency of the editing was significantly decreased for pseudouridine substitution (FIG. 33D). Additionally, dual substitution with both pseudouridine and 5-methylcytosine led to no significant increase in reporter expression.

These results indicate that MS2-directed ADAR editing of IVT mRNA can accommodate partial substitution with modified nucleotides, but that the efficiency of editing is decreased compared to unmodified transcripts.

These materials highlight the importance of the uridine-free MS2 loop as a protein-binding RNA motif that is not affected by the uridine nucleotide substitution that is commonly used in mRNA therapies.

(2) MS2 Hairpins without Uridines can Still Lead to Effective Recruitment of MCP-ADAR and Stop Codon Editing It was hypothesized that the previous result was due to destabilization of the substrate and/or MS2 motif secondary structures, so an MS2 motif and substrate was designed that was more stable and lacked uridine nucleotides at critical positions.

Figures 34A, 34B:
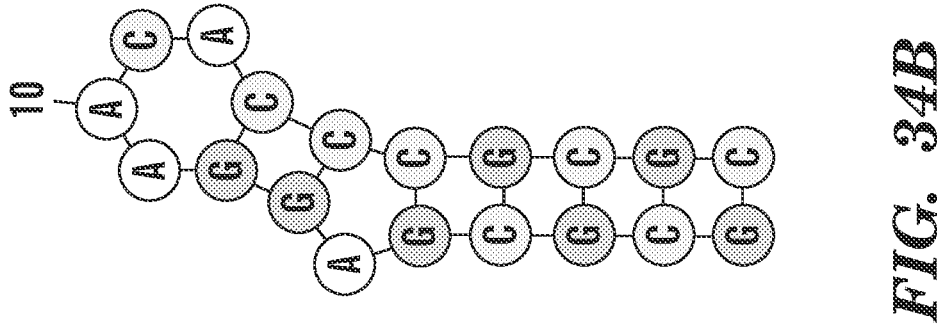
FIG. 34A-34B are a series of schematics showing exemplary MS2 binding loops.

Based on previous results showing that the only absolutely conserved nucleotides were adenosines (see e.g., FIG. 34A, adapted from F. Lim, D. S. Peabody, Nucleic Acids Res. 30, 4138-4144 (2002)), an MS2 binding loop was constructed that lacked uridines.

Such RNA hairpin lacked any uridine nucleotides, but retained the secondary structure and critical nucleotide identities (see e.g., FIG. 34B).

Figure 35:
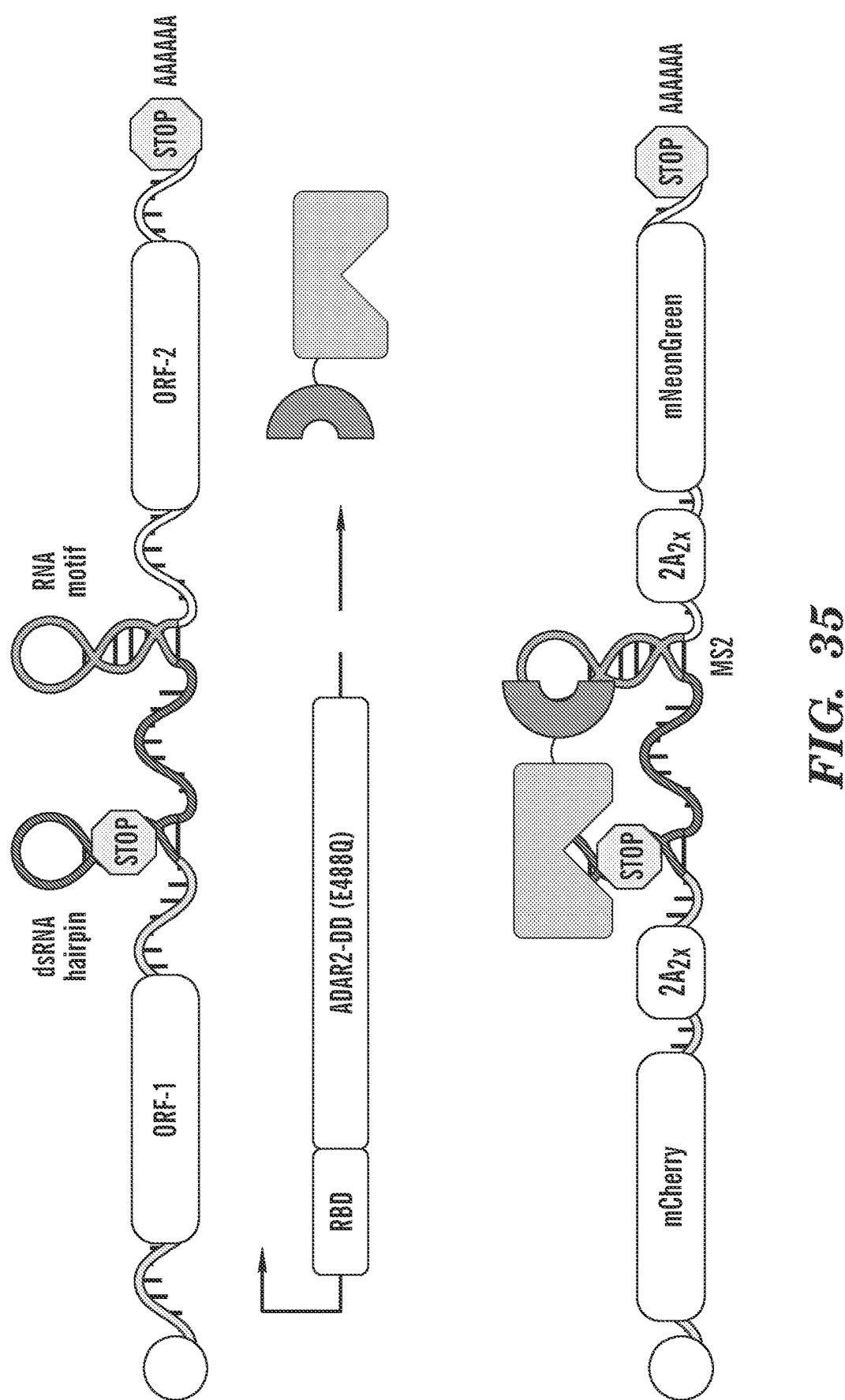
FIG. 35: Exemplary systems comprising MCP-iDAR and MS2 hairpin variants.
Figure 36:
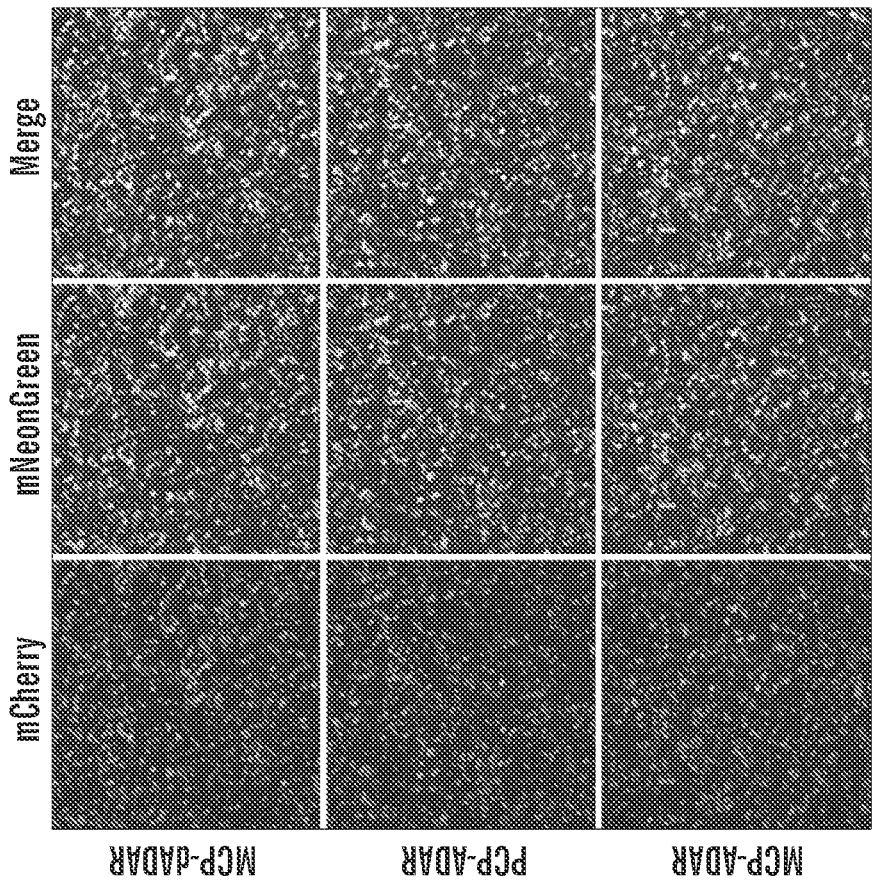
FIG. 36: Testing of MCP-ADAR with reporter variant (stop codons: 0; MS2 loop: 0; SEQ ID NO: 40, AAT-TCCGCGTGGCGCTGGCTTCCTTGCCAGCGC-CACGCGACTAGT).
Figure 36:
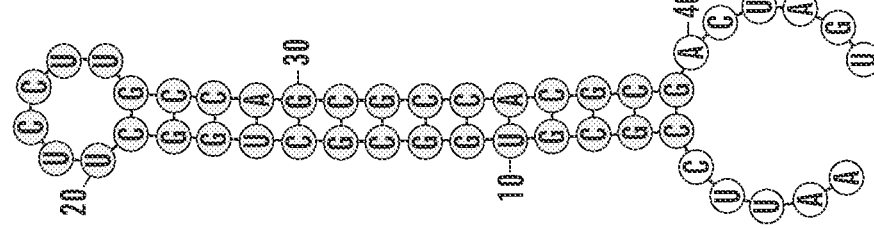
Figure 37:
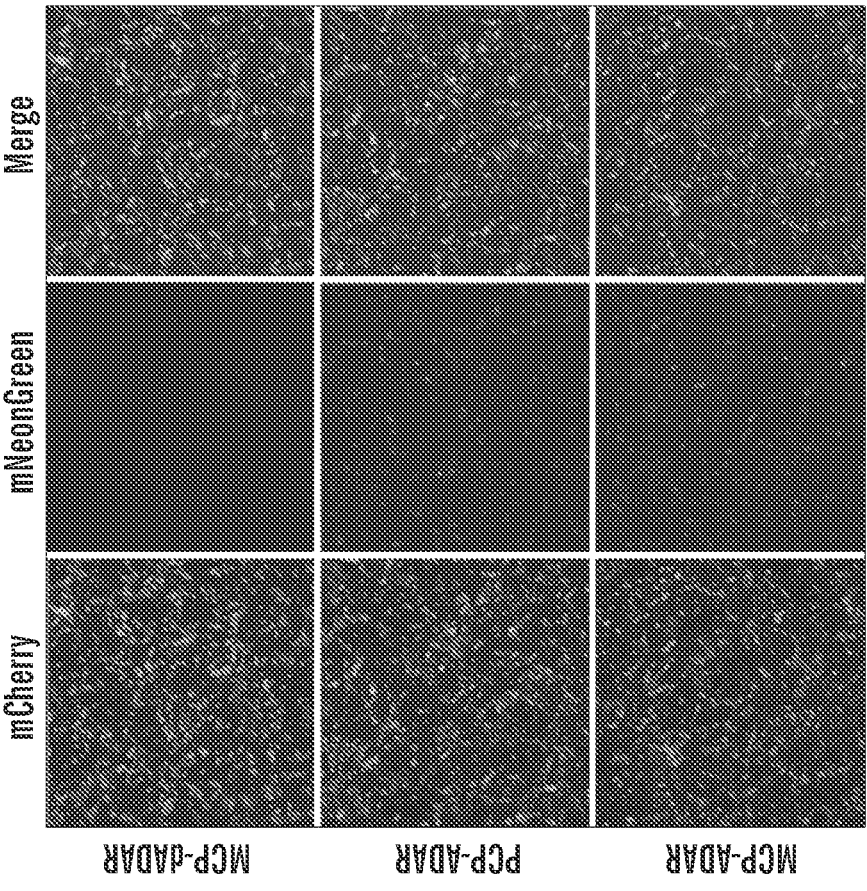
FIG. 37: Testing of MCP-ADAR with reporter variant (stop codons: 2; MS2 loop: 0; SEQ ID NO: 41, AAT-TCCGCGTAGCGCTAGCTTCCTTGCCAGCGC-CACGCGACTAGT).
Figure 37:
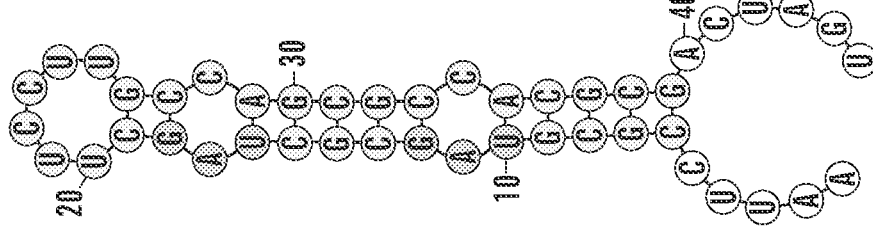
Figure 38:
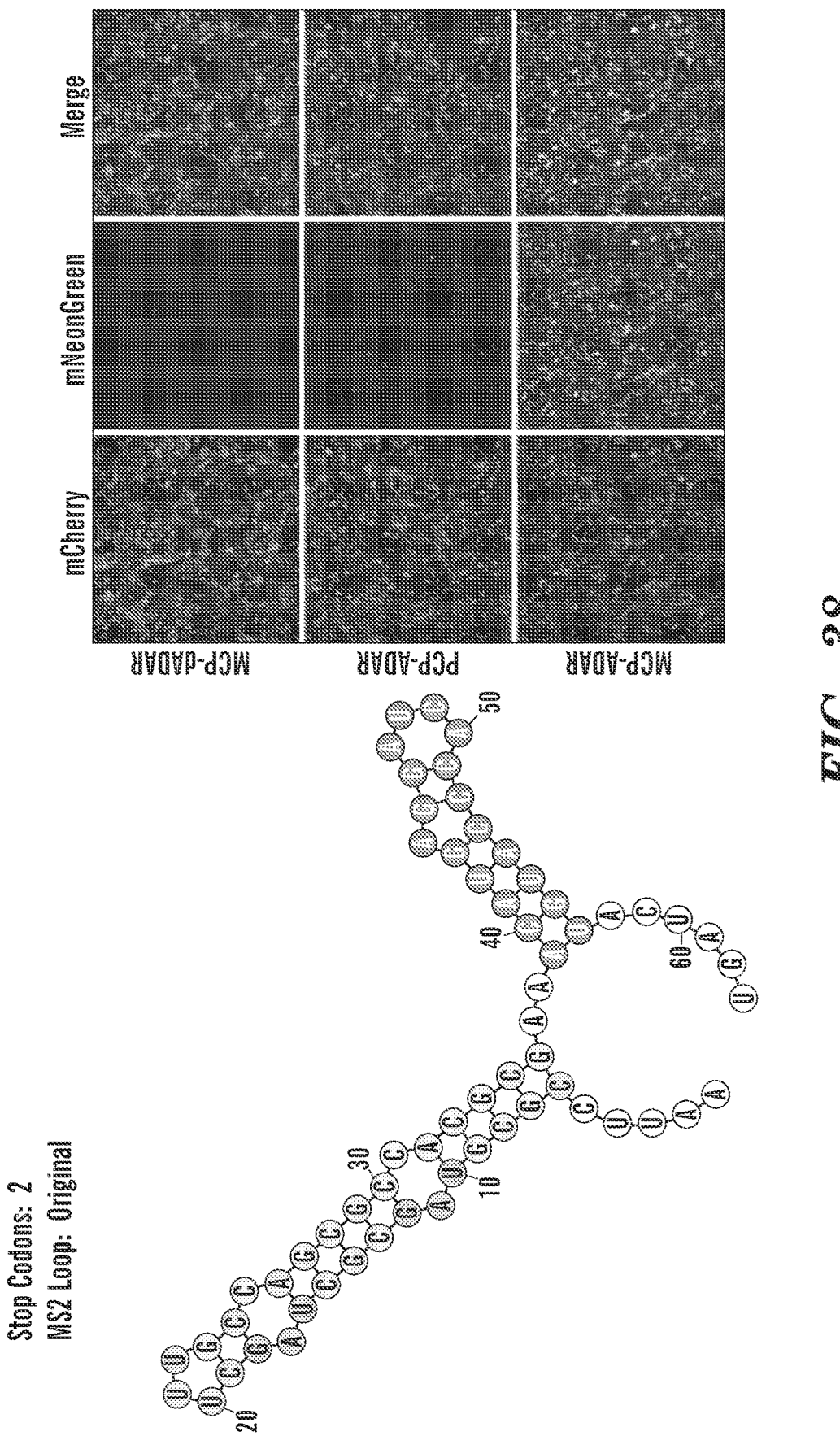
FIG. 38: Testing of MCP-ADAR with reporter variant (stop codons: 2; MS2 loop: original; SEQ ID NO: 42, AATTCCGCGTAGCGCTAGCTTTGCCAGCGC-CACGCGaaACATGAGGATcACCCATGTACTAGT).
Figure 39:
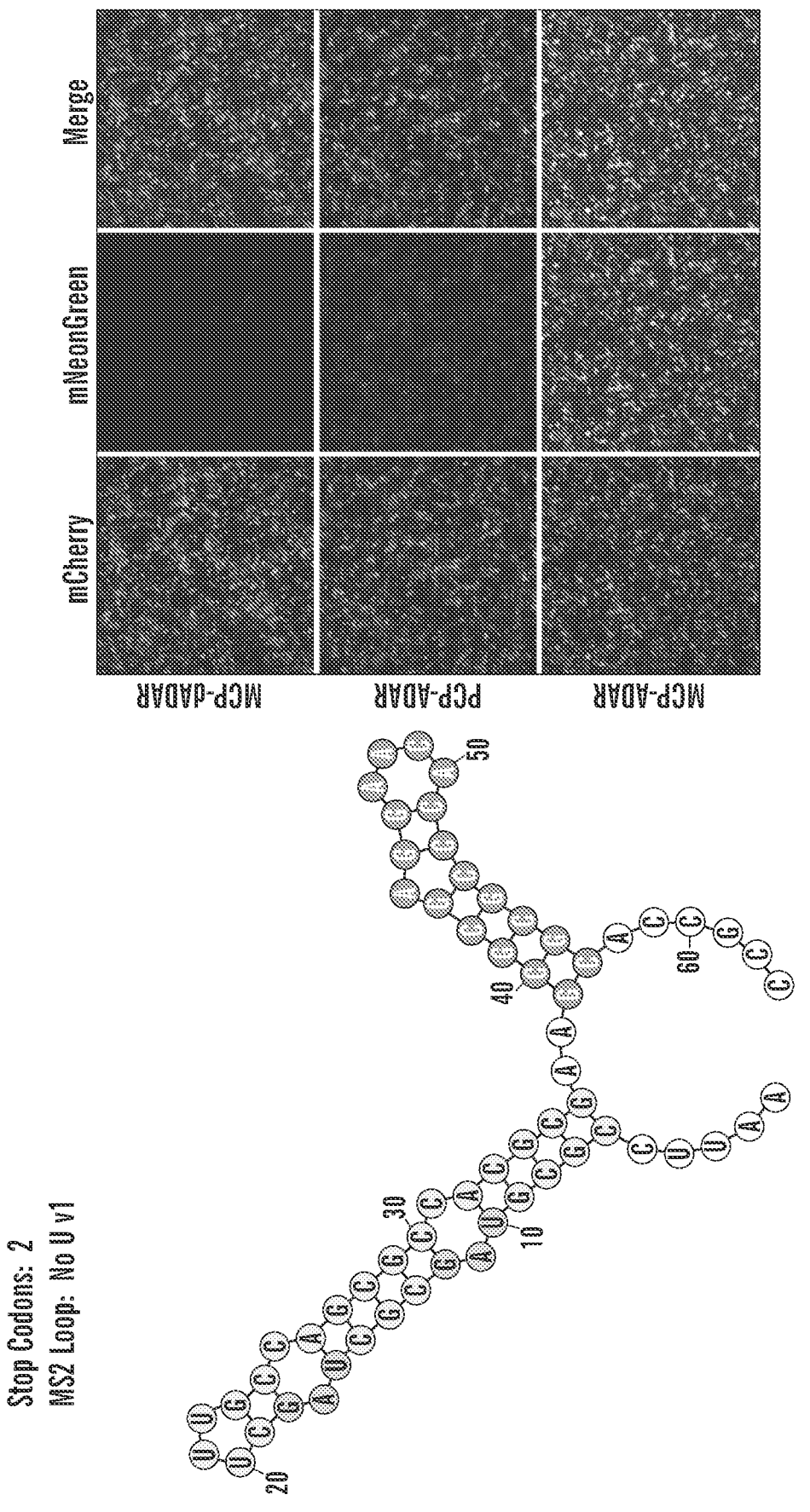
FIG. 39: Testing of MCP-ADAR with reporter variant (stop codons: 2; MS2 loop: no Uv1; SEQ ID NO: 43, AATTCCGCGTAGCGCTAGCTTTGCCAGCGC-CACGCGaaGCGCGAGGAacACCCGCGCACTAGT).

Reporter plasmids were constructed that contained an upstream mCherry fluorescent protein, RNA secondary structures representing an ADAR substrate and MS2 hairpin variants, and a downstream mNeonGreen fluorescent reporter (see e.g., FIG. 35). HEK293FT cells were then co-transfected with the reporter variants (1. no stop codons; 2. 2×UAG codons; 3. 2×UAG codons and native MS2; 4. 2×UAG codons and MS2 variant without U; 5. 2×UAG codons and MS2 variant in single hairpin) and either MCP-dADAR (catalytically inactive negative control), PCP-ADAR (non-targeted ADAR negative control), or MCP-ADAR (experimental group), see e.g., SEQ ID NOs: 30-44, with the expectation that MCP-ADAR would lead to productive editing and mNeonGreen expression, but that non-targeted (PCP) or catalytically inactive (dADAR) would not.

48 hours after transfection, HEK cells were imaged by microscopy.

The MS2 loops that were designed to lack uridine were still able to effectively recruit MCP-ADAR and led to productive editing and mNeonGreen expression, and this editing was significantly enhanced by the RNA-RNA binding domain pair (see e.g., FIG. 36-40).

This therefore demonstrates a new RNA sequence that can serve as an effective handle for MCP and dMCP, and as it is lacking any uridines, can accommodate pseudouridine and N1-methylpseudouridine.

---

Sequences:

SEQ ID NO: 30, Self-Editing MCP-ADAR with TetR:
GGAGACCCAAGCUGGcuagaggaucgaacccuuaaggccaccauggcguccaauuucacucaguuugugcugguugacaacg
gcgggaccggggacguuacgguagcccccucaaacuuugccaacgguauagcggaguggauaagcagcaauucuaggagucaagcauaca
aaguuacaugcagcgugcgccaaucuagcgcucagaaucgcaaguacaccauuaaaguagaggucccaaggggagccuggagaagcuauc
uuaacauggaguugaccauaccaaucuucgcuaccaacucugacugugaacucauugugaaagccaugcaaggucugcucaaggauggua
acccaauuccguccgcuaucgcugccaacucugggauuuacgggggcaguggggagcggugcaggaucugguaguccagcugggggagga
gcaccggguagcggugggggucucagcugcaccugccccagguucucgcagacgccguccacgccuuguacugggcaaguuuggguga
ucuuacugacaauuuuucaucuccucaugcgaggcggaaaguacucgcaggcgucgucaugacgaccggaacugacgugaaagacgccaa
agucaucucugucuccacgggcacaaagugcauaaacggggaguacaugagcgaccgggggcuggcacugaaugauugucacgcugaaau
aauaucuaggcgaucucugcuuagauuucucuacacucaacucgaauugaccuuaacaacaaagaugaccagaaacgcaguauauuuca
gaaaucagaacgcggcggaauucgacuuaaggaaaacguucaguucacuuguauacagcacaucccuugcggugacgcccgaaucuu
uuccccgcacgagccgauauuggaggagcccgcggacagacaucuaauaggaaggcuagaggccaacuucgacgaagaauugaaaagugg
ccaggguacuaucccgugcgguccaacgcuaguauucaaacgugggacggaguccuucaaggugaacggcuguugacaaugagcugcu
cagacaaaaucgcgcgcuggaauguaguggggaauccaaggcagcccucuugagcauauucguagaaccccauuauauuucucauccauuauuu
ugggcucucuguaucauggugaccaucugucaagggcuauguaccaacgaauuucuaauaucgaggaucuucuccucacucuauacacuca
auaagccucucuuguccgggauaucaaacgcugaggcccgccaggccagcuuagcuccuaacuucaggcaccgggugaccguugguguugauu
cugcgauagaggucaucaacgccacgacaggua aggaugagcucgguagagccucacgccuguguaaacacgcguuguauuguagaugga
ugagaguacaugggaaggucccaucucacuugcuccgaagcaagaucacuaagccuaaugugaucaugaucaaaacucgcggcuaaag
aauaccaggcagccaaagcucgacuuuuuacagcuuuuuuaaggcagggcucggggcaugggucgagaagccgaccgagcaggaccaau
ucucucugacggggagcggauccAGCGAGCUGAUUAAGGAGAACAUGCACAUGAAGCGCCaucggucgc
caccauggugagcaaggg cgaggaggauaacauggccaucaucaaggaguucaugcgcuucaaggugcacauggagggcuccgugaacgg
ccacgaguucgagaucgagggcgagggcgagggccgcccuacgagggcacccagaccgccaagcugaaggugaccaaggguggcccccu
gccuucgccugggacaucuguccccucaguucauguacggcuccaaggccuacgugaagcaccccgccgacauccccgacuacuugaag
cuguccuucccgagggcuucaaguggggagcgcgugaugaacucaggacggcgugggaaccggugaccccaggacuccuccccugca
ggacggcgaguucaucuacaaggugaagcugcgcggcaccaacuucccuccgacggcccccguaaugcagaagaagaccauggggcuggga
ggccuccuccgagcggauguaccccgaggacggcgcccugaagggcgagaucaagcagaggcugaagcugaaggacggcggccacuacga
cgcugaggucaagaccaccuacaaggccaagaagcccgugcagcugcccggcgccuacaacgucaacaucaaguuggacaucacccuccac
aacgaggacuacaccaucguggaacaguacgaacgcgccgaggugccgcacuccaccggcgacauggacgagcugUACaaggauuacaa
ggaugacgaugacaaaGGUAGCGGGGCAACUAAUUUUAGCUUACUCAAACAGGCUGGGGACGUCG
AGGAGAAUCCAGGCCCUGCAUCCGCUGGCUCUGGAGAAGGACGAGGCUCCUUGCUCACCU
GUGGAGAUGUCGAAGAGAACCCAGGUCCUGCAACCGGGAAUUCCGCGUAGCGCUAGCUUU
GCCAGCGCCACGCGaaACAUGAGGAUcACCCAUGUGCCGCUAUGGCAGAAAUCGGUACUGG
CUUUCCAUUCGACCCCCAUUAUGUGGAAGUCCUGGGCGAGCGCAUGCACUACGUCGAUGU
UGGUCCGCGCGAUGGCACCCCUGUGCUGUUCUGCACGGUAACCCGACCUCCUCCUACGU
GUGGCGCAACAUCAUCCCGCAUGUUGCACCGACCCAUCGCUGCAUUGCUCCAGACCUGAU
CGGUAUGGGCAAAUCCGACAAACCAGACCUGGGUUAUUUCUUCGACGACCACGUCCGCUU
CAUGGAUGCCUUCAUCGAAGCCCUGGGUCUGGAAGAGGUCGUCCUGGUCAUUCACGACUG
GGGCUCCGCUCUGGGUUUCCACUGGGCCAAGCGCAAUCCAGAGCGCGUCAAAGGUAUUGC
AUUUAUGGGAGUUCAUCCGCCCUAUCCCGACCUGGGACGAAUGGCCAGAAUUUGCCCGCGA
GACCUUCCAGGCCUUCCGCACCACCGACGUCGGCCGCAAGCUGAUCAUCGAUCAGAACGU
UUUUAUCGAGGGUACGCUGCCGAUGGGUGUCGUCCGCCCGCUGACUGAAGUCGAGAUGG
ACCAUUACCGCGAGCCGUUCCUGAAUCCUGUUGACCGCGAGCCACUGUGGCGCUUCCCAA
ACGAGCUGCCAAUCGCCGGUGAGCCAGCGAACAUCGUCGCGCUGGUCGAAGAAUACAUGG
ACUGGCUGCACCAGUCCCCUGUCCCGAAGCUGCUGUUCUGGGGCACCCCAGGCGUUCUGA
UCCCACCGGCCGAAGCCGCUCGCCUGGCCCAAAAGCCUGCCUAACUGCAAGGCUGUGGACA
UCGGCCCGGGUCUGAAUCUGCUGCAAGAAGACAACCCGGACCUGAUCGGCAGCGAGAUCG
CGCGCUGGCUGUCGACGCUCGAGAUUUCUGGCACCGGUAUGGCAUCUAUGACUGGAGGCC
AACAGAUGgGUCCUGCAACCGGGAAUUCCGCGUAGCGCUAGCUUUGCCAGCGCCACGCGaa
ACAUGAGGAUcACCCAUGUACUAGUGCCACAAACUUCUCUCUGCUAAAGCAAGCAGGUGA
UGUUGAAGAAAACCCAGGGCCUGGAGGGUCCGAGGGCAGGGGAAGUCUCCUAACAUGCG
GGGACGUGGAGGAAAAUCCCGGCCCAUCCGGAUAUCCUACGAUGUGCCCGAUUACGCUG
CUAGCUCUAGACUGGACAAGAGCAAAGUCAUAAACUCUGCUCUGGAAUUACUCAAUGAA
GUCGUAUCGAAGGCCUGACGACAAGGAAACUCGCUCAAAAGCUGGGAGUUGAGCAGCC
UACCCUGUACUGGCACGUGAAGAACAAGCGGGCCCUGCUCGAUGCCCUGGCCAAUCGAGAU
GCUGGACAGGCAUCAUACCCACUUCUGCCCCCUGGAAGGCGAGUCAUGGCAAGACUUUCU
GCGGAACAACGCCAAGUCAUUCCGCUGUGCUCUCCUCUCACAUCGCGACGGGGCUAAAGU
GCAUCUCGGCCACCCGCCCAACAGAGAAACAGUACGAAACCCUGGAAAAUCAGCUCGCGUU
CCUGUGUCAGCAAGGCUUCUCCCUGGAGAACGCACUGUACGCUGUGUCCGCCGUGGGCCA
CUUUACACUGGGCUGCGUAUUGGAGGAUCAGGAGCAUCAAGUAGCAAAAGAGGAAAGAG
AGACACCUACCACCGAUUCUAUGCCCCCACUUCUGAGACAAGCAAUUGAGCUGUUCGACC
AUCAGGGAGCCGAACCUGCCUUCCUUUUCGGCCUGGAACUAAUCAUAUGUGGCCUGGAGA
AACAGCUAAAGUGCGAAAGCGGCGGGCCGGCCGACGCCCUUGACGAUUUUGACUUAGACA
UGCUCCCAGCCGAUGCCCUUGACGACUUUGACCUUGAUAUGCUGCCUGCUGACGCUCUUG
ACGAUUUUGACCUUGACAUGCUCCCCGGGUAAUCUAGAGGGCCCGCGGUUCGAAGGUAAG Sequences:

CCUAUCCCUAACCCUCUCCUCGGUCUCGAUUCUACGCGUACCGGUCAUCAUCACCAUCAC
CAUUGAGUUUAAACCCGCUGAUCAGCCUCGACUGUGCCUUCUAGUUGCCAGCCAUCUGUU
GUUUGCCCCUCCCCCGUGCCUUCCUUGACCCUGGAAGGUGCCACUCCCACUGUCCUUUCC
UAAUAAAAUGAGGAAAUUGCAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAA
AAAAAAAAAAAAAAAAAAAAAAAAAAAAAA

SEQ ID NO: 31, Self-Editing MCP-dADAR with TetR:
GGAGACCCAAGCUGGcuagaggaucgaacccuuaaggccaccauggcguccaauuucacucaguuugugcugguugacaacg
gcgggaccggggacguuacgguagcccccucaaacuuugccaacgguauagcggaguggauaagcagcaauucuaggagucaagcauaca
aaguuacaugcagcgugcgccaaucuagcgcucagaaucgcaaguacaccauuaaaguagagguccccaagggagccuggagaagcuauc
uuaacauggaguugaccauaccaaucuucgcuaccaacucugacugugaacucauuugugaaagccaugcaaggucugcucaaggauggua
acccaauuccguccgcuaucgcugccaacucugggauuuacgggggcagugggagcggugcaggaucugguaguccagcuggggagga
gcaccggguagcgguggggggucucagcugcaccugccccaguccucgcagacgccguaucccgccuuguacugggcaaguuugguga
ucuuacugacaauuuuucaucuccucaugcgaggcggaaaguacucgcaggcgucgucaugacgaccggaacugacgugaaagacgccaa
agucaucucugucuccacgggcacaaagugcauaaacggggaguacaugaugccacaggaucgucugacugaaugauugcacgcugccau
aaauaucuaggcgaucucugcuuagauuucucuacacucaacucgaauuguaccuuaacaacaaagaugaccagaaacgcaguauauuuca
gaaaucagaacgcggcggauuucgacuuaaggaaaacguucaguuccacuuguauaucagcacaucccuugcggugacgcccgaaucuu
uucccgcacgagccgauauuggaggagcccgcggacagacauccuaauaggaaggcuagaggccaacuucggacgaagauugaaagugg
ccaggguacuaucccggugcgguccaacgcuaguauucaaacggugggagagcccucaaggugaaacacgcguuugacaaugagcugcu
cagacaaaaucgcgcgcuggaauguaguggggaauccaaggcagccucuugagcauauucguagaacccauauauuucucauccauuauuu
ugggcucucuguaucauggugaccaucugucaagggcuauguaccaacgaauuucuaauaucgaggaucuuccuccacucuauacacuca
auaagccucucuugcgggauaucaaaacgcugaggcccgccagccagggaaaagcuccuaacuucaguguuuaacuggaccguuggugauu
cugcgauagaggucaucaacgccacgacagguaaggaugagcucggaguagacccucgcguguaaacacgcguuguauuguagaugga
ugagaguacauggaagguccucaucucacuugcuccgaagcaagaucacuaaagccuaaugu guaucaugagucaaaacucgcggcuaaag
aauaccaggcagccaaagcucgacuuuuuacagcuuuuuauuaaggcagggcucggggcauggucgagaagccgaccgagcaggaccaau
ucucucugacggggagcggauccAGCGAGCUGAUUAAGGAGAACAUGCACAUGAAGCGCCCaucggucgc
caccaugguggagcaggcgaggaggauaacauggccaucaucaaggugccaacaucaaggugcaacaaggaggcgggucacauggagggcuccgugaacgg
ccacgaguucgagaucgagggcgaggcgagggccgcccccuacgagggcacccagaccgccaagcugaaggugaccaagggugggccccu
gcccuucgccuggacauccugucccccucaguucauguacggcuccaaggccuacgugaagcaccccgccgacauccccgacuacuugaag
cuguccuucccgagggcuucaagugggagcgcgugaugaacuucgaggacggggcguggugaccgugacccaggacuccucccugca
ggacggcgaguucaucuacaaggugaagcugcgcggcaccaacuucccuccgacggccccguaaugcagaagaagaccaugggcuggga
ggcccuccuccgagcggauguaccccgaggacggcgcccugaagggcgagaucaagcagaggcugaaggacgggcggccacuacga
cgcugaggucaagaccaccuacaaggccaagaagcccgugcagcugcccggcgccuacaacgucaacaucaaguuggacaucaccuccac
aacgaggacuacaccaucguggaacaguacgaacgcgccgagggcgccacuccaccggcggcauggacgagcugUA Caaggauuacaa
ggaugacgaugacaaaGGUAGCGGGGCAACUAAUUUUAGCUUACUCAAACAGGCUGGGGACGUCG
AGGAGAAUCCAGGCCCUGCAUCCGCUGGGCUCUGGAGAAGGACGAGGCUCCUUGCUCACCU
GUGGAGAUGUCGAAGAGAACCCAGGUCCUGCAACCGGGAAUUCCGCGUAGCGCUAGCUUU
GCCAGCGCCACGCGAaACAUGAGGAUcACCCAUGUGCCGCUAUGGCAGAAAUCGGUACUGG
CUUUCCAUUCGACCCCCAUUAUGUGGAAGUCCUGGGCGAGCGCAUGCACUACGUCGAUGU
UGGUCCGCGCGAUGGCACCCCUGUUCUGUUCCUGCACGGUAACCCGACCUCCUCCUUACGU
GUGGCGCAACAUCAUCCCGCAUGUUGCACCGACCCAUCGCUGCAUUGCUCCAGACCUGAU
CGGUAUGGGCAAAUCCGACAAACCAGACCUGGGUUAUUUCUUCGACGACCACGUCCGCUU
CAUGGAUGCCUUCAUCGAAGCCCUGGGUCUGGAAGAGGUCGUCCUGGUCAUUCACGACUG
GGGCUCCGCUCUGGGUUUCACUGGGCCCAAGCGCAAUCCAGACGCGUCAAAGGUAUUGC
AUUUAUGGAGUUCAUCCGCCCCUAUCCCGACCUGGGACGAAUGGCCAGAAUUUGCCCGCGA
GACCUUCCAGGCCUUCCGCACCACCGACGUCGGCCGCAAGCUGAUCAUCGAUCAGAACGU
UUUUAUCGAGGGGUACGCUGCCGAUGGGUGUCGUCCGCCCGCUGACUGAAGUCGAGAUGG
ACCAUUACCGCGAGCCGUUCCUGAAUCCUGUUGACCGCGAGCCACUGUGGCGCUUCCCAA
ACGAGCUGCCAAUCGCCGGUGAGCCAGCGAACAUCGUCGCGCUGGUCGAAGAAUACAUGG
ACUGGCUGCACCAGUCCCCUGUCCCGAAGCUGCUGUUCUGGGGCCACCCCAGGCGUUCUGA
UCCCACCGGCCGAAGCCGCUCGCCUGGCCAAAAGCCUGCCUAACUGCAAGGCUGUGGACA
UCGGCCCGGGUCUGAAUCUGCUGCAAGAAGACAACCCGGACCUGAUCGGCAGCGAGAUCG
CGCGCUGGCUGUCGACGCUCGAGAUUUCUGGCACCGGUAUGGCAUCUAUGACUGGAGGCC
AACAGAUGGgGUCCUGCAACCGGGAAUUCCGCGUAGCGCUAGCUUUGCCAGCGCCACGCGAa
ACAUGAGGAUcACCCAUGUACUAGUGCCACAAACUUCUCUCUGCUAAAGCAAGCAGGUGA
UGUUGAAGAAAACCCAGGGCCUGGAGGGUCCGAGGGCAGGGGAAGUCUCCUAACAUGCG
GGGACGUGGAGGAAAAUCCCGGCCCAUCCGGAUAUCCCUACGAUGUGCCCGAUUACGCUG
CUAGCUCUAGACUGGACAAGAGCAAAGUCAUAAACUCUGCUCUGGAAUUACUCAAUGAA
GUCGGUAUCGAAGGCCUGACGACAAGGAAACUCGCUCAAAAGCUGGGGAGUUGAGCAGCC
UACCCUGUACUGGCACGUGAAGAACAAGCGGGCCCUGCUCGAUGCCCUGGCCAAUCGAGAU
GCUGGACAGGCAUCAUACCCACUUCUGCCCCCUGGAAGGCGAGUCAUGGCAAGACUUUCU
GCGGAACAACGCCAAGUCAUUCCGCUGUGCUCUCCUCUCACAUCGCGACGGGGCUAAAGU
GCAUCUCGGCACCCGCCCAACAGAGAAACAGUACGAAACCCUGGAAAAUCAGCUCGCGUU
CCUGUGUCAGCAAGGCUUCUCCCUGGAGAACGCACUGUACGCUCUGUCCGCCGUGGGCCA
CUUUACACUGGGCUGCGUAUUGGAGGAUCAGGAGCAUCAAGUAGCAAAAGAGGAAAGAG
AGACACCUACCACCGAUUCUAUGCCCCCACUUCUGAGACAAGCAAUUGAGCUGUUCGACC
AUCAGGGAGCCGAACCUGCCUUCCUUUUCGGCCUGGAACUAAUCAUAUGUGGCCUGGAGA
AACAGCUAAAGUGCGAAAGCGGCGGGCCGGCCGACGCCCUUGACGAUUUUGACUUAGACA
UGCUCCCAGCCGAUGCCCUUGACGACUUUGACCUUGAUAUGCUGCCUGCUGACGCUCUUG
ACGAUUUUGACCUUGACAUGCUCCCCGGGUAAUCUAGAGGGCCCGCGGUUCGAAGGUAAG
CCUAUCCCUAACCCUCUCCUCGGUCUCGAUUCUACGCGUACCGGUCAUCAUCACCAUCAC
CAUUGAGUUUAAACCCGCUGAUCAGCCUCGACUGUGCCUUCUAGUUGCCAGCCAUCUGUU
GUUUGCCCCUCCCCCGUGCCUUCCUUGACCCUGGAAGGUGCCACUCCCACUGUCCUUUCC
UAAUAAAAUGAGGAAAUUGCAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAA
AAAAAAAAAAAAAAAAAAAAAAAAAAAAAA -continued Sequences:

SEQ ID NO: 32, No Stop Codon Reporter (mCherry-Flag-P2A-T2A-loop-P2A-T2A-HA-
mNeonGreen), loop is bolded (see e.g., SEQ ID NO: 40):
TAATACGACTCACTATAGGGAGACCCAAGCTGGCTAGGTAAGCTTGGTACCGAGCTCGGATC
Caccggtcgccaccatggtgagcaagggcgaggaggataacatggccatcatcaaggagttcatgcgcttcaaggtgcacatggagggctccgtgaa
cggccacgagttcgagatcgagggcgagggcgagggccgcccctacgagggcacccagaccgccaagctgaaggtgaccaagggtggccccctg
cccttcgcctgggacatcctgtcccctcagttcatgtacggctccaaggcctacgtgaagcaccccgccgacatccccgactacttgaagctgtccttccc
cgagggcttcaagtgggagcgcgtgatgaacttcgaggacggcggcgtggtgaccgtgacccaggactcctccctgcaggacggcgagttcatctac
aaggtgaagctgcgcggcaccaacttcccctccgacggccccgtaatgcagaagaagaccatgggctgggaggcctcctccgagcggatgtaccc
gaggacggcgccctgaagggcgagatcaagcagaggctgaagctgaaggacggcggccactacgacgctgaggtcaagaccacctacaaggcca
agaagccgtgcagctgcccggcgcctacaacgtcaacatcaagttggacatcacctcccacaacgaggactacaccatcgtggaacagtacgaacg
cgccgagggccgccactccaccggcggcatggacgagctgTACaaggattacaaggatgacgatgacaaaGGTAGCGGGGCAACT
AATTTTAGCTTACTCAAACAGGCTGGGGACGTCGAGGAGAATCCAGGCCCTGCATCCGCTGG
CTCTGGAGAAGGACGAGGCTCCTTGCTCACCTGTGGAGATGTCGAAGAGAACCCAGGTCCT
GCAACCGGGAATTCCGCGTGGCGCTGGCTTCCTTGCCAGCGCCACGCGACTAGTGCCAC
AAACTTCTCTCTGCTAAAGCAAGCAGGTGATGTTGAAGAAAACCCAGGGCCTGGAGGGTCC
GAGGGCAGGGGAAGTCTCCTAACATGCGGGGACGTGGAGGAAAATCCCGGCCCATCCGGAT
ATCCCTACGATGTGCCCGATTACGCTCATatggtgagcaagggcgaggaggataacatggccctctctcccagcgacacatg
agttacacatctttggctccatcaacggtgtggactttgacatggtgggtcagggcaccggcaatccaaatgatggttatgaggagttaaacctgaagtcca
ccaagggtgacctccagttctcccccctggattctggtccctcatatcgggtatggcttccatcagtacctgccctaccctgacgggatgtcgcctttccagg
ccgccatggtagatggcAGCggataccaagtccatcgcacaatgcagtttgaagatggtgcctcccttactgttaactaccgctacacctacgagggaa
gccacatcaaaggagaggcccaggtgaaggggactggtttccctgctgacggtcctgtgatgaccaactcgctgaccgctgcggactggtgcaggtcg
aagaagacttacccaacgacaaaaccatcatcagtacctttaagtggagttacaccactggaaatggcaagAGAtaccggagcactgcgcggacca
cctacacctttgccaagccaatggcggctaactatctgaagaaccagccgatgtacgtgttccgtaagacggagctcaagcactccaagaccgagctca
acttcaaggagtggcaaaaggcctttaccgatgtgatgGGAatggacGAGCTGTATaagGCTAGCTAAGCGGCCGCTCG
AGTCTAGAGGGCCCGCGGTTCGAAGGTAAGCCTATCCCTAACCCTCTCCTCGGTCTCGATTC
TACGCGTACCGGTCATCATCACCATCACCATTGAGTTTAAACCCGCTGATCAGCCTCGACTG
TGCCTTCTA SEQ ID NO: 33, 2xUAG Stop Codon Reporter (mCherry-Flag-P2A-T2A-loop-P2A-T2A-
HA-mNeonGreen); loop is bolded (see e.g., SEQ ID NO: 41):
TAATACGACTCACTATAGGGAGACCCAAGCTGGCTAGGTAAGCTTGGTACCGAGCTCGGATC
Caccggtcgccaccatggtgagcaagggcgaggaggataacatggccatcatcaaggagttcatgcgcttcaaggtgcacatggagggctccgtgaa
cggccacgagttcgagatcgagggcgagggcgagggccgcccctacgagggcacccagaccgccaagctgaaggtgaccaagggtggccccctg
cccttcgcctgggacatcctgtcccctcagttcatgtacggctccaaggcctacgtgaagcaccccgccgacatccccgactacttgaagctgtccttccc
cgagggcttcaagtgggagcgcgtgatgaacttcgaggacggcggcgtggtgaccgtgacccaggactcctccctgcaggacggcgagttcatctac
aaggtgaagctgcgcggcaccaacttcccctccgacggccccgtaatgcagaagaagaccatgggctgggaggcctcctccgagcggatgtaccc
gaggacggcgccctgaagggcgagatcaagcagaggctgaagctgaaggacggcggccactacgacgctgaggtcaagaccacctacaaggcca
agaagccgtgcagctgcccggcgcctacaacgtcaacatcaagttggacatcacctcccacaacgaggactacaccatcgtggaacagtacgaacg
cgccgagggccgccactccaccggcggcatggacgagctgTA CaaggattacaaggatgacgatgacaaaGGTAGCGGGGCAACT
AATTTTAGCTTACTCAAACAGGCTGGGGACGTCGAGGAGAATCCAGGCCCTGCATCCGCTGG
CTCTGGAGAAGGACGAGGCTCCTTGCTCACCTGTGGAGATGTCGAAGAGAACCCAGGTCCT
GCAACCGGGAATTCCGCGTAGCGCTAGCTTCCTTGCCAGCGCCACGCGACTAGTGCCAC
AAACTTCTCTCTGCTAAAGCAAGCAGGTGATGTTGAAGAAAACCCAGGGCCTGGAGGGTCC
GAGGGCAGGGGAAGTCTCCTAACATGCGGGGACGTGGAGGAAAATCCCGGCCCATCCGGAT
ATCCCTACGATGTGCCCGATTACGCTCATatggtgagcaagggcgaggaggataacatggccctctctcccagcgacacatg
agttacacatctttggctccatcaacggtgtggactttgacatggtgggtcagggcaccggcaatccaaatgatggttatgaggagttaaacctgaagtcca
ccaagggtgacctccagttctcccccctggattctggtccctcatatcgggtatggcttccatcagtacctgccctaccctgacgggatgtcgcctttccagg
ccgccatggtagatggcAGCggataccaagtccatcgcacaatgcagtttgaagatggtgcctcccttactgttaactaccgctacacctacgagggaa
gccacatcaaaggagaggcccaggtgaaggggactggtttccctgctgacggtcctgtgatgaccaactcgctgaccgctgcggactggtgcaggtcg
aagaagacttacccaacgacaaaaccatcatcagtacctttaagtggagttacaccactggaaatggcaagAGAtaccggagcactgcgcggacca
cctacacctttgccaagccaatggcggctaactatctgaagaaccagccgatgtacgtgttccgtaagacggagctcaagcactccaagaccgagctca
acttcaaggagtggcaaaaggcctttaccgatgtgatgGGAatggacGAGCTGTATaagGCTAGCTAAGCGGCCGCTCG
AGTCTAGAGGGCCCGCGGTTCGAAGGTAAGCCTATCCCTAACCCTCTCCTCGGTCTCGATTC
TACGCGTACCGGTCATCATCACCATCACCATTGAGTTTAAACCCGCTGATCAGCCTCGACTG
TGCCTTCTA SEQ ID NO: 34, 2xUAG and MS2 Reporter (mCherry-Flag-P2A-T2A-loop and MS2-P2A-
T2A-HA-mNeonGreen), loop and MS2 is bolded (see e.g., SEQ ID NO: 42):
TAATACGACTCACTATAGGGAGACCCAAGCTGGCTAGGTAAGCTTGGTACCGAGCTCGGATC
Caccggtcgccaccatggtgagcaagggcgaggaggataacatggccatcatcaaggagttcatgcgcttcaaggtgcacatggagggctccgtgaa
cggccacgagttcgagatcgagggcgagggcgagggccgcccctacgagggcacccagaccgccaagctgaaggtgaccaagggtggccccctg
cccttcgcctgggacatcctgtcccctcagttcatgtacggctccaaggcctacgtgaagcaccccgccgacatccccgactacttgaagctgtccttccc
cgagggcttcaagtgggagcgcgtgatgaacttcgaggacggcggcgtggtgaccgtgacccaggactcctccctgcaggacggcgagttcatctac
aaggtgaagctgcgcggcaccaacttcccctccgacggccccgtaatgcagaagaagaccatgggctgggaggcctcctccgagcggatgtaccc
gaggacggcgccctgaagggcgagatcaagcagaggctgaagctgaaggacggcggccactacgacgctgaggtcaagaccacctacaaggcca
agaagccgtgcagctgcccggcgcctacaacgtcaacatcaagttggacatcacctcccacaacgaggactacaccatcgtggaacagtacgaacg
cgccgagggccgccactccaccggcggcatggacgagctgTA CaaggattacaaggatgacgatgacaaaGGTAGCGGGGCAACT
AATTTTAGCTTACTCAAACAGGCTGGGGACGTCGAGGAGAATCCAGGCCCTGCATCCGCTGG
CTCTGGAGAAGGACGAGGCTCCTTGCTCACCTGTGGAGATGTCGAAGAGAACCCAGGTCCT
GCAACCGGG**AATTCCGCGTAGCGCTAGCTTTGCCAGCGCCACGCGaaACATGAGGATcA
CCCATGTACTAGT**GCCACAAACTTCTCTCTGCTAAAGCAAGCAGGTGATGTTGAAGAAAAC
CCAGGGCCTGGAGGGTCCGAGGGCAGGGGAAGTCTCCTAACATGCGGGGACGTGGAGGAA
AATCCCGGCCCATCCGGATATCCCTACGATGTGCCCGATTACGCTCATatggtgagcaagggcgaggag
gataacatggcctctctctcccagcgacacatgagttacacatctttggctccatcaacggtgtggactttgacatggtgggtcagggcaccggcaatccaaa
tgatggttatgaggagttaaacctgaagtccaccaagggtgacctccagttctcccccctggattctggtccctcatatcgggtatggcttccatcagtacctg
ccctaccctgacgggatgtcgcctttccaggccgccatggtagatggcAGCggataccaagtccatcgcacaatgcagtttgaagatggtgcctccctt Sequences:

```
actgttaactaccgctacacctacgagggaagccacatcaaaggagaggcccaggtgaaggggactggtttccctgctgacggtcctgtgatgaccaac
tcgctgaccgctgcggactggtgcaggtcgaagaagacttaccccaacgacaaaaccatcatcagtacctttaagtggagttacaccactggaaatggc
aagAGAtaccggagcactgcgcggaccacctacacctttgccaagccaatggcggctaactatctgaagaaccagccgatgtacgtgttccgtaaga
cggagctcaagcactccaagaccgagctcaacttcaaggagtggcaaaaggcctttaccgatgtgatgGGAatggacGAGCTGTATaagG
CTAGCTAAGCGGCCGCTCGAGTCTAGAGGGCCCGCGGTTCGAAGGTAAGCCTATCCCTAACC
CTCTCCTCGGTCTCGATTCTACGCGTACCGGTCATCATCACCATCACCATTGAGTTTAAACCC
GCTGATCAGCCTCGACTGTGCCTTCTA SEQ ID NO: 35, 2xUAG and MS2 without U Reporter (mCherry-Flag-P2A-T2A-loop and
MS2(no U)-P2A-T2A-HA-mNeonGreen), loop and MS2(no U) is bolded (see e.g., SEQ ID NO: 43):
TAATACGACTCACTATAGGGAGACCCAAGCTGGCTAGGTAAGCTTGGTACCGAGCTCGGATC
Caccggtcgccaccatggtgagcaagggcgaggaggataacatggccatcatcaaggagttcatgcgcttcaaggtgcacatggagggctccgtgaa
cggccacgagttcgagatcgagggcgagggcgagggccgcccctacgagggcacccagaccgccaagctgaaggtgaccaagggtggccccctg
cccttcgcctgggacatcctgtcccctcagttcatgtacggctccaaggcctacgtgaagcaccccgccgacatccccgactacttgaagctgtccttccc
cgagggcttcaagtgggagcgcgtgatgaacttcgaggacggcggcgtggtgaccgtgacccaggactcctccctgcaggacggcgagttcatctac
aaggtgaagctgcgcggcaccaacttcccctccgacggccccgtaatgcagaagaagaccatgggctgggaggcctcctccgagcggatgtaccccc
gaggacggcgccctgaagggcgagatcaagcagaggctgaagctgaaggacggcggccactacgacgctgaggtcaagaccacctacaaggcca
agaagcccgtgcagctgcccggcgcctacaacgtcaacatcaagttggacatcacctcccacaacgaggactacaccatcgtggaacagtacgaacg
cgccgagggcgccactccaccggcggcatggacgagctgTA CaaggattacaaggatgacgatgacaaaGGTAGCGGGGCAACT
AATTTTAGCTTACTCAAACAGGCTGGGGACGTCGAGGAGAATCCAGGCCCTGCATCCGCTGG
CTCTGGAGAAGGACGAGGCTCCTTGCTCACCTGTGGAGATGTCGAAGAGAACCCAGGTCCT
GCAACCGGGAATTCCGCGTAGCGCTAGCTTTGCCAGCGCCACGCGaaGCGCGAGGAacA
CCCGCGCACTAGTGCCACAAACTTCTCTCTGCTAAAGCAAGCAGGTGATGTTGAAGAAAC
CCAGGGCCTGGAGGGTCCGAGGGCAGGGGAAGTCTCCTAACATGCGGGGACGTGGAGGAA
AATCCCGGCCCATCCGGATATCCCTACGATGTGCCCGATTACGCTCATatggtgagcaagggcgaggag
gataacatggcctctctcccagcgacacatgagttacacatctttggctccatcaacggtgtggactttgacatggtgggtcagggcaccggcaatccaaa
tgatggttatgaggagttaaacctgaagtccaccaagggtgacctccagttctcccctggattctggtccctcatatcgggtatggcttccatcagtacctg
ccctaccctgacgggatgtcgcctttccaggccgccatggtagatggcAGCggataccaagtccatcgcacaatgcagtttgaagatggtgcctcctt
actgttaactaccgctacacctacgagggaagccacatcaaaggagaggcccaggtgaaggggactggtttccctgctgacggtcctgtgatgaccaac
tcgctgaccgctgcggactggtgcaggtcgaagaagacttaccccaacgacaaaaccatcatcagtacctttaagtggagttacaccactggaaatggc
aagAGAtaccggagcactgcgcggaccacctacacctttgccaagccaatggcggctaactatctgaagaaccagccgatgtacgtgttccgtaaga
cggagctcaagcactccaagaccgagctcaacttcaaggagtggcaaaaggcctttaccgatgtgatgGGAatggacGAGCTGTATaagG
CTAGCTAAGCGGCCGCTCGAGTCTAGAGGGCCCGCGGTTCGAAGGTAAGCCTATCCCTAACC
CTCTCCTCGGTCTCGATTCTACGCGTACCGGTCATCATCACCATCACCATTGAGTTTAAACCC
GCTGATCAGCCTCGACTGTGCCTTCTA SEQ ID NO: 36, 2xUAG and MS2 without U as single Hairpin Reporter (mCherry-Flag-
P2A-T2A-loop with MS2(no U)-P2A-T2A-HA-mNeonGreen), loop with MS2(no U) is bolded (see e.g.,
SEQ ID NO: 44):
TAATACGACTCACTATAGGGAGACCCAAGCTGGCTAGGTAAGCTTGGTACCGAGCTCGGATC
Caccggtcgccaccatggtgagcaagggcgaggaggataacatggccatcatcaaggagttcatgcgcttcaaggtgcacatggagggctccgtgaa
cggccacgagttcgagatcgagggcgagggcgagggccgcccctacgagggcacccagaccgccaagctgaaggtgaccaagggtggccccctg
cccttcgcctgggacatcctgtcccctcagttcatgtacggctccaaggcctacgtgaagcaccccgccgacatccccgactacttgaagctgtccttccc
cgagggcttcaagtgggagcgcgtgatgaacttcgaggacggcggcgtggtgaccgtgacccaggactcctccctgcaggacggcgagttcatctac
aaggtgaagctgcgcggcaccaacttcccctccgacggccccgtaatgcagaagaagaccatgggctgggaggcctcctccgagcggatgtaccccc
gaggacggcgccctgaagggcgagatcaagcagaggctgaagctgaaggacggcggccactacgacgctgaggtcaagaccacctacaaggcca
agaagcccgtgcagctgcccggcgcctacaacgtcaacatcaagttggacatcacctcccacaacgaggactacaccatcgtggaacagtacgaacg
cgccgagggcgccactccaccggcggcatggacgagctgTACaaggattacaaggatgacgatgacaaaGGTAGCGGGGCAACT
AATTTTAGCTTACTCAAACAGGCTGGGGACGTCGAGGAGAATCCAGGCCCTGCATCCGCTGG
CTCTGGAGAAGGACGAGGCTCCTTGCTCACCTGTGGAGATGTCGAAGAGAACCCAGGTCCT
GCAACCGGGAATTCCGCGTAGCGCTAGCCaaGCGCGAGGAacACCCGCGCaGGCCAGCG
CCACGCGACTAGTGCCACAAACTTCTCTCTGCTAAAGCAAGCAGGTGATGTTGAAGAAAC
CCAGGGCCTGGAGGGTCCGAGGGCAGGGGAAGTCTCCTAACATGCGGGGACGTGGAGGAA
AATCCCGGCCCATCCGGATATCCCTACGATGTGCCCGATTACGCTCATatggtgagcaagggcgaggag
gataacatggcctctctcccagcgacacatgagttacacatctttggctccatcaacggtgtggactttgacatggtgggtcagggcaccggcaatccaaa
tgatggttatgaggagttaaacctgaagtccaccaagggtgacctccagttctcccctggattctggtccctcatatcgggtatggcttccatcagtacctg
ccctaccctgacgggatgtcgcctttccaggccgccatggtagatggcAGCggataccaagtccatcgcacaatgcagtttgaagatggtgcctcctt
actgttaactaccgctacacctacgagggaagccacatcaaaggagaggcccaggtgaaggggactggtttccctgctgacggtcctgtgatgaccaac
tcgctgaccgctgcggactggtgcaggtcgaagaagacttaccccaacgacaaaaccatcatcagtacctttaagtggagttacaccactggaaatggc
aagAGAtaccggagcactgcgcggaccacctacacctttgccaagccaatggcggctaactatctgaagaaccagccgatgtacgtgttccgtaaga
cggagctcaagcactccaagaccgagctcaacttcaaggagtggcaaaaggcctttaccgatgtgatgGGAatggacGAGCTGTATaagG
CTAGCTAAGCGGCCGCTCGAGTCTAGAGGGCCCGCGGTTCGAAGGTAAGCCTATCCCTAACC
CTCTCCTCGGTCTCGATTCTACGCGTACCGGTCATCATCACCATCACCATTGAGTTTAAACCC
GCTGATCAGCCTCGACTGTGCCTTCTA
```

Sequences:

SEQ ID NO: 37, MCP-ADAR2-DD(E488Q)-TagBFP Protein Sequence:
MASNFTQFVLVDNGGTGDVTVAPSNFANGIAEWISSNSRSQAYKVTCSVRQSSAQNRKYTIKVE
VPKGAWRSYLNMELTIPIFATNSDCELIVKAMQGLLKDGNPIPSAIAANSGIYGGSGSGAGSGSPA
GGGAPGSGGGSQLHLPQVLADAVSRLVLGKFGDLTDNFSSPHARRKVLAGVVMTTGTDVKDA
KVISVSTGTKCINGEYMSDRGLALNDCHAEIISRRSLLRFLYTQLELYLNNKDDQKRSIFQKSERG
GFRLKENVQFHLYISTSPCGDARIFSPHEPILEEPADRHPNRKARGQLRTKIESGQGTIPVRSNASIQ
TWDGVLQGERLLTMSCSDKIARWNVVGIQGSLLSIFVEPIYFSSIILGSLYHGDHLSRAMYQRISNI
EDLPPLYTLNKPLLSGISNAEARQPGKAPNFSVNWTVGDSAIEVINATTGKDELGRASRLCKHAL
YCRWMRVHGKVPSHLLRSKITKPNVYHESKLAAKEYQAAKARLFTAFIKAGLGAWVEKPTEQD
QFSLTGSGSSELIKENMHMKLYMEGTVDNHHFKCTSEGEGKPYEGTQTMRIKVVEGGPLPFAFD
ILATSFLYGSKTFINHTQGIPDFFKQSFPEGFTWERVTTYEDGGVLTATQDTSLQDGCLIYNVKIR
GVNFTSNGPVMQKKTLGWEAFTETLYPADGGLEGRNDMALKLVGGSHLIANIKTTYRSKKPAK
NLKMPGVYYVDYRLERIKEANNETYVEQHEVAVARYCDLPSKLGHKLN*

SEQ ID NO: 38, MCP-dADAR2-DD(E488Q & E396A)-TagBFP Protein Sequence:
MASNFTQFVLVDNGGTGDVTVAPSNFANGIAEWISSNSRSQAYKVTCSVRQSSAQNRKYTIKVE
VPKGAWRSYLNMELTIPIFATNSDCELIVKAMQGLLKDGNPIPSAIAANSGIYGGSGSGAGSGSPA
GGGAPGSGGGSQLHLPQVLADAVSRLVLGKFGDLTDNFSSPHARRKVLAGVVMTTGTDVKDA
KVISVSTGTKCINGEYMSDRGLALNDCHAAIISRRSLLRFLYTQLELYLNNKDDQKRSIFQKSERG
GFRLKENVQFHLYISTSPCGDARIFSPHEPILEEPADRHPNRKARGQLRTKIESGQGTIPVRSNASIQ
TWDGVLQGERLLTMSCSDKIARWNVVGIQGSLLSIFVEPIYFSSIILGSLYHGDHLSRAMYQRISNI
EDLPPLYTLNKPLLSGISNAEARQPGKAPNFSVNWTVGDSAIEVINATTGKDELGRASRLCKHAL
YCRWMRVHGKVPSHLLRSKITKPNVYHESKLAAKEYQAAKARLFTAFIKAGLGAWVEKPTEQD
QFSLTGSGSSELIKENMHMKLYMEGTVDNHHFKCTSEGEGKPYEGTQTMRIKVVEGGPLPFAFD
ILATSFLYGSKTFINHTQGIPDFFKQSFPEGFTWERVTTYEDGGVLTATQDTSLQDGCLIYNVKIR
GVNFTSNGPVMQKKTLGWEAFTETLYPADGGLEGRNDMALKLVGGSHLIANIKTTYRSKKPAK
NLKMPGVYYVDYRLERIKEANNETYVEQHEVAVARYCDLPSKLGHKLN*

SEQ ID NO: 39, PCP-ADAR2-DD(E488Q)-TagBFP Protein Sequence:
MSKTIVLSVGEATRTLTEIQSTADRQIFEEKVGPLVGRLRLTASLRQNGAKTAYRVNLKLDQADV
VDSGLPKVRYTQVWSHDVTIVANSTEASRKSLYDLTKSLVATSQVEDLVVNLVPLGRASTGSGI
YGGSGSGAGSGSPAGGGAPGSGGGSQLHLPQVLADAVSRLVLGKFGDLTDNFSSPHARRKVLA
GVVMTTGTDVKDAKVISVSTGTKCINGEYMSDRGLALNDCHAEIISRRSLLRFLYTQLELYLNNK
DDQKRSIFQKSERGGFRLKENVQFHLYISTSPCGDARIFSPHEPILEEPADRHPNRKARGQLRTKIE
SGQGTIPVRSNASIQTWDGVLQGERLLTMSCSDKIARWNVVGIQGSLLSIFVEPIYFSSIILGSLYH
GDHLSRAMYQRISNIEDLPPLYTLNKPLLSGISNAEARQPGKAPNFSVNWTVGDSAIEVINATTGK
DELGRASRLCKHALYCRWMRVHGKVPSHLLRSKITKPNVYHESKLAAKEYQAAKARLFTAFIK
AGLGAWVEKPTEQDQFSLTGSGSSELIKENMHMKLYMEGTVDNHHFKCTSEGEGKPYEGTQTM
RIKVVEGGPLPFAFDILATSFLYGSKTFINHTQGIPDFFKQSFPEGFTWERVTTYEDGGVLTATQD
TSLQDGCLIYNVKIRGVNFTSNGPVMQKKTLGWEAFTETLYPADGGLEGRNDMALKLVGGSHLI
ANIKTTYRSKKPAKNLKMPGVYYVDYRLERIKEANNETYVEQHEVAVARYCDLPSKLGHKLN*

Example 14

(1) cpMCP With N-terminal Degron: Data demonstrating that cpMCP can be granted MS2-RNA dependent stability with an N-degron instead of a C-degron.

(2) Structural Similarities Between MCP/PCP: A comparison between MCP and PCP structures is shown to demonstrate that techniques applied to MCP to create proteins like dmMCP can be extended to PCP.

(1) cpMCP with N-Terminal Degron

Figure 41A:
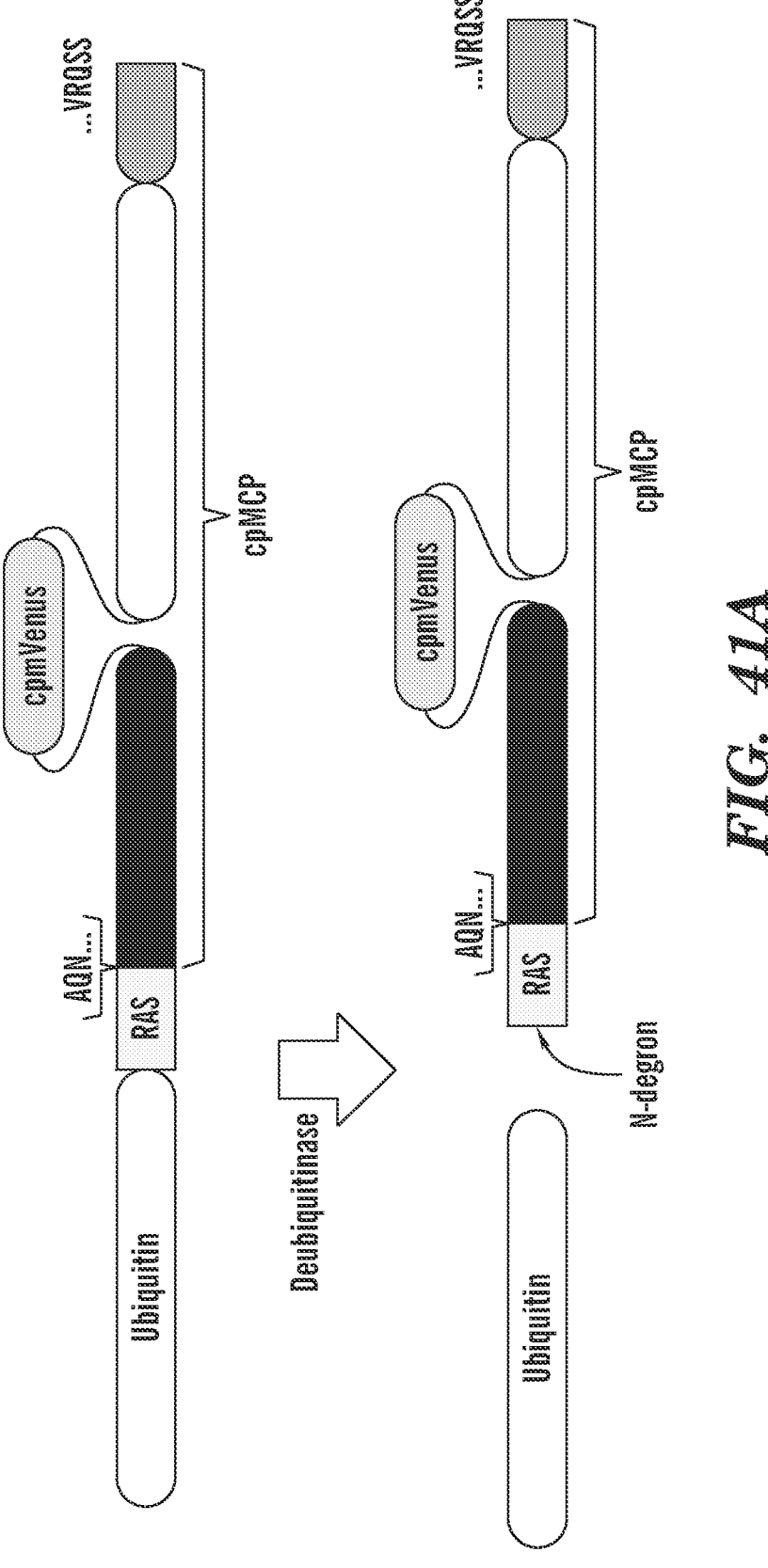
FIG. 41A-41B are a series of schematics and images.
Figure 41B:
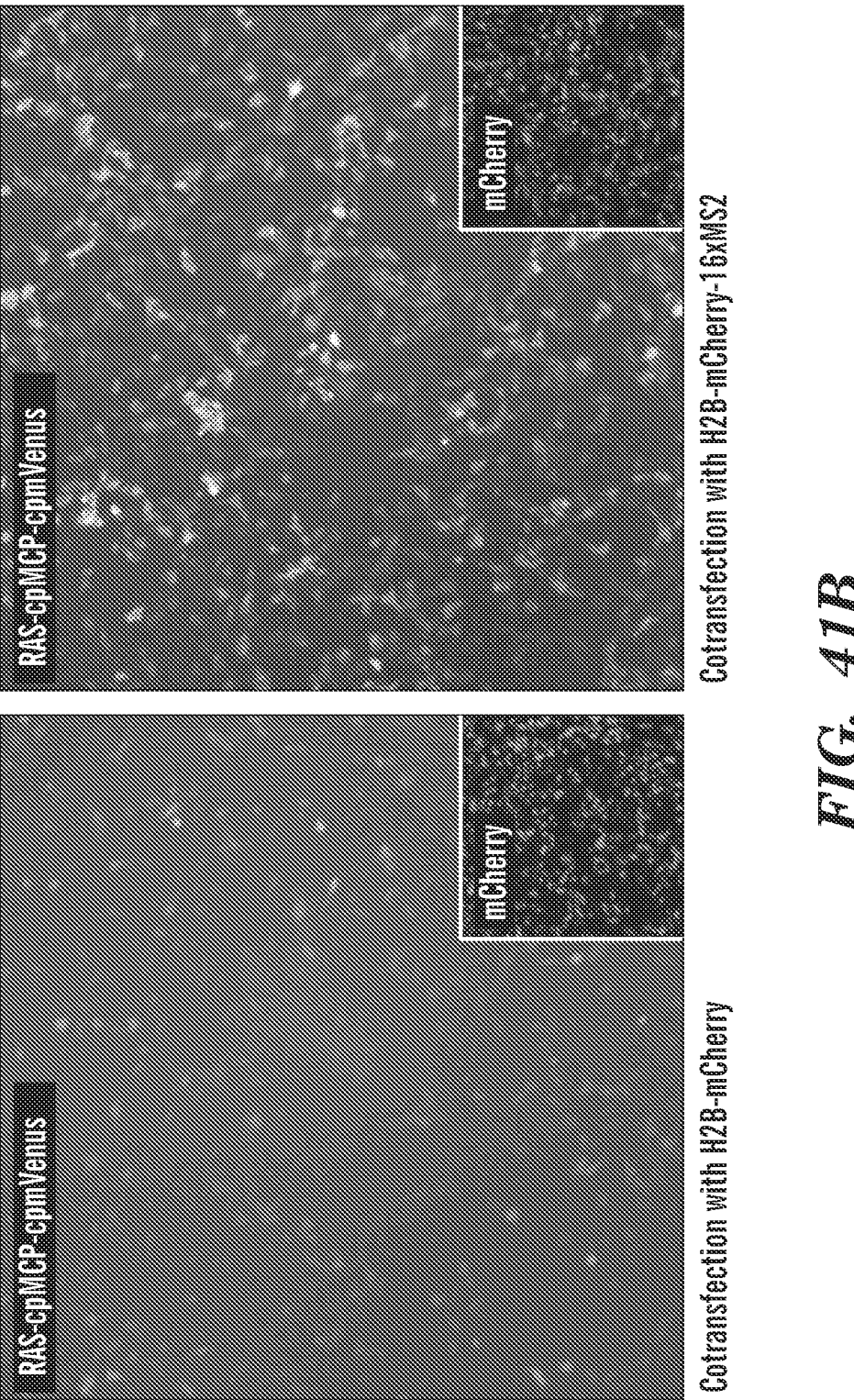

An N-terminal degron was added to the N-terminus of cpMCP through the ubiquitin fusion technique (see e.g., Bachmair et al. (1986). Science 234(4773), 179-186). This technique allows for the creation of proteins with specific N-terminal amino acids, rather than the usual methionine encoded by the AUG start codon. Ubiquitin fusion involves inserting the sequence for a protein of interest directly after the sequence for ubiquitin. When this fusion protein is translated, deubiquitinases cleave ubiquitin at its C-terminus, generating one ubiquitin and one protein whose N-terminus is the amino acid sequence following ubiquitin. Exposed N-terminal arginine (R) amino acids act as degrons and trigger protein degradation, so ubiquitin fusion was used to add the sequence 'RAS' to the N-terminus of cpMCP. The resulting protein had MS2-RNA dependent stability, as seen by an increase in fluorescent signal when co-expressed with MS2-RNA (see e.g., FIG. 41A-41B).

(2) Structural Similarities Between MCP/PCP

Figure 42:
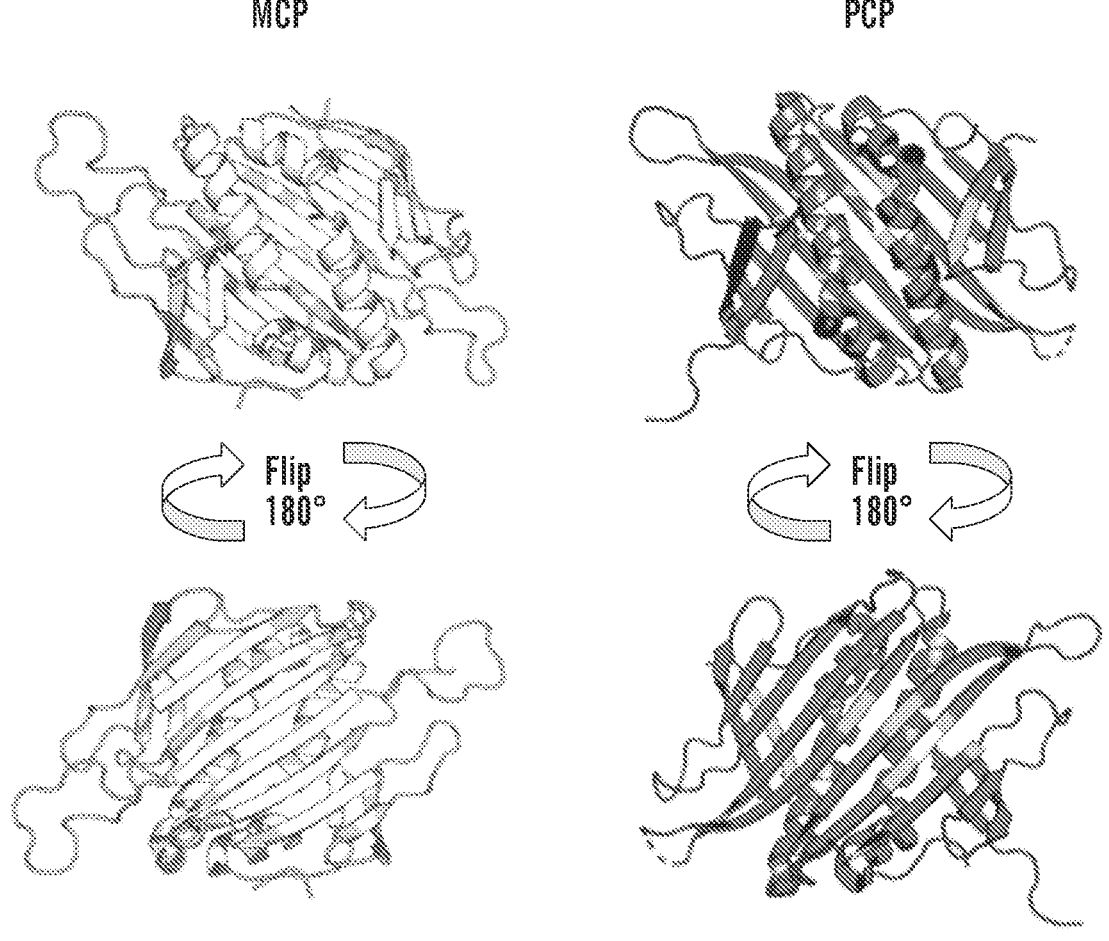
FIG. 42: Comparison between structures of wildtype MS2
coat protein homodimer (PDB ID: 2MS2) and wildtype PP7
coat protein homodimer (PDB ID: 2QUD). Note that both
wildtype MCP and PCP form homodimers with a
10-stranded beta sheet on one side and with interdigitated
alpha helices on the other.

As described herein, cpMCP and dMCP could be split in half to create 'cpmMCP' and 'dmMCP'. These proteins exhibit MS2-RNA dependent stability and it is expected that, when expressed in cells, pairs of cpmMCP and dmMCP proteins form homodimers that match the structure of cpMCP and dMCP respectively. It is expected that a similar outcome of PP7-RNA dependent stability can be achieved when splitting cpPCP and dPCP in half because the PCP and MCP structures are highly similar. Note in FIG. 42 that both wildtype MCP and PCP form homodimers with a 10-stranded beta sheet stretching the length of each structure on one side and with interdigitated alpha helices on the other. It is also expected that such 'cpmPCP' and 'dmPCP' proteins can comprise the same solubilizing mutations used to make dPCP in order to prevent their aggregation (e.g., at least one mutation corresponds to S22R, L36A, and/or L71A in SEQ ID NO: 24).

As such, any of the fusion constructs comprising an engineered MCP protein can comprise an engineered PCP protein in place of the engineered MCP protein, and any of the RNA molecules described herein comprising a MS2 hairpin loop can comprise a PP7 hairpin loop in place of the MS2 hairpin loop.

Relevant Annotated Amino Acid Sequence

TABLE 9

| | |
|---|---|
| SEQ ID NO: 51, Ubiquitin is shown in dotted underlined text; RAS is shown in zigzag underlined text; C_half_MCP is shown in bolded text; MCP is shown in italicized text; cpm Venus is show with double-underlined text; N_half_MCP is shown in bolded italicized text | |

| Construct | Sequence (Amino Acid) |
|---|---|
| Ubiquitin-RAS-dMCP with cpm Venus Inserted at Fused Termini Site A (Ubiquitin-RAS-C_half_MCP-MCP-cpm Venus-N_half_MCP); SEQ ID NO: 51 | MQIFVKTLTGKTITLEVEPSDTIENVKAKIQDKEGIPPDQQRLIFAG KQLEDGRTLSDYNIQKESTLHLVLRLRGGRASARASAQNRKYTIKVEV PKGAWRSYLNMELTIPIFATNSDCELIVKAMQGLLKDGNPIPS AIAANSGIY_ANFTQFVLVDNGGTGDVTVAPSNFANGIAEWISSNSRS_ _QAYKVTCSVRQSSAQNRKYTIKVEVPKGAWRSYLNMELTIPIFATNSD_ _CELIVKAMQGLLKDGNPIPSAIAANSGIYGS_VQLADHYQQNTPIGD GPVLLPDNHYLSYQSKLSKDPNEKRDHMVLLEFVTAAGITLGMD ELYKGGTGGSMVSKGEELFTGVVPILVELDGDVNGHKFSVSGEG EGDATYGKLTLKLICTTGKLPVPWPTLVTTLGYGLQCFARYPDH MKQHDFFKSAMPEGYVQERTIFFKDDGNYKTRAEVKFEGDTLV NRIELKGIDFKEDGNILGHKLEYNYNSHNVYITADKOKNGIKANF KIRHNTS_ANFTQFVLVDNGGTGDVTVAPSNFANGIAEWISSNSRS_ _QAYKVTCSRQSS_ |

What is claimed herein is:

1. An engineered MS2 coat protein (MCP) comprising an engineered RNA-binding domain; wherein the engineered MCP protein is stable when the engineered RNA-binding domain is bound to an MS2 RNA hairpin loop; wherein when the engineered RNA-binding domain is not bound to the MS2 RNA hairpin loop, the engineered MCP protein is unstable and degradation of the engineered MCP protein increases; wherein the engineered RNA-binding domain comprises:

(a) a C-terminal portion of a first MCP monomer; and
(b) an N-terminal portion of the first MCP monomer;
wherein the first MCP monomer is split into the N-terminal portion and the C-terminal portion at a binding pocket for the MS2 RNA hairpin loop.

2. An engineered MS2 coat protein (MCP) comprising an engineered RNA-binding domain and a degron; wherein the degron is hidden upon binding of the engineered RNA-binding domain to an MS2 RNA hairpin loop; wherein when the engineered RNA-binding domain is not bound to the MS2 RNA hairpin loop, the degron is exposed and degradation of the engineered MCP protein increases; wherein the engineered RNA-binding domain comprises:

(a) a C-terminal portion of a first MCP monomer; and
(b) an N-terminal portion of the first MCP monomer;
wherein the first MCP monomer is split into the N-terminal portion and the C-terminal portion at a binding pocket for the MS2 RNA hairpin loop.

3. The engineered MCP protein of claim 2, wherein the degron is a C-terminal degron that is C-terminal of the engineered RNA-binding domain.

4. The engineered MCP protein of claim 3, wherein C-terminal degron comprises RRRG (SEQ ID NO: 10).

5. The engineered MCP protein of claim 2, wherein the degron is a N-terminal degron that is N-terminal of the engineered RNA-binding domain.

6. The engineered MCP protein of claim 5, wherein the N-terminal degron comprises ubiquitin and Arg-Ala-Ser (RAS).

7. The engineered MCP protein of claim 2, wherein the engineered RNA-binding domain comprises a tandem dimer of MCP monomers.

8. The engineered MCP protein of claim 2, wherein the engineered RNA-binding domain comprises circular permutation of MCP monomers.

9. The engineered MCP protein of claim 2, wherein the engineered RNA-binding domain comprises:

(a) the C-terminal portion of the first MCP monomer;
(b) a second MCP monomer; and
(c) the N-terminal portion of the first MCP monomer.

10. The engineered MCP protein of claim 9, wherein:

(a) the C-terminal portion of the first MCP monomer comprises SEQ ID NO: 19 or an amino acid sequence that is at least 80% identical to SEQ ID NO: 19;
(b) the second MCP monomer comprises SEQ ID NO: 20 or an amino acid sequence that is at least 80% identical to SEQ ID NO: 20; and/or
(c) the N-terminal portion of the first MCP monomer comprises SEQ ID NO: 21 or an amino acid sequence that is at least 80% identical to SEQ ID NO: 21.

11. The engineered MCP protein of claim 2, wherein the engineered RNA-binding domain comprises from N-terminus to C-terminus:

(a) the C-terminal portion of the first MCP monomer; and
(b) the N-terminal portion of the first MCP monomer.

12. The engineered MCP protein of claim 2, wherein the binding pocket for the MS2 RNA hairpin loop comprises SEQ ID NO: 25.

13. The engineered MCP protein of claim 2, wherein the first MCP monomer is split into the N-terminal portion and the C-terminal portion at residue 48, 49, 50, 51, 52, 53, 54, or 55 of SEQ ID NO: 22 or at residue 49, 50, 51, 52, 53, 54, 55, or 56 of SEQ ID NO: 23.

14. The engineered MCP protein of claim 2, wherein:
(a) the C-terminal portion of the first MCP monomer comprises at least residues 53-116 of SEQ ID NO: 22 or at least residues 54-117 of SEQ ID NO: 23; and/or
(b) the N-terminal portion of the first MCP monomer comprises at least residues 3-50 of SEQ ID NO: 22 or at least residues 4-51 of SEQ ID NO: 23.

15. The engineered MCP protein of claim 2, wherein the MS2 RNA hairpin loop comprises one of SEQ ID NOs: 27, 29, 42-44, 47, 54 or a nucleic acid sequence that is at least 80% identical to one of SEQ ID NOs: 27, 29, 42-44, 47, 54.

16. The engineered MCP protein of claim 2, wherein the MS2 RNA hairpin loop comprises NNNNNRNNAN-YANNNNNNN, wherein "R" indicates a purine, "Y" indicates a pyrimidine, and the following "N" nucleotide positions are complementary: 1 and 19, 2 and 18, 3 and 17, 4 and 16, 5 and 15, 7 and 13, 8 and 13.

17. The engineered MCP protein of claim 2 comprising SEQ ID NO: 4, SEQ ID NO: 50, or an amino acid sequence that is at least 80% identical to SEQ ID NO: 4 or SEQ ID NO: 50.

18. The engineered MCP protein of claim 2, comprising from N-terminus to C-terminus:
(a) the engineered RNA-binding domain comprising from N-terminus to C-terminus:
(i) the C-terminal portion of the first MCP monomer;
(ii) a second MCP monomer; and
(iii) the N-terminal portion of the first MCP monomer; and
(b) the degron.

19. The engineered MCP protein of claim 2, comprising from N-terminus to C-terminus:
(a) the engineered RNA-binding domain comprising from N-terminus to C-terminus:
(i) the C-terminal portion of the first MCP monomer; and
(ii) the N-terminal portion of the first MCP monomer; and
(b) the degron.

20. A fusion protein comprising the engineered MCP protein of claim 2 linked to at least one effector protein.

21. The fusion protein of claim 20, wherein the at least one effector protein is selected from the group consisting of:
(a) a detectable marker;
(b) a trafficking domain and/or targeting sequence;
(c) a Cas protein that binds to an RNA guide sequence;
(d) an RNA-cleaving and/or RNA-modifying enzyme;
(e) a translation-regulating and translation-associated domain;
(f) a cell-cycle regulated degron;
(g) a proximity-labeling and/or substrate-labeling enzyme; and
(h) an antigen-binding domain.

22. The fusion protein of claim 20, further comprising a linker between the engineered RNA-binding domain and the at least one effector protein;
wherein the linker is selected from the group consisting of:
(a) drug-inducible heterodimerization domains;
(b) drug-dissociable heterodimerization domains;
(c) drug-preservable domains;
(d) a gas-vesicle associated domain that is released by ultrasound;
(e) light-regulated protein-protein interaction domains; and
(f) protein-protein interaction domains dependent on an extracellular or intracellular signal.

23. The fusion protein of claim 20, further comprising a transmembrane domain.

24. A complex comprising the fusion protein of claim 20 bound to an RNA molecule comprising at least one hairpin loop specifically bound by the engineered RNA-binding domain of the fusion protein.

25. A nucleic acid encoding the fusion protein of claim 20.

26. A vector comprising the nucleic acid of claim 25.

27. A system comprising:
(a) a fusion protein comprising the engineered MCP protein of claim 2 linked to at least one effector protein; and
(b) an RNA molecule comprising at least one MS2 RNA hairpin loop.

\* \* \* \* \*